US010040791B2

(12) United States Patent
Saito et al.

(10) Patent No.: US 10,040,791 B2
(45) Date of Patent: Aug. 7, 2018

(54) ISOXAZOLE DERIVATIVE AS MUTANT ISOCITRATE DEHYDROGENASE 1 INHIBITOR

(71) Applicants: Daiichi Sankyo Company, Limited, Chuo-ku, Tokyo (JP); National Cancer Center, Chuo-ku, Tokyo (JP)

(72) Inventors: Shoichi Saito, Shinagawa-ku (JP); Masao Itoh, Shinagawa-ku (JP); Tetsunori Fujisawa, Edogawa-ku (JP); Hironao Saito, Shinagawa-ku (JP); Yohei Kiyotsuka, Shinagawa-ku (JP); Hideaki Watanabe, Shinagawa-ku (JP); Hironori Matsunaga, Shinagawa-ku (JP); Yoshiko Kagoshima, Shinagawa-ku (JP); Tetsuya Suzuki, Shinagawa-ku (JP); Yoko Ogawara, Chuo-ku (JP); Kazuo Kitabayashi, Chuo-ku (JP)

(73) Assignees: Daiichi Sankyo Company, Limited, Chuo-ku (JP); National Cancer Center, Chuo-ko (JP)

( * ) Notice: Subject to any disclaimer, the term of this patent is extended or adjusted under 35 U.S.C. 154(b) by 0 days.

(21) Appl. No.: 15/516,362

(22) PCT Filed: Oct. 1, 2015

(86) PCT No.: PCT/JP2015/077916
§ 371 (c)(1),
(2) Date: Mar. 31, 2017

(87) PCT Pub. No.: WO2016/052697
PCT Pub. Date: Apr. 7, 2016

(65) Prior Publication Data
US 2017/0313696 A1 Nov. 2, 2017

(30) Foreign Application Priority Data

Oct. 1, 2014 (JP) .................. 2014-203475
Jun. 9, 2015 (JP) .................. 2015-116774

(51) Int. Cl.
*A61K 31/437* (2006.01)
*A61K 31/454* (2006.01)
*A61K 31/5377* (2006.01)
*A61K 31/422* (2006.01)
*A61K 31/4439* (2006.01)
*A61K 31/496* (2006.01)
*C07D 413/06* (2006.01)
*C07D 413/14* (2006.01)
*C07D 471/04* (2006.01)

(52) U.S. Cl.
CPC ......... *C07D 471/04* (2013.01); *C07D 413/06* (2013.01); *C07D 413/14* (2013.01)

(58) Field of Classification Search
CPC ............... A61K 31/437; A61K 31/454; A61K 31/5377; A61K 31/422; A61K 31/4439; A61K 31/496; C07D 413/06; C07D 413/14; C07D 471/04
USPC ....... 514/292, 293, 300, 303, 322, 323, 378, 514/380; 546/82, 84, 113, 199; 548/245, 548/246, 248
See application file for complete search history.

(56) References Cited

U.S. PATENT DOCUMENTS 3,336,307 A    8/1967  Shen

FOREIGN PATENT DOCUMENTS

| GB | 2 284 600 A | 6/1995 |
| JP | 2013-536168 A | 9/2013 |
| JP | 2014-519518 A | 8/2014 |
| WO | 94/10145 A1 | 5/1994 |
| WO | 94/24095 A1 | 10/1994 |
| WO | 2004/072051 A1 | 8/2004 |
| WO | 2012/171506 A1 | 12/2012 |
| WO | 2012/173682 A2 | 12/2012 |
| WO | 2013/046136 A1 | 4/2013 |
| WO | 2013/107291 A1 | 7/2013 |
| WO | 2013/107405 A1 | 7/2013 |

OTHER PUBLICATIONS

International Preliminary Report on Patentability dated Apr. 4, 2017, issued in corresponding International Application No. PCT/JP2015/077916, filed Oct. 1, 2015, 6 pages.
Amary, M.F., et al., "Ollier Disease and Maffucci Syndrome Are Caused by Somatic Mosaic Mutations of IDH1 and IDH2," Nature Genetics 43(12):1262-1266, Dec. 2011.
Borger, D.R., et al., "Frequent Mutation of Isocitrate Dehydrogenase (IDH)1 and IDH2 in Cholangiocarcinoma Identified Through Broad-Based Tumor Genotyping," Oncologist 17(1):72-79, 2012.
Cairns, R.A., et al., "IDH2 Mutations Are Frequent in Angioimmunoblastic T-Cell Lymphoma," Blood 119(8):1901-1903, Feb. 2012.
Dang, L., et al., "Cancer-Associated IDH1 Mutations Produce 2-Hydroxyglutarate," Nature 462(7274):739-744, Dec. 2009.
Database Registry, RN 443778-21-0, Aug. 2002, Chemical Library, 1 page.
Database Registry, RN 732270-62-1, Aug. 2004, Chemical Library, 1 page.
Gross, S., et al., "Cancer-Associated Metabolite 2-Hydroxyglutarate Accumulates in Acute Myelogenous Leukemia With Isocitrate Dehydrogenase 1 and 2 Mutations," Journal of Experimental Medicine 207(2):339-344, Feb. 2010.

(Continued)

Primary Examiner — Brenda L Coleman
(74) Attorney, Agent, or Firm — Christensen O'Connor Johnson Kindness PLLC

(57) ABSTRACT

It has been found that a compound of the general formula (I) having an isoxazole skeleton has excellent inhibitory activity against mutant IDH1 protein and inhibits the production of 2-HG by this protein, while the compound is also capable of effectively inhibiting the growth of various tumors expressing the protein. In the formula, $R^1$, $R^2$, $R^3$, Y, and Z are as defined in claim 1.

15 Claims, 4 Drawing Sheets

(56) References Cited

OTHER PUBLICATIONS

Hemerly, J.P., et al., "Identification of Several Novel Non-p.R132 IDH1 Variants in Thyroid Carcinomas," European Journal of Endocrinology 163(5):747-755, Nov. 2010.

Kang, M.R., et al., "Mutational Analysis of IDH1 Codon 132 in Glioblastomas and Other Common Cancers," International Journal of Cancer 125(2):353-355, Jul. 2009.

Kosmider, O., et al., "Mutations of IDH1 and IDH2 Genes in Early and Accelerated Phases of Myelodysplastic Syndromes and MDS/Myeloproliferative Neoplasms," Leukemia 24(5):1094-1096, May 2010.

Liu, X., et al., "Isocitrate Dehydrogenase 2 Mutation Is a Frequent Event in Osteosarcoma Detected by a Multi-Specific Monoclonal Antibody MsMab-1," Cancer Medicine 2(6):803-814, Dec. 2013.

Losman, J.-A., et al., "(R)-2-Hydroxyglutarate Is Sufficient to Promote Leukemogenesis and Its Effects Are Reversible," Science 339(6127):1621-1625, Mar. 2013.

Mardis, E.R., et al., "Recurring Mutations Found by Sequencing an Acute Myeloid Leukemia Genome," New England Journal of Medicine 36(11):1058-1066, Sep. 2009.

Pansuriya, T.C., et al., "Somatic Mosaic IDH1 and IDH2 Mutations Are Associated With Enchondroma and Spindle Cell Hemangioma in Ollier Disease and Maffucci Syndrome," Nature Genetics 43(12):1256-1261, Nov. 2011.

Parsons, D.W., et al., "An Integrated Genomic Analysis of Human Glioblastoma Multiforme," Science 321(5897):1807-1812, Sep. 2008.

Paschka, P., et al., "IDH1 and IDH2 Mutations Are Frequent Genetic Alterations in Acute Myeloid Leukemia and Confer Adverse Prognosis in Cytogenetically Normal Acute Myeloid Leukemia With NPM1 Mutation Without FLT3 Internal Tandem Duplication," Journal of Clinical Oncology 28(22):3636-3643, Aug. 2010.

Shibata, T., et al., "Mutant IDH1 Confers an In Vivo Growth in a Melanoma Cell Line With BRAF Mutation," American Journal of Pathology 178(3):1395-1402, Mar. 2011.

Sjöblom, T., et al., "The Concensus Coding Sequences of Human Breast and Colorectal Cancers," Science 314(5797):267-274, Oct. 2006.

Tefferi, A., et al., "IDH1 and IDH2 Mutation Studies in 1473 Patients With Chronic-, Fibrotic- or Blast-Phase Essential Thrombocythemia, Polycythemia Vera or Myelofibrosis," Leukemia 24(7):1302-1309, Jul. 2010.

Vissers, L.E.L.M., et al., "Whole-Exome Sequencing Detects Somatic Mutations of IDH1 in Metaphyseal Chondromatosis With D-2-Hydroxyglutaric Aciduria (MC-HGA)," American Journal of Medical Genetics, Part A 155A(11):2609-2616, Nov. 2011.

Ward, P.S., et al., "Identification of Additional IDH Mutations Associated With Oncometabolite R(-)-2-Hydroxyglutarate Production," Oncogene 31(19):2491-2498, May 2012. (Author Manuscript provided, PMCID:PMC3271133, available in PMC May 12, 2012, 12 pages.).

Ward, P.S., et al., "The Common Feature of Leukemia-Associated IDH1 and IDH2 Mutations Is a Neomorphic Enzyme Activity Converting α-Ketoglutarate to 2-Hydroxyglutarate," Cancer Cell 17(3):225-234, Mar. 2010.

Yan, H., et al., "IDH1 and IDH2 Mutations in Gliomas," New England Journal of Medicine 360(8):765-773, Feb. 2009.

Yang, H., et al., "IDH1 and IDH2 Mutations in Tumorigenesis: Mechanistic Insights and Clinical Perspectives," Clinical Cancer Research 18(20):5562-5571, Oct. 2012.

ISOXAZOLE DERIVATIVE AS MUTANT ISOCITRATE DEHYDROGENASE 1 INHIBITOR

TECHNICAL FIELD

The present invention relates to a compound and a pharmaceutically acceptable salt thereof which have excellent inhibitory activity against mutant isocitrate dehydrogenase 1 (hereinafter, also referred to as "IDH1").

BACKGROUND ART

Isocitrate dehydrogenases (IDHs) are an enzyme group that converts isocitrate to 2-oxoglutarate (α-ketoglutarate). This enzyme group is further divided into NAD+ dependent isocitrate dehydrogenases (EC 1.1.1.41) and NADP+ dependent isocitrate dehydrogenases (EC 1.1.1.42).

IDH1 (isocitrate dehydrogenase 1 (NADP+), soluble) protein and IDH2 (isocitrate dehydrogenase 2 (NADP+), mitochondrial) protein are enzymes that are classified into the NADP+ dependent isocitrate dehydrogenases (EC 1.1.1.42). IDH1 gene mutations or IDH2 gene mutations have been found in various cancers. Specific examples thereof can include glioma and glioblastoma, acute myeloid leukemia, myelodysplastic syndrome, myeloproliferative tumor, peripheral T-cell lymphoma, chondrosarcoma, osteosarcoma, bile duct cancer, primitive neuroectodermal tumor, B-cell lymphoblastic lymphoma, malignant melanoma, prostate cancer, colorectal cancer, and thyroidal cancer (Non Patent References 1 to 16).

Also, a great majority of Ollier's disease or Maffucci syndrome patients often having chondrosarcoma have been reported to naturally retain a mosaic IDH1 gene mutation or IDH2 gene mutation (Non Patent References 8 and 9).

Features common in various literature reports are that the gene mutations in IDH1 and IDH2 are point mutations and the mutation sites are focused on amino acids important for the enzymatic reactions or amino acids close thereto. Particularly, a mutation to substitute arginine at the 132-position (hereinafter, indicated as R132) of the IDH1 protein by another amino acid accounts for a great majority of the IDH1 gene mutations. As an example, a mutation to convert arginine at the 132-position to histidine (indicated as R132H) or a mutation to convert this arginine to cytosine (R132C), leucine (R132L), serine (R132S), glycine (R132G), valine (R132V), or the like has been found to occur frequently. In addition, cases where a mutation occurs in G97, R100, H133, A134, or the like are known. The IDH2 gene mutations are mostly mutations to convert R140 or R172 to another amino acid. For example, R140Q mutation or R172K or R172S mutation is known. A great majority of mutation cases also indicate that one of the alleles resides in a wild-type form. Such features of the mutations suggest that the mutated IDH1 gene and the mutated IDH2 gene function as activating mutations.

From the functional analysis of IDH1R132H protein, it has been reported that the IDH1R132H protein has enzymatic activity totally different from that of wild-type IDH1, i.e., has the activity of converting 2-oxoglutarate and NADPH to D-2-hydroxyglutarate (hereinafter, referred to as 2-HG) and NADP+ (Non Patent Reference 17). 2-HG has been produced at a high concentration in glioma or acute myeloid leukemia cells or cultured cells having a mutation such as R132H, R132S, R132C, R132G, or G97D of IDH1, or R140Q or R172K of IDH2. Similar reports have also been made as to other IDH1 mutations (Non Patent References 18 to 20). From these reports, the possibility is suggested that mutant IDH1 protein expressed in a tumor influences the properties of the tumor via 2-HG produced by the enzymatic activity different from that of wild-type IDH.

It has been shown that acute myeloid leukemia cell line TF-1 cells caused to express IDH1R132H can grow even in a medium free from GM-CSF (granulocyte macrophage colony-stimulating factor). It has also been shown that TF-1 cells expressing IDH1R132H are hindered from differentiating into erythrocytes through erythropoietin (Non Patent Reference 21). From such reports, it is suggested that tumors are induced by the function of mutant IDH1 protein to have properties such as promoted growth or suppressed differentiation.

In patients with the aforementioned Ollier's disease or Maffucci syndrome as well, a high concentration of 2-HG is reportedly detected. There is also a report stating that IDH1 gene mutations were detected in some D-2-hydroxyglutaric aciduria patients (Non Patent Reference 22). Thus, 2-HG produced by mutant IDH protein also seems to contribute to the pathologic conditions of these diseases.

Against this backdrop, drugs inhibiting the activity of the mutant IDH1 protein have been expected to be useful as therapeutic drugs that specifically act on diseases related to IDH1 mutations, such as cancers.

Amide derivatives (Patent References 6, 7, and 8), bicyclic compounds (Patent Reference 9), aminopyridine derivatives (Patent References 10 and 11), aminopyrimidine derivatives (Patent Reference 12), and the like have been reported as compounds inhibiting the activity of the mutant IDH1 protein.

However, there is still a demand for the development of a compound with a novel structure having excellent inhibitory activity against the mutant IDH1 protein.

CITATION LIST

Patent References

Patent Reference 1: U.S. Pat. No. 3,336,307
Patent Reference 2: WO1994/010145
Patent Reference 3: WO1994/024095
Patent Reference 4: GB2284600
Patent Reference 5: WO2004/072051
Patent Reference 6: WO2012/009678
Patent Reference 7: WO2013/107291
Patent Reference 8: WO2013/107405
Patent Reference 9: WO2012/173682
Patent Reference 10: WO2012/171506
Patent Reference 11: WO2012/171337
Patent Reference 12: WO2013/046136

Non Patent References

Non Patent Reference 1: H. Yang et al., Clin Cancer Res 18 (2012) 5562-5571.
Non Patent Reference 2: D. W. Parsons et al., Science 321 (2008) 1807-1812.
Non Patent Reference 3: H. Yan et al., N Engl J Med 360 (2009) 765-773.
Non Patent Reference 4: E. R. Mardis et al., N Engl J Med 361 (2009) 1058-1066.
Non Patent Reference 5: P. Paschka et al., J Clin Oncol 28 (2010) 3636-3643.
Non Patent Reference 6: O. Kosmider et al., Leukemia 24 (2010) 1094-1096.

Non Patent Reference 7: A. Tefferi et al., Leukemia 24 (2010) 1302-1309.

Non Patent Reference 8: T. C. Pansuriya et al., Nat Genet 43 (2011) 1256-1261.

Non Patent Reference 9: M. F. Amary et al., Nat Genet 43 (2011) 1262-1265.

Non Patent Reference 10: D. R. Borger et al., Oncologist 17 (2012) 72-79.

Non Patent Reference 11: T. Shibata et al., Am J Pathol 178 (2011) 1395-1402.

Non Patent Reference 12: M. R. Kang et al., Int J Cancer 125 (2009) 353-355.

Non Patent Reference 13: T. Sjoblom et al., Science 314 (2006) 268-274.

Non Patent Reference 14: J. P. Hemerly et al., Eur J Endocrinol 163 (2010) 747-755.

Non Patent Reference 15: R. A. Cairns et al., Blood 119 (2012) 1901-1903.

Non Patent Reference 16: X. Liu et al., Cancer Med 2 (2013) 803-814.

Non Patent Reference 17: L. Dang et al., Nature 462 (2009) 739-744.

Non Patent Reference 18: P. S. Ward et al., Cancer Cell 17 (2010) 225-234.

Non Patent Reference 19: S. Gross et al., J Exp Med 207 (2010) 339-344.

Non Patent Reference 20: P. S. Ward et al., Oncogene 31 (2012) 2491-2498.

Non Patent Reference 21: J. A. Losman et al., Science 339 (2013) 1621-1625.

Non Patent Reference 22: L. E. Vissers et al., Am J Med Genet A 155A (2011) 2609-2616.

SUMMARY OF INVENTION

Technical Problem

The present invention has been made in light of these circumstances, and an object of the present invention is to provide a compound with a novel structure having excellent inhibitory activity against mutant IDH1 protein.

Solution to Problem

To attain the object, the present inventors have synthesized compounds having various structures and tested their inhibitory activity against mutant IDH1 protein. As a result, the present inventors have found that a particular compound having an isoxazole skeleton has excellent inhibitory activity against mutant IDH1 protein and inhibits the production of 2-HG by this protein, while the compound is also capable of effectively inhibiting the growth of various tumors expressing the protein. On the basis of these findings, the present invention has been completed.

Thus, the present invention relates to a compound that has an isoxazole skeleton and has inhibitory activity against mutant IDH1 protein, a pharmaceutically acceptable salt thereof, and use thereof and more specifically provides the following:

[1] A compound represented by the general formula (I) or a pharmaceutically acceptable salt thereof:

[Formula 1]

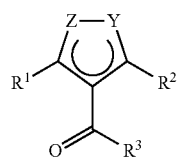

(I)

wherein

Z—Y represents N—O or O—N;

$R^1$ represents a phenyl group optionally having 1 to 3 substituents independently selected from the following group A, or a pyridyl group optionally having 1 to 3 substituents independently selected from the following group A;

$R^2$ represents —$NR^{21}R^{22}$, a $C_1$ to $C_6$ alkyl group optionally having 1 to 3 substituents independently selected from the following group B, a $C_3$ to $C_6$ cycloalkyl group optionally having 1 to 3 substituents independently selected from the following group C, or a 4- to 6-membered heterocyclic group having 1 or 2 heteroatoms independently selected from the group consisting of a nitrogen atom and an oxygen atom in the ring, wherein the 4- to 6-membered heterocyclic group optionally has 1 to 3 substituents independently selected from the following group C, and a bridged structure is optionally bonded within the heterocyclic ring, or one $C_3$ to $C_6$ cycloalkyl ring is optionally bonded onto the heterocyclic ring via a spiro bond;

$R^{21}$ and $R^{22}$ each independently represent a hydrogen atom, a $C_1$ to $C_6$ alkyl group, or —C(=O)$R^{23}$;

$R^{23}$ represents a $C_2$ to $C_6$ alkenyl group or a $C_2$ to $C_6$ alkynyl group;

$R^3$ represents any of the following formulae (II) to (IV):

[Formula 2]

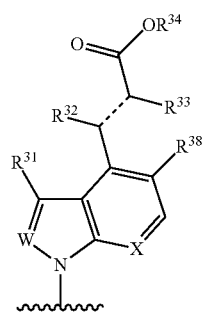

(II)

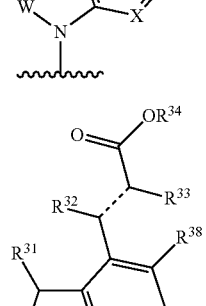

(III)

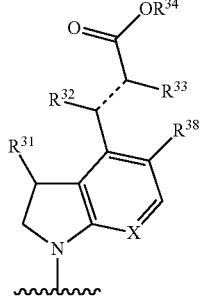

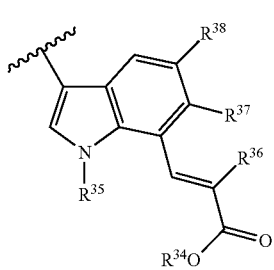

(IV)

wherein
$R^{31}$ represents a hydrogen atom, a halogen atom, a $C_1$ to $C_6$ alkyl group optionally substituted by 1 to 3 halogen atoms, a $C_3$ to $C_6$ cycloalkyl group, or a $C_1$ to $C_6$ alkylcarbonyl group, $R^{32}$ represents a hydrogen atom or a $C_1$ to $C_6$ alkyl group, or $R^{31}$ and $R^{32}$ optionally together form a cyclohexane ring, $R^{33}$ represents a hydrogen atom or a $C_1$ to $C_6$ alkyl group, or $R^{32}$ and $R^{33}$ optionally together form a cyclopropane ring, $R^{34}$ represents a hydrogen atom or a $C_1$ to $C_6$ alkyl group, $R^{35}$ represents a $C_1$ to $C_6$ alkyl group, $R^{36}$ represents a hydrogen atom or a $C_1$ to $C_6$ alkyl group, $R^{37}$ represents a hydrogen atom or a $C_1$ to $C_6$ alkyl group, or $R^{36}$ and $R^{37}$ optionally together form a benzene ring, $R^{38}$ represents a hydrogen atom or a halogen atom, X represents a nitrogen atom or CH, W represents a nitrogen atom or CH, and the broken line represents a single bond or a double bond;

group A consists of a halogen atom, a $C_1$ to $C_6$ alkyl group and a $C_1$ to $C_6$ alkoxy group;

group B consists of a halogen atom, a hydroxy group, a $C_1$ to $C_6$ alkoxy group, a $C_1$ to $C_6$ alkylamino group, and a di-$C_1$ to $C_6$ alkylamino group, group C consists of a $C_2$ to $C_6$ alkenyl group, a halogen atom, a hydroxy group, a cyano group, a $C_1$ to $C_6$ alkyl group optionally having 1 to 3 substituents independently selected from the following group D, a $C_1$ to $C_6$ alkoxy group, —NR$^{211}$R$^{212}$, —C(=O)R$^{213}$, and —SO$_2$R$^{213}$;

$R^{211}$ and $R^{212}$ each independently represent a hydrogen atom or a $C_1$ to $C_6$ alkyl group;

$R^{213}$ represents a $C_2$ to $C_6$ alkenyl group or a $C_2$ to $C_6$ alkynyl group; and group D consists of an amino group, a $C_1$ to $C_6$ alkoxy group, a di-$C_1$ to $C_6$ alkylamino group, an oxo group, and a $C_3$ to $C_6$ cycloalkyl group.

[2] A compound according to [1] or a pharmaceutically acceptable salt thereof, wherein in the formula (I), $R^1$ represents a phenyl group optionally having 1 to 3 substituents independently selected from the group A.

[3] A compound according to [1] or [2] or a pharmaceutically acceptable salt thereof, wherein in the formula (I), $R^2$ represents a $C_1$ to $C_6$ alkyl group optionally having 1 to 3 substituents independently selected from the group B, or a 4- to 6-membered aliphatic heterocyclic group having 1 or 2 heteroatoms independently selected from the group consisting of a nitrogen atom and an oxygen atom in the ring, wherein the 4- to 6-membered aliphatic heterocyclic group optionally has 1 to 3 substituents independently selected from the group C.

[4] A compound according to any one of [1] to [3] or a pharmaceutically acceptable salt thereof,
wherein in the formula (I),
$R^2$ represents any of the following formulae:

[Formula 3]

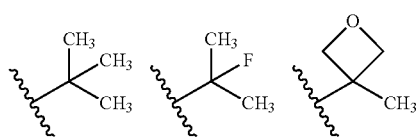

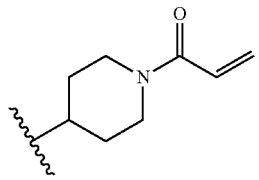

[5] A compound according to any one of [1] to [4] or a pharmaceutically acceptable salt thereof, wherein in the formula (I),
$R^3$ represents the following formula (IV) or (V):

[Formula 4]

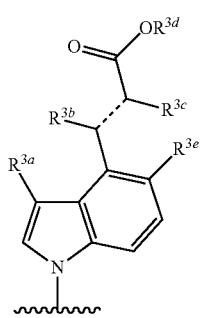
(IV)

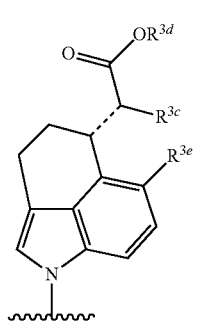
(V)

wherein
$R^{3a}$ represents a hydrogen atom or a $C_1$ to $C_6$ alkyl group optionally substituted by 1 to 3 halogen atoms, $R^{3b}$ represents a hydrogen atom or a $C_1$ to $C_6$ alkyl group, $R^{3c}$ represents a hydrogen atom or a $C_1$ to $C_6$ alkyl group, $R^{3d}$ represents a hydrogen atom or a $C_1$ to $C_6$ alkyl group, $R^{3e}$ represents a hydrogen atom or a halogen atom, and the broken line represents a single bond or a double bond.

[6] A compound according to any one of [1] to [5] or a pharmaceutically acceptable salt thereof,
wherein in the formula (I),
$R^3$ represents any of the following formulae:

[Formula 5]

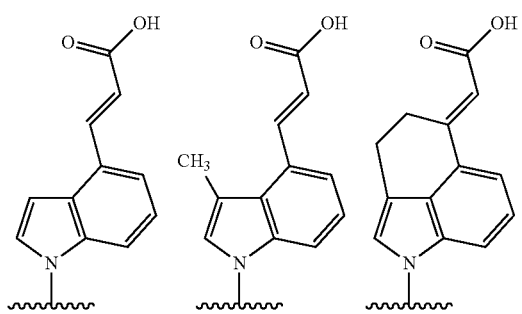

[7] A compound represented by the general formula VI or a pharmaceutically acceptable salt thereof:

[Formula 6]

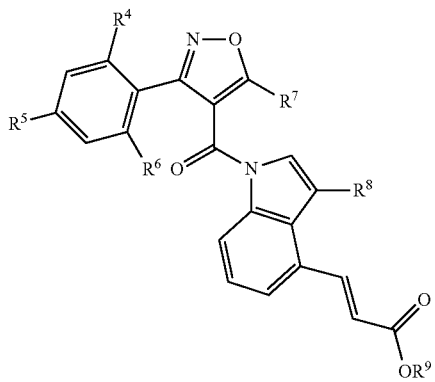

wherein
$R^4$, $R^5$, and $R^6$ each independently represent a hydrogen atom or a halogen atom,
$R^7$ represents any of the following formulae:

[Formula 7]

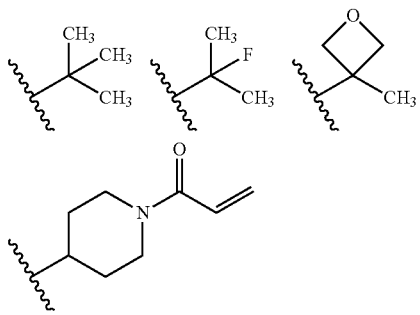

and
$R^8$ and $R^9$ each independently represent a hydrogen atom or a $C_1$ to $C_6$ alkyl group.

[8] A compound represented by the general formula VII or a pharmaceutically acceptable salt thereof:

[Formula 8]

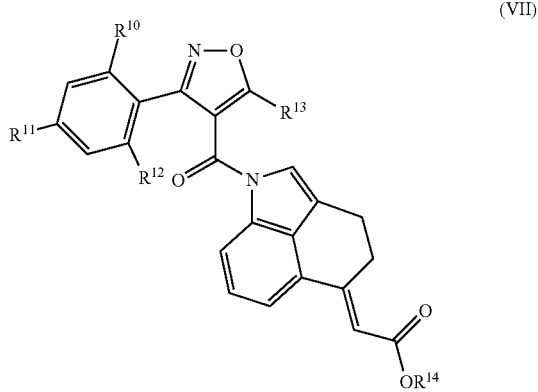

wherein
$R^{10}$, $R^{11}$, and $R^{12}$ each independently represent a hydrogen atom or a halogen atom,
$R^{13}$ represents any of the following formulae:

[Formula 9]

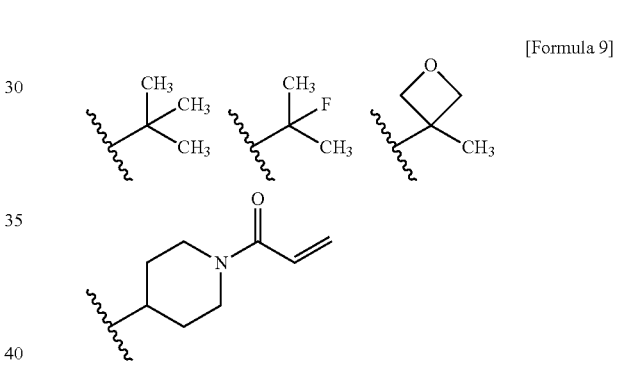

and
$R^{14}$ represents a hydrogen atom or a $C_1$ to $C_6$ alkyl group.

[9] A compound selected from the following group or a pharmaceutically acceptable salt thereof:
(2E)-3-(1-{[5-(3-methyloxetan-3-yl)-3-(2,4,6-trichlorophenyl)-1,2-oxazol-4-yl]carbonyl}-1H-indol-4-yl)prop-2-enoic acid
(2E)-3-(1-{[5-(2-fluoropropan-2-yl)-3-(2,4,6-trichlorophenyl)-1,2-oxazol-4-yl]carbonyl}-3-methyl-1H-indol-4-yl)prop-2-enoic acid
(2E)-3-(1-{[5-(tert-butyl)-3-(2,4,6-trichlorophenyl)-1,2-oxazol-4-yl]carbonyl}-1H-indol-4-yl)prop-2-enoic acid
(2E)-3-(1-{[3-(2,4-dichloro-6-fluorophenyl)-5-(2-fluoropropan-2-yl)-1,2-oxazol-4-yl]carbonyl}-3-methyl-1H-indol-4-yl)prop-2-enoic acid
(2E)-3-(1-{[3-(2,4-dichlorophenyl)-5-(2-fluoropropan-2-yl)-1,2-oxazol-4-yl]carbonyl}-3-methyl-1H-indol-4-yl)prop-2-enoic acid
(2E)-[1-{[5-(1-acryloylpiperidin-4-yl)-3-(2,4,6-trichlorophenyl)-1,2-oxazol-4-yl]carbonyl}-3,4-dihydrobenzo[cd]indol-5(1H)-ylidene]ethanoic acid
(2E)-3-(1-{[5-(1-acryloylpiperidin-4-yl)-3-(2,4,6-trichlorophenyl)-1,2-oxazol-4-yl]carbonyl}-3-methyl-1H-indol-4-yl)prop-2-enoic acid
(2E)-[1-{[5-(1-acryloylpiperidin-4-yl)-3-(2,4-dichloro-6-fluorophenyl)-1,2-oxazol-4-yl]carbonyl}-3,4-dihydrobenzo[cd]indol-5(1H)-ylidene]ethanoic acid (2E)-[1-{[5-(1-acryloylpiperidin-4-yl)-3-(2,4-dichloro-5-fluorophenyl)-1,2-oxazol-4-yl]carbonyl}-3,4-dihydrobenzo[cd]indol-5(1H)-ylidene]ethanoic acid (2E)-[1-{[5-(1-acryloylpiperidin-4-yl)-3-(2,4-dichlorophenyl)-1,2-oxazol-4-yl]carbonyl}-3,4-dihydrobenzo[cd]indol-5(1H)-ylidene]ethanoic acid.

[10] (2E)-3-(1-{[5-(2-fluoropropan-2-yl)-3-(2,4,6-trichlorophenyl)-1,2-oxazol-4-yl]carbonyl}-3-methyl-1H-indol-4-yl)prop-2-enoic acid or a pharmaceutically acceptable salt thereof.

[11] (2E)-3-(1-{[5-(2-Fluoropropan-2-yl)-3-(2,4,6-trichlorophenyl)-1,2-oxazol-4-yl]carbonyl}-3-methyl-1H-indol-4-yl)prop-2-enoic acid tert-butylamine salt.

[12] (2E)-[1-{[5-(1-Acryloylpiperidin-4-yl)-3-(2,4,6-trichlorophenyl)-1,2-oxazol-4-yl]carbonyl}-3,4-dihydrobenzo[cd]indol-5(1H)-ylidene]ethanoic acid or a pharmaceutically acceptable salt thereof.

[13] (2E)-[1-{[5-(1-Acryloylpiperidin-4-yl)-3-(2,4,6-trichlorophenyl)-1,2-oxazol-4-yl]carbonyl}-3,4-dihydrobenzo[cd]indol-5(1H)-ylidene]ethanoic acid tert-butylamine salt.

[14] A mutant isocitrate dehydrogenase 1 inhibitor comprising a compound according to any one of [1] to [13] or a pharmaceutically acceptable salt thereof as an active ingredient.

[15] A D-2-hydroxyglutarate production inhibitor comprising a compound according to any one of [1] to [13] or a pharmaceutically acceptable salt thereof as an active ingredient.

[16] A pharmaceutical composition comprising a compound according to any one of [1] to [13] or a pharmaceutically acceptable salt thereof as an active ingredient.

An antitumor agent against a tumor having an isocitrate dehydrogenase 1 gene mutation, comprising a compound according to any one of [1] to [13] or a pharmaceutically acceptable salt thereof as an active ingredient.

[18] The antitumor agent according to [17], wherein the tumor is brain tumor (including glioma), acute myeloid leukemia, myelodysplastic syndrome, myeloproliferative tumor, peripheral T-cell lymphoma, chondrosarcoma, osteosarcoma, bile duct cancer, primitive neuroectodermal tumor, B-cell lymphoblastic lymphoma, malignant melanoma, prostate cancer, colorectal cancer, or thyroidal cancer.

[19] The compound according to any one of [1] to [13] or a pharmaceutically acceptable salt thereof for use in a method for treating a tumor having an isocitrate dehydrogenase 1 gene mutation.

[20] The compound according to [19] or a pharmaceutically acceptable salt thereof, wherein the tumor is brain tumor (including glioma), acute myeloid leukemia, myelodysplastic syndrome, myeloproliferative tumor, peripheral T-cell lymphoma, chondrosarcoma, osteosarcoma, bile duct cancer, primitive neuroectodermal tumor, B-cell lymphoblastic lymphoma, malignant melanoma, prostate cancer, colorectal cancer, or thyroidal cancer.

[21] Use of a compound according to any one of [1] to [13] or a pharmaceutically acceptable salt thereof for the production of a pharmaceutical composition for the treatment of a tumor having an isocitrate dehydrogenase 1 gene mutation.

[22] Use according to [21], wherein the tumor is brain tumor (including glioma), acute myeloid leukemia, myelodysplastic syndrome, myeloproliferative tumor, peripheral T-cell lymphoma, chondrosarcoma, osteosarcoma, bile duct cancer, primitive neuroectodermal tumor, B-cell lymphoblastic lymphoma, malignant melanoma, prostate cancer, colorectal cancer, or thyroidal cancer.

[23] A method for treating a tumor having an isocitrate dehydrogenase 1 gene mutation, comprising administering a compound according to any one of [1] to [13] or a pharmaceutically acceptable salt thereof.

[24] A method for treating according to [23], wherein the tumor is brain tumor (including glioma), acute myeloid leukemia, myelodysplastic syndrome, myeloproliferative tumor, peripheral T-cell lymphoma, chondrosarcoma, osteosarcoma, bile duct cancer, primitive neuroectodermal tumor, B-cell lymphoblastic lymphoma, malignant melanoma, prostate cancer, colorectal cancer, or thyroidal cancer.

Compounds having an isoxazole skeleton have been reported so far as anti-inflammatory agents (Patent Reference 1), dopamine receptor subtype ligands (Patent Reference 2), immunosuppressants (Patent Reference 3), herbicides (Patent Reference 4), or heat shock protein inhibitors (Patent Reference 5). However, such a compound inhibiting the activity of mutant IDH protein has not yet been reported.

Advantageous Effects of Invention

The compound of the present invention or a pharmaceutically acceptable salt thereof has a strong activity inhibitory effect on mutant IDH1 protein and can thereby inhibit the production of 2-HG in cells expressing the protein and suppress the growth thereof. Since mutations in IDH1 protein have been found in various tumors, the compound of the present invention or a pharmaceutically acceptable salt thereof is particularly useful as an antitumor agent.

BRIEF DESCRIPTION OF DRAWINGS

FIG. 1A shows the 2-HG concentrations in plasma, and FIG. 1B shows the 2-HG levels in bone marrow cells.

FIG. 2A shows the proportion of EGFP-positive AML cells in bone marrow cells, and FIG. 2B shows the proportion of EGFP-positive AML cells in peripheral blood cells. Mean±dispersion is also shown.

DESCRIPTION OF EMBODIMENTS

Figure 1:
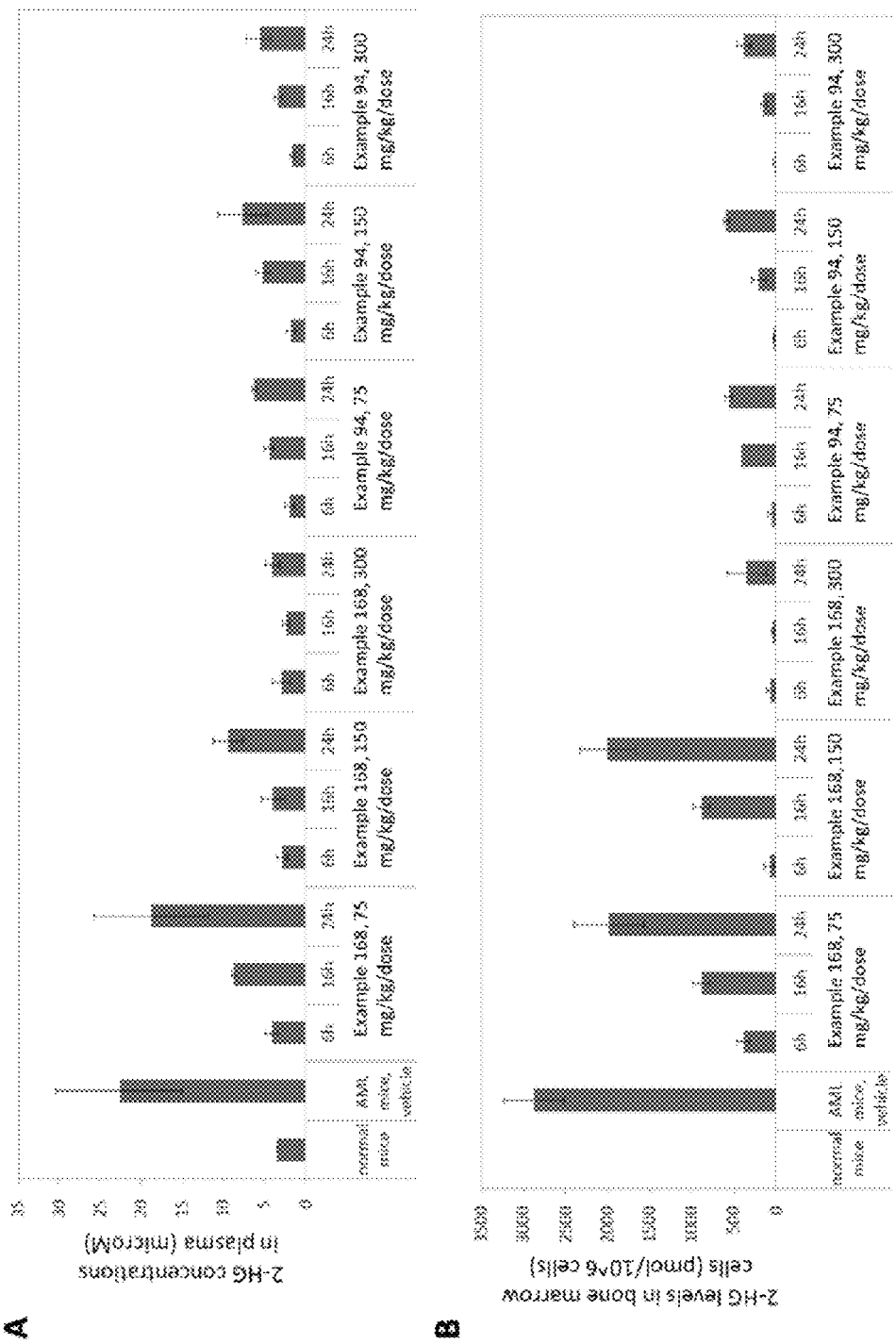
FIG. 1 is a graph showing the results of measuring the 2-HG production inhibitory activity of compounds of the present invention in acute myeloid leukemia (AML) mouse models harboring 4 genes including IDH1R132H.

The present invention provides a compound represented by the following general formula (I) or a pharmaceutically acceptable salt thereof:

[Formula 10]

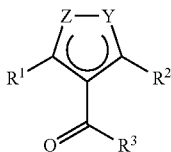

(I)

In the formula, Z—Y represents N—O or O—N.

In the formula, $R^1$ represents a phenyl group optionally having 1 to 3 substituents independently selected from group A given below, or a pyridyl group optionally having 1 to 3 substituents independently selected from group A given below. $R^1$ is preferably a phenyl group optionally having 1 to 3 substituents independently selected from group A given below.

Group A consists of a halogen atom, a $C_1$ to $C_6$ alkyl group, and a $C_1$ to $C_6$ alkoxy group.

In the present invention, a "halogen atom" is a fluorine atom, a chlorine atom, a bromine atom, or an iodine atom.

In the present invention, a "$C_1$ to $C_6$ alkyl group" is a linear or branched alkyl group having 1 to 6 carbon atoms. Examples thereof include a methyl group, an ethyl group, a propyl group, an isopropyl group, a butyl group, an isobutyl group, a s-butyl group, a t-butyl group, a pentyl group, an isopentyl group, a 2-methylbutyl group, a neopentyl group, a 1-ethylpropyl group, a hexyl group, an isohexyl group, and a 4-methylpentyl group.

In the present invention, a "$C_1$ to $C_6$ alkoxy group" refers to a group in which an oxy group is bonded to the aforementioned $C_1$-$C_6$ alkyl group. Examples thereof include a methoxy group, an ethoxy group, a n-propoxy group, an isopropoxy group, a butoxy group, an isobutoxy group, a s-butoxy group, a t-butoxy group, a pentoxy group, an isopentoxy group, a 2-methylbutoxy group, hexyloxy, and an isohexyloxy group.

In the formula, $R^2$ represents —$NR^{21}R^{22}$, a $C_1$ to $C_6$ alkyl group optionally having 1 to 3 substituents independently selected from group B given below, a $C_3$ to $C_6$ cycloalkyl group optionally having 1 to 3 substituents independently selected from group C given below, or a 4- to 6-membered heterocyclic group having 1 or 2 heteroatoms independently selected from the group consisting of a nitrogen atom and an oxygen atom in the ring.

In this context, $R^{21}$ and $R^{22}$ in "—$NR^{21}R^{22}$" each independently represent a hydrogen atom, a $C_1$ to $C_6$ alkyl group, or —$C(=O)R^{23}$. $R^{23}$ represents a $C_2$ to $C_6$ alkenyl group or a $C_2$ to $C_6$ alkynyl group. The "4- to 6-membered heterocyclic group" optionally has 1 to 3 substituents independently selected from group C given below, and a bridged structure is optionally bonded within the heterocyclic ring, or one $C_3$ to $C_6$ cycloalkyl ring is optionally bonded onto the heterocyclic ring via a spiro bond.

Group B consists of a halogen atom, a hydroxy group, a $C_1$ to $C_6$ alkoxy group, a $C_1$ to $C_6$ alkylamino group, and a di-$C_1$ to $C_6$ alkylamino group.

Group C consists of a $C_2$ to $C_6$ alkenyl group, a halogen atom, a hydroxy group, a cyano group, a $C_1$ to $C_6$ alkyl group optionally having 1 to 3 substituents independently selected from group D given below, a $C_1$ to $C_6$ alkoxy group, —$NR^{211}R^{212}$, —$C(=O)R^{213}$, and —$SO_2R^{213}$.

In this context, $R^{211}$ and $R^{212}$ in "—$NR^{211}R^{212}$" each independently represent a hydrogen atom or a $C_1$ to $C_6$ alkyl group. $R^{213}$ in "—$C(=O)R^{213}$" or "—$SO_2R^{213}$" represents a $C_2$ to $C_6$ alkenyl group or a $C_2$ to $C_6$ alkynyl group.

Group D consists of an amino group, a $C_1$ to $C_6$ alkoxy group, a di-$C_1$ to $C_6$ alkylamino group, an oxo group, and a $C_3$ to $C_6$ cycloalkyl group.

In the present invention, a "$C_3$ to $C_6$ cycloalkyl group" is a cyclopropyl group, a cyclobutyl group, a cyclopentyl group, or a cyclohexyl group.

In the present invention, a "$C_1$ to $C_6$ alkylamino group" means a group in which an amino group is substituted by one aforementioned $C_1$ to $C_6$ alkyl group. Examples thereof include a methylamino group, an ethylamino group, a propylamino group, an isopropylamino group, a butylamino group, an isobutylamino group, a s-butylamino group, a t-butylamino group, a pentylamino group, an isopentylamino group, a 2-methylbutylamino group, a neopentylamino group, a 1-ethylpropylamino group, a hexylamino group, and an isohexylamino group.

In the present invention, a "di-$C_1$ to $C_6$ alkylamino group" means a group in which an amino group is substituted by two identical or different aforementioned $C_1$ to $C_6$ alkyl groups. Examples thereof include a dimethylamino group, a diethylamino group, a dipropylamino group, a diisopropylamino group, a dibutylamino group, a diisobutylamino group, a dipentylamino group, a dineopentylamino group, a dihexylamino group, a N-ethyl-N-methylamino group, a N-methyl-N-propylamino group, a N-isopropyl-N-methylamino group, a N-butyl-N-methylamino group, a N-isobutyl-N-methylamino group, a N-ethyl-N-propylamino group, a N-ethyl-N-isopropylamino group, a N-butyl-N-ethylamino group, and a N-ethyl-N-isopentylamino group.

In the present invention, a "$C_2$ to $C_6$ alkenyl group" refers to a linear or branched alkenyl group having 2 to 6 carbon atoms and having one double bond in the molecule. Examples thereof include a vinyl group, an allyl group, and an isopropenyl group.

In the present invention, a "$C_2$ to $C_6$ alkynyl group" refers to a linear or branched $C_2$-$C_6$ alkynyl group having 2 to 6 carbon atoms and having one triple bond in the molecule. Examples thereof include an ethynyl group, a prop-1-ynyl group, a prop-2-ynyl group, and a but-3-ynyl group.

In the present invention, a "heterocyclic group" means a group derived from a monocyclic aromatic or aliphatic compound containing 1 or 2 atoms each independently selected from the group consisting of a nitrogen atom and an oxygen atom, in addition to carbon as ring-constituting atoms. Examples thereof include a furyl group, a pyrrolyl group, an oxazolyl group, an isoxazolyl group, an imidazolyl group, a pyrazolyl group, a pyridyl group, a pyrazyl group, a pyrimidinyl group, a pyridazinyl group, an oxiranyl group, an aziridinyl group, an oxetanyl group, an azetidinyl group, a tetrahydrofuranyl group, a pyrrolidinyl group, a tetrahydropyranyl group, a piperazinyl group, a tetrahydrothiopyranyl group, a morpholino group, a morpholinyl group, and a piperazinyl group.

$R^2$ is preferably a $C_1$ to $C_6$ alkyl group optionally having 1 to 3 substituents independently selected from group B, or a 4- to 6-membered heterocyclic group having 1 or 2 heteroatoms independently selected from the group consisting of a nitrogen atom and an oxygen atom in the ring.

$R^2$ more preferably represents any of the following formulae:

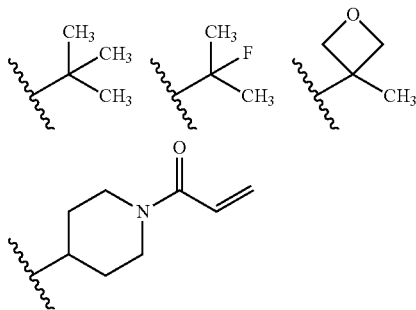

In the formula, R³ represents any of the following formulae (II) to (IV):

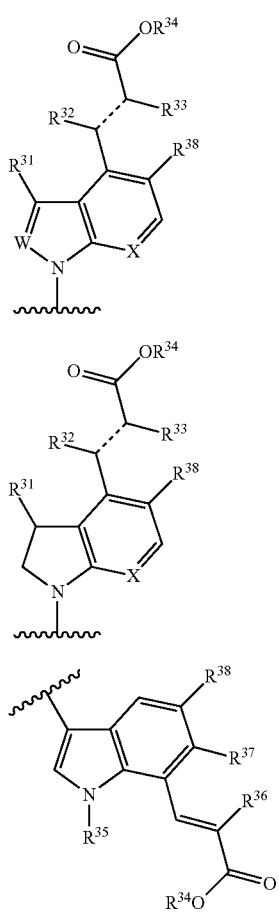

In these formulae, R³¹ represents a hydrogen atom, a halogen atom, a $C_1$ to $C_6$ alkyl group optionally substituted by 1 to 3 halogen atoms, a $C_3$ to $C_6$ cycloalkyl group, or a $C_1$ to $C_6$ alkylcarbonyl group, R³² represents a hydrogen atom or a $C_1$ to $C_6$ alkyl group, or R³¹ and R³² optionally together form a cyclohexane ring, R³³ represents a hydrogen atom or a $C_1$ to $C_6$ alkyl group, or R³² and R³³ optionally together form a cyclopropane ring, R³⁴ represents a hydrogen atom or a $C_1$ to $C_6$ alkyl group, R³⁵ represents a $C_1$ to $C_6$ alkyl group, R³⁶ represents a hydrogen atom or a $C_1$ to $C_6$ alkyl group, R³⁷ represents a hydrogen atom or a $C_1$ to C6 alkyl group, or R³⁶ and R³⁷ optionally together form a benzene ring, R³⁸ represents a hydrogen atom or a halogen atom, X represents a nitrogen atom or CH, W represents a nitrogen atom or CH, and the broken line represents a single bond or a double bond.

In the present invention, a "$C_1$ to $C_6$ alkylcarbonyl group" refers to a group in which a carbonyl group is bonded to the aforementioned $C_1$-$C_6$ alkyl group. Examples thereof include a methylcarbonyl group, an ethylcarbonyl group, a n-propylcarbonyl group, and an isopropylcarbonyl group.

R³ preferably represents the following formula (IV') or (V):

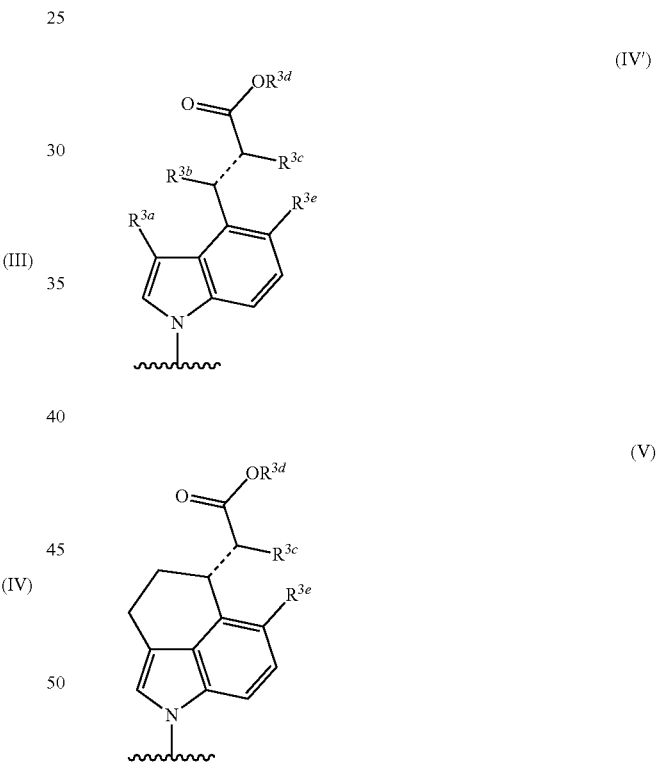

In the formulae (IV') and (V),

R³ᵃ represents a hydrogen atom or a $C_1$ to $C_6$ alkyl group optionally substituted by 1 to 3 halogen atoms, R³ᵇ represents a hydrogen atom or a $C_1$ to $C_6$ alkyl group, R³ᶜ represents a hydrogen atom or a $C_1$ to $C_6$ alkyl group, R³ᵈ represents a hydrogen atom or a $C_1$ to $C_6$ alkyl group, R³ᵉ represents a hydrogen atom or a halogen atom, and the broken line represents a single bond or a double bond.

R³ more preferably represents any of the following formulae:

[Formula 14]

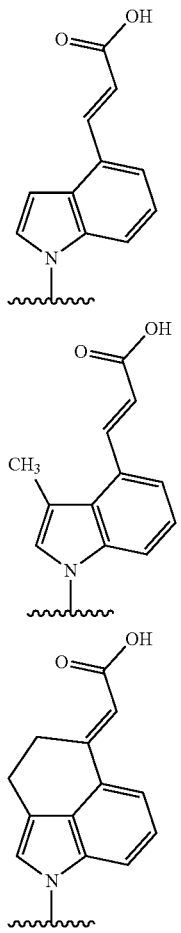

The compound represented by the general formula I is more preferably a compound represented by the following general formula (VI) or (VII):

[Formula 15]

(VI)

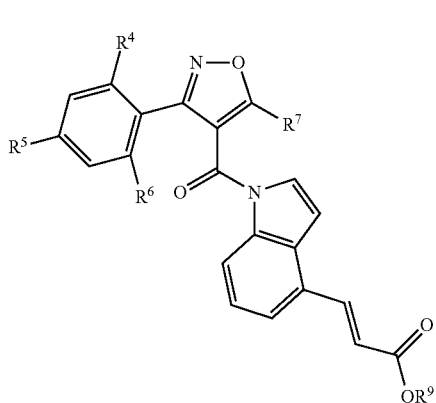

wherein
$R^4$, $R^5$, and $R^6$ each independently represent a hydrogen atom or a halogen atom, $R^7$ represents any of the following formulae:

[Formula 16]

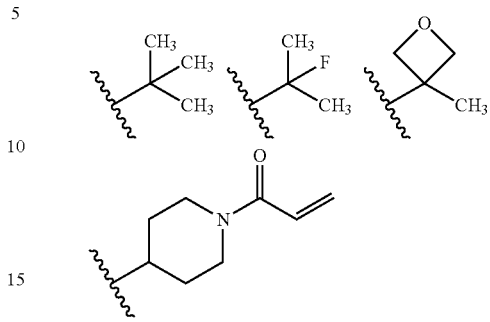

and $R^8$ and $R^9$ each independently represent a hydrogen atom or a $C_1$ to $C_6$ alkyl group; and

[Formula 17]

(VII)

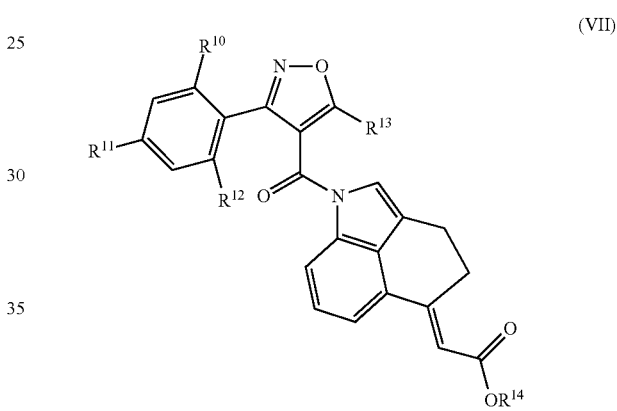

wherein
$R^{10}$, $R^{11}$, and $R^{12}$ each independently represent a hydrogen atom or a halogen atom, $R^{13}$ represents any of the following formulae:

[Formula 18]

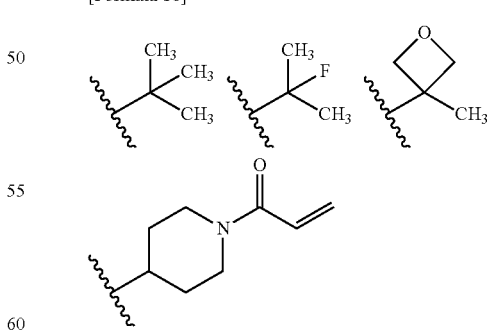

and $R^{14}$ represents a hydrogen atom or a $C_1$ to $C_6$ alkyl group.

A compound represented by the general formula (I) is particularly preferably any compound selected from the following group:

(2E)-3-(1-{[5-(3-methyloxetan-3-yl)-3-(2,4,6-trichlorophenyl)-1,2-oxazol-4-yl]carbonyl}-1H-indol-4-yl)prop-2-enoic acid (2E)-3-(1-{[5-(2-fluoropropan-2-yl)-3-(2,4,6-trichlorophenyl)-1,2-oxazol-4-yl]carbonyl}-3-methyl-1H-indol-4-yl)prop-2-enoic acid (2E)-3-(1-{[5-(tert-butyl)-3-(2,4,6-trichlorophenyl)-1,2-oxazol-4-yl]carbonyl}-1H-indol-4-yl)prop-2-enoic acid (2E)-3-(1-{[3-(2,4-dichloro-6-fluorophenyl)-5-(2-fluoropropan-2-yl)-1,2-oxazol-4-yl]carbonyl}-3-methyl-1H-indol-4-yl)prop-2-enoic acid (2E)-3-(1-{[3-(2,4-dichlorophenyl)-5-(2-fluoropropan-2-yl)-1,2-oxazol-4-yl]carbonyl}-3-methyl-1H-indol-4-yl)prop-2-enoic acid (2E)-[1-{[5-(1-acryloylpiperidin-4-yl)-3-(2,4,6-trichlorophenyl)-1,2-oxazol-4-yl]carbonyl}-3,4-dihydrobenzo[cd]indol-5(1H)-ylidene]ethanoic acid (2E)-3-(1-{[5-(1-acryloylpiperidin-4-yl)-3-(2,4,6-trichlorophenyl)-1,2-oxazol-4-yl]carbonyl}-3-methyl-1H-indol-4-yl)prop-2-enoic acid (2E)-[1-{[5-(1-acryloylpiperidin-4-yl)-3-(2,4-dichloro-6-fluorophenyl)-1,2-oxazol-4-yl]carbonyl}-3,4-dihydrobenzo[cd]indol-5(1H)-ylidene]ethanoic acid (2E)-[1-{[5-(1-acryloylpiperidin-4-yl)-3-(2,4-dichloro-5-fluorophenyl)-1,2-oxazol-4-yl]carbonyl}-3,4-dihydrobenzo[cd]indol-5(1H)-ylidene]ethanoic acid (2E)-[1-{[5-(1-acryloylpiperidin-4-yl)-3-(2,4-dichlorophenyl)-1,2-oxazol-4-yl]carbonyl}-3,4-dihydrobenzo[cd]indol-5(1H)-ylidene]ethanoic acid.

The compound of the present invention is most preferably (2E)-3-(1-{[5-(2-fluoropropan-2-yl)-3-(2,4,6-trichlorophenyl)-1,2-oxazol-4-yl]carbonyl}-3-methyl-1H-indol-4-yl)prop-2-enoic acid or a pharmaceutically acceptable salt thereof, or (2E)-[1-{[5-(1-acryloylpiperidin-4-yl)-3-(2,4,6-trichlorophenyl)-1,2-oxazol-4-yl]carbonyl}-3,4-dihydrobenzo[cd]indol-5(1H)-ylidene]ethanoic acid or a pharmaceutically acceptable salt thereof. Preferred forms of the pharmaceutically acceptable salts of these compounds are tert-butylamine salts (t-butylamine salts).

In the present invention, a "pharmaceutically acceptable salt" refers to a salt that has no significant toxicity and can be used in a pharmaceutical composition. A compound of the present invention can form a salt through reaction with an acid when having a basic group or through reaction with a base when having an acidic group. Examples of a salt based on a basic group can include, but are not limited to: hydrohalides such as hydrofluoride, hydrochloride, hydrobromide, and hydroiodide; inorganic acid salts such as nitrate, perchlorate, sulfate, and phosphate; $C_1$-$C_6$ alkylsulfonates such as methanesulfonate, trifluoromethanesulfonate, and ethanesulfonate; arylsulfonates such as benzenesulfonate and p-toluenesulfonate; and carboxylates such as acetate, oxalate, tartrate, and maleate.

On the other hand, examples of a salt based on an acidic group can include, but are not limited to: metal salts including alkali metal salts such as sodium salt, potassium salt, and lithium salt, alkaline earth metal salts such as calcium salt and magnesium salt, and others such as aluminum salt and iron salt; amine salts including inorganic salts such as ammonium salt, and organic salts such as t-butylamine salt, t-octylamine salt, dibenzylamine salt, morpholine salt, glucosamine salt, phenylglycine alkyl ester salt, ethylenediamine salt, N-methylglucamine salt, guanidine salt, diethylamine salt, triethylamine salt, dicyclohexylamine salt, N,N'-dibenzylethylenediamine salt, chloroprocaine salt, procaine salt, diethanolamine salt, N-benzylphenethylamine salt, piperazine salt, tetramethylammonium salt, and tris (hydroxymethyl)aminomethane salt; and amino acid salts such as glycine salt, lysine salt, arginine salt, ornithine salt, glutamate, and aspartate.

The compound of the present invention or a pharmaceutically acceptable salt thereof, when left in air or recrystallized, may incorporate a water molecule to form a hydrate. Such a hydrate is also included in a salt of the present invention.

The compound of the present invention or a pharmaceutically acceptable salt thereof, when left in a solvent or recrystallized, may absorb a certain kind of solvent to form a solvate. Such a solvate is also included in a salt of the present invention.

The compound of the present invention or a pharmaceutically acceptable salt thereof encompasses all isomers (diastereomers, optical isomers, geometric isomers, rotational isomers, etc.).

For the compound of the present invention, these isomers and mixtures of these isomers are all represented by a single formula. Thus, the present invention includes all of these isomers and even mixtures of these isomers in arbitrary ratios.

The present invention also provides a mutant IDH1 inhibitor comprising a compound of the present invention or a pharmaceutically acceptable salt thereof as an active ingredient. In the present invention, examples of the mutation in the "mutant IDH1" include, but are not limited to, mutations of arginine at the 132-position (hereinafter, referred to as R132), mutations of G97, mutations of R100, mutations of H133, and mutations of A134 in IDH1. Examples of the mutations of R132 include, but are not limited to, a mutation to histidine (R132H), a mutation to cytosine (R132C), a mutation to leucine (R132L), a mutation to serine (R132S), a mutation to glycine (R132G), and a mutation to valine (R132V). The compound of the present invention or a pharmaceutically acceptable salt thereof is particularly suitable as an inhibitor of an R132 mutant of IDH1.

The typical amino acid sequence of human-derived wild-type IDH1 is described in NP_005887.2 of GenBank or O75874 of UniprotKB.

Particular mutant IDH1 has been found to have the enzymatic activity of converting 2-oxoglutarate and NADPH to 2-HG and NADP+, which is not possessed by wild-type IDH1, and the production of 2-HG at a high concentration has been confirmed in cells having a particular IDH1 mutation (Non Patent References 17 to 20). In the present Test Examples (Test Examples 1, 2, 3, and 5), the compound of the present invention has been found to inhibit the production of 2-HG by inhibiting the enzymatic activity. Thus, the present invention provides a 2-HG production inhibitor comprising a compound of the present invention or a pharmaceutically acceptable salt thereof as an active ingredient.

The compound of the present invention or a pharmaceutically acceptable salt thereof can be prepared as a pharmaceutical composition and can also be prepared as a reagent for the purpose of research.

The compound of the present invention may also contain unnatural proportions of atomic isotopes at one or more of the atoms constituting such a compound. Examples of the atomic isotopes include deuterium ($^2$H), tritium ($^3$H), iodine-125 ($^{125}$I), and carbon-14 ($^{14}$C). The compound may be radiolabeled, for example, with a radioisotope such as tritium ($^3$H), iodine-125 ($^{125}$I), or carbon-14 ($^{14}$C). The radiolabeled compound is useful as a therapeutic or prophylactic agent, a research reagent (e.g., an assay reagent), and a diagnostic agent (e.g., an in vivo diagnostic imaging agent). All isotopic variants of the compound of the present invention are included in the scope of the present invention, regardless of being radioactive or not.

IDH1 gene mutations or IDH2 gene mutations have been found in patients with cancers such as brain tumor (including glioma), acute myeloid leukemia, myelodysplastic syndrome, myeloproliferative tumor, peripheral T-cell lymphoma, chondrosarcoma, osteosarcoma, bile duct cancer, primitive neuroectodermal tumor, B-cell lymphoblastic lymphoma, malignant melanoma, prostate cancer, colorectal cancer, and thyroidal cancer, or with Ollier's disease or Maffucci syndrome (Non Patent References 1 to 16). In the present Test Examples (Test Examples 4 and 7), the compound of the present invention has been found to inhibit the growth of various tumor cells. Thus, a pharmaceutical composition comprising the compound of the present invention or a pharmaceutically acceptable salt thereof as an active ingredient can target, for example, these diseases and is particularly suitable as an antitumor agent.

The presence of an IDH1 gene mutation can be confirmed in test tissues (collected by, for example, blood collection or biopsy) from patients by use of a method known in the art such as analysis using Western blot, ELISA, DNA chips, FISH assay, immunohistological staining, other gene analysis methods known in the art {e.g., Sanger sequence analysis, next-generation DNA sequencing analysis (NGS), PCR, LCR (ligase chain reaction), SDA (strand displacement amplification), NASBA (nucleic acid sequence-based amplification), ICAN (isothermal and chimeric primer-initiated amplification), and LAMP (loop-mediated isothermal amplification)}, or the like, or a pathological approach.

In the present invention, the "tumor" is not limited to a malignant tumor and includes every type of tumor. Examples thereof include carcinomas, sarcomas, and benign tumors. Particularly, a malignant tumor is also expressed as a "cancer".

The antitumor agent of the present invention may be used in combination with an additional antitumor agent or an additional treatment method (e.g., radiotherapy or immunotherapy).

Examples of the additional antitumor agent include alkylating agents, various antimetabolites, antitumor antibiotics, antitumor plant components, BRM (biological response modifiers), hormones, vitamins, antitumor antibodies, molecular target drugs, and other antitumor agents.

More specifically, examples of the alkylating agents include: alkylating agents such as nitrogen mustard, nitrogen mustard N-oxide, and chlorambucil; aziridine alkylating agents such as carboquone and thiotepa; epoxide alkylating agents such as dibromomannitol and dibromodulcitol; nitrosourea alkylating agents such as carmustine, lomustine, semustine, nimustine hydrochloride, streptozocin, chlorozotocin, and ranimustine; and others such as busulfan, improsulfan tosylate, and dacarbazine.

Examples of the various antimetabolites include: purine antimetabolites such as 6-mercaptopurine, 6-thioguanine, and thioinosine; pyrimidine antimetabolites such as fluorouracil, tegafur, tegafur uracil, carmofur, doxifluridine, broxuridine, cytarabine, and enocitabine; and antifolates such as methotrexate and trimetrexate.

Examples of the antitumor antibiotics include: anthracycline antibiotic antitumor agents such as mitomycin C, bleomycin, peplomycin, daunorubicin, aclarubicin, doxorubicin, pirarubicin, THP-adriamycin, 4'-epidoxorubicin, and epirubicin; and others such as chromomycin A3 and actinomycin D.

Examples of the antitumor plant components include: vinca alkaloids such as vindesine, vincristine, and vinblastine; taxanes such as paclitaxel and docetaxel; and epipodophyllotoxins such as etoposide and teniposide.

Examples of the BRM include tumor necrosis factors and indomethacin.

Examples of the hormones include hydrocortisone, dexamethasone, methylprednisolone, prednisolone, prasterone, betamethasone, triamcinolone, oxymetholone, nandrolone, metenolone, fosfestrol, ethynyl estradiol, chlormadinone, and medroxyprogesterone.

Examples of the vitamins include vitamin C and vitamin A.

Examples of the antitumor antibodies and the molecular target drugs include trastuzumab, rituximab, cetuximab, nimotuzumab, denosumab, bevacizumab, infliximab, imatinib mesylate, gefitinib, erlotinib, sunitinib, lapatinib, and sorafenib.

Examples of other antitumor agents include cisplatin, carboplatin, oxaliplatin, tamoxifen, camptothecin, ifosfamide, cyclophosphamide, melphalan, L-asparaginase, aceglatone, sizofiran, picibanil, procarbazine, pipobroman, neocarzinostatin, hydroxyurea, ubenimex, and krestin.

A compound of the present invention or a pharmaceutically acceptable salt thereof may be conjugated with an auxiliary moiety that potentiates therapeutically useful characteristics. Typical examples of the useful characteristics include the promotion of delivery of the compound to a target region (e.g., a tumor), the sustention of the therapeutic concentration of the compound in the target region, the alteration of the pharmacokinetic or pharmacodynamic characteristics of the compound, and improvement in the therapeutic index or safety profile of the compound. For example, an antibody specifically recognizing the target region or a ligand for a receptor expressed in the target region can be utilized as a suitable auxiliary moiety.

In the case of preparing a compound of the present invention or a pharmaceutically acceptable salt thereof as a pharmaceutical composition, examples of the pharmaceutically acceptable carrier used include, but are not limited to, sterilized water, physiological saline, plant oils, solvents, bases, emulsifiers, suspending agents, surfactants, stabilizers, flavors, fragrances, excipients, vehicles, antiseptics, binders, diluents, tonicity agents, soothing agents, expanders, disintegrants, buffers, coating agents, lubricants, colorants, sweeteners, thickeners, corrigents, solubilizers, and other additives. The compound of the present invention or a pharmaceutically acceptable salt thereof can be made into various forms such as tablets, powders, granules, capsules, and solutions according to a therapeutic purpose, etc. The compound of the present invention or a pharmaceutically acceptable salt thereof can also be administered, for example, in the form of a liposome delivery system. The aforementioned auxiliary moiety (e.g., an antibody or a ligand) that potentiates therapeutically useful characteristics may be added to the liposome.

The administration to a patient may be oral administration or may be parenteral administration. Examples of the parenteral administration include intravenous administration, intra-arterial administration, intramuscular administration, intrathoracic administration, intraperitoneal administration, and direct administration to a target site (e.g., a tumor).

The dose is not particularly limited as long as the dose is an amount effective for the treatment of a disease of interest. The dose can be appropriately selected according to the age, body weight, symptoms, health condition, degree of progression of the disease, etc., of a patient. The dosing frequency is not particularly limited and can be appropriately selected according to a purpose. For example, the daily dose may be administered once a day or may be administered in two or more divided portions. In the case of administering the drug of the present invention to a human, the dose range of the active ingredient is usually approximately 0.01 mg/kg body weight to approximately 500 mg/kg body weight, preferably approximately 0.1 mg/kg body weight to approximately 100 mg/kg body weight, per day. For the administration to a human, the daily dose is preferably administered once a day or in two to four divided portions, and the administration is preferably repeated at appropriate intervals.

In the case of preparing a compound of the present invention or a pharmaceutically acceptable salt thereof as a reagent, the reagent can optionally contain other components acceptable for the reagent, such as sterilized water, physiological saline, buffers, and preservatives. The reagent can be administered at a dose appropriate for the purpose to a recipient (e.g., cells or fractions thereof, tissues, and laboratory animals) appropriate for the purpose, for example, to inhibit mutant IDH1, to inhibit the production of 2-HG, or to inhibit tumor growth.

Next, a typical method for producing a compound represented by the general formula (I) will be described. The compound of the present invention can be produced by various production methods. The production methods shown below are given for illustrative purposes. It should be understood that the present invention is not limited by these examples. The compound represented by the general formula (I) and intermediates for production thereof can be produced through the use of various reactions known in the art as described below. In this respect, functional groups in starting materials or intermediates may be protected with appropriate protective groups. Examples of such functional groups can include a hydroxy group, a carboxy group, and an amino group. For the types of their protective groups as well as conditions for the introduction and removal of these protective groups, see those described in, for example, Protective Groups in Organic Synthesis (T. W. Greene and P. G. M. Wuts, John Wiley & Sons, Inc., New York, 2006).

[Production method 1]

Among the compounds represented by formula I, compound 1a given below can be produced by, for example, the following reaction scheme:

[Formula 19]

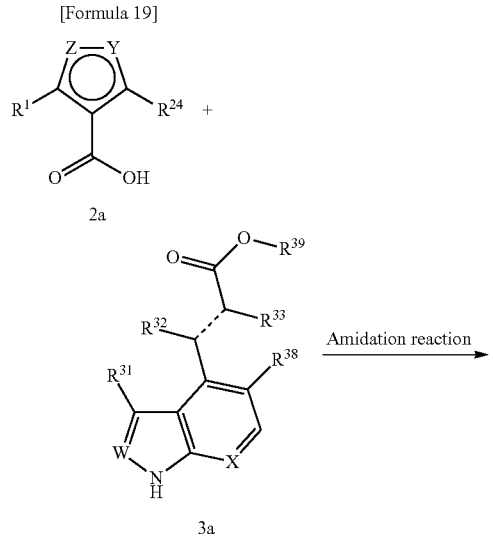

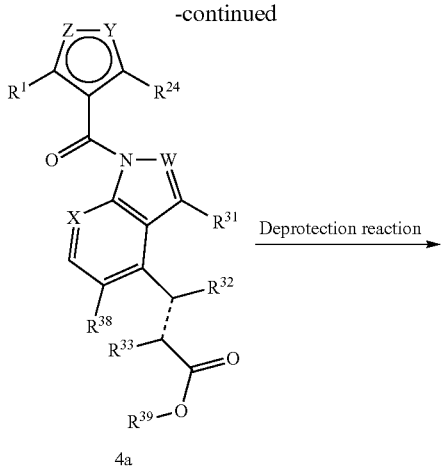

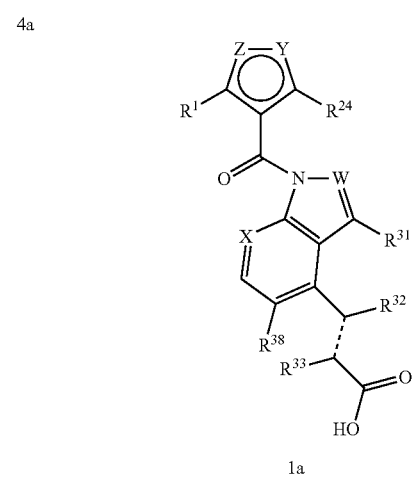

In the scheme, $R^1$, $R^{31}$, $R^{32}$, $R^{33}$, $R^{38}$, W, X, Y, and Z are as defined above. In the scheme, the broken line represents a single bond or a double bond. $R^{39}$ represents a protective group for a carboxy group.

$R^{24}$ represents a $C_1$ to $C_6$ alkyl group optionally having 1 to 3 substituents independently selected from group B given below, a $C_3$ to $C_6$ cycloalkyl group optionally having 1 to 3 substituents independently selected from group C given below, or a 4- to 6-membered aliphatic heterocyclic group having one oxygen atom in the ring. The 4- to 6-membered aliphatic heterocyclic group optionally has 1 to 3 substituents independently selected from group C given below.

Group B consists of a halogen atom, a hydroxy group, and a $C_1$ to $C_6$ alkoxy group.

Group C consists of a halogen atom, a hydroxy group, a $C_1$ to $C_6$ alkyl group, a $C_1$ to $C_6$ alkoxy group, and a di-$C_1$ to $C_6$ alkylamino group.

(1) Conversion of Compound 2a to Compound 4a

The conversion of compound 2a to compound 4a can be carried out by the reaction of a carboxylic acid halide or a carboxylic acid active ester derived from the carboxylic acid compound 2a in the presence of an appropriate base (e.g., sodium hydride, triethylamine, N,N-di(propan-2-yl)ethylamine, N-methylmorpholine, 4-dimethylaminopyridine, or a mixture thereof) in an appropriate solvent that has no adverse effect on the reaction (e.g., benzene, toluene, diethyl ether, dichloromethane, tetrahydrofuran, or N,N-dimethylformamide, or a mixed solvent thereof) at −30° C. to the boiling point of the solvent used in the reaction, preferably 0° C. to 100° C. A catalytic amount or an excessive amount can be used as the amount of the base. The reaction time is preferably 10 minutes to 72 hours, more preferably 30 minutes to 24 hours.

(2) Conversion of Compound 4a to Compound 1a

The conversion of compound 4a to compound 1a differs in deprotection reaction conditions depending on the type of $R^{39}$. When $R^{39}$ is a methyl group, an ethyl group, a benzyl group, or the like, the conversion can be carried out by treatment with an appropriate base (e.g., sodium hydroxide, potassium hydroxide, lithium hydroxide, or potassium tert-butoxide) in an appropriate solvent that has no adverse effect on the reaction (examples thereof include methanol, ethanol, water, tetrahydrofuran, dioxane, and mixed solvents thereof, and water and an organic solvent miscible therewith at an arbitrary ratio are preferred) at −30° C. to the boiling point of the solvent used in the reaction, preferably room temperature to 100° C. The reaction time is preferably 10 minutes to 72 hours, more preferably 30 minutes to 24 hours.

When $R^{39}$ is a tert-butyl group or the like, the conversion can be carried out by treatment with, for example, trifluoroacetic acid, hydrochloric acid, or formic acid, in an appropriate solvent that has no adverse effect on the reaction (e.g., dichloromethane, chloroform, methanol, tetrahydrofuran, 1,4-dioxane, or a mixed solvent thereof) at −30° C. to the boiling point of the solvent used in the reaction, preferably −20° C. to room temperature. The reaction time is preferably 10 minutes to 72 hours, more preferably 30 minutes to 24 hours.

Compounds 2a and 3a, which are starting materials for production, can be synthesized according to methods described in the Reference Examples.

[Production method 2]

Among the compounds represented by formula I compound 1b given below can be produced by, for example, the following reaction scheme:

[Formula 20]

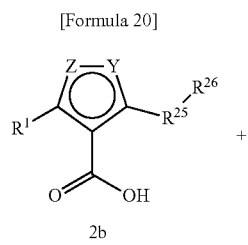

2b

+

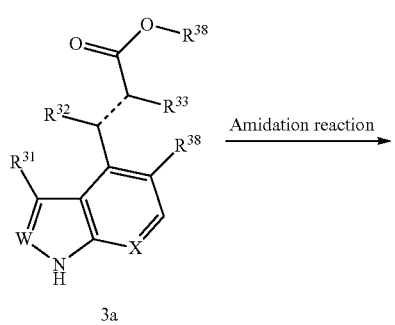

3a

Amidation reaction →

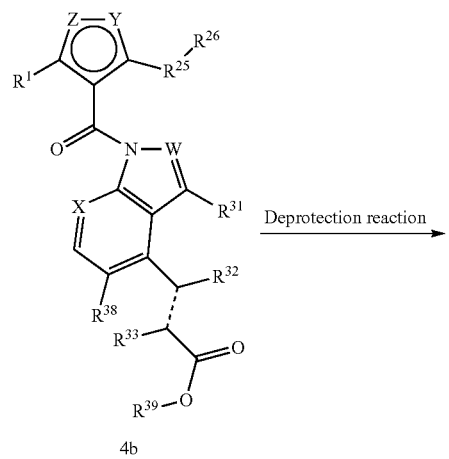

4b

Deprotection reaction →

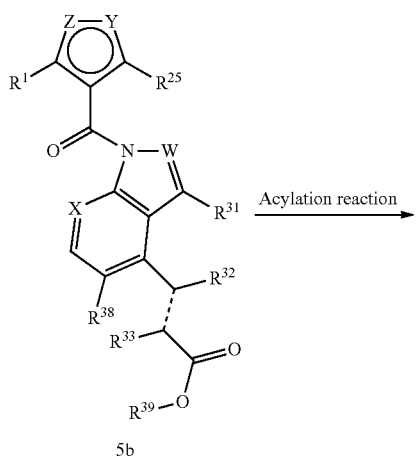

5b

Acylation reaction →

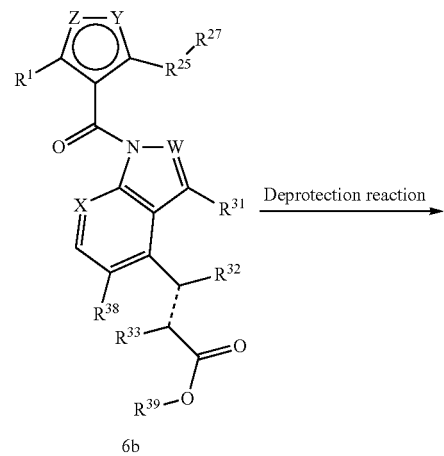

6b

Deprotection reaction →

-continued

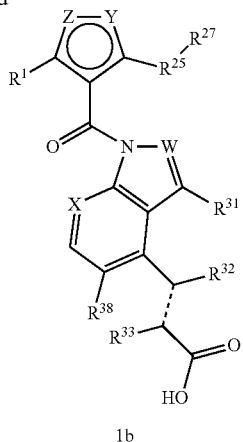

1b

In the scheme, $R^1$, $R^{31}$, $R^{32}$, $R^{33}$, $R^{38}$, W, X, Y, and Z are as defined above. In the scheme, the broken line represents a single bond or a double bond. $R^{39}$ represents a protective group for a carboxy group.

$R^{25}$ represents a 4- to 6-membered aliphatic heterocyclic group having one nitrogen atom in the ring.

The 4- to 6-membered aliphatic heterocyclic ring is bonded to $R^{26}$ via the nitrogen atom on the ring. This 4- to 6-membered aliphatic heterocyclic ring optionally has 1 to 3 substituents independently selected from group C given below, and a bridged structure is optionally bonded within the heterocyclic ring, or one $C_3$ to $C_6$ cycloalkyl ring is optionally bonded onto the heterocyclic ring via a spiro bond.

$R^{26}$ represents a protective group for an amino group, and examples thereof include a 2-nitrophenylsulfonyl group.

$R^{27}$ represents —C(=O)$R^{23}$ or —SO$_2$$R^{23}$.

$R^{23}$ represents a $C_2$ to $C_6$ alkenyl group or a $C_2$ to $C_6$ alkynyl group.

Group C consists of a halogen atom, a hydroxy group, a cyano group, a $C_1$ to $C_6$ alkyl group optionally having 1 to 3 substituents independently selected from group D given below, a $C_1$ to $C_6$ alkoxy group, and —NR$^{21}$R$^{22}$.

In this context, $R^{21}$ and $R^{22}$ each independently represent a hydrogen atom, a $C_1$ to $C_6$ alkyl group, or —C(=O)$R^{23}$. $R^{23}$ represents a $C_2$ to $C_6$ alkenyl group or a $C_2$ to $C_6$ alkynyl group.

Group D consists of an amino group, a $C_1$ to $C_6$ alkoxy group, a di-$C_1$ to $C_6$ alkylamino group, an oxo group, and a $C_3$ to $C_6$ cycloalkyl group.

(1) Conversion of compound 2b to compound 4b

The conversion of compound 2b to compound 4b can be carried out by a general coupling reaction similar to the method described above in (1) of [Production method 1].

(2) Conversion of Compound 4b to Compound 5b

When $R^{26}$ is a 2-nitrophenylsulfonyl group or the like, the conversion of compound 4b to compound 5b can be carried out by treatment with an appropriate base (e.g., potassium carbonate or cesium carbonate) and a thiol derivative (e.g., benzenethiol) in an appropriate solvent that has no adverse effect on the reaction (e.g., acetonitrile, N,N-dimethylformamide, or a mixed solvent thereof) at −30° C. to the boiling point of the solvent used in the reaction, preferably −20° C. to room temperature. The reaction time is preferably 10 minutes to 72 hours, more preferably 30 minutes to 24 hours.

(3) Conversion of Compound 5b to Compound 6b

The conversion of compound 5b to compound 6b can be carried out by the reaction of the compound 5b with a carboxylic acid halide or a sulfonic acid halide in the presence of an appropriate base (e.g., an organic base such as triethylamine, N,N-di(propan-2-yl)ethylamine, 4-dimethylaminopyridine, N-methylmorpholine, pyridine, 2,6-lutidine, or diazabicyclo[5.4.0]undec-7-ene, or an inorganic base such as potassium carbonate, sodium carbonate, or sodium bicarbonate) in an appropriate solvent that has no adverse effect on the reaction (e.g., dichloromethane, chloroform, tetrahydrofuran, ethyl acetate, toluene, or a mixed solvent thereof). The reaction temperature is usually in the range of −78° C. to 100° C. or the boiling point of the solvent and is preferably −10° C. to around room temperature. As another method, the present compound 6b can also be obtained by the reaction of the compound 5b with a carboxylic acid or a sulfonic acid in the presence of an appropriate condensing agent (e.g., N,N'-dicyclohexylcarbodiimide or 1-ethyl-3-(3-dimethylaminopropyl)carbodiimide) in an appropriate solvent that has no adverse effect on the reaction (e.g., dichloromethane, N,N-dimethylformamide, tetrahydrofuran, ethyl acetate, or a mixed solvent thereof). The reaction temperature is usually in the range of −78° C. to 100° C. or the boiling point of the solvent and is preferably 0° C. to 50° C. If necessary, a base such as triethylamine, N,N-di(propan-2-yl)ethylamine, N-methylmorpholine, or 4-dimethylaminopyridine can be added thereto. Further, a reaction accelerator such as 1-hydroxybenzotriazole or N-hydroxysuccinimide may also be added thereto.

(4) Conversion of Compound 6b to Compound 1b

The conversion of compound 6b to compound 1b can be carried out by a general deprotection method similar to the method described above in (2) of [Production method 1].

[Production Method 3]

When $R^{26}$ is a tert-butoxycarbonyl group and $R^{39}$ is a tert-butyl group in [Production method 2], compound 1b can also be synthesized by the following production method:

[Formula 21]

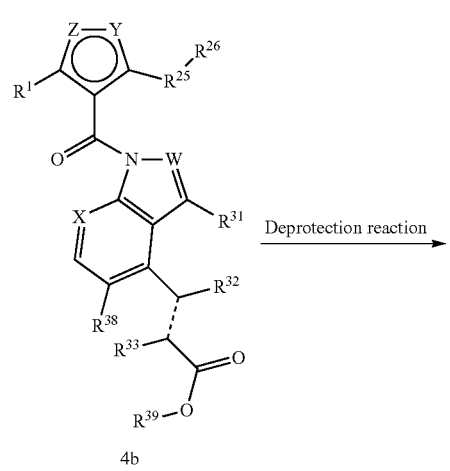

4b

Deprotection reaction →

-continued

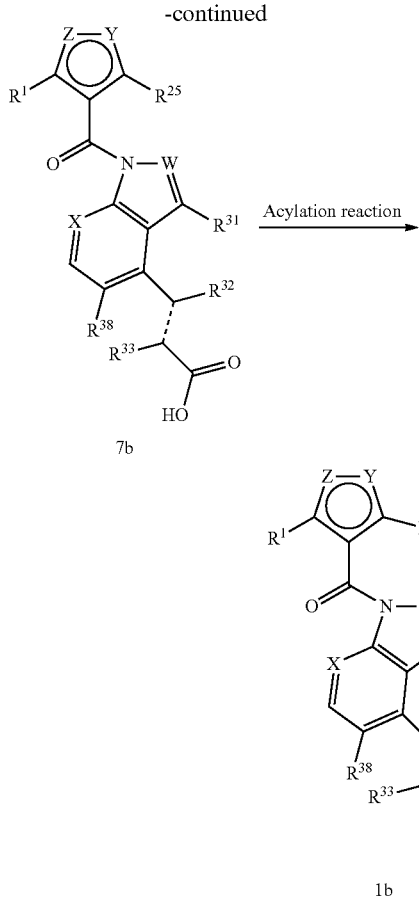

7b

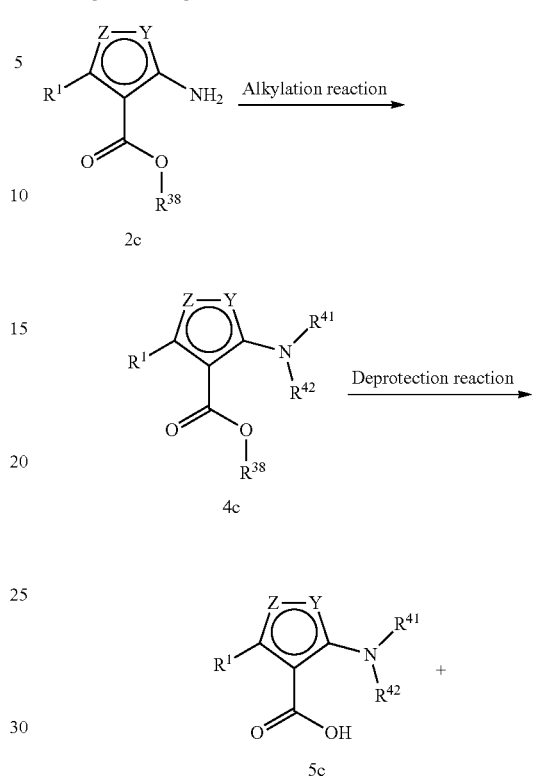

[Formula 22]

2c

4c

5c

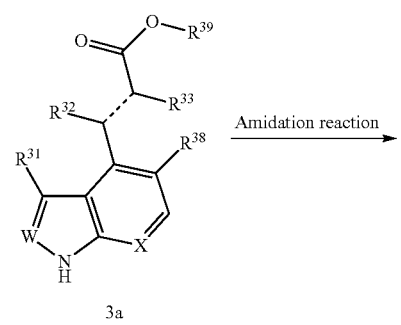

3a

6c

1b (1) Conversion of Compound 4b to Compound 7b

The conversion of compound 4b to compound 7b can be carried out by treatment with, for example, trifluoroacetic acid, hydrochloric acid, or formic acid, in an appropriate solvent that has no adverse effect on the reaction (e.g., dichloromethane, chloroform, methanol, tetrahydrofuran, 1,4-dioxane, or a mixed solvent thereof) at −30° C. to the boiling point of the solvent used in the reaction, preferably 0° C. to room temperature. The reaction time is preferably 10 minutes to 72 hours, more preferably 30 minutes to 24 hours.

(2) Conversion of Compound 7b to Compound 1b

The conversion of compound 7b to compound 1b can be carried out by a Schotten-Baumann reaction. Specifically, the conversion can be carried out by reaction with a carboxylic acid halide or a sulfonic acid halide under two-layer system conditions using an appropriate solvent that has no adverse effect on the reaction (e.g., dichloromethane or chloroform) and an aqueous solution of a base such as sodium bicarbonate or sodium hydroxide. The reaction temperature is preferably 0° C. to room temperature. The reaction time is preferably 10 minutes to 72 hours, more preferably 30 minutes to 24 hours.

[Production method 4]

Among the compounds represented by formula I, compound 1c given below can be produced by, for example, the following reaction scheme:

-continued

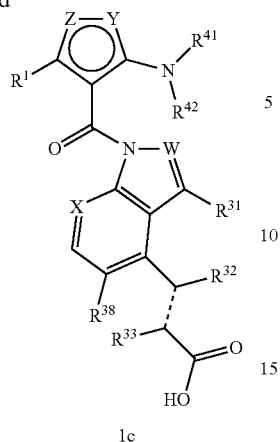

1c

In the scheme, $R^1$, $R^{31}$, $R^{32}$, $R^{33}$, $R^{38}$, W, X, Y, and Z are as defined above. In the scheme, the broken line represents a single bond or a double bond. $R^{39}$ represents a protective group for a carboxy group.

$R^{41}$ and $R^{42}$ each independently represent a hydrogen atom or a $C_1$ to $C_6$ alkyl group, or $R^{41}$ and $R^{42}$ optionally together form a cycloalkyl ring or an aliphatic heterocyclic ring having an oxygen atom in the ring.

(1) Conversion of Compound 2c to Compound 4c

The conversion of compound 2c to compound 4c can be carried out by reaction with an alkyl halide in the presence of an appropriate base (e.g., potassium carbonate, cesium carbonate, or a mixture thereof) in an appropriate solvent that has no adverse effect on the reaction (e.g., N,N-dimethylformamide, acetone, or a mixed solvent thereof) at room temperature to the boiling point of the solvent used in the reaction, preferably 50° C. to 100° C. An excessive amount can be used as the amount of the base. The reaction time is preferably 1 hour to 72 hours, more preferably 8 hours to 24 hours.

(2) Conversion of Compound 4c to Compound 5c

The conversion of compound 4c to compound 5c can be carried out by a general deprotection reaction similar to the method described above in (2) of [Production method 1].

(3) Conversion of Compound 5c to Compound 6c

The conversion of compound 5c to compound 6c can be carried out by a general amidation reaction similar to the method described above in (1) of [Production method 1].

(4) Conversion of Compound 6c to Compound 1c

The conversion of compound 6c to compound 1c can be carried out by a general deprotection reaction similar to the method described above in (2) of [Production method 1].

Compound 2c, which is a starting material for production, can be synthesized according to a method described in the Reference Examples.

[Production method 5]

Among the compounds represented by formula I, compound 1c given below can also be produced by, for example, the following reaction scheme:

[Formula 23]

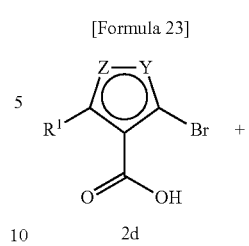

2d

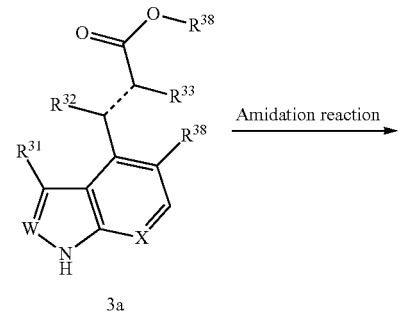

3a

Amidation reaction

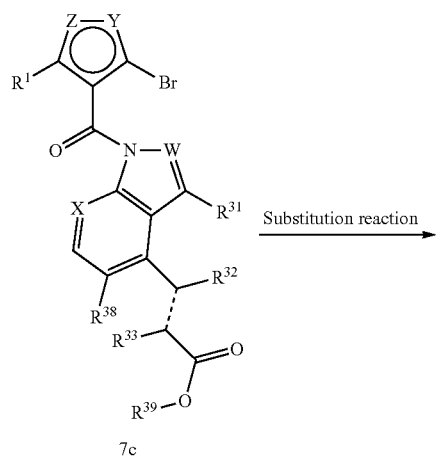

7c

Substitution reaction

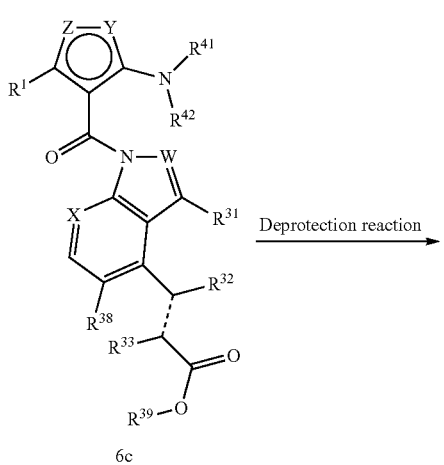

6c

Deprotection reaction

[Formula 24]

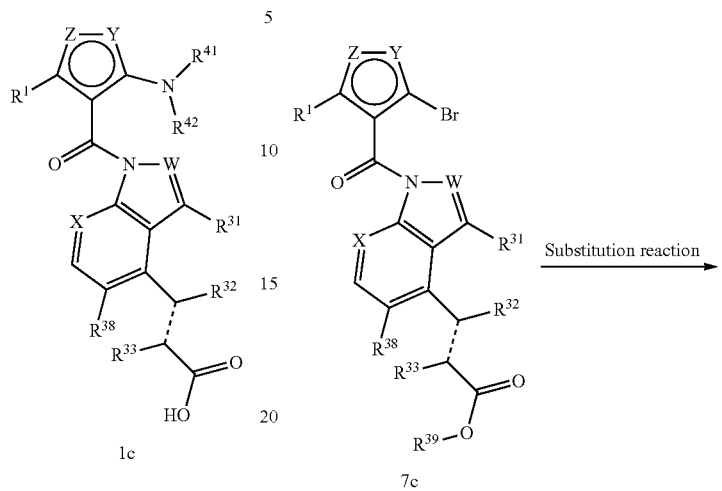

1c

In the scheme, $R^1$, $R^{31}$, $R^{32}$, $R^{33}$, $R^{38}$, W, X, Y, and Z are as defined above. In the scheme, the broken line represents a single bond or a double bond. $R^{39}$ represents a protective group for a carboxy group.

$R^{41}$ and $R^{42}$ each independently represent a hydrogen atom or a $C_1$ to $C_6$ alkyl group, or $R^{41}$ and $R^{42}$ optionally together form a cycloalkyl ring or an aliphatic heterocyclic ring having an oxygen atom in the ring.

(1) Conversion of Compound 2d to Compound 7c

The conversion of compound 2d to compound 7c can be carried out by a general amidation reaction similar to the method described above in (1) of [Production method 1].

(2) Conversion of Compound 7c to Compound 6c

The conversion of compound 7c to compound 6c can be carried out by the reaction of the corresponding amine in an appropriate solvent that has no adverse effect on the reaction (e.g., N,N-dimethylformamide, acetone, or a mixed solvent thereof) at −30° C. to the boiling point of the solvent used in the reaction, preferably 0° C. to 100° C. In this reaction, an appropriate base (e.g., triethylamine, N,N-di(propan-2-yl)ethylamine, N-methylmorpholine, potassium carbonate, or a mixture thereof) can also be used in an excessive amount. The reaction time is preferably 10 minutes to 72 hours, more preferably 30 minutes to 24 hours.

(3) Conversion of Compound 6c to Compound 1c

The conversion of compound 6c to compound 1c can be carried out by a general deprotection reaction similar to the method described above in (2) of [Production method 1].

Compound 2d, which is a starting material for production, can be synthesized according to a method described in the Reference Examples.

[Production method 6]

Among the compounds represented by formula I, compound 1d given below can be produced by, for example, the following reaction scheme:

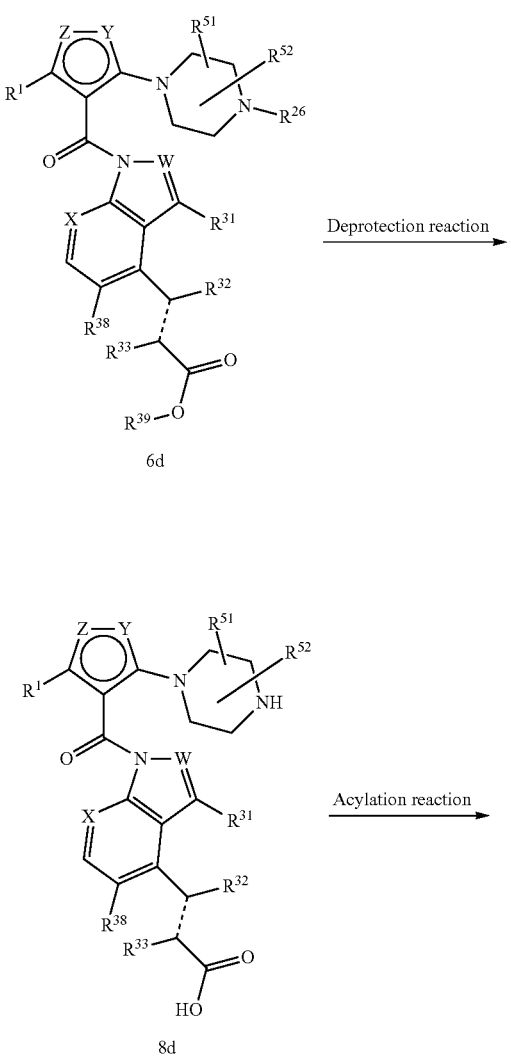

-continued

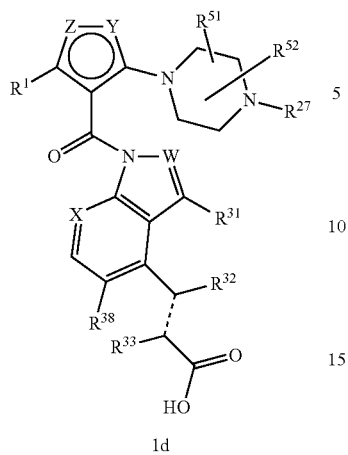

1d

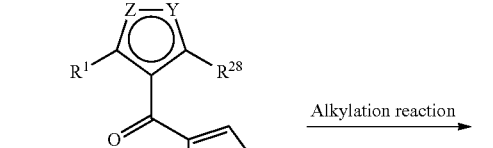

4e

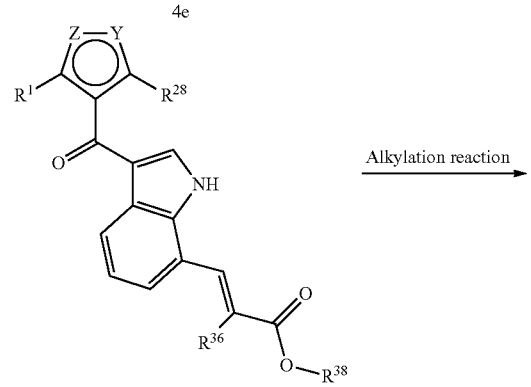

5e

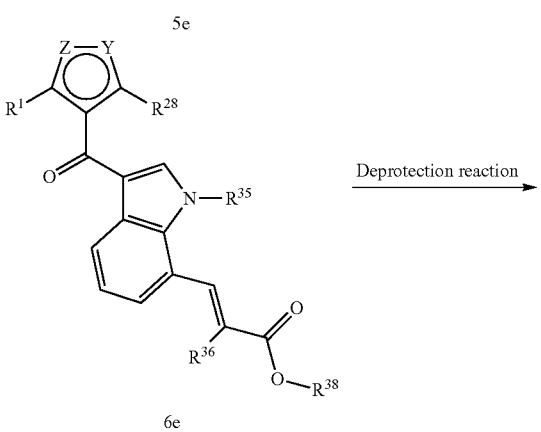

6e

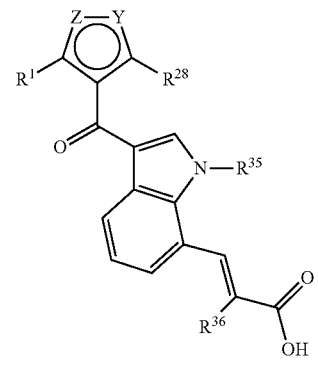

1e

In the scheme, $R^1$, $R^{31}$, $R^{32}$, $R^{33}$, $R^{38}$, W, X, Y, and Z are as defined above. In the scheme, the broken line represents a single bond or a double bond. $R^{39}$ represents a protective group for a carboxy group, and examples thereof include a tert-butyl group.

$R^{51}$ and $R^{52}$ each independently represent a hydrogen atom or a $C_1$ to $C_6$ alkyl group, or $R^{51}$ and $R^{52}$ optionally together form a cycloalkyl ring.

$R^{26}$ represents a protective group for an amino group, and examples thereof include a tert-butoxycarbonyl group.

$R^{27}$ represents —C(=O)$R^{23}$ or —SO$_2$$R^{23}$.

(1) Conversion of Compound 7c to Compound 6d

The conversion of compound 7c to compound 6d can be carried out by a general substitution reaction similar to the method described above in (2) of [Production method 5].

(2) Conversion of Compound 6d to Compound 8d

The conversion of compound 6d to compound 8d can be carried out by a general deprotection reaction similar to the method described above in (1) of [Production method 3].

(3) Conversion of Compound 8d to Compound 1d

The conversion of compound 8d to compound 1d can be carried out by an acylation reaction similar to the method described above in (2) of [Production method 3].

[Production method 7]

Among the compounds represented by formula I, compound 1e given below can be produced by, for example, the following reaction scheme:

[Formula 25]

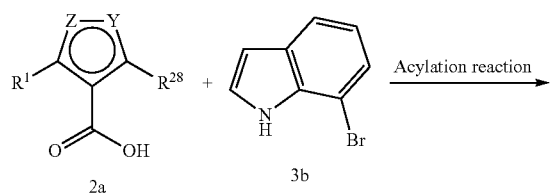

In the scheme, $R^1$, $R^{31}$, $R^{32}$, $R^{33}$, $R^{35}$, $R^{36}$, Y, and Z are as defined above. $R^{39}$ represents a protective group for a carboxy group.

$R^{28}$ represents a $C_1$ to $C_6$ alkyl group optionally having 1 to 3 substituents independently selected from group B given below, a $C_3$ to $C_6$ cycloalkyl group optionally having 1 to 3 substituents independently selected from group C given below, or a 4- to 6-membered aliphatic heterocyclic group having one oxygen atom in the ring. The 4- to 6-membered aliphatic heterocyclic group optionally has 1 to 3 substituents independently selected from group C given below.

Group B consists of a halogen atom, a hydroxy group, and a $C_1$ to $C_6$ alkoxy group.

Group C consists of a halogen atom, a hydroxy group, a $C_1$ to $C_6$ alkyl group, a $C_1$ to $C_6$ alkoxy group, and a di-$C_1$ to $C_6$ alkylamino group.

(1) Conversion of Compound 2a to Compound 4e

The conversion of compound 2a to compound 4e can be carried out by a Friedel-Crafts reaction. Specifically, the conversion can be carried out by use of a carboxylic acid chloride prepared from the compound 2a, compound 3b, and a metal chloride (e.g., anhydrous aluminum chloride or anhydrous zinc chloride) in an appropriate solvent that has no effect on the reaction (e.g., dichloromethane). The reaction temperature can be −20° C. to the boiling point of the solvent used in the reaction, preferably 0° C. to room temperature. The metal chloride used is preferably used at 1 to excessive molar equivalents.

(2) Conversion of Compound 4e to Compound 5e

The conversion of compound 4e to compound 5e can be carried out by a Heck reaction. Specifically, the conversion is carried out by the addition of an organic base or an inorganic base (e.g., sodium carbonate, potassium carbonate, tripotassium phosphate, or N,N-di(propan-2-yl)ethylamine) and a ligand (e.g., triphenylphosphine) in the presence of the corresponding acrylic acid ester and an appropriate transition metal catalyst (e.g., a palladium compound) in an appropriate solvent that has no adverse effect on the reaction (e.g., N,N-dimethylformamide, tetrahydrofuran, toluene, 1,4-dioxane, or water, or a mixed solvent thereof). The acrylic acid ester is commercially available or can be produced by a method known in the art. For the coupling reaction, the reaction temperature is preferably 0° C. to 300° C., more preferably room temperature to 200° C. (the optimum temperature is 80° C. to 100° C.). The reaction can also be carried out by treatment in a sealed tube or under microwave irradiation. The acrylic acid ester and the base are each preferably used at 1 to excessive molar equivalents with respect to the compound 4e. More preferably, the acrylic acid ester is used at 1 to 1.5 molar equivalents, and the base is at 1 to 5 molar equivalents. The reaction time is preferably 1 minute to 60 hours, more preferably 5 minutes to 24 hours.

(3) Conversion of Compound 5e to Compound 6e

The conversion of compound 5e to compound 6e can be carried out by reaction with an alkyl halide in the presence of an appropriate base (e.g., sodium hydride) in an appropriate solvent that has no adverse effect on the reaction (e.g., N,N-dimethylformamide or tetrahydrofuran) or a mixed solvent thereof at −20° C. to the boiling point of the solvent used in the reaction, preferably 0° C. to room temperature. An excessive amount can be used as the amount of the base. The reaction time is preferably 1 hour to 72 hours, more preferably 8 hours to 24 hours.

(4) Conversion of Compound 6e to Compound 1e

The conversion of compound 6e to compound 1e can be carried out by a general deprotection reaction similar to the method described above in (2) of [Production method 1].

[Production method 8]

Among the compounds represented by formula I, compound if given below can be produced by, for example, the following reaction scheme:

[Formula 26]

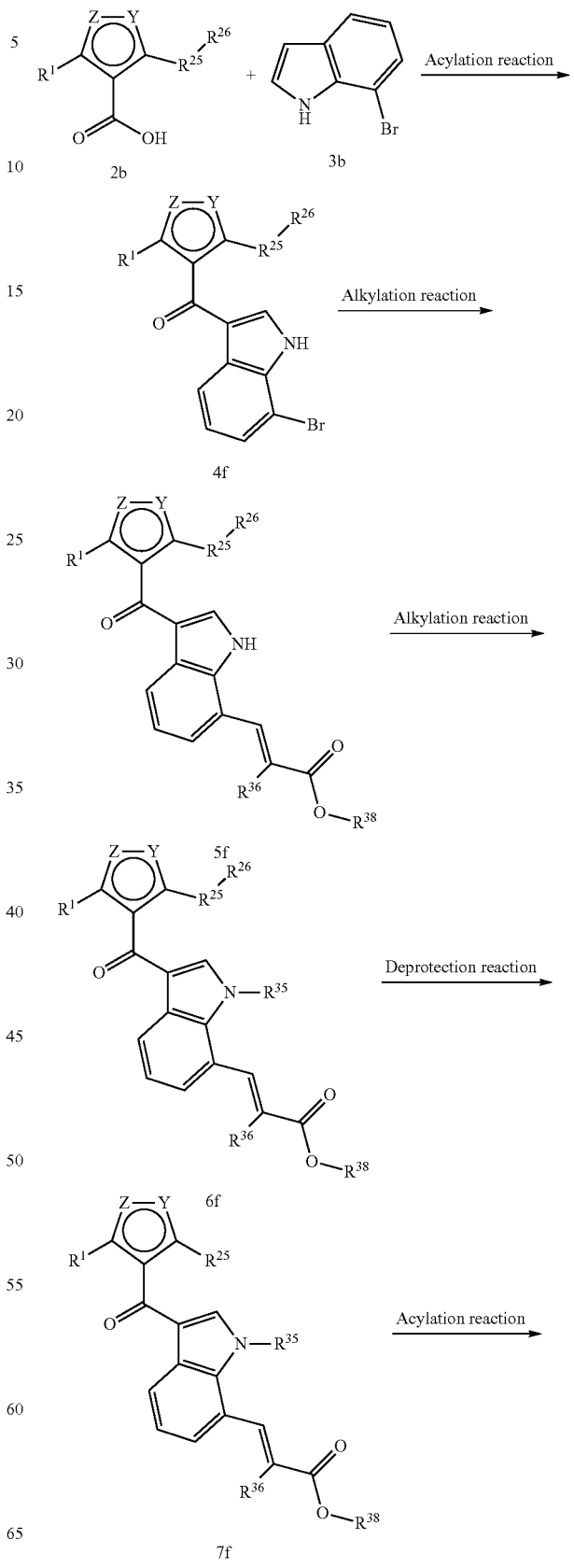

-continued

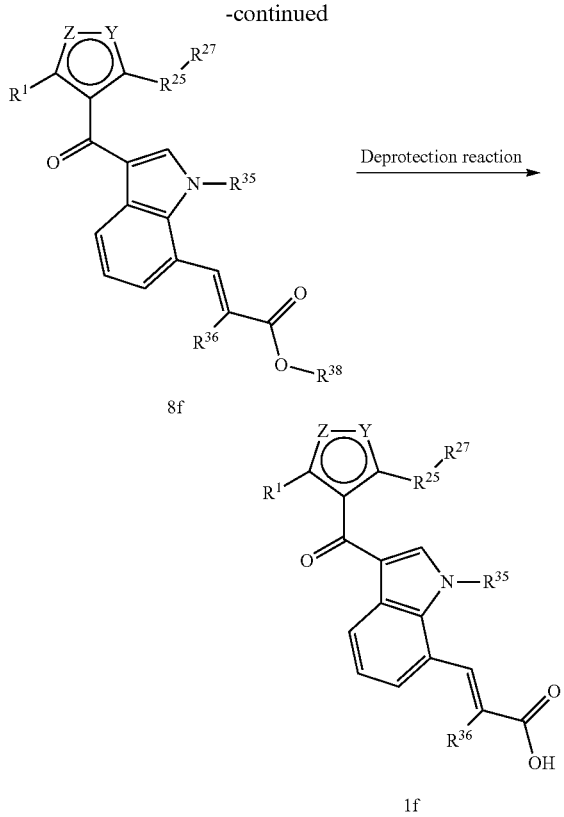

In the scheme, $R^1$, $R^{31}$, $R^{32}$, $R^{33}$, $R^{35}$, $R^{36}$, Y, and Z are as defined above. $R^{39}$ represents a protective group for a carboxy group.

$R^{25}$ represents a 4- to 6-membered aliphatic heterocyclic group having one nitrogen atom in the ring. The 4- to 6-membered aliphatic heterocyclic ring is bonded to $R^{26}$ via the nitrogen atom on the ring. This 4- to 6-membered aliphatic heterocyclic ring optionally has 1 to 3 substituents independently selected from group C given below, and a bridged structure is optionally bonded within the heterocyclic ring, or one $C_3$ to $C_6$ cycloalkyl ring is optionally bonded onto the heterocyclic ring via a spiro bond.

$R^{26}$ represents a protective group for an amino group, and examples thereof include a 2-nitrophenylsulfonyl group.

$R^{27}$ represents —C(=O)$R^{23}$ or —SO$_2R^{23}$.

$R^{23}$ represents a $C_2$ to $C_6$ alkenyl group or a $C_2$ to $C_6$ alkynyl group.

Group C consists of a halogen atom, a hydroxy group, a cyano group, a $C_1$ to $C_6$ alkyl group optionally having 1 to 3 substituents independently selected from group D given below, a $C_1$ to $C_6$ alkoxy group, and —NR$^{21}$R$^{22}$.

In this context, $R^{21}$ and $R^{22}$ each independently represent a hydrogen atom, a $C_1$ to $C_6$ alkyl group, or —C(=O)$R^{23}$. $R^{23}$ represents a $C_2$ to $C_6$ alkenyl group or a $C_2$ to $C_6$ alkynyl group.

Group D consists of an amino group, a $C_1$ to $C_6$ alkoxy group, a di-$C_1$ to $C_6$ alkylamino group, an oxo group, and a $C_3$ to $C_6$ cycloalkyl group.

(1) Conversion of Compound 2b to Compound 4f

The conversion of compound 2b to compound 4f can be carried out by a general coupling reaction similar to the method described above in (1) of [Production method 7].

(2) Conversion of Compound 4f to Compound 5f

The conversion of compound 4f to compound 5f can be carried out by a general alkylation reaction similar to the method described above in (2) of [Production method 7].

(3) Conversion of Compound 5f to Compound 6f

The conversion of compound 5f to compound 6f can be carried out by a general alkylation reaction similar to the method described above in (3) of [Production method 7].

(4) Conversion of Compound 6f to Compound 7f

The conversion of compound 6f to compound 7f can be carried out by a general deprotection reaction similar to the method described above in (2) of [Production method 2].

(5) Conversion of Compound 7f to Compound 8f

The conversion of compound 7f to compound 8f can be carried out by a general acylation reaction similar to the method described above in (3) of [Production method 2].

(6) Conversion of Compound 8f to Compound 1f

The conversion of compound 8f to compound 1f can be carried out by a general deprotection method similar to the method described above in (2) of [Production method 1].

EXAMPLES

Hereinafter, the present invention will be described in more detail with reference to the Reference Examples, Examples, and Test Examples. However, the scope of the present invention is not intended to be limited by these examples.

Elution in column chromatography in the Reference Examples and Examples was carried out under observation by thin layer chromatography (TLC). In the TLC observation, silica gel 60 $F_{254}$ or silica gel 60 NH$_2$F$_{254}$S manufactured by Merck KGaA was used as a TLC plate; a solvent used as an eluting solvent in column chromatography was used as a developing solvent; and a UV detector was adopted in a detection method. Silica gel SK-85 (230 to 400 mesh) also manufactured by Merck KGaA or Chromatorex NH (200 to 350 mesh) manufactured by Fuji Silysia Chemical Ltd. was used as silica gel for columns. In addition to general column chromatography, an automatic purification apparatus from Yamazen Corp. (YFLC-5404-FC) or an automatic purification apparatus from Biotage Japan Ltd. (HORIZON, SP1, or Isolera) was appropriately used. The eluting solvent used was a solvent specified on a Reference Example or Example basis. The abbreviations used in the Reference Examples and Examples are as defined below.

mg: milligram, g: gram, μl: microliter, ml: milliliter, L: liter, and MHz: megahertz.

In Examples below, nuclear magnetic resonance (hereinafter, referred to as $^1$H-NMR: 400 MHz) spectra were indicated by chemical shift δ values (ppm) determined with tetramethylsilane as a standard. Splitting patterns were indicated by s=singlet, d=doublet, t=triplet, q=quartet, m=multiplet, and br=broad.

Reference Example K-1

Ethyl 3-(3-methyloxetan-3-yl)-3-oxopropanoate

[Formula 27]

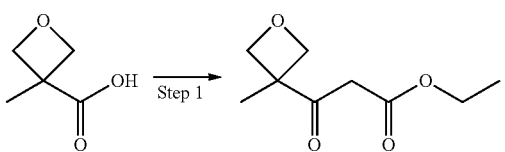

[Step 1]

To a solution of 3-methyloxetane-3-carboxylic acid (4.78 g) in tetrahydrofuran (80 ml), 1,1'-carbonyldiimidazole (7.35 g) was added, and the mixture was stirred at room temperature for 1 hour. Potassium monoethyl malonate (7.01 g) and magnesium chloride (3.92 g) were added to the reaction solution, and the mixture was stirred at 60° C. for 1 hour. After cooling, the reaction solution was diluted with ethyl acetate and filtered. The filtrate was rendered acidic by the addition of 1 N hydrochloric acid and then separated into two layers. The organic layer was washed with saturated saline and then dried over anhydrous sodium sulfate. The solvent was distilled off under reduced pressure to obtain the title compound (5.98 g).

$^1$H-NMR (CDCl$_3$) δ: 1.29 (3H, t, J=7.3 Hz), 1.60 (3H, s), 3.62 (2H, s), 4.21 (2H, q, J=7.3 Hz), 4.45 (2H, d, J=6.7 Hz), 4.91 (2H, d, J=6.7 Hz).

The following compounds were obtained by the same method as in step 1 of Reference Example K-1.

TABLE 1

| Reference Example No. | Name and structure | Instrumental data |
|---|---|---|
| K-2 | Ethyl 3-(3-ethyloxetan-3-yl)-3-oxopropanoate | $^1$H-NMR(CDCl$_3$)δ: 0.88(3H, t, J = 7.3 Hz), 1.29 (3H, t, J = 7.3 Hz), 2.07(2H, q, J = 7.5 Hz), 3.51 (2H, s), 4.21(2H, q, J = 7.3 Hz), 4.45(2H, d, J = 6.7 Hz), 4.87(2H, d, J = 6.7 Hz). |
| K-3 | Ethyl 3-(1-methylcyclobutyl)-3-oxopropanoate | $^1$H-NMR(CDCl$_3$)δ: 1.28(3H, t, J = 7.3 Hz), 1.41 (3H, s), 1.73-1.85(3H, m), 1.93-2.04(1H, m), 2.40-2.50(2H, m), 3.46(2H, s), 4.20(2H, q, J = 7.3 Hz). |
| K-4 | Ethyl 3-(1-methoxycyclobutyl)-3-oxopropanoate | $^1$H-NMR(CDCl$_3$)δ: 1.28(3H, t, J = 7.3 Hz), 1.60-1.86(2H, m), 2.10-2.19(2H, m), 2.34-2.42(2H, m), 3.17(3H, s), 3.58(2H, s), 4.20 (2H, q, J = 7.3 Hz). |
| K-5 | Ethyl 3-(1-methylcyclopropyl)-3-oxopropanoate | $^1$H-NMR(CDCl$_3$)δ: 0.81(2H, q, J = 3.6 Hz), 1.26-1.31(5H, m), 1.37(3H, s), 3.46(2H, s), 4.20 (2H, q, J = 7.1 Hz). |
| K-6 | Ethyl 4-methoxy-4-methyl-3-oxopentanoate | $^1$H-NMR(CDCl$_3$)δ: 1.28(3H, t, J = 7.3 Hz), 1.32 (6H, s), 3.25(3H, s), 3.64(2H, s), 4.19(2H, q, J = 7.3 Hz). |
| K-7 | Ethyl 3-[1-(tert-butoxycarbonylamino)cyclopropyl]-3-oxopropanoate | $^1$H-NMR(CDCl$_3$)δ: 1.18-1.23(2H, m), 1.29(3H, t, J = 7.3 Hz), 1.47(9H, s), 1.62-1.66(2H, m), 3.67(2H, s), 4.21(2H, q, J = 7.3 Hz), 5.26(1H, brs). |

TABLE 1-continued

| Reference Example No. | Name and structure | Instrumental data |
|---|---|---|
| K-8 | Ethyl 3-[1-(tert-butoxycarbonylamino)cyclobutyl]-3-oxopropanoate 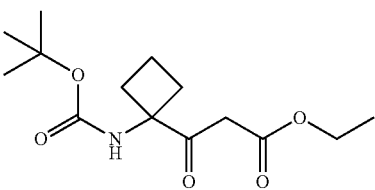 | $^1$H-NMR(CDCl$_3$)δ: 1.28(3H, t, J = 7.3 Hz), 1.44 (9H, brs), 1.82-2.10(4H, m), 2.62-2.71(2H, m), 3.55(2H, s), 4.19(2H, q, J = 7.3 Hz), 5.06-5.23(1H, m). |

TABLE 2

| | | |
|---|---|---|
| K-9 | Ethyl 4-(tert-butoxycarbonylamino)-4-methyl-3-oxopentanoate 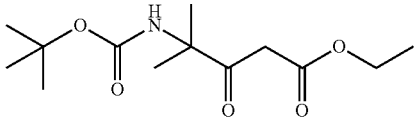 | $^1$H-NMR(CDCl$_3$)δ: 1.27(3H, t, J = 7.3 Hz), 1.41 (6H, brs), 1.44(9H, s), 3.63(2H, s), 4.19(2H, q, J = 7.3 Hz), 4.70-5.04(1H, m). |
| K-10 | tert-Butyl 3-(3-ethoxy-3-oxopropanoyl)-3-methylazetidine-1-carboxylate 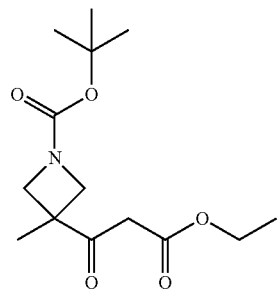 | $^1$H-NMR(CDCl$_3$)δ: 1.29(3H, t, J = 7.3 Hz), 1.44 (9H, s), 1.54(3H, s), 3.56(2H, s), 3.62-3.69(2H, m), 4.10-4.25(4H, m). |
| K-11 | tert-Butyl 4-(3-ethoxy-3-oxopropanoyl)-4-methylpiperidine-1-carboxylate 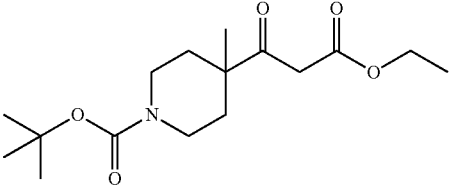 | $^1$H-NMR(CDCl$_3$)δ: 1.19(3H, s), 1.28(3H, t, J = 7.3 Hz), 1.38-1.52(10H, m), 1.97(2H, ddd, J = 13.6, 3.3, 1.7 Hz), 3.19-3.26(2H, m), 3.46-3.64(4H, m), 4.20(2H, q, J = 7.3 Hz). |
| K-12 | tert-Butyl 6-(3-ethoxy-3-oxopropanoyl)-3-azabicyclo[3.1.0]hexane-3-carboxylate 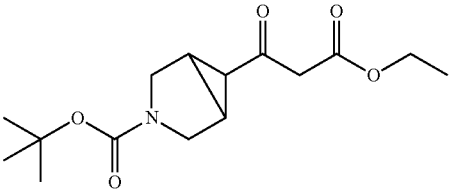 | $^1$H-NMR(CDCl$_3$)δ: 1.29(3H, t, J = 7.3 Hz), 1.45 (9H, s), 1.92(1H, t, J = 3.0 Hz), 2.11-2.21(2H, m), 3.39-3.48(2H, m), 3.56(2H, s), 3.59(1H, d, J = 11.5 Hz), 3.68(1H, d, J = 11.5 Hz), 4.21(2H, q, J = 7.1 Hz). |

TABLE 2-continued

| K-13 | | $^1$H-NMR(CDCl$_3$)δ: 1.35(3H, t, J = 7.0 Hz), 3.98 (1H, s), 4.29(2H, q, J = 7.0 Hz), 5.68(1H, s), 7.40(1H, d, J = 8.5 Hz), 8.01(1H, dd, J = 8.5, 2.4 Hz), 8.77(1H, d, J = 2.4 Hz). MS (m/z): 228(M + H)$^+$. |
|---|---|---|
| | Ethyl 3-(6-chloro-3-pyridyl)-3-oxopropanoate 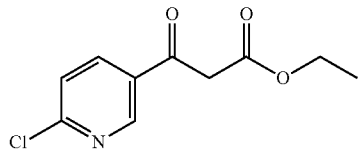 | |

TABLE 3

| K-14 | | $^1$H-NMR(CDCl$_3$)δ: 1.29(3H, t, J = 7.3 Hz), 1.51 (3H, s), 2.34-2.45(2H, m), 2.94-3.08(2H, m), 3.53(2H, s), 4.21(2H, q, J = 7.3 Hz). |
|---|---|---|
| | Ethyl 3-(3,3-difluoro-1-methylcyclobutyl)-3-oxopropanoate 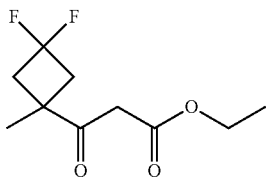 | |

Reference Example K-15

Ethyl 4-fluoro-4-methyl-3-oxopentanoate

[Formula 28]

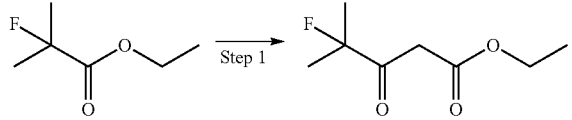

[Step 1]

To a suspension of sodium hydride (55% oil, 6.10 g) in tetrahydrofuran (40 ml), a mixture of ethyl 2-fluoro-2-methylpropanoate (12.5 g) and ethyl acetate (12.3 g) was added dropwise over 20 minutes, and the mixture was stirred at room temperature for 3 hours. The reaction solution was neutralized by the addition of 1 N hydrochloric acid, followed by extraction with n-hexane. The extract was washed with saturated saline and then dried over anhydrous magnesium sulfate. The solvent was distilled off under reduced pressure, and the residue was dried. The supernatant oil was removed to obtain a crude form of the title compound (16.60 g), which was directly used in the next reaction.

$^1$H-NMR (CDCl$_3$) δ: 1.29 (3H, t, J=7.3 Hz), 1.50 (6H, d, J=21.2 Hz), 3.66 (2H, d, J=3.6 Hz), 4.21 (2H, q, J=7.3 Hz).

Reference Example K-16 tert-Butyl 4,4-difluoro-3-oxopentanoate

[Formula 29]

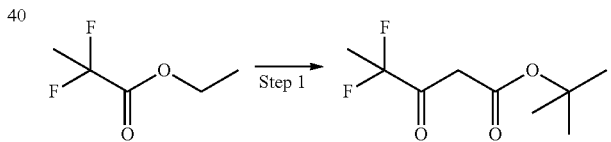

[Step 1]

To a solution of lithium di(propan-2-yl)amide (1.12 mol solution in tetrahydrofuran, 36 ml) in tetrahydrofuran (50 ml), tert-butyl acetate (4.83 ml) was added at −78° C., and the mixture was stirred at the same temperature as above for 30 minutes. Ethyl 2,2-difluoropropanoate (3 g) was added to the reaction solution, and the mixture was stirred at the same temperature as above for 2 hours. 1 N hydrochloric acid was added to the reaction solution, followed by extraction with n-hexane. The extract was washed with 1 N hydrochloric acid and saturated saline in this order and then dried over anhydrous magnesium sulfate. The solvent was distilled off under reduced pressure to obtain a crude form of the title compound (5.10 g), which was directly used in the next reaction.

$^1$H-NMR (CDCl3) δ: 1.47 (9H, s), 1.74 (3H, t, J=19.3 Hz), 3.62 (2H, s).

The following compound was obtained by the same method as in step 1 of Reference Example K-16.

TABLE 4

| Reference Example No. | Name and structure | Instrumental data |
|---|---|---|
| K-17 | tert-Butyl 4,4,4-trifluoro-3-oxobutanoate 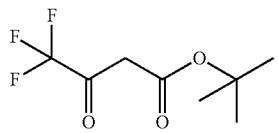 | $^1$H-NMR(CDCl$_3$)δ: 1.51(9H, s), 3.63-3.77(2H, m). |

Reference Example K-18

Ethyl 3-[1-(methoxymethoxymethyl)cyclobutyl]-3-oxopropanoate

[Formula 30]

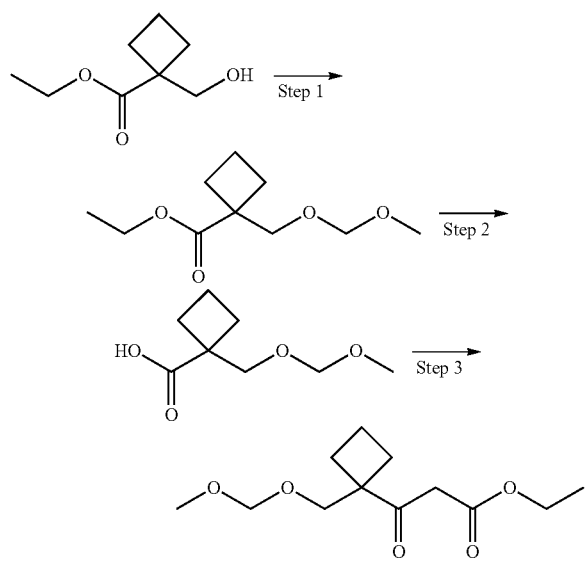

[Step 1] Ethyl 1-(methoxymethoxymethyl)cyclobutanecarboxylate

To a solution of ethyl 1-(hydroxymethyl)cyclobutanecarboxylate (2.50 g) in dichloromethane (30 ml), N,N-di(propan-2-yl)ethylamine (4.06 ml), and chloromethyl methyl ether (1.43 ml) were added, and the mixture was stirred at room temperature for 1 hour. Chloromethyl methyl ether (0.595 ml) and N,N-di(propan-2-yl)ethylamine (1.62 ml) were further added to the reaction solution, and the mixture was stirred for another 1 hour. Water and dichloromethane were added to the reaction solution, which was then separated into two layers. The organic layer was washed with 0.25 N hydrochloric acid and a saturated aqueous solution of sodium bicarbonate in this order and then dried over anhydrous sodium sulfate. The solvent was distilled off under reduced pressure to obtain the title compound (2.98 g).

$^1$H-NMR (CDCl$_3$) δ: 1.27 (3H, t, J=7.3 Hz), 1.89-2.05 (4H, m), 2.39-2.48 (2H, m), 3.35 (3H, s), 3.79 (2H, s), 4.18 (2H, q, J=7.3 Hz), 4.63 (2H, s).

[Step 2] 1-(Methoxymethoxymethyl)cyclobutanecarboxylic acid

To a mixed solution of the compound (2.98 g) obtained in the preceding step 1 in methanol (20 ml) and tetrahydrofuran (20 ml), a 1 N aqueous sodium hydroxide solution (20 ml) was added, and the mixture was stirred at 45° C. for 1.5 hours. After being allowed to cool, the reaction solution was rendered weakly acidic by the addition of 1 N hydrochloric acid, followed by extraction with ethyl acetate. The extract was washed with saturated saline and then dried over anhydrous sodium sulfate. The solvent was distilled off under reduced pressure to obtain the title compound (2.05 g).

$^1$H-NMR (CDCl$_3$) δ: 1.93-2.07 (4H, m), 2.42-2.53 (2H, m), 3.37 (3H, s), 3.82 (2H, s), 4.66 (2H, s).

[Step 3] Ethyl 3-[1-(methoxymethoxymethyl)cyclobutyl]-3-oxopropanoate

The title compound (2.49 g) was obtained by the same method as in step 1 of Reference Example K-1 using the compound (2.05 g) obtained in the preceding step 2.

$^1$H-NMR (CDCl$_3$) δ: 1.28 (3H, t, J=7.3 Hz), 1.81-2.03 (4H, m), 2.40-2.48 (2H, m), 3.36 (3H, s), 3.54 (2H, s), 3.81 (2H, s), 4.19 (2H, q, J=7.3 Hz), 4.61 (2H, s).

Reference Example K-19

Ethyl 3-[1-(methoxymethyl)cyclobutyl]-3-oxopropanoate

[Formula 31]

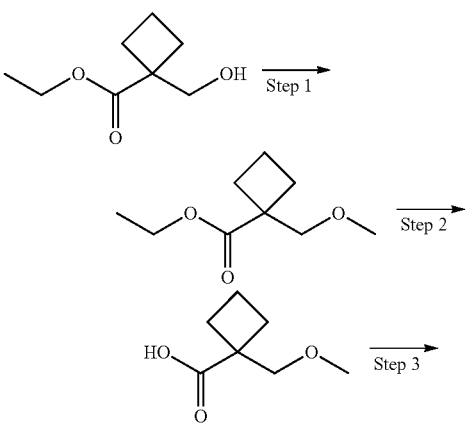

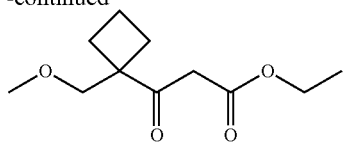

[Step 1] Ethyl 1-(methoxymethyl)cyclobutanecarboxylate

To a solution of ethyl 1-(hydroxymethyl)cyclobutanecarboxylate (0.690 g) in dichloromethane (25 ml), a 42% aqueous tetrafluoroboric acid solution (0.793 ml) was added, subsequently (trimethylsilyl)diazomethane (2.0 mol solution in n-hexane, 4.36 ml) was added in small portions, and the mixture was stirred at room temperature for 15 minutes. Water and dichloromethane were added to the reaction solution, which was then separated into two layers. The organic layer was dried over anhydrous sodium sulfate. The solvent was distilled off under reduced pressure to obtain the title compound (0.720 g).

$^1$H-NMR (CDCl$_3$) δ: 1.27 (3H, t, J=7.3 Hz), 1.88-2.05 (4H, m), 2.36-2.45 (2H, m), 3.36 (3H, s), 3.63 (2H, s), 4.18 (2H, q, J=7.3 Hz).

[Step 2] 1-(Methoxymethyl)cyclobutanecarboxylic acid

The title compound (300 mg) was obtained by the same method as in step 2 of Reference Example K-18 using the compound (720 mg) obtained in the preceding step 1.

$^1$H-NMR (CDCl$_3$) δ: 1.92-2.06 (4H, m), 2.40-2.51 (2H, m), 3.41 (3H, s), 3.66 (2H, s).

[Step 3] Ethyl 3-[1-(methoxymethyl)cyclobutyl]-3-oxopropanoate

The title compound (308 mg) was obtained by the same method as in step 1 of Reference Example K-1 using the compound (285 mg) obtained in the preceding step 2.

$^1$H-NMR (CDCl$_3$) δ: 1.28 (3H, t, J=7.3 Hz), 1.81-2.00 (4H, m), 2.38-2.44 (2H, m), 3.34 (3H, s), 3.51 (2H, s), 3.64 (2H, s), 4.19 (2H, q, J=7.3 Hz).

Reference Example K-20

Ethyl 3-(1-methoxycyclopropyl)-3-oxopropanoate

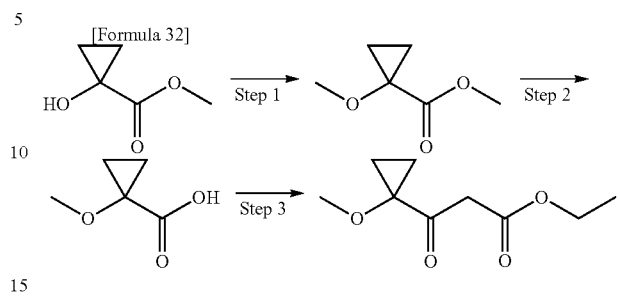

[Formula 32]

[Step 1] Methyl 1-methoxycyclopropanecarboxylate

To a solution of methyl 1-hydroxycyclopropanecarboxylate (3.2 g) in tetrahydrofuran (40 ml), sodium hydride (55% oil, 1.3 g) was added under ice cooling, and the mixture was stirred at the same temperature as above for 15 minutes. Methyl iodide (2.3 ml) was added to the reaction solution, and the mixture was stirred overnight at room temperature. 1 N hydrochloric acid was added to the reaction solution, followed by extraction with a n-hexane-ethyl acetate mixed solution. The extract was washed with saturated saline and then dried over anhydrous magnesium sulfate. The solvent was distilled off under reduced pressure to obtain the title compound (4.0 g).

$^1$H-NMR (CDCl$_3$) δ: 1.13-1.32 (4H, m), 3, 42 (3H, s), 3.75 (3H, s).

[Step 2] 1-Methoxycyclopropanecarboxylic acid

The title compound (2.0 g) was obtained by the same method as in step 2 of Reference Example K-18 using the compound (4.0 g) obtained in the preceding step 1.

$^1$H-NMR (CDCl$_3$) δ: 1.22-1.26 (2H, m), 1.36-1.40 (2H, m), 3.45 (3H, s).

[Step 3] Ethyl 3-(1-methoxycyclopropyl)-3-oxopropanoate

The title compound (3.1 g) was obtained by the same method as in step 1 of Reference Example K-1 using the compound (2.0 g) obtained in the preceding step 2.

$^1$H-NMR (CDCl$_3$) δ: 1.22-1.39 (7H, m), 3.38 (3H, s), 3.72 (2H, s), 4.21 (2H, q, J=7.3 Hz).

The following compound was obtained by the same method as in Reference Example K-20.

TABLE 5

| Reference Example No. | Name and structure | Instrumental data |
| --- | --- | --- |
| K-21 | Ethyl 5-methoxy-4,4-dimethyl-3-oxopentanoate | $^1$H-NMR(CDCl$_3$)δ: 1.16(6H, s), 1.28(3H, t, J = 7.0 Hz), 3.32(3H, s), 3.35(2H, s), 3.57(2H, s), 4.19(2H, q, J = 7.0 Hz). |

Reference Example K-22

Ethyl 3-{1-[(2-nitrophenyl)sulfonyl]piperidin-4-yl}-3-oxopropanoate

[Formula 33]

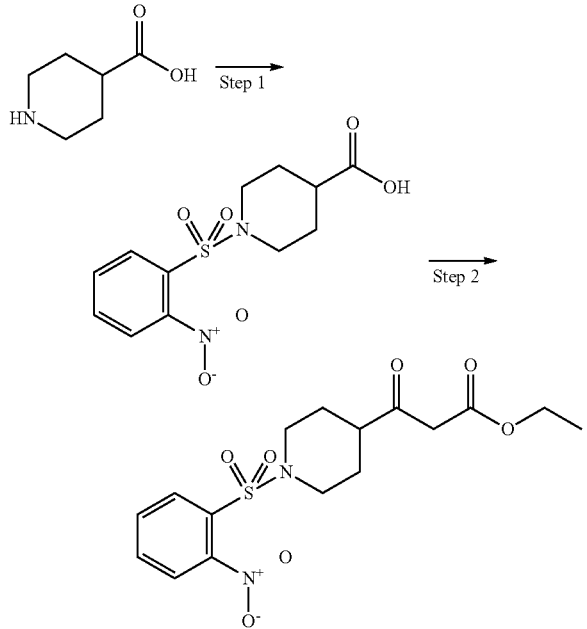

[Step 1] 1-(2-Nitrophenyl)sulfonylpiperidine-4-carboxylic acid

To an aqueous solution (1000 ml) of piperidine-4-carboxylic acid (30 g), sodium carbonate (73.9 g) and 2-nitrobenzenesulfonyl chloride (61.8 g) were added in small portions under ice cooling, and the mixture was stirred overnight at room temperature. Ethyl acetate was added to the reaction solution, which was then separated into two layers. The aqueous layer was rendered acidic by the addition of concentrated hydrochloric acid under ice cooling, followed by extraction with ethyl acetate. The extract was washed with water and saturated saline in this order and then dried over anhydrous sodium sulfate. The solvent was distilled off under reduced pressure, and n-hexane was added to the residue obtained. The resulting solid was collected by filtration to obtain the title compound (69 g).

$^1$H-NMR (CDCl$_3$) δ: 1.78-1.90 (2H, m), 1.99-2.07 (2H, m), 2.45-2.52 (1H, m), 2.93-3.02 (2H, m), 3.76 (2H, dt, J=12.7, 3.6 Hz), 7.61-7.74 (3H, m), 8.00 (1H, dd, J=7.3, 1.8 Hz).

[Step 2] Ethyl 3-{1-[(2-nitrophenyl)sulfonyl]piperidin-4-yl}-3-oxopropanoate The title compound (14 g) was obtained by the same method as in step 1 of Reference Example K-1 using the compound (10 g) obtained in the preceding step 1.

$^1$H-NMR (CDCl$_3$) δ: 1.26 (3H, t, J=7.3 Hz), 1.68-1.79 (2H, m), 1.84-2.01 (2H, m), 2.57-2.66 (1H, m), 2.88-2.97 (2H, m), 3.48 (2H, s), 3.79-3.86 (2H, m), 4.19 (2H, q, J=7.3 Hz), 7.60-7.74 (3H, m), 7.98-8.02 (1H, m).

The following compounds were obtained by the same method as in Reference Example K-22.

TABLE 6

| Reference Example No. | Name and structure | Instrumental data |
| --- | --- | --- |
| K-23 | Ethyl 3-{1-[(2-nitrophenyl)sulfonyl]piperidin-3-yl}-3-oxopropanoate | $^1$H-NMR(CDCl$_3$)δ: 1.29(3H, t, J = 7.3 Hz), 1.41-1.73(2H, m), 1.80-1.90(1H, m), 2.03-2.11(1H, m), 2.72-2.98(3H, m), 3.54(2H, s), 3.71-3.84(1H, m), 3.88-3.98(1H, m), 4.21(2H, q, J = 7.1 Hz), 7.60-7.65(1H, m), 7.67-7.75(2H, m), 7.97-8.02(1H, m). |
| K-24 | Ethyl 3-{1-[(2-nitrophenyl)sulfonyl]azetidin-3-yl}-3-oxopropanoate | $^1$H-NMR(CDCl$_3$)δ: 1.28(3H, t, J = 7.3 Hz), 3.46(2H, s), 3.64-3.73(1H, m), 4.16-4.36(6H, m), 7.69-7.77(3H, m), 8.01-8.07(1H, m). |

Reference Example K-25 tert-Butyl 4-(3-ethoxy-3-oxopropanoyl)-4-(methoxymethyl)piperidine-1-carboxylate

[Formula 34]

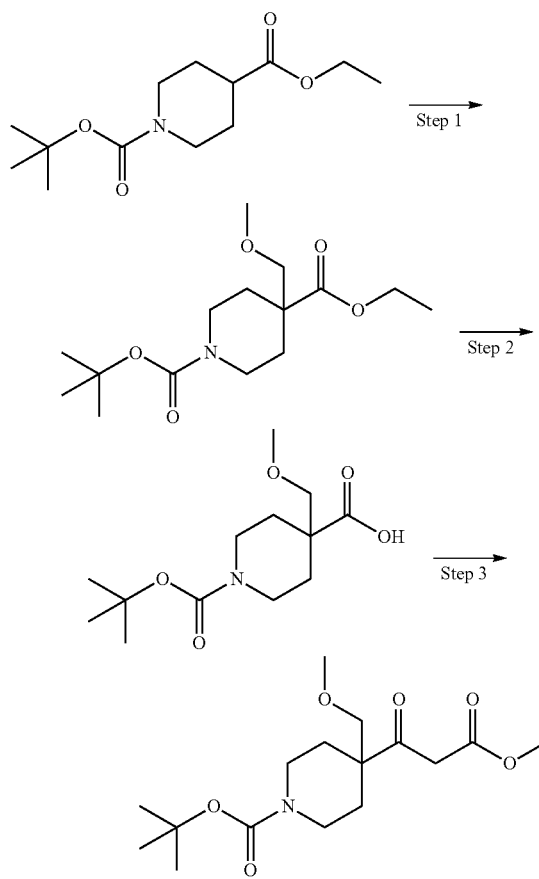

[Step 1] 1-tert-Butyl 4-ethyl 4-(methoxymethyl)piperidine-1,4-dicarboxylate To a solution of 1-tert-butyl 4-ethyl piperidine-1,4-dicarboxylate (1.00 g) in tetrahydrofuran (20 ml), lithium di(propan-2-yl)amide (1.09 mol solution in tetrahydrofuran, 5.35 ml) was added at −78° C. under a nitrogen atmosphere, and the mixture was stirred at the same temperature as above for 1 hour. Chloromethyl methyl ether (0.73 ml) was added to the reaction solution, and the mixture was gradually heated to room temperature and stirred overnight at room temperature. An aqueous ammonium chloride solution (20 ml) was added to the reaction solution, which was then separated into two layers. The aqueous layer was subjected to extraction with ethyl acetate. The organic layers were combined, washed with water and saturated saline in this order and then dried over anhydrous sodium sulfate. The solvent was distilled off under reduced pressure, and the residue obtained was purified by silica gel column chromatography (n-hexane/ethyl acetate) to obtain the title compound (917 mg).

$^1$H-NMR (CDCl$_3$) δ: 1.27 (3H, t, J=7.0 Hz), 1.38-1.48 (11H, m), 2.04-2.12 (2H, m), 2.85-3.06 (2H, brm), 3.30 (3H, s), 3.38 (2H, brs), 3.75-3.95 (2H, brm), 4.20 (2H, q, J=7.1 Hz).

[Step 2] 1-tert-Butoxycarbonyl-4-(methoxymethyl)piperidine-4-carboxylic acid The title compound (852 mg) was obtained by the same method as in step 3 of Reference Example K-18 using the compound (910 mg) obtained in the preceding step 1.

$^1$H-NMR (CDCl$_3$) δ: 1.39-1.50 (11H, m), 2.03-2.12 (2H, m), 2.99-3.14 (2H, brm), 3.36 (3H, s), 3.44 (2H, brs), 3.75-3.91 (2H, brm).

MS (m/z): 272 (M−H)$^-$.

[Step 3] tert-Butyl 4-(3-ethoxy-3-oxopropanoyl)-4-(methoxymethyl)piperidine-1-carboxylate The title compound (835 mg) was obtained by the same method as in step 1 of Reference Example K-1 using the compound (825 mg) obtained in the preceding step 2.

$^1$H-NMR (CDCl$_3$) δ: 1.27 (3H, t, J=7.3 Hz), 1.44 (9H, s), 1.46-1.57 (2H, brm), 2.03 (2H, ddd, J=13.9, 4.1, 2.0 Hz), 3.08-3.24 (2H, m), 3.30 (3H, s), 3.40 (2H, s), 3.57 (2H, s), 3.58-3.72 (2H, brm), 4.19 (2H, q, J=7.3 Hz).

Reference Example K-26 tert-Butyl 4-(3-ethoxy-3-oxopropanoyl)-4-methoxypiperidine-1-carboxylate

[Formula 35]

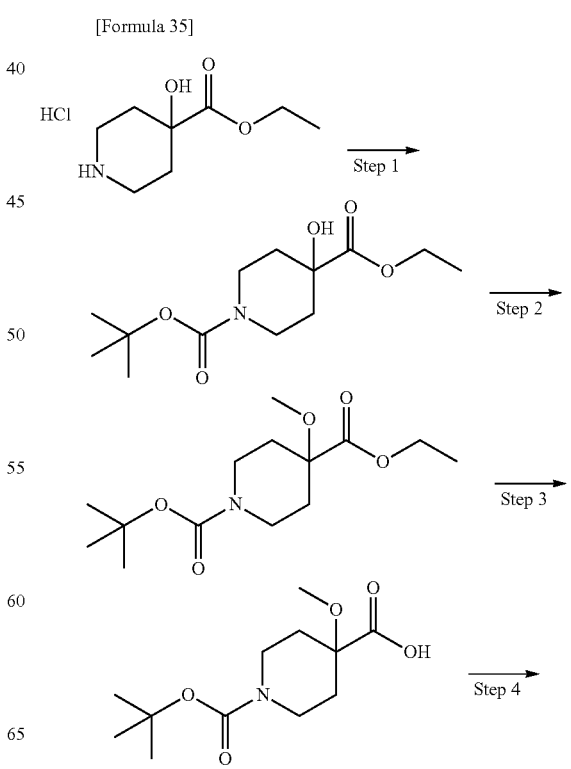

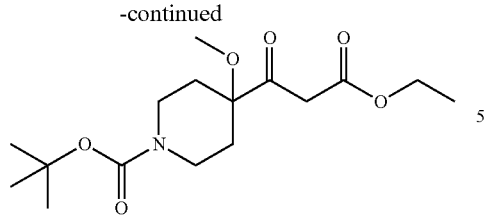

[Step 1] 1-tert-Butyl 4-ethyl 4-hydroxypiperidine-1,4-dicarboxylate

To a suspension of ethyl 4-hydroxypiperidine-4-carboxylate hydrochloride (1.02 g) in dichloromethane (10 ml), triethylamine (1.69 ml) and di-tert-butyl dicarbonate (1.23 ml) were added, and the mixture was stirred overnight at room temperature. The reaction solution was concentrated under reduced pressure, and the residue obtained was purified by silica gel column chromatography (n-hexane/ethyl acetate) to obtain the title compound (1.35 g).

$^1$H-NMR (CDCl$_3$) δ: 1.30 (3H, t, J=7.3 Hz), 1.47 (9H, s), 1.53-1.62 (2H, brm), 1.95 (2H, td, J=12.7, 4.8 Hz), 3.05 (1H, s), 3.07-3.25 (2H, brm), 3.86-4.08 (2H, brm), 4.25 (2H, q, J=7.3 Hz).

[Step 2] 1-tert-Butyl 4-ethyl 4-methoxypiperidine-1,4-dicarboxylate

The title compound (483 mg) was obtained by the same method as in step 1 of Reference Example K-20 using the compound (685 mg) obtained in the preceding step 1.

$^1$H-NMR (CDCl$_3$) δ: 1.30 (3H, t, J=7.0 Hz), 1.46 (9H, s), 1.82-1.96 (4H, brm), 3.10-3.23 (2H, brm), 3.27 (3H, s), 3.69-3.85 (2H, brm), 4.23 (2H, q, J=7.3 Hz).

[Step 3] 1-(tert-Butoxycarbonyl)-4-methoxypiperidine-4-carboxylic acid

The title compound (430 mg) was obtained by the same method as in step 3 of Reference Example K-18 using the compound (483 mg) obtained in the preceding step 2.

$^1$H-NMR (CDCl$_3$) δ: 1.46 (9H, s), 1.85-1.99 (4H, m), 3.08-3.23 (2H, brm), 3.33 (3H, s), 3.75-3.92 (2H, brm).

[Step 4] tert-Butyl 4-(3-ethoxy-3-oxopropanoyl)-4-methoxypiperidine-1-carboxylate The title compound (488 mg) was obtained by the same method as in step 1 of Reference Example K-1 using the compound (430 mg) obtained in the preceding step 3.

$^1$H-NMR (CDCl$_3$) δ: 1.28 (3H, t, J=7.3 Hz), 1.45 (9H, s), 1.71-1.95 (4H, m), 3.08-3.22 (2H, m), 3.23 (3H, s), 3.63 (2H, s), 3.82-3.84 (2H, brm), 4.20 (2H, q, J=7.3 Hz).

Reference Example K-27

Ethyl 3-{4-(methoxymethoxy)-1-[(2-nitrophenyl)sulfonyl]piperidin-4-yl}-3-oxopropanoate

[Formula 36]

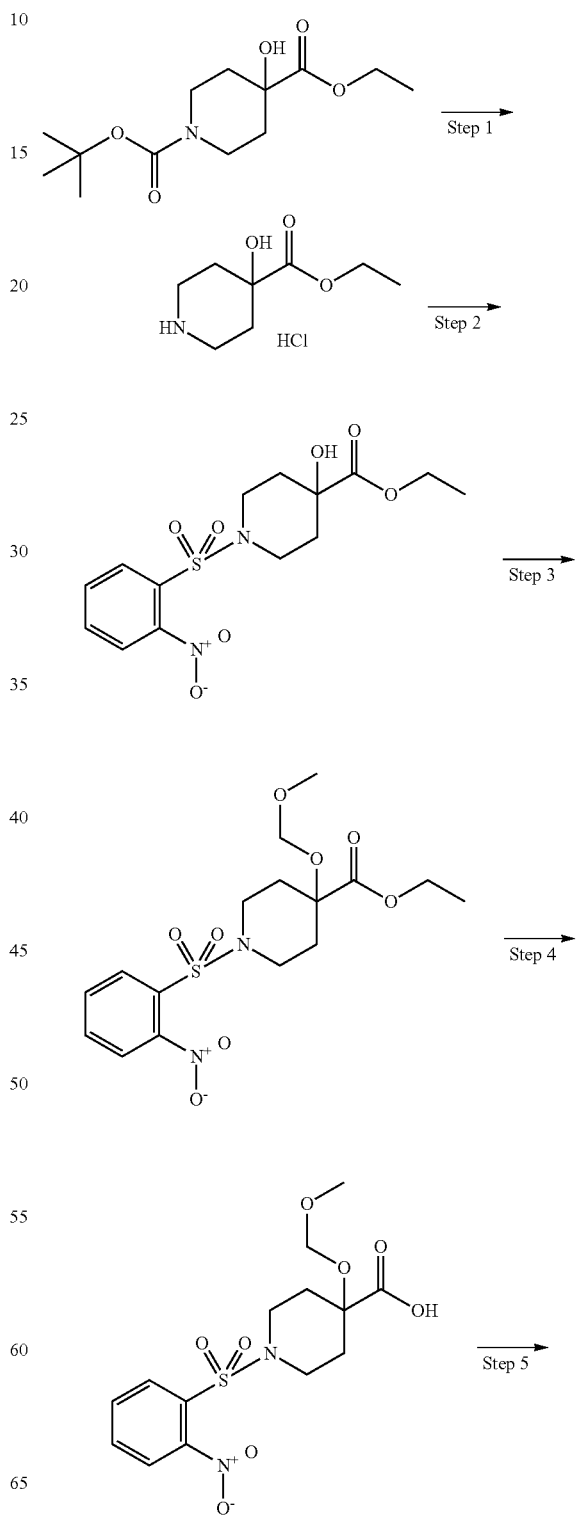

-continued

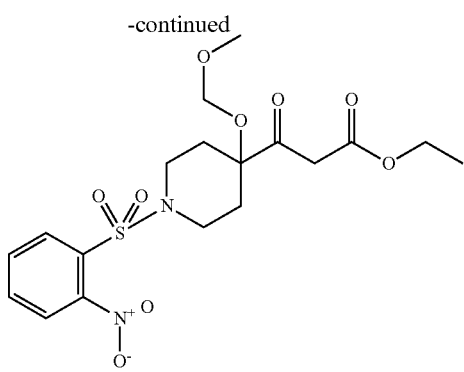

[Step 1] Ethyl 4-hydroxypiperidine-4-carboxylate hydrochloride

To a solution of the compound (2.78 g) obtained in step 1 of Reference Example K-26 in ethanol (30 ml), a solution of 4 N hydrochloric acid in 1,4-dioxane (10 ml) was added under ice cooling, and the mixture was stirred overnight at room temperature. The reaction solution was concentrated under reduced pressure to obtain the title compound (2.12 g).
$^1$H-NMR (DMSO-$d_6$) δ: 1.22 (3H, t, J=7.3 Hz), 1.77-1.80 (2H, m), 2.02 (2H, ddd, J=13.1, 4.0, 2.0 Hz), 3.02-3.05 (2H, m), 3.14-3.17 (2H, m), 4.14 (2H, q, J=7.1 Hz), 5.86 (1H, brs), 8.51 (1H, brs), 8.67 (1H, brs).

[Step 2] Ethyl 4-hydroxy-1-[(2-nitrophenyl)sulfonyl]piperidine-4-carboxylate

To a solution of the compound (2.12 g) obtained in the preceding step 1 and triethylamine (4.24 ml) in dichloromethane (35 ml), 2-nitrobenzenesulfonyl chloride (2.47 g) was added under ice cooling, and the mixture was stirred overnight at room temperature. The reaction solution was diluted with dichloromethane, and then, water was added thereto. After separation into two layers, the organic layer was washed with water and saturated saline in this order and then dried over anhydrous sodium sulfate. The solvent was distilled off under reduced pressure, and the residue obtained was purified by silica gel column chromatography (n-hexane/ethyl acetate) to obtain the title compound (3.38 g).
$^1$H-NMR (CDCl$_3$) δ: 1.31 (3H, t, J=7.3 Hz), 1.68-1.71 (2H, m), 2.15 (2H, ddd, J=13.1, 4.6, 2.3 Hz), 3.11 (1H, s), 3.16 (2H, ddd, J=12.7, 2.4, 1.2 Hz), 3.78-3.81 (2H, m), 4.26 (2H, q, J=7.1 Hz), 7.59-7.65 (1H, m), 7.67-7.73 (2H, m), 7.98 (1H, dd, J=7.3, 1.8 Hz).
MS (m/z): 359 (M+H)$^+$.

[Step 3] Ethyl 4-(methoxymethoxy)-1-[(2-nitrophenyl)sulfonyl]piperidine-4-carboxylate To a solution of the compound (1.51 g) obtained in the preceding step 2 and chloromethyl methyl ether (0.64 ml) in N,N-dimethylformamide (16.9 ml), sodium hydride (55% oil, 369 mg) was added under ice cooling, and the mixture was stirred at room temperature for 30 minutes. The reaction solution was diluted with ethyl acetate, and then, ice was added to the reaction solution, which was then separated into two layers. The organic layer was washed with water and saturated saline in this order and then dried over anhydrous sodium sulfate. The solvent was distilled off under reduced pressure, and the residue obtained was purified by silica gel column chromatography (n-hexane/ethyl acetate) to obtain the title compound (1.12 g).
$^1$H-NMR (CDCl$_3$) δ: 1.28 (3H, t, J=7.0 Hz), 2.01-2.13 (4H, m), 3.21-3.27 (2H, m), 3.34 (3H, s), 3.60 (2H, ddd, J=8.6, 4.2, 2.1 Hz), 4.19 (2H, q, J=7.1 Hz), 4.70 (2H, s), 7.61-7.74 (3H, m), 7.99-8.02 (1H, m).

[Step 4] 4-(Methoxymethoxy)-1-[(2-nitrophenyl)sulfonyl]piperidine-4-carboxylic acid The title compound (1.07 g) was obtained by the same method as in step 3 of Reference Example K-18 using the compound (1.12 g) obtained in the preceding step 3.
$^1$H-NMR (CDCl$_3$) δ: 2.07-2.17 (4H, m), 3.21-3.28 (2H, m), 3.38 (3H, s), 3.64 (2H, ddd, J=8.5, 4.0, 2.0 Hz), 4.75 (2H, s), 7.62-7.64 (1H, m), 7.67-7.74 (2H, m), 8.00-8.02 (1H, m).

[Step 5] Ethyl 3-{4-(methoxymethoxy)-1-[(2-nitrophenyl)sulfonyl]piperidin-4-yl}-3-oxopropanoate The title compound (958 mg) was obtained by the same method as in step 1 of Reference Example K-1 using the compound (1.07 g) obtained in the preceding step 4.
$^1$H-NMR (CDCl$_3$) δ: 1.26 (3H, t, J=7.3 Hz), 1.91-2.02 (4H, m), 3.23-3.30 (2H, m), 3.35 (3H, s), 3.61-3.64 (4H, m), 4.18 (2H, q, J=7.3 Hz), 4.61 (2H, s), 7.62-7.64 (1H, m), 7.69-7.72 (2H, m), 7.99-8.02 (1H, m).
MS (m/z): 443 (M−H)$^−$.

Reference Example K-28

Ethyl 3-{4-(tert-butoxycarbonylamino)-1-[(2-nitrophenyl)sulfonyl]piperidin-4-yl}-3-oxopropanoate

[Formula 37]

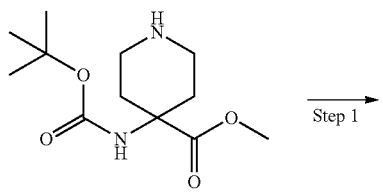
Step 1

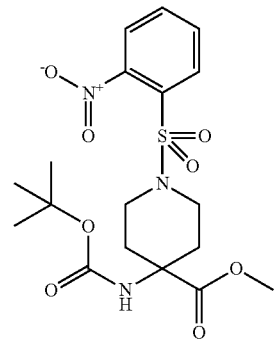
Step 2

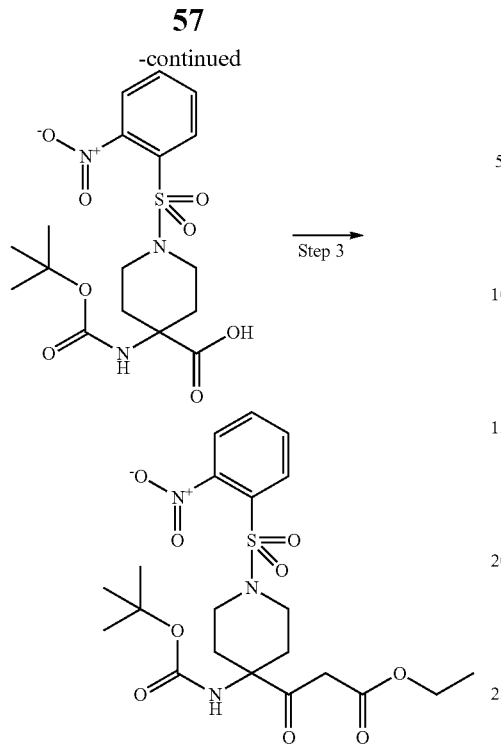

[Step 1] Methyl 4-(tert-butoxycarbonylamino)-1-[(2-nitrophenyl)sulfonyl]piperidine-4-carboxylate To a mixed solution of methyl 4-(tert-butoxycarbonylamino)piperidine-4-carboxylate (1.06 g) in tetrahydrofuran (11 ml) and water (11 ml), sodium carbonate (1.30 g) and 2-nitrobenzenesulfonyl chloride (1.09 g) were added under ice cooling, and the mixture was stirred overnight at room temperature. The reaction solution was concentrated under reduced pressure, and the residue obtained was diluted with ethyl acetate, washed with water and saturated saline in this order and then dried over anhydrous sodium sulfate. The solvent was distilled off under reduced pressure, and the residue obtained was purified by silica gel column chromatography (n-hexane/ethyl acetate) to obtain the title compound (1.66 g).
$^1$H-NMR (CDCl$_3$) δ: 1.42 (9H, s), 2.01-2.09 (2H, m), 2.17-2.25 (2H, m), 3.17-3.26 (2H, m), 3.62 (2H, td, J=8.9, 4.2 Hz), 3.73 (3H, s), 4.64 (1H, brs), 7.63 (1H, dd, J=7.3, 1.8 Hz), 7.67-7.75 (2H, m), 8.00 (1H, dd, J=7.0, 2.7 Hz).

[Step 2] 4-(tert-Butoxycarbonylamino)-1-[(2-nitrophenyl)sulfonyl]piperidine-4-carboxylic acid The title compound (1.46 g) was obtained by the same method as in step 3 of Reference Example K-18 using the compound (1.66 g) obtained in the preceding step 1.
$^1$H-NMR (CDCl$_3$) δ: 1.43 (9H, s), 2.01-2.12 (2H, m), 2.19-2.29 (2H, m), 3.25 (2H, t, J=11.2 Hz), 3.57-3.67 (2H, m), 4.80 (1H, brs), 7.62-7.77 (3H, m), 7.97-8.04 (1H, m).

[Step 3] Ethyl 3-{4-(tert-butoxycarbonylamino)-1-[(2-nitrophenyl)sulfonyl]piperidin-4-yl}-3-oxopropanoate The title compound (1.23 g) was obtained by the same method as in step 1 of Reference Example K-1 using the compound (1.46 g) obtained in the preceding step 2.

$^1$H-NMR (CDCl$_3$) δ: 1.26 (3H, t, J=7.3 Hz), 1.43 (9H, s), 1.85-1.97 (2H, brm), 2.16-2.32 (2H, m), 3.27-3.38 (2H, m), 3.51-3.61 (2H, m), 3.59 (2H, s), 4.17 (2H, q, J=7.3 Hz), 4.83 (1H, brs), 7.62-7.76 (3H, m), 7.99 (1H, dd, J=7.9, 1.8 Hz).

Reference Example X-1

3-(2,6-Dichlorophenyl)-5-(propan-2-yl)-1,2-oxazole-4-carboxylic acid

[Formula 38]

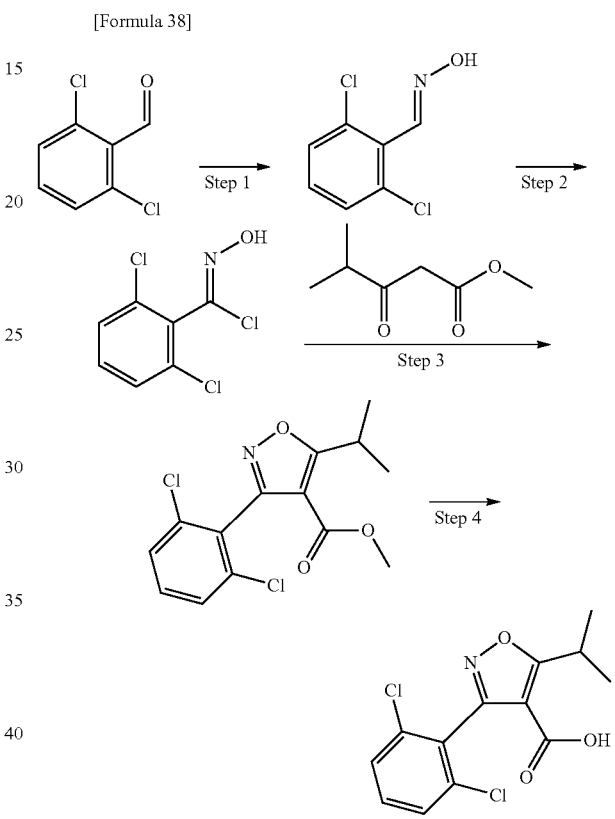

[Step 1] (1E)-2,6-Dichlorobenzaldehyde oxime 2,6-Dichlorobenzaldehyde (1.24 g) was suspended in water (20 ml). To the suspension, hydroxylamine hydrochloride (652 mg) and sodium carbonate (488 mg) were added, and the mixture was heated to reflux for 2 hours. After cooling, the reaction solution was subjected to extraction with dichloromethane. The extract was dried over anhydrous sodium sulfate. The solvent was distilled off under reduced pressure to obtain the title compound (1.31 g).
$^1$H-NMR (CDCl$_3$) δ: 7.24 (1H, dd, J=8.6, 7.4 Hz), 7.37 (2H, d, J=8.0 Hz), 7.88 (1H, brs), 8.38 (1H, s).

[Step 2] (1Z)-2,6-Dichloro-N-hydroxybenzenecarboximidoyl chloride

To a solution of the compound (1.00 g) obtained in the preceding step 1 in N,N-dimethylformamide (13 ml), N-chlorosuccinimide (737 mg) was added under cooling in a water bath, and the mixture was stirred overnight at room temperature. Water was added to the reaction solution, followed by extraction with diethyl ether. The extract was washed with saturated saline and then dried over anhydrous sodium sulfate. The solvent was distilled off under reduced pressure to obtain the title compound (1.28 g), which was used in the next reaction without being purified.

$^1$H-NMR (CDCl$_3$) δ: 7.27-7.41 (3H, m), 9.64-9.94 (1H, m).

[Step 3] Methyl 3-(2,6-dichlorophenyl)-5-(propan-2-yl)-1,2-oxazole-4-carboxylate To a solution of methyl 4-methyl-3-oxopentanoate (0.79 ml) in tetrahydrofuran (6 ml), a solution of sodium methoxide (28% solution in methanol, 1.07 ml) in methanol (10 ml) was added dropwise under ice cooling, and the mixture was stirred at room temperature for 1 hour. A solution of the compound (1.28 g) obtained in the preceding step 2 in tetrahydrofuran (3 ml) was added dropwise to the reaction solution under ice cooling, and the mixture was stirred overnight at room temperature. The reaction solution was concentrated under reduced pressure, and water was added to the residue obtained, followed by extraction with diethyl ether. The extract was washed with saturated saline and then dried over anhydrous sodium sulfate. The solvent was distilled off under reduced pressure to obtain the title compound (1.34 g).

$^1$H-NMR (CDCl$_3$) δ: 1.44 (6H, d, J=7.3 Hz), 3.67 (3H, s), 3.83-3.90 (1H, m), 7.29-7.44 (3H, m).

[Step 4] 3-(2,6-Dichlorophenyl)-5-(propan-2-yl)-1,2-oxazole-4-carboxylic acid

To a solution of the compound (1.34 g) obtained in the preceding step 3 in methanol (10 ml), a 1 N aqueous sodium hydroxide solution (10 ml) was added, and the mixture was stirred at 55° C. for 9 hours. The reaction solution was concentrated under reduced pressure, and ethyl acetate was added to the residue obtained, which was then separated into two layers. The aqueous layer was rendered acidic using 1 N hydrochloric acid under ice cooling, followed by extraction with ethyl acetate. The extract was dried over anhydrous sodium sulfate, and then, the solvent was distilled off under reduced pressure to obtain the title compound (1.11 g).

$^1$H-NMR (CDCl$_3$) δ: 1.43 (6H, d, J=6.7 Hz), 3.85-3.92 (1H, m), 7.30-7.43 (3H, m).

The following compounds were obtained by the same method as in Reference Example X-1 using commercially available esters or the esters described in the Reference Examples.

TABLE 7

| Reference Example No. | Reference Example No. (ester) | Name and structure | Instrumental data |
|---|---|---|---|
| X-2 | — | 5-(Propan-2-yl)-3-(2,4,6-trichlorophenyl)-1,2-oxazole-4-carboxylic acid 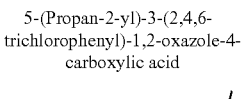 | $^1$H-NMR(CDCl$_3$)δ: 1.43(6H, d, J = 6.8 Hz), 3.82-3.95(1H, m), 7.44(2H, s). |
| X-3 | — | 3-(2,6-Dichloro-3-fluorophenyl)-5-(propan-2-yl)-1,2-oxazole-4-carboxylic acid 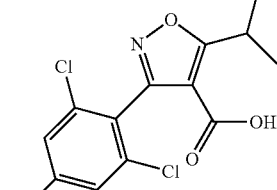 | $^1$H-NMR(CDCl$_3$)δ: 1.44(6H, d, J = 7.2 Hz), 3.83-3.95(1H, m), 7.23(1H, t, J = 8.4 Hz), 7.38(1H, dd, J = 8.6, 4.5 Hz). |

TABLE 7-continued

| Reference Example No. | Reference Example No. (ester) | Name and structure | Instrumental data |
|---|---|---|---|
| X-4 | — | 5-(tert-Butyl)-3-(2,6-dichlorophenyl)-1,2-oxazole-4-carboxylic acid | $^1$H-NMR(CDCl$_3$)δ: 1.56(9H, s), 7.31-7.40(3H, m). |
| X-5 | — | 5-(tert-Butyl)-3-(2,4,6-trichlorophenyl)-1,2-oxazole-4-carboxylic acid | $^1$H-NMR(CDCl$_3$)δ: 1.56(9H, s), 7.43(2H, s). |

TABLE 8

| X-6 | — | 5-(tert-Butyl)-3-(2,4-dichloro-6-fluorophenyl)-1,2-oxazole-4-carboxylic acid | $^1$H-NMR(CDCl$_3$)δ: 1.55 (9H, s), 7.15 (1H, dd, J = 8.8, 2.1 Hz), 7.33 (1H, t, J = 1.5 Hz). |
| X-7 | — | 5-(tert-Butyl)-3-(2,6-dichloro-4-methylphenyl)-1,2-oxazole-4-carboxylic acid | $^1$H-NMR(CDCl$_3$)δ: 1.55 (9H, s), 2.38 (3H, s), 7.22(2H, s). MS(m/z): 328 (M + H)$^+$. |
| X-8 | — | 3-(2-Bromo-6-chlorophenyl)-5-(tert-butyl)-1,2-oxazole-4-carboxylic acid | $^1$H-NMR(CDCl$_3$)δ: 1.56 (9H, s), 7.24-7.28 (1H, m), 7.44(1H, d, J = 7.9 Hz), 7.57 (1H, d, J = 7.9 Hz). |
| X-9 | — | 5-(tert-Butyl)-3-(2,4-dichloro-6-methylphenyl)-1,2-oxazole-4-carboxylic acid | $^1$H-NMR(CDCl$_3$)δ: 1.55 (9H, s), 2.16 (3H, s), 7.19-7.20 (1H, m), 7.31-7.32 (1H, m). |
| X-10 | — | 3-(2,6-Dichlorophenyl)-5-(3-methyloxetan-3-yl)-1,2-oxazole-4-carboxylic acid | $^1$H-NMR(CDCl$_3$)δ: 1.89 (3H, s), 4.67 (2H, d, J = 6.8 Hz), 5.18 (2H, d, J = 6.8 Hz), 7.34-7.44(3H, m). |

TABLE 9

| | | | |
|---|---|---|---|
| X-11 | K-1 | 5-(3-Methyloxetan-3-yl)-3-(2,4,6-trichlorophenyl)-1,2-oxazole-4-carboxylic acid | ¹H-NMR(CDCl₃)δ: 1.89(3H, s), 4.68(2H, d, J = 6.7 Hz), 5.18 (2H, d, J = 6.7 Hz), 7.45(2H, s). |

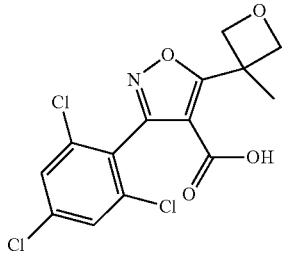

| | | | |
|---|---|---|---|
| X-12 | K-1 | 3-(2,4-Dichlorophenyl)-5-(3-methyloxetan-3-yl)-1,2-oxazole-4-carboxylic acid | ¹H-NMR(CDCl₃)δ: 1.88(3H, s), 4.67(2H, d, J = 6.7 Hz), 5.16 (2H, d, J = 6.7 Hz), 7.36-7.38(2H, m), 7.51-7.52(1H, m). |

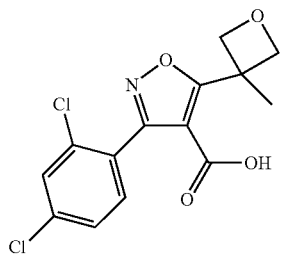

| | | | |
|---|---|---|---|
| X-13 | K-2 | 5-(3-Ethyloxetan-3-yl)-3-(2,4,6-trichlorophenyl)-1,2-oxazole-4-carboxylic acid | ¹H-NMR(CDCl₃)δ: 0.87(3H, t, J = 7.6 Hz), 2.35(2H, q, J = 7.5 Hz), 4.71(2H, d, J = 6.7 Hz), 5.15 (2H, d, J = 6.7 Hz), 7.45(2H, s). |

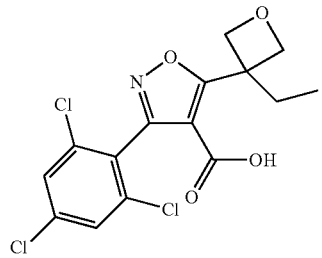

| | | | |
|---|---|---|---|
| X-14 | K-3 | 5-(1-Methylcyclobutyl)-3-(2,4,6-trichlorophenyl)-1,2-oxazole-4-carboxylic acid | ¹H-NMR(CDCl₃)δ: 1.67(3H, s), 1.86-1.95(1H, m), 2.11-2.26(3H, m), 2.65-2.74(2H, m), 7.43(2H, s). |

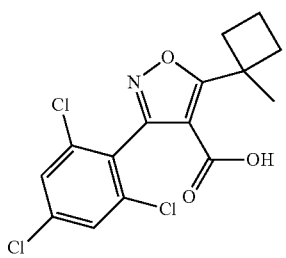

TABLE 10

| X-15 | K-4 | 5-(1-Methoxycyclobutyl)-3-(2,4,6-trichlorophenyl)-1,2-oxazole-4-carboxylic acid | ¹H-NMR(CDCl₃)δ: 1.96-2.17(2H, m), 2.60-2.68(2H, m), 2.74-2.81(2H, m), 3.33(3H, s), 7.45 (2H, s). |
|---|---|---|---|
| X-16 | K-4 | 3-(2,4-Dichloro-6-fluorophenyl)-5-(1-methoxycyclobutyl)-1,2-oxazole-4-carboxylic acid | ¹H-NMR(CDCl₃)δ: 1.94-2.15(2H, m), 2.59-2.67(2H, m), 2.74-2.81(2H, m), 3.32(3H, s), 7.17 (1H, dd, J = 8.8, 2.0 Hz), 7.35 (1H, t, J = 2.0 Hz). |
| X-17 | K-5 | 5-(1-Methylcyclopropyl)-3-(2,4,6-trichlorophenyl)-1,2-oxazole-4-carboxylic acid | ¹H-NMR(CDCl₃)δ: 0.96-0.98(2H, m), 1.30-1.32(2H, m), 1.55(3H, s), 7.43 (2H, s). |
| X-18 | K-6 | 3-(2,6-Dichlorophenyl)-5-(1-methoxy-1-methylethyl)-1,2-oxazole-4-carboxylic acid | ¹H-NMR(CDCl₃)δ: 1.83(6H, s), 3.47(3H, s), 7.32-7.44(3H, m). |
| X-19 | K-15 | 3-(2,6-Dichlorophenyl)-5-(2-fluoropropan-2-yl)-1,2-oxazole-4-carboxylic acid | MS(m/z): 318(M + H)⁺. |

TABLE 11

| | | | |
|---|---|---|---|
| X-20 | K-15 | 5-(2-Fluoropropan-2-yl)-3-(2,4,6-trichlorophenyl)-1,2-oxazole-4-carboxylic acid 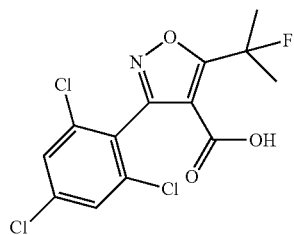 | ¹H-NMR(CDCl₃)δ: 1.95(6H, d, J = 21.2 Hz), 7.44 (2H, s). |
| X-21 | K-15 | 3-(3,5-Dichloro-4-pyridyl)-5-(2-fluoropropan-2-yl)-1,2-oxazole-4-carboxylic acid 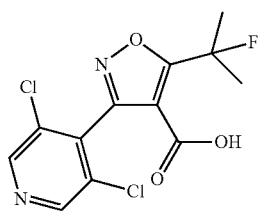 | ¹H-NMR(CDCl₃)δ: 1.96(6H, d, J = 21.8 Hz), 8.62 (2H, s). |

TABLE 11-continued

| | | | |
|---|---|---|---|
| X-22 | K-15 | 3-(2,4-Dichlorophenyl)-5-(2-fluoropropan-2-yl)-1,2-oxazole-4-carboxylic acid 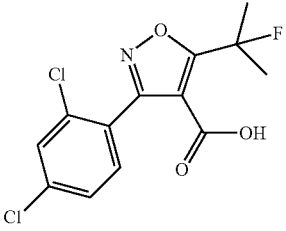 | ¹H-NMR(CDCl₃)δ: 1.93(6H, d, J = 22.4 Hz), 7.35-7.41(2H, m), 7.49-7.52(1H, m). MS(m/z): 318(M + H)⁺. |
| X-23 | K-15 | 3-(2,4-Dichloro-6-fluorophenyl)-5-(2-fluoropropan-2-yl)-1,2-oxazole-4-carboxylic acid 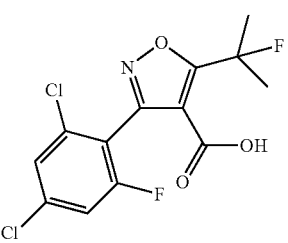 | ¹H-NMR(CDCl₃)δ: 1.94(6H, d, J = 21.8 Hz), 7.17 (1H, dd, J = 8.5, 1.8 Hz), 7.35 (1H, s). MS(m/z): 336(M + H)⁺. |

TABLE 12

| | | | |
|---|---|---|---|
| X-24 | K-15 | 3-(2,6-Dichloro-4-methylphenyl)-5-(2-fluoropropan-2-yl)-1,2-oxazole-4-carboxylic acid 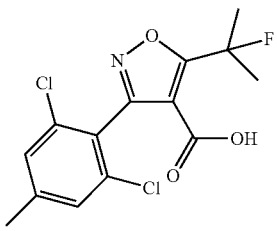 | ¹H-NMR(CDCl₃)δ: 1.94(6H, d, J = 21.8 Hz), 2.39(3H, s), 7.23 (2H, s). MS(m/z): 332(M + H)⁺. |
| X-25 | K-15 | 3-(2,4-Dichloro-6-methylphenyl)-5-(2-fluoropropan-2-yl)-1,2-oxazole-4-carboxylic acid 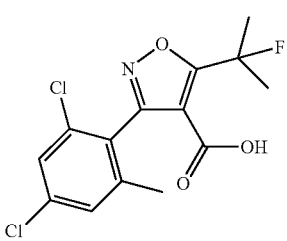 | ¹H-NMR(CDCl₃)δ: 1.94(6H, d, J = 22.4 Hz), 2.17(3H, s), 7.22-7.22(1H, m), 7.33-7.34(1H, m). |

TABLE 12-continued

| X-26 | K-15 | 3-(2,6-Dichloro-4-fluorophenyl)-5-(2-fluoropropan-2-yl)-1,2-oxazole-4-carboxylic acid 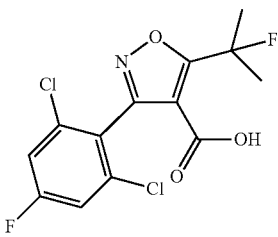 | $^{1}$H-NMR(CDCl$_3$)δ: 1.95(6H, d, J = 21.8 Hz), 7.20(2H, d, J = 7.9 Hz).<br>MS(m/z): 336(M + H)$^{+}$. |
|---|---|---|---|
| X-27 | K-15 | 3-(2-Chloro-6-fluorophenyl)-5-(2-fluoropropan-2-yl)-1,2-oxazole-4-carboxylic acid 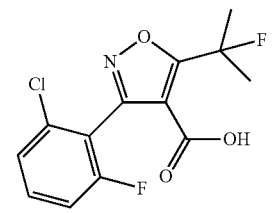 | MS(m/z): 302(M + H)$^{+}$. |

TABLE 13

| X-28 | K-15 | 3-(4-Chloro-2,6-difluorophenyl)-5-(2-fluoropropan-2-yl)-1,2-oxazole-4-carboxylic acid 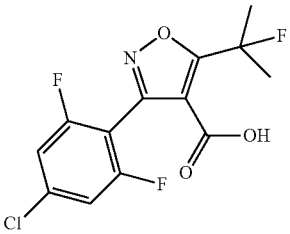 | $^{1}$H-NMR(CDCl$_3$)δ: 1.93(6H, d, J = 21.8 Hz), 7.07(2H, d, J = 7.3 Hz). |
|---|---|---|---|
| X-29 | K-15 | 5-(2-Fluoropropan-2-yl)-3-(2,4,6-trimethylphenyl)-1,2-oxazole-4-carboxylic acid 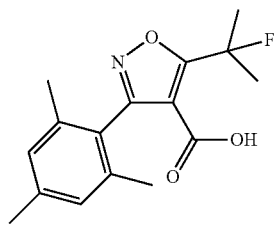 | MS(m/z): 292(M + H)$^{+}$. |

TABLE 13-continued

| | | | |
|---|---|---|---|
| X-30 | K-15 | 3-(4-Chloro-2,6-dimethylphenyl)-5-(2-fluoropropan-2-yl)-1,2-oxazole-4-carboxylic acid | $^1$H-NMR(CDCl$_3$)δ: 1.93(6H, d, J = 22.4 Hz), 2.09(6H, s), 7.11 (2H, s). MS(m/z): 312(M + H)$^+$. |
| X-31 | K-15 | 3-(2,4-Dichloro-6-methoxyphenyl)-5-(2-fluoropropan-2-yl)-1,2-oxazole-4-carboxylic acid | $^1$H-NMR(CDCl$_3$)δ: 1.93(6H, d, J = 21.8 Hz), 3.76(3H, s), 6.88 (1H, d, J = 1.8 Hz), 7.13(1H, d, J = 1.8 Hz). |

TABLE 14

| | | | |
|---|---|---|---|
| X-32 | K-15 | 3-(2,4-Dichloro-5-fluorophenyl)-5-(2-fluoropropan-2-yl)-1,2-oxazole-4-carboxylic acid | $^1$H-NMR(CDCl$_3$)δ: 1.93(6H, d, J = 21.8 Hz), 7.28(1H, d, J = 7.5 Hz), 7.55(1H, d, J = 7.5 Hz). |
| X-33 | K-18 | 5-[1-(Methoxymethoxymethyl)cyclobutyl]-3-(2,4,6-trichlorophenyl)-1,2-oxazole-4-carboxylic acid | $^1$H-NMR(DMSO-d$_6$)δ: 1.86-1.95(1H, m), 2.05-2.17(1H, m), 2.29-2.36(2H, m), 2.53-2.61(2H, m), 3.08(3H, s), 4.00 (2H, s), 4.51(2H, s), 7.88 (2H, s), 13.10(1H, brs). |

TABLE 14-continued

| | | | |
|---|---|---|---|
| X-34 | K-19 | 5-[1-(Methoxymethyl)cyclobutyl]-3-(2,4,6-trichlorophenyl)-1,2-oxazole-4-carboxylic acid | No data |

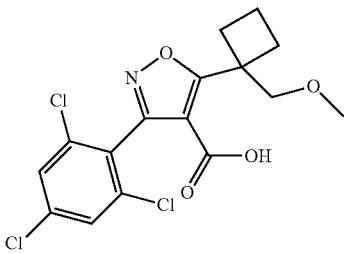

| | | | |
|---|---|---|---|
| X-35 | K-20 | 5-(1-Methoxycyclopropyl)-3-(2,4,6-trichlorophenyl)-1,2-oxazole-4-carboxylic acid | $^1$H-NMR(CDCl$_3$)δ: 1.57(4H, s), 3.52(3H, s), 7.44(2H, s). |

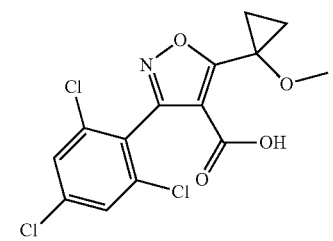

TABLE 15

| | | | |
|---|---|---|---|
| X-36 | K-21 | 5-(2-Methoxy-1,1-dimethylethyl)-3-(2,4,6-trichlorophenyl)-1,2-oxazole-4-carboxylic acid | $^1$H-NMR(CDCl$_3$)δ: 1.58(6H, s), 3.43(3H, s), 3.68(2H, s), 7.42-7.44(2H, m). |
| X-37 | K-22 | 3-(2,6-Dichlorophenyl)-5-{1-[(2-nitrophenyl)sulfonyl]piperidin-4-yl}-1,2-oxazole-4-carboxylic acid | $^1$H-NMR(CDCl$_3$)δ: 2.04-2.19(4H, m), 2.97-3.06(2H, m), 3.64-3.77(1H, m), 3.97-4.05(2H, m), 7.33-7.43(3H, m), 7.66(1H, dd, J = 6.7, 2.4 Hz), 7.69-7.78(2H, m), 8.05(1H, dd, J = 7.3, 1.8 Hz). |

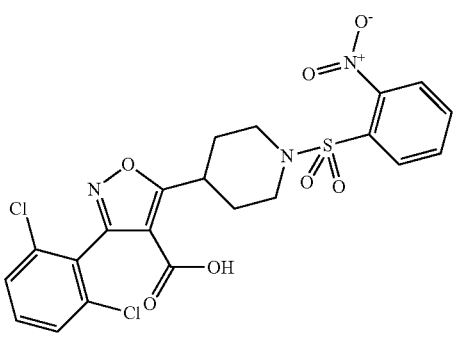 [SMILES: O=C(O)c1c(-c2c(Cl)cccc2Cl)noc1C1CCN(S(=O)(=O)c2ccccc2[N+](=O)[O-])CC1]

TABLE 15-continued

| | | | |
|---|---|---|---|
| X-38 | K-22 | 5-{1-[(2-Nitrophenyl)sulfonyl]piperidin-4-yl}-3-(2,4,6-trichlorophenyl)-1,2-oxazole-4-carboxylic acid | $^1$H-NMR(CDCl$_3$)δ: 2.06-2.15(4H, m), 2.96-3.06(2H, m), 3.63-3.75(1H, m), 4.00(2H, dt, J = 12.7, 3.0 Hz), 7.26(2H, s), 7.64-7.78(3H, m), 8.03-8.07(1H, m). |
| X-39 | K-22 | 5-{1-[(2-Nitrophenyl)sulfonyl]piperidin-4-yl}-3-(2,4,6-trimethylphenyl)-1,2-oxazole-4-carboxylic acid | $^1$H-NMR(CDCl$_3$)δ: 2.04(6H, s), 2.05-2.13(4H, m), 2.32(3H, s), 2.97-3.05(2H, m), 3.64-3.73(1H, m), 4.00(2H, d, J = 13.3 Hz), 6.92(2H, s), 7.64-7.77(3H, m), 8.02-8.06(1H, m). |

TABLE 16

| | | | |
|---|---|---|---|
| X-40 | K-22 | 3-(2,4-Dichlorophenyl)-5-{1-[(2-nitrophenyl)sulfonyl]piperidin-4-yl}-1,2-oxazole-4-carboxylic acid | $^1$H-NMR(CDCl$_3$)δ: 2.04-2.13(4H, m), 2.93-3.07(2H, m), 3.61-3.70(1H, m), 3.97-4.04(2H, m), 7.35(2H, s), 7.49(1H, s), 7.65(1H, dd, J = 7.0, 2.1 Hz), 7.69-7.77(2H, m), 8.04(1H, dd, J = 6.7, 2.4 Hz). |

TABLE 16-continued

| | | | |
|---|---|---|---|
| X-41 | K-22 | 3-(2,4-Dichloro-6-fluorophenyl)-5-{1-[(2-nitrophenyl)sulfonyl]piperidin-4-yl}-1,2-oxazole-4-carboxylic acid | $^1$H-NMR(CDCl$_3$)δ: 2.06-2.15(4H, m), 2.96-3.07(2H, m), 3.61-3.75(1H, m), 3.97-4.05(2H, m), 7.15(1H, dd, J = 8.5, 1.8 Hz), 7.34(1H, d, J = 1.8 Hz), 7.66(1H, dd, J = 7.0, 2.1 Hz), 7.69-7.78(2H, m), 8.04(1H, dd, J = 7.3, 2.4 Hz). |
| X-42 | K-22 | 3-(2,6-Dichloro-4-fluorophenyl)-5-{1-[(2-nitrophenyl)sulfonyl]piperidin-4-yl}-1,2-oxazole-4-carboxylic acid | $^1$H-NMR(CDCl$_3$)δ: 2.04-2.18(4H, m), 2.96-3.06(2H, m), 3.63-3.74(1H, m), 3.97-4.05(2H, m), 7.19(2H, d, J = 7.9 Hz), 7.64-7.68(1H, m), 7.69-7.78(2H, m), 8.02-8.07(1H, m). |

TABLE 17

| | | | |
|---|---|---|---|
| X-43 | K-22 | 3-(4-Chloro-2,6-dimethylphenyl)-5-{1-[(2-nitrophenyl)sulfonyl]piperidin-4-yl}-1,2-oxazole-4-carboxylic acid | $^1$H-NMR(CDCl$_3$)δ: 2.05(6H, s), 2.05-2.13(4H, m), 2.96-3.05(2H, m), 3.63-3.72(1H, m), 4.01(2H, d, J = 12.1 Hz), 7.10(2H, s), 7.64-7.77(3H, m), 8.02-8.06(1H, m). |

TABLE 17-continued

| | | | |
|---|---|---|---|
| X-44 | K-22 | 3-(2,4-Dichloro-5-fluorophenyl)-5-{1-[(2-nitrophenyl)sulfonyl]piperidin-4-yl}-1,2-oxazole-4-carboxylic acid | 1H-NMR(CDCl$_3$)δ: 2.02-2.15(4H, m), 2.94-3.05(2H, m), 3.61-3.71(1H, m), 3.97-4.06(2H, m), 7.23(1H, d, J = 8.5 Hz), 7.54(1H, d, J = 6.7 Hz), 7.64-7.67(1H, m), 7.69-7.77(2H, m), 8.03-8.06(1H, m). |
| X-45 | K-23 | 5-{1-[(2-Nitrophenyl)sulfonyl]piperidin-3-yl}-3-(2,4,6-trichlorophenyl)-1,2-oxazole-4-carboxylic acid | $^1$H-NMR(CDCl$_3$)δ: 1.75-2.00(3H, m), 2.22(1H, d, J = 12.7 Hz), 2.91(1H, dt, J = 2.4, 12.1 Hz), 3.19(1H, t, J = 11.8 Hz), 3.85-3.99(2H, m), 4.12-4.19(1H, m), 7.43-7.46(2H, m), 7.65(1H, dd, J = 7.0, 2.1 Hz), 7.69-7.75(2H, m), 8.03(1H, dd, J = 7.3, 1.8 Hz). |

TABLE 18

| | | | |
|---|---|---|---|
| X-46 | K-24 | 5-{1-[(2-Nitrophenyl)sulfonyl]azetidin-3-yl}-3-(2,4,6-trichlorophenyl)-1,2-oxazole-4-carboxylic acid | $^1$H-NMR(CDCl$_3$)δ: 4.47-4.66(5H, m), 7.45(2H, s), 7.73-7.79(3H, m), 8.07-8.12(1H, m). |

TABLE 18-continued

| | | | |
|---|---|---|---|
| X-47 | K-27 | 5-{4-(Methoxymethoxy)-1-[(2-nitrophenyl)sulfonyl]piperidin-4-yl}-3-(2,4,6-trichlorophenyl)-1,2-oxazole-4-carboxylic acid | $^1$H-NMR(CDCl$_3$)δ: 2.37-2.47(2H, m), 2.58(2H, d, J = 13.3 Hz), 3.34-3.42(2H, m), 3.34(3H, s), 3.70-3.77(2H, m), 4.74(2H, s), 7.44 (2H, s), 7.65-7.67(1H, m), 7.68-7.77(2H, m), 8.05(1H, dd, J = 7.0, 2.7 Hz). |
| X-48 | K-15 | 3-(2,4-Dichloro-3-fluorophenyl)-5-(2-fluoropropan-2-yl)-1,2-oxazole-4-carboxylic acid | $^1$H-NMR(CDCl$_3$)δ: 1.93(6H, d, J = 21.8 Hz), 7.21(1H, dd, J = 8.5, 1.8 Hz), 7.43(1H, dd, J = 8.5, 6.7 Hz). |

TABLE 19

| | | | |
|---|---|---|---|
| X-49 | K-15 | 3-(4-Bromo-2,6-dichlorophenyl)-5-(2-fluoropropan-2-yl)-1,2-oxazole-4-carboxylic acid | $^1$H-NMR(CDCl$_3$)δ: 1.95(6H, d, J = 21.8 Hz), 7.59(2H, s). MS(m/z): 396(M + H)$^+$. |
| X-50 | K-22 | 3-(2,4-Dichloro-3-fluorophenyl)-5-{1-[(2-nitrophenyl)sulfonyl]piperidin-4-yl}-1,2-oxazole-4-carboxylic acid | $^1$H-NMR(CDCl$_3$)δ: 2.03-2.17(4H, m), 2.95-3.05(2H, m), 3.66(1H, dt, J = 17.5, 6.0 Hz), 3.97-4.06(2H, m), 7.17(1H, dd, J = 8.5, 1.8 Hz), 7.42(1H, dd, J = 8.2, 7.0 Hz), 7.66(1H, dd, J = 7.0, 2.1 Hz), 7.70-7.77(2H, m), 8.04(1H, dd, J = 7.0, 2.7 Hz). |

| | | | |
|---|---|---|---|
| X-51 | K-14 | 5-(3,3-Difluoro-1-methylcyclobutyl)-3-(2,4,6-trichlorophenyl)-1,2-oxazole-4-carboxylic acid | $^1$H-NMR(DMSO-$d_6$)δ: 1.66(3H, s), 2.86-2.95(2H, m), 3.21-3.32(2H, m), 7.89(2H, s), 13.37 (1H, brs). |

Reference Example X-52

5-(1,1-Difluoroethyl)-3-(2,4,6-trichlorophenyl)-1,2-oxazole-4-carboxylic acid

[Formula 39]

[Step 1] tert-Butyl 5-(1,1-difluoroethyl)-3-(2,4,6-trichlorophenyl)-1,2-oxazole-4-carboxylate To a solution of (1E)-2,4,6-trichlorobenzaldehyde oxime (1.90 g) in N,N-dimethylformamide (30 ml), N-chlorosuccinimide (1.19 g) was added, and the mixture was stirred at room temperature for 45 minutes. The compound (3.52 g) obtained in step 1 of Reference Example K-16 and triethylamine (1.88 g) were added to the reaction solution, and the mixture was stirred overnight at room temperature. The reaction solution was diluted with ethyl acetate, washed with water and saturated saline in this order and then dried over anhydrous magnesium sulfate. The solvent was distilled off under reduced pressure, and the residue obtained was purified by silica gel column chromatography (n-hexane/ethyl acetate) to obtain the title compound (3.00 g).

$^1$H-NMR (CDCl$_3$) δ: 1.33 (9H, s), 2.20 (3H, t, J=18.7 Hz), 7.47 (2H, s).

[Step 2] 5-(1,1-Difluoroethyl)-3-(2,4,6-trichlorophenyl)-1,2-oxazole-4-carboxylic acid A mixture of the compound (3.00 g) obtained in the preceding step 1, trifluoroacetic acid (5 ml), and dichloromethane (15 ml) was stirred at room temperature for 3 hours. The reaction solution was diluted with chloroform, washed with water and saturated saline in this order and then dried over anhydrous magnesium sulfate. The solvent was distilled off under reduced pressure, and the residue obtained was washed with n-hexane to obtain the title compound (2.07 g).

$^1$H-NMR (CDCl$_3$) δ: 2.21 (3H, t, J=18.4 Hz), 7.46 (2H, s).

The following compound was obtained by the same method as in Reference Example X-52 using the ester described in the Reference Example.

TABLE 20

| Reference Example No. | Reference Example No. (ester) | Name and structure | Instrumental data |
|---|---|---|---|
| X-53 | K-17 | 3-(2,4,6-Trichlorophenyl)-5-(trifluoromethyl)-1,2-oxazole-4-carboxylic acid 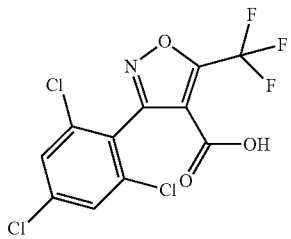 [SMILES: O=C(O)c1c(-c2c(Cl)cc(Cl)cc2Cl)noc1C(F)(F)F] | $^1$H-NMR(CDCl$_3$)δ: 7.48(2H, s). |

Reference Example X-54

5-(6-Chloropyridin-3-yl)-3-(2,4,6-trichlorophenyl)-1,2-oxazole-4-carboxylic acid

[Formula 40]

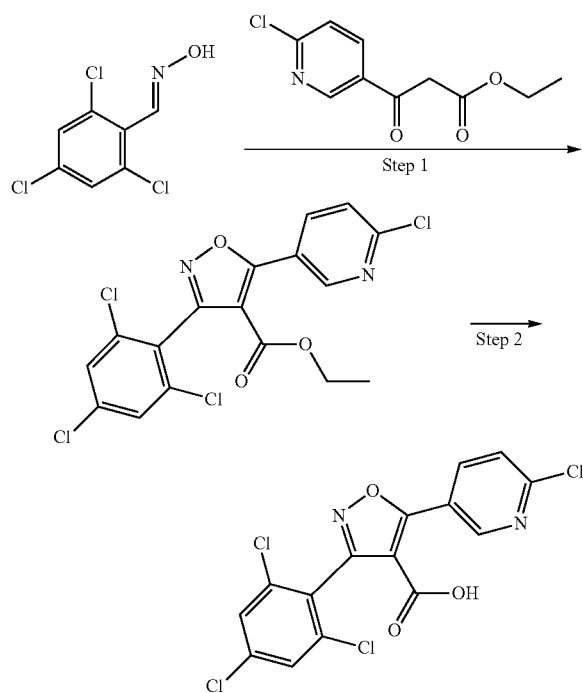

[Step 1] Ethyl 5-(6-chloropyridin-3-yl)-3-(2,4,6-trichlorophenyl)-1,2-oxazole-4-carboxylate To a solution of (1E)-2,4,6-trichlorobenzaldehyde oxime (1.00 g) in N,N-dimethylformamide (18 ml), N-chlorosuccinimide (625 mg) was added, and the mixture was stirred overnight at room temperature. The reaction solution was poured into water, followed by extraction with diethyl ether. The extract was washed with water and saturated saline in this order and then dried over anhydrous sodium sulfate. The solvent was distilled off under reduced pressure, and the residue obtained was dissolved in N,N-dimethylformamide (18 ml). To this solution, the compound (1.52 g) obtained in Reference Example K-13 and triethylamine (1.55 ml) were added in this order, and the mixture was stirred at room temperature for 6 hours. The reaction solution was poured into a mixed solution of ethyl acetate, n-hexane, and water and separated into two layers. The organic layer was washed with water and saturated saline in this order and then dried over anhydrous sodium sulfate. The solvent was distilled off under reduced pressure, and the residue obtained was purified by silica gel column chromatography (n-hexane/ethyl acetate) to obtain the title compound (1.08 g).

$^1$H-NMR (CDCl$_3$) δ: 1.03 (3H, t, J=7.0 Hz), 4.15 (2H, q, J=7.0 Hz), 7.48 (2H, s), 7.53 (1H, d, J=8.5 Hz), 8.48 (1H, dd, J=8.5, 2.4 Hz), 9.13 (1H, d, J=2.4 Hz).

MS (m/z): 431 (M+H)$^+$.

[Step 2] 5-(6-Chloropyridin-3-yl)-3-(2,4,6-trichlorophenyl)-1,2-oxazole-4-carboxylic acid To a mixed solution of the compound (570 mg) obtained in the preceding step 1 in tetrahydrofuran (5 ml) and methanol (5 ml), a 1 N aqueous sodium hydroxide solution (5 ml) was added, and the mixture was heated to reflux for 1 hour. After cooling, the reaction solution was concentrated under reduced pressure, and 1 N hydrochloric acid (7 ml) was added to the residue obtained under ice cooling. The deposited solid was collected by filtration, washed with water and n-hexane in this order and then dried by heating under reduced pressure to obtain a crude form of the title compound (497 mg), which was directly used in the next reaction.

$^1$H-NMR (CDCl$_3$) δ: 7.48 (2H, s), 7.54 (1H, d, J=8.5 Hz), 8.40 (1H, dd, J=7.9, 2.4 Hz), 9.14 (1H, s).

MS (m/z): 403 (M+H)$^+$.

Reference Example X-55

5-{3-Methyl-1-[(2-nitrophenyl)sulfonyl]azetidin-3-yl}-3-(2,4,6-trichlorophenyl)-1,2-oxazole-4-carboxylic acid

[Formula 41]

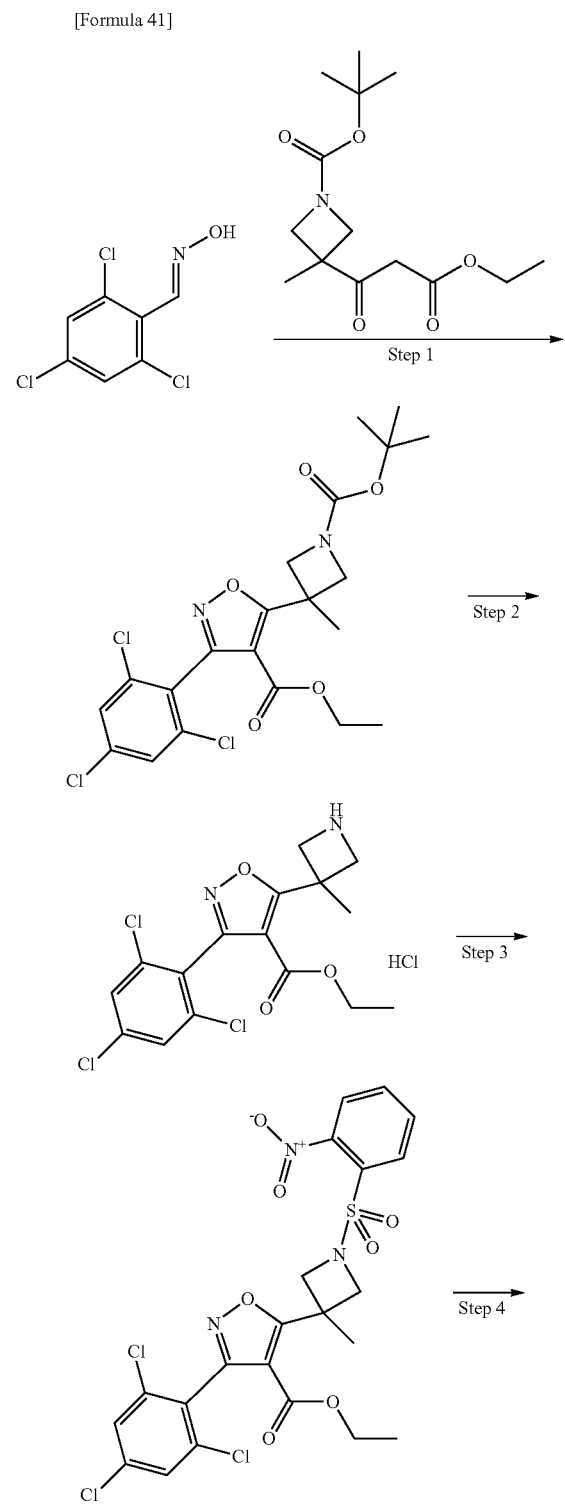

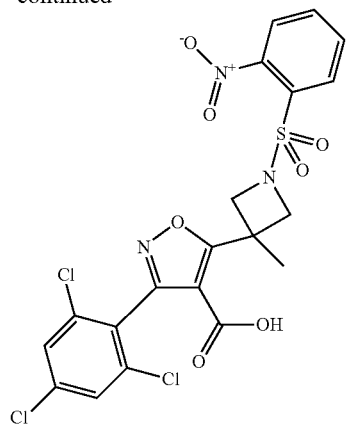

[Step 1] Ethyl 5-[1-(tert-butoxycarbonyl)-3-methyl-azetidin-3-yl]-3-(2,4,6-trichlorophenyl)-1,2-oxazole-4-carboxylate To a solution of (1E)-2,4,6-trichlorobenzaldehyde oxime (536 mg) in N,N-dimethylformamide (6 ml), N-chlorosuccinimide (319 mg) was added, and the mixture was stirred overnight at room temperature. Sodium methoxide (28% solution in methanol, 0.48 ml) was added to the reaction solution under ice cooling, and then, an enolate solution prepared by mixing a solution of the compound (681 mg) obtained in Reference Example K-10 in tetrahydrofuran (7 ml) with a solution of sodium methoxide (28% solution in methanol, 0.48 ml) in methanol (5 ml) was added dropwise thereto. The mixture was stirred overnight at room temperature and then concentrated under reduced pressure. The residue obtained was diluted with ethyl acetate, washed with water and saturated saline in this order and then dried over anhydrous sodium sulfate. The solvent was distilled off under reduced pressure, and the residue obtained was purified by silica gel column chromatography (n-hexane/ethyl acetate) to obtain the title compound (0.80 g).

$^1$H-NMR (CDCl$_3$) δ: 1.46 (9H, s), 1.80 (3H, s), 4.03 (2H, d, J=9.1 Hz), 4.14 (2H, q, J=7.1 Hz), 4.46 (2H, d, J=9.1 Hz), 7.45 (2H, s).

[Step 2] Ethyl 5-(3-methylazetidin-3-yl)-3-(2,4,6-trichlorophenyl)-1,2-oxazole-4-carboxylate hydrochloride To the compound (0.80 g) obtained in the preceding step 1, 4 N hydrochloric acid-1,4-dioxane (8 ml) was added, and the mixture was stirred at room temperature for 1.5 hours. The reaction solution was concentrated under reduced pressure to obtain the title compound, which was directly used in the next reaction.

[Step 3] Ethyl 5-{3-methyl-1-[(2-nitrophenyl)sulfonyl]azetidin-3-yl}-3-(2,4,6-trichlorophenyl)-1,2-oxazole-4-carboxylate To a suspension of the compound obtained in the preceding step 2 in dichloromethane (8 ml), triethylamine (0.91 ml)

and 2-nitrobenzenesulfonyl chloride (470 mg) were added under ice cooling, and the mixture was stirred overnight at room temperature. The reaction solution was diluted with dichloromethane, washed with water and saturated saline in this order and then dried over anhydrous sodium sulfate. The solvent was distilled off under reduced pressure, and the residue obtained was purified by silica gel column chromatography (n-hexane/ethyl acetate) to obtain the title compound (454 mg).

$^1$H-NMR (CDCl$_3$) δ: 1.08 (3H, t, J=7.0 Hz), 1.81 (3H, s), 4.08-4.21 (4H, m), 4.67 (2H, d, J=8.5 Hz), 7.44 (2H, s), 7.69-7.75 (3H, m), 8.08 (1H, dd, J=7.3, 2.4 Hz).

[Step 4] 5-{3-Methyl-1-[(2-nitrophenyl)sulfonyl]azetidin-3-yl}-3-(2,4,6-trichlorophenyl)-1,2-oxazole-4-carboxylic acid The title compound (312 mg) was obtained by the same method as in step 4 of Reference Example X-1 using the compound (334 mg) obtained in the preceding step 3.

$^1$H-NMR (CDCl$_3$) δ: 1.83 (3H, s), 4.16 (2H, d, J=8.5 Hz), 4.69 (2H, d, J=8.5 Hz), 7.44 (2H, s), 7.70-7.76 (3H, m), 8.06-8.11 (1H, m).

The following compounds were obtained by the same method as in Reference Example X-55 using the esters described in the Reference Examples.

TABLE 21

| Reference Example No. | Reference Example No. (ester) | Name and structure | Instrumental data |
|---|---|---|---|
| X-56 | K-11 | 5-{4-Methyl-1-[(2-nitrophenyl)sulfonyl]piperidin-4-yl}-3-(2,4,6-trichlorophenyl)-1,2-oxazole-4-carboxylic acid | $^1$H-NMR(CDCl$_3$)δ: 1.54(3H, s), 1.88-1.95(2H, m), 2.71(2H, d, J = 14.5 Hz), 3.05-3.12(2H, m), 3.66(2H, ddd, J = 9.1, 4.2, 2.1 Hz), 7.43(2H, s), 7.61-7.63(1H, m), 7.66-7.73(2H, m), 7.98-8.00(1H, m). MS(m/z): 574(M + H)$^+$. |
| X-57 | K-12 | 5-{3-[(2-Nitrophenyl)sulfonyl]-3-azabicyclo[3.1.0]hexan-6-yl}-3-(2,4,6-trichlorophenyl)-1,2-oxazole-4-carboxylic acid | $^1$H-NMR(CDCl$_3$)δ: 2.48-2.52(2H, m), 2.94(1H, t, J = 3.3 Hz), 3.65(2H, d, J = 10.9 Hz), 3.92(2H, d, J = 10.3 Hz), 7.43 (2H, s), 7.62-7.66(1H, m), 7.69-7.75(2H, m), 8.03-8.07(1H, m). |

TABLE 21-continued

| Reference Example No. | Reference Example No. (ester) | Name and structure | Instrumental data |
|---|---|---|---|
| X-58 | K-25 | 5-{4-(Methoxymethyl)-1-[(2-nitrophenyl)sulfonyl]piperidin-4-yl}-3-(2,4,6-trichlorophenyl)-1,2-oxazole-4-carboxylic acid | $^1$H-NMR(CDCl$_3$)δ: 1.89-1.97(2H, m), 2.76(2H, d, J = 14.5 Hz), 2.86-2.93(2H, m), 3.34(3H, s), 3.73 (2H, s), 3.81(2H, ddd, J = 13.7, 3.3, 1.7 Hz), 7.42(2H, s), 7.61(1H, dd, J = 7.3, 1.8 Hz), 7.65-7.73(2H, m), 7.96(1H, dd, J = 7.3, 1.8 Hz). MS(m/z): 604(M + H)$^+$. |

TABLE 22

| | | | |
|---|---|---|---|
| X-59 | K-26 | 5-{4-Methoxy-1-{(2-nitrophenyl)sulfonyl]piperidin-4-yl}-3-(2,4,6-trichlorophenyl)-1,2-oxazole-4-carboxylic acid | $^1$H-NMR(CDCl$_3$)δ: 2.34-2.52(4H, m), 3.26-3.37(5H, m), 3.77-3.85(2H, m), 7.44(2H, s), 7.68 (1H, dd, J = 7.0, 2.1 Hz), 7.70-7.79(2H, m), 8.05(1H, dd, J = 7.0, 2.1 Hz). |

Reference Example X-60

5-[1-(Dimethylamino)cyclobutyl]-3-(2,4,6-trichlorophenyl)-1,2-oxazole-4-carboxylic acid

[Formula 42]

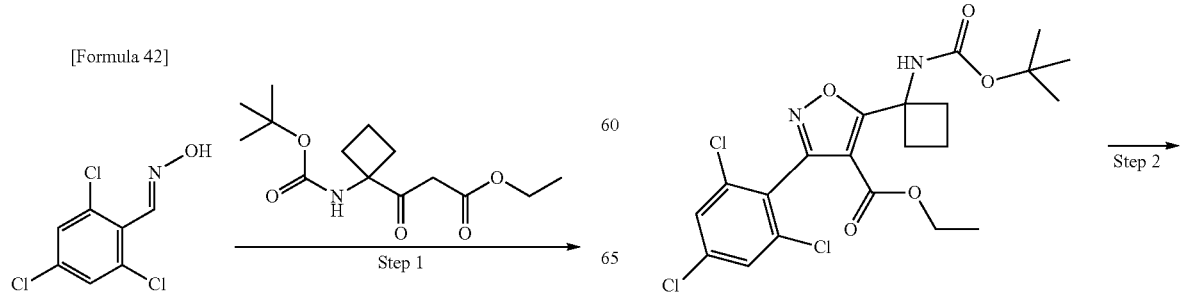

Step 1 → Step 2 →

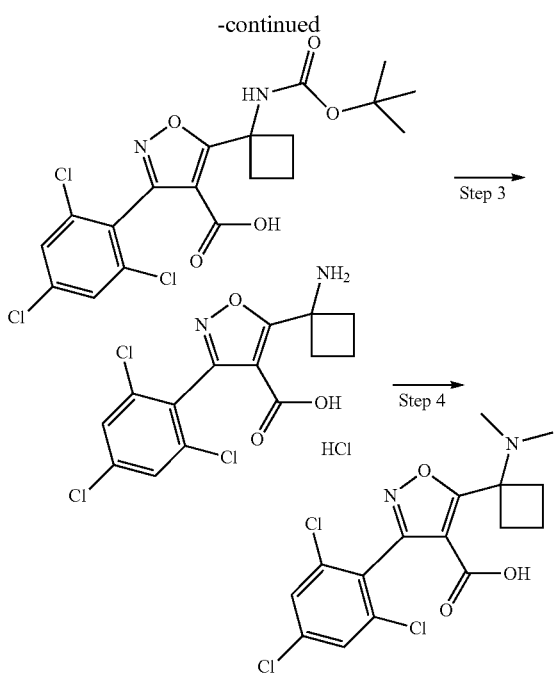

[Step 1] Ethyl 5-[1-(tert-butoxycarbonylamino)cyclobutyl]-3-(2,4,6-trichlorophenyl)-1,2-oxazole-4-carboxylate The title compound (21 mg) was obtained by the same method as in step 1 of Reference Example X-55 using (1E)-2,4,6-trichlorobenzaldehyde oxime (79 mg) and the compound (100 mg) obtained in Reference Example K-8.

$^1$H-NMR (CDCl$_3$) δ: 1.01 (3H, t, J=7.3 Hz), 1.34 (9H, s), 1.93-2.04 (1H, m), 2.13-2.24 (1H, m), 2.48-2.55 (2H, m), 2.84-2.91 (2H, m), 4.10 (2H, q, J=7.3 Hz), 5.79 (1H, brs), 7.44 (1H, s).

MS (m/z): 489 (M+H)$^+$.

[Step 2] 5-[1-(tert-Butoxycarbonylamino)cyclobutyl]-3-(2,4,6-trichlorophenyl)-1,2-oxazole-4-carboxylic acid The title compound (2.45 g) was obtained by the same method as in step 4 of Reference Example X-1 using the compound (2.50 g) obtained in the preceding step 1.

$^1$H-NMR (DMSO-d$_6$) δ: 1.28 (9H, brs), 1.80-1.88 (1H, m), 2.00-2.11 (1H, m), 2.41-2.48 (2H, m), 2.70-2.77 (2H, m), 7.87 (2H, s), 13.01 (1H, brs).

[Step 3] 5-(1-Aminocyclobutyl)-3-(2,4,6-trichlorophenyl)-1,2-oxazole-4-carboxylic acid hydrochloride To a suspension of the compound (2.45 g) obtained in the preceding step 2 in methanol (20 ml), a solution of 4 N hydrochloric acid in 1,4-dioxane (15 ml) was added, and the mixture was stirred at room temperature for 1 hour. A solution of 4 N hydrochloric acid in 1,4-dioxane (5 ml) was further added to the reaction solution, and the mixture was stirred at room temperature for another 1 hour. The reaction solution was concentrated under reduced pressure, and small amounts of diethyl ether and n-hexane were added to the residue obtained. The resulting solid was collected by filtration to obtain the title compound (1.55 g).

$^1$H-NMR (DMSO-d$_6$) δ: 1.88-1.99 (1H, m), 2.21-2.32 (1H, m), 2.67-2.75 (2H, m), 2.81-2.90 (2H, m), 7.93 (2H, s), 9.20 (3H, brs).

[Step 4] 5-[1-(Dimethylamino)cyclobutyl]-3-(2,4,6-trichlorophenyl)-1,2-oxazole-4-carboxylic acid To a suspension of the compound (1.55 g) obtained in the preceding step 3 in 1,2-dichloroethane (20 ml), formaldehyde (37% aqueous solution, 1.45 ml), N,N-di(propan-2-yl)ethylamine (0.666 ml), and sodium triacetoxyborohydride (4.13 g) were added, and the mixture was stirred at room temperature for 2 hours. Water and dichloromethane were added to the reaction solution, which was then separated into two layers. The aqueous layer was subjected to extraction with dichloromethane. The organic layers were combined and dried over anhydrous sodium sulfate. The solvent was distilled off under reduced pressure, and n-hexane was added to the residue obtained. The resulting solid was collected by filtration to obtain the title compound (1.25 g).

$^1$H-NMR (DMSO-d$_6$) δ: 1.91-1.99 (2H, m), 2.42-2.52 (2H, m), 2.43 (6H, s), 2.71-2.80 (2H, m), 7.87 (2H, s).

MS (m/z): 389 (M+H)$^+$.

The following compound was obtained by the same method as in Reference Example X-60 using the ester described in the Reference Example.

TABLE 23

| Reference Example No. | Reference Example No. (ester) | Name and structure | Instrumental data |
| --- | --- | --- | --- |
| X-61 | K-28 | 5-{4-(Dimethylamino)-1-[(2-nitrophenyl)sulfonyl]piperidin-4-yl}-3-(2,4,6-trichlorophenyl)-1,2-oxazole-4-carboxylic acid | $^1$H-NMR(DMSO-d$_6$)δ: 2.27-2.38(2H, m), 2.40-2.53(8H, m), 2.84(2H, t, J = 1.8 Hz), 3.82(2H, d, J = 13.3 Hz), 7.84-7.89(3H, m), 7.93(1H, td, J = 7.6, 1.2 Hz), 8.02(1H, dd, J = 7.9, 1.2 Hz), 8.05(1H, dd, J = 7.9, 1.2 Hz). |

Reference Example X-62

5-(1-{Methyl-[(2-nitrophenyl)sulfonyl]amino}cyclobutyl)-3-(2,4,6-trichlorophenyl)-1,2-oxazole-4-carboxylic acid

[Formula 43]

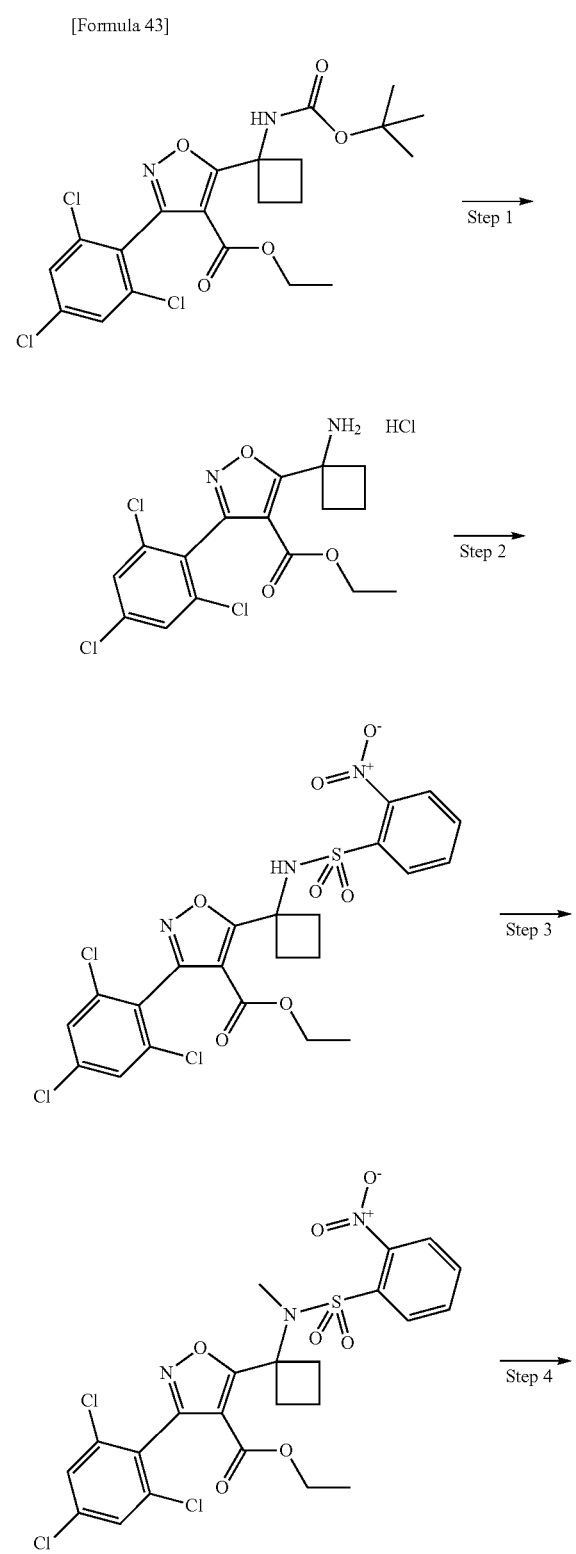

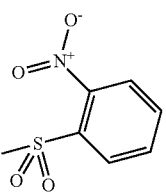

[Step 1] Ethyl 5-(1-aminocyclobutyl)-3-(2,4,6-trichlorophenyl)-1,2-oxazole-4-carboxylate hydrochloride To a solution of the compound (1.00 g) obtained in step 1 of Reference Example X-60 in dichloromethane (5 ml), 4 N hydrochloric acid-1,4-dioxane (10 ml) was added, and the mixture was stirred at room temperature for 1 hour. The reaction solution was concentrated under reduced pressure to obtain the title compound, which was directly used in the next reaction.

[Step 2] Ethyl 5-(1-{[(2-nitrophenyl)sulfonyl]amino}cyclobutyl)-3-(2,4,6-trichlorophenyl)-1,2-oxazole-4-carboxylate To a suspension of the compound obtained in the preceding step 1 in dichloromethane (20 ml), triethylamine (0.848 ml) and 2-nitrobenzenesulfonyl chloride (0.452 g) were added, and the mixture was stirred at room temperature for 1 hour. Triethylamine (0.283 ml) and 2-nitrobenzenesulfonyl chloride (0.206 g) were further added to the reaction solution, and the mixture was stirred at room temperature for another 30 minutes. Water and dichloromethane were added to the reaction solution, which was then separated into two layers. The organic layer was dried over anhydrous sodium sulfate. The solvent was distilled off under reduced pressure, and the residue obtained was purified by silica gel column chromatography (n-hexane/ethyl acetate) to obtain the title compound (0.66 g), which was directly used in the next reaction.

[Step 3] Ethyl 5-[(1-{methyl-[(2-nitrophenyl)sulfonyl]amino}cyclobutyl)-3-(2,4,6-trichlorophenyl)-1,2-oxazole-4-carboxylate To a solution of the compound (53 mg) obtained in the preceding step 2 in N,N-dimethylformamide (3 ml), methyl iodide (0.017 ml) and sodium hydride (55% oil, 6 mg) were added, and the mixture was stirred at room temperature for 15 minutes. Water and ethyl acetate were added to the reaction solution, which was then separated into two layers.

The organic layer was washed with saturated saline and then dried over anhydrous sodium sulfate. The solvent was distilled off under reduced pressure, and the residue obtained was purified by silica gel column chromatography (n-hexane/ethyl acetate) to obtain the title compound (31 mg).

$^1$H-NMR (CDCl$_3$) δ: 0.95 (3H, t, J=7.3 Hz), 1.71-1.83 (1H, m), 1.88-1.97 (1H, m), 2.83-2.93 (2H, m), 2.98-3.04 (2H, m), 3.11 (3H, s), 4.05 (2H, q, J=7.3 Hz), 7.44 (2H, s), 7.57-7.71 (3H, m), 7.92-7.95 (1H, m).

[Step 4] 5-(1-{Methyl-[(2-nitrophenyl)sulfonyl]amino}cyclobutyl)-3-(2,4,6-trichlorophenyl)-1,2-oxazole-4-carboxylic acid The title compound was obtained by the same method as in step 4 of Reference Example X-1 using the compound obtained in the preceding step 3. The compound obtained was directly used in the next reaction.

The following compounds were obtained by the same method as in Reference Examples X-60 and X-62 using the esters described in the Reference Examples.

TABLE 24

| Reference Example No. | Reference Example No. (ester) | Name and structure | Instrumental data |
| --- | --- | --- | --- |
| X-63 | K-9 | 5-(2-{Methyl-[(2-nitrophenyl)sulfonyl]amino}propan-2-yl)-3-(2,4,6-trichlorophenyl)-1,2-oxazole-4-carboxylic acid | $^1$H-NMR(CDCl$_3$)δ: 1.97(6H, s), 3.03(3H, s), 7.44(2H, s), 7.57-7.70(3H, m), 7.91-7.94(1H, m). |
| X-64 | K-7 | 5-(1-{Methyl-[(2-nitrophenyl)sulfonyl]amino}cyclopropyl)-3-(2,4,6-trichlorophenyl)-1,2-oxazole-4-carboxylic acid | $^1$H-NMR(CDCl$_3$)δ: 1.71-1.81(4H, m), 3.26(3H, s), 7.41(2H, s), 7.60(1H, dd, J = 7.3, 1.8 Hz), 7.65-7.74(2H, m), 8.13(1H, dd, J = 7.9, 1.8 Hz). |

Reference Example X-65

5-{1-[(tert-Butoxycarbonyl)(prop-2-en-1-yl)amino]cyclobutyl}-3-(2,4,6-trichlorophenyl)-1,2-oxazole-4-carboxylic acid

[Formula 44]

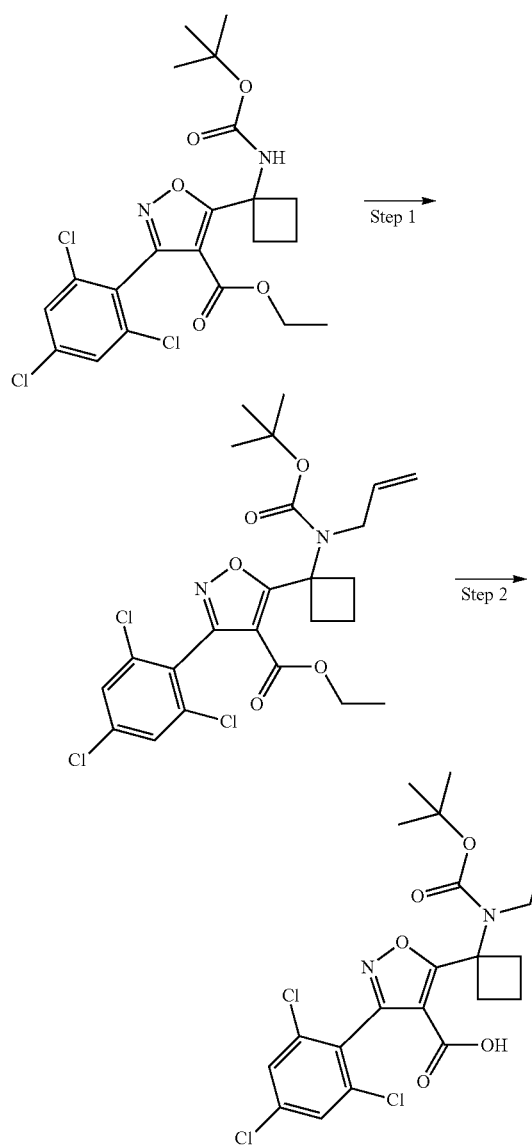

[Step 1] Ethyl 5-{1-[(tert-butoxycarbonyl)(prop-2-en-1-yl)amino]cyclobutyl}-3-(2,4,6-trichlorophenyl)-1,2-oxazole-4-carboxylate To a suspension of sodium hydride (55% oil, 0.260 g) in N,N-dimethylformamide (5 ml), the compound (1.46 g) obtained in step 1 of Reference Example X-60 was added, and the mixture was stirred at room temperature for 5 minutes. Allyl bromide (1.80 g) was added to the reaction solution under ice cooling, and the mixture was stirred at room temperature for 1 hour. Water and ethyl acetate were added under ice cooling to the reaction solution, which was then separated into two layers. The aqueous layer was subjected to extraction with ethyl acetate. The organic layers were combined, washed with saturated saline and then dried over anhydrous sodium sulfate. The solvent was distilled off under reduced pressure, and the residue obtained was purified by silica gel column chromatography (n-hexane/ethyl acetate) to obtain the title compound (0.871 g).

$^1$H-NMR (CDCl$_3$) δ: 0.96 (3H, t, J=7.3 Hz), 1.35 (9H, s), 1.86-1.96 (2H, m), 2.66-2.74 (2H, m), 2.90-2.96 (2H, m), 4.05 (2H, q, J=7.3 Hz), 4.16-4.23 (2H, m), 5.19-5.30 (2H, m), 5.94-6.05 (1H, m), 7.44 (2H, s).

MS (m/z): 529 (M+H)$^+$.

[Step 2] 5-{1-[(tert-Butoxycarbonyl)(prop-2-en-1-yl)amino]cyclobutyl}-3-(2,4,6-trichlorophenyl)-1,2-oxazole-4-carboxylic acid The title compound was obtained by the same method as in step 4 of Reference Example X-1 using the compound (0.871 g) obtained in the preceding step 1. The compound obtained was directly used in the next reaction.

$^1$H-NMR (CDCl$_3$) δ: 1.40 (9H, s), 1.80-1.88 (1H, m), 1.90-2.00 (1H, m), 2.66-2.76 (2H, m), 2.89-2.99 (2H, m), 4.04-4.08 (2H, m), 5.21-5.27 (2H, m), 5.89-5.98 (1H, m), 7.43 (2H, s).

Reference Example X-66

5-[1-(Dimethylamino)cyclopropyl]-3-(2,4,6-trichlorophenyl)-1,2-oxazole-4-carboxylic acid

[Formula 45]

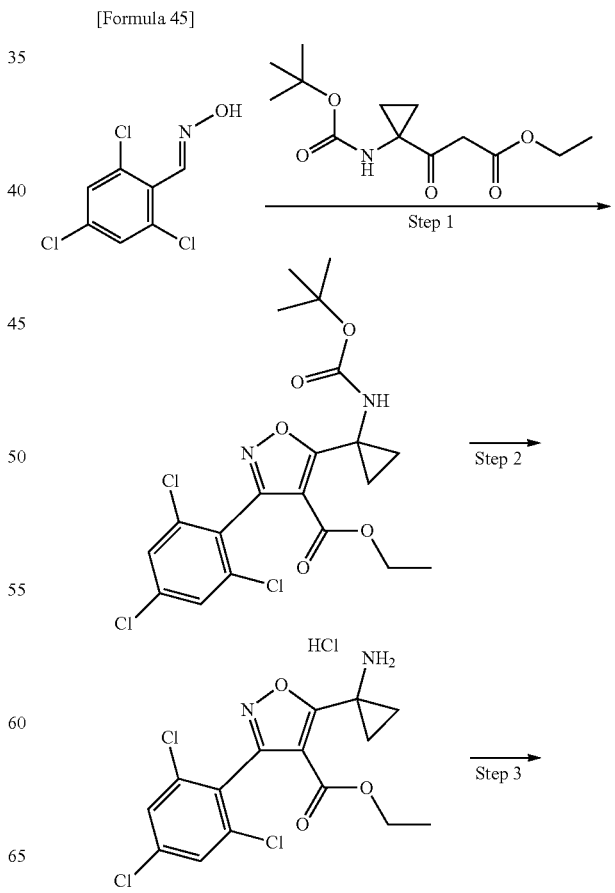

-continued

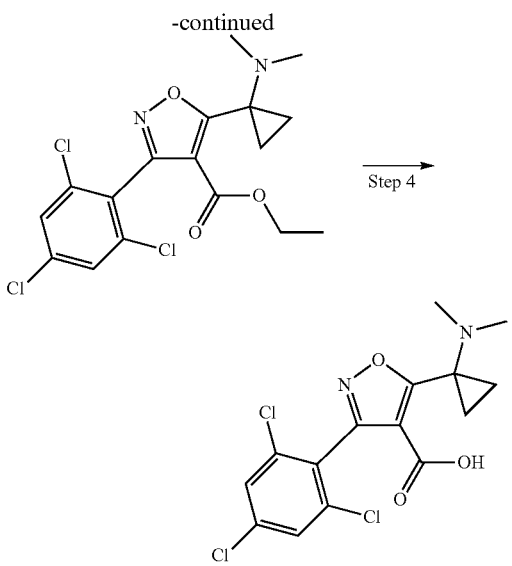

[Step 1] Ethyl 5-[1-(tert-butoxycarbonylamino)cyclopropyl]-3-(2,4,6-trichlorophenyl)-1,2-oxazole-4-carboxylate The title compound (3.32 g) was obtained by the same method as in step 1 of Reference Example X-55 using (1E)-2,4,6-trichlorobenzaldehyde oxime (2.42 g) and the compound (2.93 g) obtained in Reference Example K-7.

$^1$H-NMR (CDCl$_3$) δ: 1.03 (3H, t, J=7.3 Hz), 1.39 (9H, s), 1.40-1.44 (2H, m), 1.61-1.66 (2H, m), 4.14 (2H, q, J=7.3 Hz), 6.03 (1H, brs), 7.43 (2H, s).

MS (m/z): 475 (M+H)$^+$.

[Step 2] Ethyl 5-(1-aminocyclopropyl)-3-(2,4,6-trichlorophenyl)-1,2-oxazole-4-carboxylate hydrochloride The title compound (2.40 g) was obtained by the same method as in step 1 of Reference Example X-62 using the compound (3.32 g) obtained in the preceding step 1.

$^1$H-NMR (DMSO-d$_6$) δ: 1.02 (3H, t, J=7.3 Hz), 1.68-1.72 (4H, m), 4.13 (2H, q, J=7.3 Hz), 7.96 (2H, s), 9.14 (3H, brs).

[Step 3] Ethyl 5-[1-(dimethylamino)cyclopropyl]-3-(2,4,6-trichlorophenyl)-1,2-oxazole-4-carboxylate The title compound (584 mg) was obtained by the same method as in step 4 of Reference Example X-60 using the compound (1.00 g) obtained in the preceding step 2.

$^1$H-NMR (CDCl$_3$) δ: 1.10 (3H, t, J=7.3 Hz), 1.20-1.21 (4H, m), 2.38 (6H, s), 4.14 (2H, q, J=7.3 Hz), 7.44 (2H, s).

[Step 4] 5-[1-(Dimethylamino)cyclopropyl]-3-(2,4,6-trichlorophenyl)-1,2-oxazole-4-carboxylic acid The title compound was obtained by the same method as in step 4 of Reference Example X-1 using the compound (584 mg) obtained in the preceding step 3. The compound obtained was directly used in the next reaction.

Reference Example X-67

3-(2,6-Dichlorophenyl)-5-(3-methoxyoxetan-3-yl)-1,2-oxazole-4-carboxylic acid

[Formula 46]

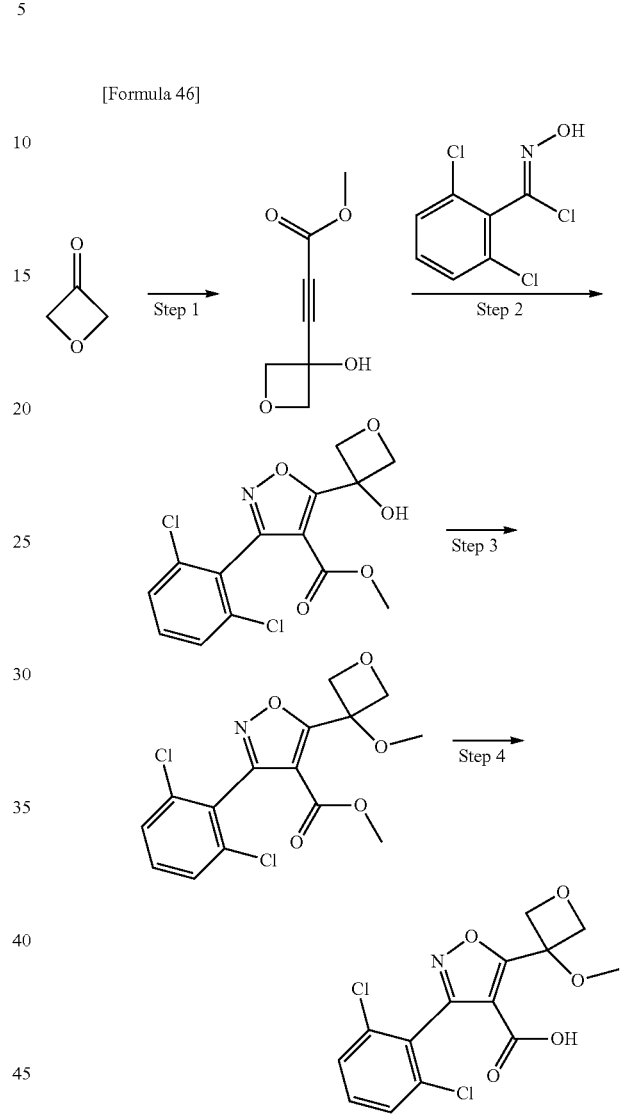

[Step 1] Methyl 3-(3-hydroxyoxetan-3-yl)prop-2-ynoate

To a solution of lithium bis(trimethylsilyl)amide (1.09 mol solution in tetrahydrofuran, 9.2 ml), a solution of methyl propiolate (0.83 ml) in tetrahydrofuran (10 ml) was added dropwise at −78° C., and the mixture was stirred at the same temperature as above for 30 minutes. Oxetan-3-one (360 mg) was added to the reaction solution, and the mixture was stirred for 1.5 hours and then poured into ethyl acetate and a saturated aqueous solution of ammonium chloride and vigorously stirred. After separation into two layers, the organic layer was washed with water and saturated saline in this order and then dried over anhydrous sodium sulfate. The solvent was distilled off under reduced pressure, and the residue obtained was purified by silica gel column chromatography (n-hexane/ethyl acetate) to obtain the title compound (152 mg).

¹H-NMR (CDCl₃) δ: 2.76 (1H, s), 3.82 (3H, s), 4.73 (2H, d, J=6.7 Hz), 4.88 (2H, d, J=6.7 Hz).

[Step 2] Methyl 3-(2,6-dichlorophenyl)-5-(3-hydroxyoxetan-3-yl)-1,2-oxazole-4-carboxylate To a solution of the compound (190 mg) obtained in step 1 of Reference Example X-1 in N,N-dimethylformamide (2 ml), N-chlorosuccinimide (134 mg) was added, and the mixture was stirred overnight at room temperature. A solution of triethylamine (0.34 ml) and the compound (152 mg) obtained in the preceding step 1 in N,N-dimethylformamide (2 ml) was added to the reaction solution under ice cooling, and the mixture was stirred at room temperature for 2 days. The reaction solution was diluted with ethyl acetate, washed with water and saturated saline in this order and then dried over anhydrous sodium sulfate. The solvent was distilled off under reduced pressure, and the residue obtained was purified by silica gel column chromatography (n-hexane/ethyl acetate) to obtain the title compound (281 mg).

¹H-NMR (CDCl₃) δ: 3.66 (3H, s), 4.97 (2H, d, J=7.7 Hz), 5.15 (2H, d, J=7.7 Hz), 5.87 (1H, s), 7.36-7.46 (3H, m).

[Step 3] Methyl 3-(2,6-dichlorophenyl)-5-(3-methoxyoxetan-3-yl)-1,2-oxazole-4-carboxylate To a solution of the compound (124 mg) obtained in the preceding step 2 in N,N-dimethylformamide (2 ml), methyl iodide (0.050 ml) and sodium hydride (55% oil, 22 mg) were added under ice cooling, and the mixture was stirred at room temperature for 20 minutes. The reaction solution was diluted with ethyl acetate under ice cooling, washed with water and saturated saline in this order and then dried over anhydrous sodium sulfate. The solvent was distilled off under reduced pressure, and the residue obtained was purified by silica gel column chromatography (n-hexane/ethyl acetate) to obtain the title compound (93.3 mg).

¹H-NMR (CDCl₃) δ: 3.23 (3H, s), 3.67 (3H, s), 4.98 (2H, d, J=6.8 Hz), 5.18 (2H, d, J=6.8 Hz), 7.34-7.50 (3H, m).

[Step 4] 3-(2,6-Dichlorophenyl)-5-(3-methoxyoxetan-3-yl)-1,2-oxazole-4-carboxylic acid The title compound (67 mg) was obtained by the same method as in step 4 of Reference Example X-1 using the compound (73 mg) obtained in the preceding step 3.

¹H-NMR (CDCl₃) δ: 3.26 (3H, s), 4.97 (2H, d, J=7.7 Hz), 5.18 (2H, d, J=7.7 Hz), 7.36-7.46 (3H, m).

The following compounds were obtained by the same method as in Reference Example X-67.

TABLE 25

| Reference Example No. | Name and structure | Instrumental data |
|---|---|---|
| X-68 | 5-(1-Methoxy-1-methylethyl)-3-(2,4,6-trichlorophenyl)-1,2-oxazole-4-carboxylic acid 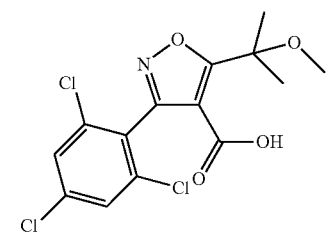 [SMILES: COC(C)(C)c1onc(-c2c(Cl)cc(Cl)cc2Cl)c1C(=O)O] | ¹H-NMR(CDCl₃)δ: 1.82(6H, s), 3.47(3H, s), 7.44(2H, s). |
| X-69 | 5-(3-Methoxyoxetan-3-yl)-3-(2,4,6-trichlorophenyl)-1,2-oxazole-4-carboxylic acid 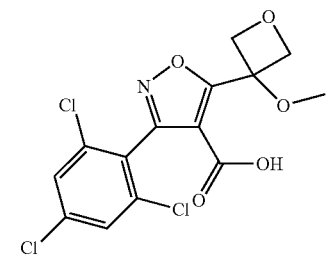 [SMILES: COC1(c2onc(-c3c(Cl)cc(Cl)cc3Cl)c2C(=O)O)COC1] | ¹H-NMR(CDCl₃)δ: 3.27(3H, s), 4.99(2H, d, J = 7.9 Hz), 5.18 (2H, d, J = 7.9 Hz), 7.47(2H, s). |

Reference Example X-70

5-(3-Fluorooxetan-3-yl)-3-(2,4,6-trichlorophenyl)-1,2-oxazole-4-carboxylic acid

[Formula 47]

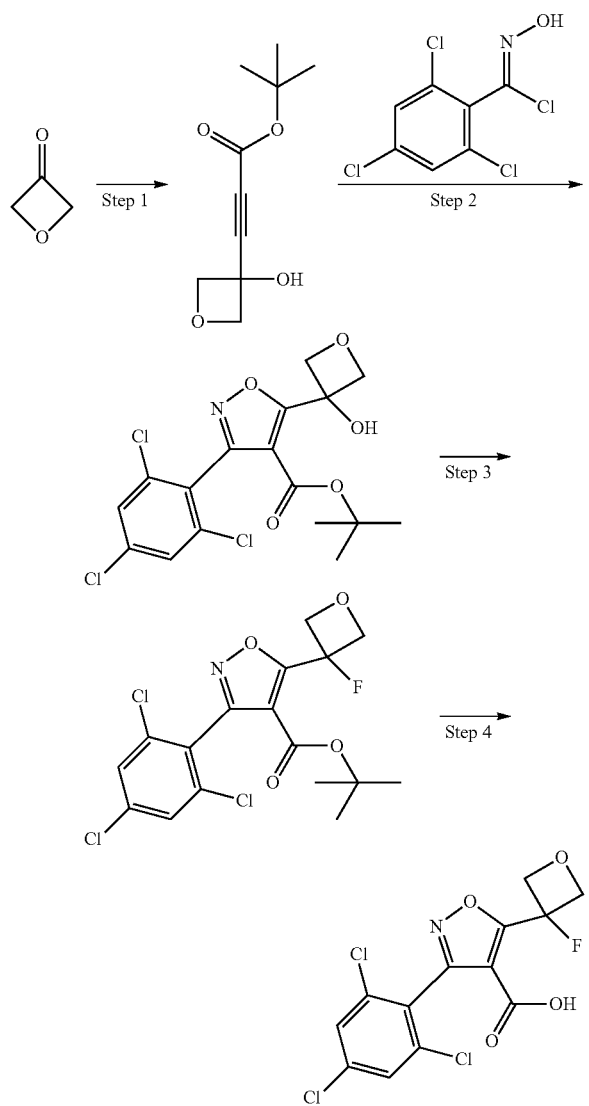

[Step 1] tert-Butyl 3-(3-hydroxyoxetan-3-yl)prop-2-ynoate

The title compound (8.25 g) was obtained by the same method as in step 1 of Reference Example X-67 using oxetan-3-one (3.0 g).
$^1$H-NMR (CDCl$_3$) δ: 1.51 (9H, s), 3.16 (1H, s), 4.72 (2H, d, J=6.7 Hz), 4.89 (2H, d, J=6.7 Hz).

[Step 2] tert-Butyl 5-(3-hydroxyoxetan-3-yl)-3-(2,4,6-trichlorophenyl)-1,2-oxazole-4-carboxylate The title compound (1.27 g) was obtained by the same method as in step 2 of Reference Example X-67 using the compound (861 mg) obtained in the preceding step 1.
$^1$H-NMR (CDCl$_3$) δ: 1.25 (9H, s), 4.96 (2H, d, J=7.3 Hz), 5.13 (2H, d, J=7.3 Hz), 6.33 (1H, s), 7.47 (2H, s).

[Step 3] tert-Butyl 5-(3-fluorooxetan-3-yl)-3-(2,4,6-trichlorophenyl)-1,2-oxazole-4-carboxylate To a solution of the compound (87 mg) obtained in the preceding step 2 in dichloromethane (1 ml), (diethylamino)sulfur trifluoride (0.030 ml) was added at −78° C., and the mixture was stirred at the same temperature as above for 30 minutes and then stirred at 0° C. for 1 hour. The reaction solution was diluted with dichloromethane, washed with water and saturated saline in this order and then dried over anhydrous sodium sulfate. The solvent was distilled off under reduced pressure, and the residue obtained was purified by silica gel column chromatography (n-hexane/ethyl acetate) to obtain the title compound (66 mg).
$^1$H-NMR (CDCl$_3$) δ: 1.31 (9H, s), 5.18 (2H, dd, J=20.9, 8.8 Hz), 5.26 (2H, dd, J=22.4, 8.5 Hz), 7.47 (2H, s).

[Step 4] 5-(3-Fluorooxetan-3-yl)-3-(2,4,6-trichlorophenyl)-1,2-oxazole-4-carboxylic acid The title compound (57 mg) was obtained by the same method as in step 2 of Reference Example X-52 using the compound (66 mg) obtained in the preceding step 3.
$^1$H-NMR (CDCl$_3$) δ: 5.18 (2H, dd, J=22.1, 9.4 Hz), 5.28 (2H, dd, J=22.4, 9.1 Hz), 7.47 (2H, s).

Reference Example X-71

3-(2,6-Dichlorophenyl)-5-[1-(methoxymethoxy)-1-methylethyl]-1,2-oxazole-4-carboxylic acid

[Formula 48]

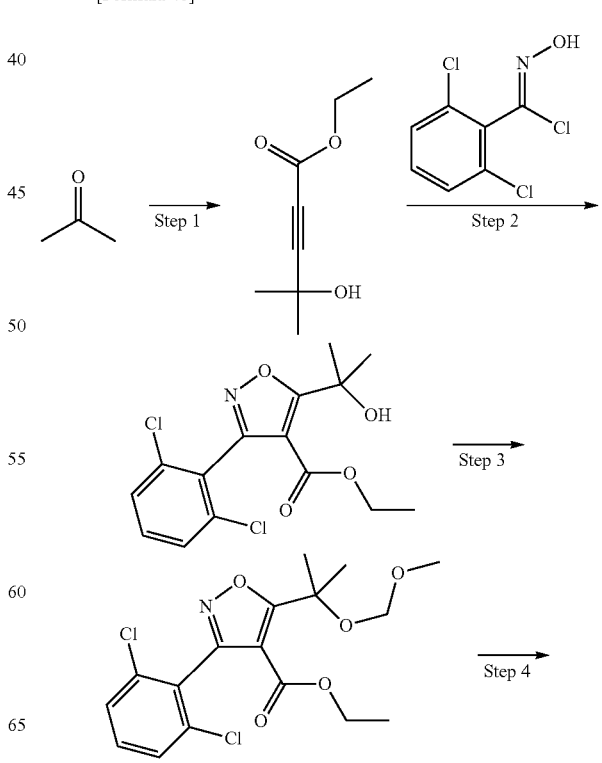

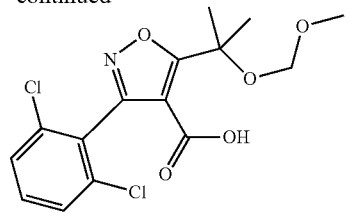

[Step 1] Ethyl 4-hydroxy-4-methylpent-2-ynoate

The title compound (1.64 g) was obtained by the same method as in step 1 of Reference Example X-67 using ethyl propiolate (1.02 ml).
$^1$H-NMR (CDCl$_3$) δ: 1.32 (3H, t, J=7.3 Hz), 1.57 (6H, s), 2.05 (1H, s), 4.24 (2H, q, J=7.1 Hz).

[Step 2] Ethyl 3-(2,6-dichlorophenyl)-5-(1-hydroxy-1-methylethyl)-1,2-oxazole-4-carboxylate The title compound (627 mg) was obtained by the same method as in step 2 of Reference Example X-67 using the compound (781 mg) obtained in the preceding step 1.
$^1$H-NMR (CDCl$_3$) δ: 0.89 (3H, t, J=7.3 Hz), 1.73 (6H, s), 4.10 (2H, q, J=7.1 Hz), 5.96 (1H, s), 7.33-7.43 (3H, m).

[Step 3] Ethyl 3-(2,6-dichlorophenyl)-5-[1-(methoxymethoxy)-1-methylethyl]-1,2-oxazole-4-carboxylate To a solution of the compound (304 mg) obtained in the preceding step 2 in N,N-dimethylformamide (3 ml), chloromethyl methyl ether (0.13 ml) and sodium hydride (55% oil, 77 mg) were added under ice cooling, and the mixture was stirred overnight at room temperature. The reaction solution was diluted with ethyl acetate, washed with water and saturated saline in this order and then dried over anhydrous sodium sulfate. The solvent was distilled off under reduced pressure, and the residue obtained was purified by silica gel column chromatography (n-hexane/ethyl acetate) to obtain the title compound (317 mg).
$^1$H-NMR (CDCl$_3$) δ: 0.93 (3H, t, J=7.0 Hz), 1.86 (6H, s), 3.36 (3H, s), 4.07 (2H, q, J=7.3 Hz), 4.78 (2H, s), 7.31-7.45 (3H, m).

[Step 4] 3-(2,6-Dichlorophenyl)-5-[1-(methoxymethoxy)-1-methylethyl]-1,2-oxazole-4-carboxylic acid The title compound (296 mg) was obtained by the same method as in step 4 of Reference Example X-1 using the compound (317 mg) obtained in the preceding step 3.
$^1$H-NMR (CDCl$_3$) δ: 1.89 (6H, s), 3.44 (3H, s), 4.96 (2H, s), 7.33-7.43 (3H, m).

Reference Example X-72

3-(2,6-Dichlorophenyl)-5-(2-methyloxetan-2-yl)-1,2-oxazole-4-carboxylic acid

[Formula 49]

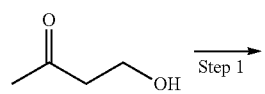

[Step 1] 4-[tert-Butyl(dimethyl)silyl]oxybutan-2-one

To a solution of 4-hydroxybutan-2-one (881 mg) in dichloromethane (26 ml), triethylamine (4.2 ml), 4-dimeth-

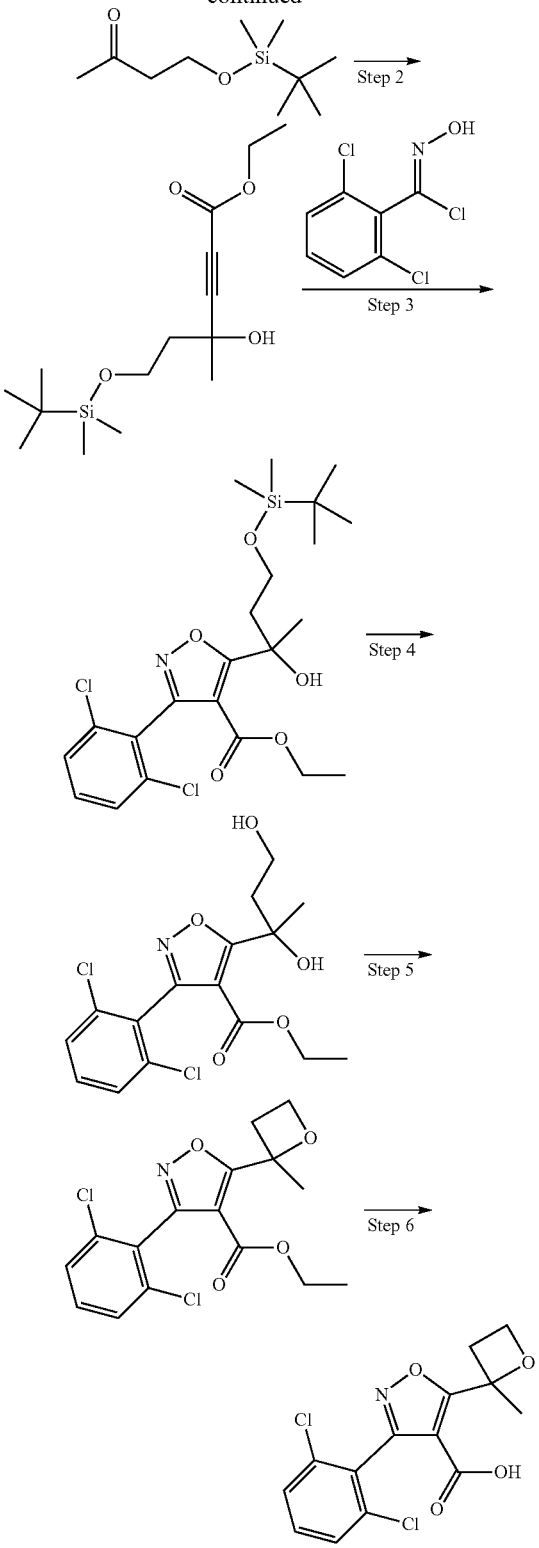

ylaminopyridine (244 mg) and tert-butyldimethylchlorosilane (1.81 g) were added in this order under ice cooling, and the mixture was stirred overnight at room temperature. The reaction solution was diluted with dichloromethane, washed with water and saturated saline in this order and then dried over anhydrous sodium sulfate. The solvent was distilled off under reduced pressure, and the residue obtained was purified by silica gel column chromatography (n-hexane/ethyl acetate) to obtain the title compound (1.63 g).
$^1$H-NMR (CDCl$_3$) δ: 0.05 (6H, s), 0.88 (9H, s), 2.18 (3H, s), 2.62 (2H, t, J=6.0 Hz), 3.89 (2H, t, J=6.3 Hz).

[Step 2] Ethyl 6-[tert-butyl(dimethyl)silyl]oxy-4-hydroxy-4-methylhex-2-ynoate

The title compound (1.09 g) was obtained by the same method as in step 1 of Reference Example X-67 using the compound (809 mg) obtained in the preceding step 1.
$^1$H-NMR (CDCl$_3$) δ: 0.89 (3H, t, J=7.3 Hz), 1.73 (6H, s), 4.10 (2H, q, J=7.1 Hz), 5.96 (1H, s), 7.33-7.43 (3H, m).

[Step 3] Ethyl 5-[3-[tert-butyl(dimethyl)silyl]oxy-1-hydroxy-1-methylpropyl]-3-(2,6-dichlorophenyl)-1,2-oxazole-4-carboxylate The title compound (850 mg) was obtained by the same method as in step 2 of Reference Example X-67 using the compound (1.09 g) obtained in the preceding step 2.
$^1$H-NMR (CDCl$_3$) δ: 0.04 (3H, s), 0.05 (3H, s), 0.88 (3H, t, J=7.3 Hz), 0.89 (9H, s), 1.74 (3H, s), 2.22 (1H, td, J=14.5, 7.5 Hz), 2.32-2.40 (1H, m), 3.74 (2H, t, J=7.0 Hz), 4.07 (2H, q, J=7.1 Hz), 5.90 (1H, s), 7.32-7.46 (3H, m).

[Step 4] Ethyl 3-(2,6-dichlorophenyl)-5-(1,3-dihydroxy-1-methylpropyl)-1,2-oxazole-4-carboxylate To a mixed solution of the compound (434 mg) obtained in the preceding step 3 in methanol (5 ml) and tetrahydrofuran (5 ml), pyridinium p-toluenesulfonate (223 mg) was added, and the mixture was stirred overnight at room temperature. The reaction solution was concentrated under reduced pressure, and the residue obtained was purified by silica gel column chromatography (n-hexane/ethyl acetate) to obtain the title compound (293 mg).
$^1$H-NMR (CDCl$_3$) δ: 0.89 (3H, t, J=7.3 Hz), 1.74 (3H, s), 2.17-2.25 (1H, m), 2.43-2.51 (1H, m), 2.70 (1H, t, J=5.4 Hz), 3.76-3.85 (1H, m), 3.88-3.96 (1H, m), 4.10 (2H, q, J=7.3 Hz), 6.47 (1H, s), 7.34-7.44 (3H, m).

[Step 5] Ethyl 3-(2,6-dichlorophenyl)-5-(2-methyloxetan-2-yl)-1,2-oxazole-4-carboxylate To a solution of the compound (355 mg) obtained in the preceding step 4 in dichloromethane (5 ml), triethylamine (0.18 ml) and methanesulfonyl chloride (0.090 ml) were added under ice cooling, and the mixture was stirred at the same temperature as above for 15 minutes. Tetrahydrofuran (20 ml) and potassium tert-butoxide (426 mg) were added to the reaction solution, and the mixture was stirred at room temperature for 20 minutes. The reaction solution was diluted with ethyl acetate under ice cooling, washed with water and saturated saline in this order and then dried over anhydrous sodium sulfate. The solvent was distilled off under reduced pressure, and the residue obtained was purified by silica gel column chromatography (n-hexane/ethyl acetate) to obtain the title compound (55.2 mg).
$^1$H-NMR (CDCl$_3$) δ: 0.99 (3H, t, J=7.3 Hz), 1.96 (3H, s), 2.97 (1H, dt, J=14.5, 5.9 Hz), 3.22 (1H, dt, J=14.5, 5.7 Hz), 4.09 (2H, q, J=7.3 Hz), 4.66-4.73 (2H, m), 7.32-7.43 (3H, m).

[Step 6] 3-(2,6-Dichlorophenyl)-5-(2-methyloxetan-2-yl)-1,2-oxazole-4-carboxylic acid The title compound (68 mg) was obtained by the same method as in step 4 of Reference Example X-1 using the compound (95 mg) obtained in the preceding step 5.
$^1$H-NMR (CDCl$_3$) δ: 2.03 (3H, s), 3.05-3.14 (1H, m), 3.20 (1H, ddd, J=13.8, 7.1, 4.7 Hz), 4.88 (1H, dt, J=11.3, 4.5 Hz), 4.92-5.00 (1H, m), 7.33-7.44 (3H, m).

Reference Example X-73

5-[3-Methoxy-1-(2-nitrophenyl)sulfonylazetidin-3-yl]-3-(2,4,6-trichlorophenyl)-1,2-oxazole-4-carboxylic acid

[Formula 50]

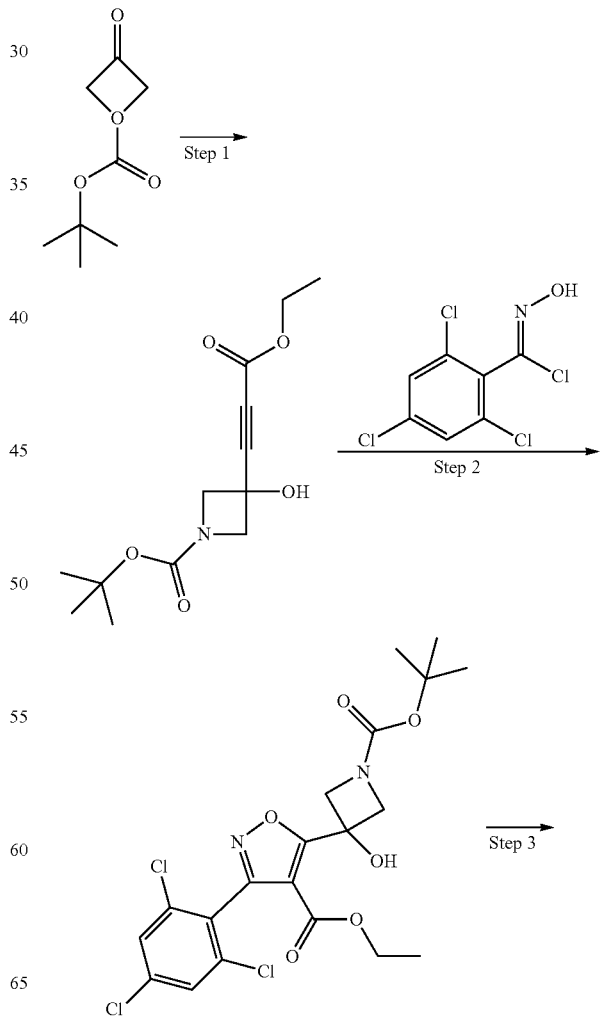

-continued

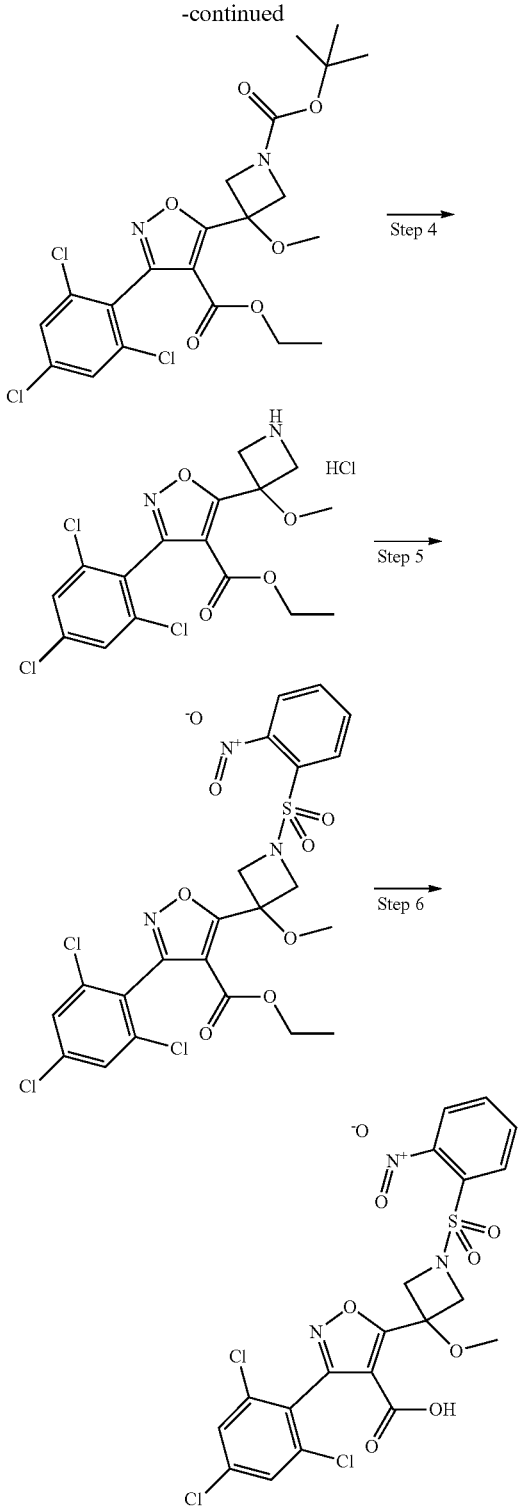

[Step 1] tert-Butyl 3-(3-ethoxy-3-oxo-1-propynyl)-3-hydroxyazetidine-1-carboxylate The title compound (758 mg) was obtained by the same method as in step 1 of Reference Example X-67 using tert-butyl 3-oxoazetidine-1-carboxylate (856 mg).
$^1$H-NMR (CDCl$_3$) δ: 1.33 (3H, t, J=7.0 Hz), 1.44 (9H, s), 2.87 (1H, brs), 4.05 (2H, d, J=9.1 Hz), 4.23-4.30 (4H, m).

[Step 2] Ethyl 5-[1-(tert-butoxycarbonyl)-3-hydroxyazetidin-3-yl]-3-(2,4,6-trichlorophenyl)-1,2-oxazole-4-carboxylate The title compound (876 mg) was obtained by the same method as in step 2 of Reference Example X-67 using the compound (758 mg) obtained in the preceding step 1.
$^1$H-NMR (CDCl$_3$) δ: 1.01 (3H, t, J=7.3 Hz), 1.48 (9H, s), 4.16 (2H, q, J=7.5 Hz), 4.22-4.28 (2H, m), 4.43-4.56 (2H, m), 6.09 (1H, s), 7.47 (2H, s).

[Step 3] Ethyl 5-[1-(tert-butoxycarbonyl)-3-methoxyazetidin-3-yl]-3-(2,4,6-trichlorophenyl)-1,2-oxazole-4-carboxylate The title compound (732 mg) was obtained by the same method as in step 3 of Reference Example X-67 using the compound (876 mg) obtained in the preceding step 2.
$^1$H-NMR (CDCl$_3$) δ: 1.10 (3H, t, J=7.0 Hz), 1.47 (9H, s), 3.20 (3H, s), 4.16 (2H, q, J=7.3 Hz), 4.31 (2H, d, J=10.3 Hz), 4.52 (2H, d, J=10.3 Hz), 7.46 (2H, s).

[Step 4] Ethyl 5-(3-methoxyazetidin-3-yl)-3-(2,4,6-trichlorophenyl)-1,2-oxazole-4-carboxylate hydrochloride The title compound was obtained by the same method as in step 1 of Reference Example X-62 using the compound (732 mg) obtained in the preceding step 3. The compound obtained was directly used in the next reaction.

[Step 5] Ethyl 5-[3-methoxy-1-(2-nitrophenyl)sulfonylazetidin-3-yl]-3-(2,4,6-trichlorophenyl)-1,2-oxazole-4-carboxylate The title compound (831 mg) was obtained by the same method as in step 2 of Reference Example X-62 using the compound obtained in the preceding step 4.
$^1$H-NMR (CDCl$_3$) δ: 1.11 (3H, t, J=7.3 Hz), 3.17 (3H, s), 4.17 (2H, q, J=7.3 Hz), 4.54 (2H, d, J=9.7 Hz), 4.76 (2H, d, J=9.7 Hz), 7.46 (2H, s), 7.71-7.76 (3H, m), 8.07-8.12 (1H, m).

[Step 6] 5-[3-Methoxy-1-(2-nitrophenyl)sulfonylazetidin-3-yl]-3-(2,4,6-trichlorophenyl)-1,2-oxazole-4-carboxylic acid The title compound (674 mg) was obtained by the same method as in step 4 of Reference Example X-1 using the compound (831 mg) obtained in the preceding step 5.
$^1$H-NMR (CDCl$_3$) δ: 3.20 (3H, s), 4.53 (2H, d, J=9.7 Hz), 4.75 (2H, d, J=9.7 Hz), 7.47 (2H, s), 7.72-7.78 (3H, m), 8.07-8.12 (1H, m).

Reference Example X-74

3-(2,6-Dichloro-4-cyclopropylphenyl)-5-(2-fluoropropan-2-yl)-1,2-oxazole-4-carboxylic acid

[Formula 51]

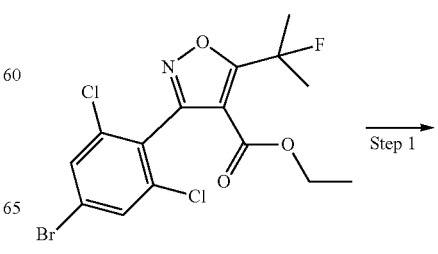

-continued

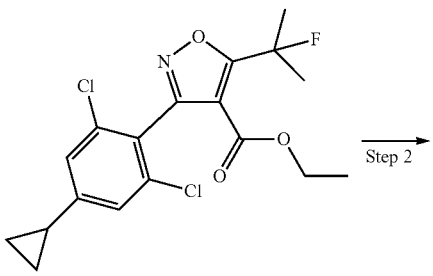
Step 2

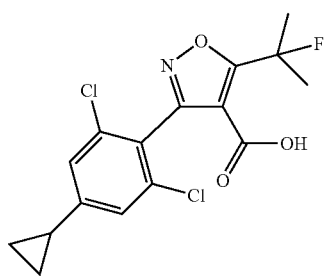

[Step 1] Ethyl 3-(2,6-dichloro-4-cyclopropylphenyl)-5-(2-fluoropropan-2-yl)-1,2-oxazole-4-carboxylate To a suspension of the compound (1.69 g) obtained in Reference Example X-49, tricyclohexylphosphine (200 mg), cyclopropylboronic acid (368 mg), and tripotassium phosphate (2.27 g) in toluene (17.8 ml) and water (3.6 ml), palladium acetate (80 mg) was added, and the mixture was stirred at 100° C. for 3 hours. After cooling, ethyl acetate and water were added to the reaction solution, which was then separated into two layers. The organic layer was washed with water and saturated saline in this order and then dried over anhydrous sodium sulfate. The solvent was distilled off under reduced pressure, and the residue obtained was purified by silica gel column chromatography (n-hexane/ethyl acetate) to obtain the title compound (1.09 g).

$^1$H-NMR (CDCl$_3$) δ: 0.74-0.78 (2H, m), 1.01 (3H, t, J=7.3 Hz), 1.05-1.10 (2H, m), 1.86-1.99 (7H, m), 4.11 (2H, q, J=7.3 Hz), 7.09 (2H, s).

MS (m/z): 386 (M+H)$^+$.

[Step 2] 3-(2,6-Dichloro-4-cyclopropylphenyl)-5-(2-fluoropropan-2-yl)-1,2-oxazole-4-carboxylic acid The title compound (655 mg) was obtained by the same method as in step 4 of Reference Example X-1 using the compound (1.09 g) obtained in the preceding step 1.

$^1$H-NMR (CDCl$_3$) δ: 0.78 (2H, ddd, J=5.7, 4.2, 2.1 Hz), 1.05-1.11 (2H, m), 1.87-1.99 (7H, m), 7.09 (2H, s).

Reference Example X-75

3-(tert-Butyl)-5-(2,4,6-trichlorophenyl)-1,2-oxazole-4-carboxylic acid

[Formula 52]

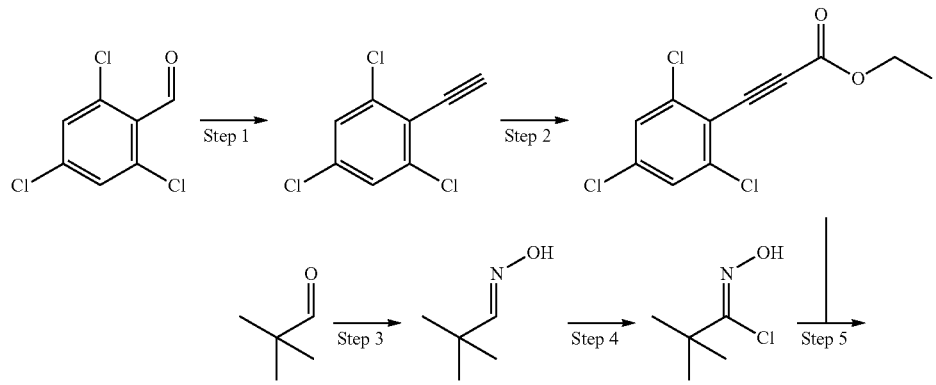

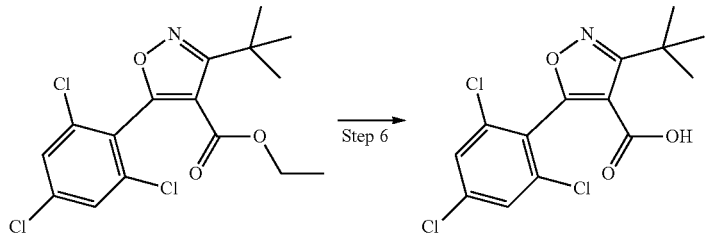

[Step 1] 1,3,5-Trichloro-2-ethynylbenzene

To a solution of 2,4,6-trichlorobenzaldehyde (1.68 g) in methanol (80 ml), potassium carbonate (2.22 g) and dimethyl (1-diazo-2-oxopropyl)phosphonate (1.44 ml) were added, and the mixture was stirred at room temperature for 2 days. A saturated aqueous solution of sodium bicarbonate was added to the reaction solution under ice cooling, and the mixture was concentrated under reduced pressure. Ethyl acetate was added to the residue obtained, washed with water and saturated saline in this order and then dried over anhydrous sodium sulfate. The solvent was distilled off under reduced pressure, and the residue obtained was purified by silica gel column chromatography (n-hexane/ethyl acetate) to obtain the title compound (1.35 g).

$^1$H-NMR (CDCl$_3$) δ: 3.71 (1H, s), 7.37 (2H, s).

[Step 2] Ethyl 3-(2,4,6-trichlorophenyl)prop-2-ynoate

To a solution of the compound (1.35 g) obtained in the preceding step 1 in tetrahydrofuran (14 ml), n-butyllithium (1.58 mol solution in n-hexane, 4.6 ml) was added at −78° C., and the mixture was stirred at the same temperature as above for 30 minutes. Ethyl chloroformate (0.82 ml) was added to the reaction solution, and the mixture was stirred at the same temperature as above for 1.5 hours and then poured into ethyl acetate and a saturated aqueous solution of ammonium chloride and vigorously stirred. After separation into two layers, the organic layer was washed with water and saturated saline in this order and then dried over anhydrous sodium sulfate. The solvent was distilled off under reduced pressure, and the residue obtained was purified by silica gel column chromatography (n-hexane/ethyl acetate) to obtain the title compound (732 mg).

$^1$H-NMR (CDCl$_3$) δ: 1.37 (3H, t, J=7.3 Hz), 4.33 (2H, q, J=7.1 Hz), 7.39 (2H, s).

[Step 3] (1E)-2,2-Dimethylpropanal oxime

To a solution of 2,2-dimethylpropanal (2.0 ml) in ethanol (11 ml), hydroxylamine hydrochloride (1.4 g) and a 1 N aqueous sodium hydroxide solution (45 ml) were added under ice cooling, and the mixture was stirred at room temperature for 2 hours. The reaction solution was rendered acidic by the addition of concentrated hydrochloric acid under ice cooling, followed by extraction with diethyl ether. The extract was washed with saturated saline and then dried over anhydrous sodium sulfate, and the solvent was distilled off under reduced pressure to obtain the title compound (790 mg).

$^1$H-NMR (CDCl$_3$) δ: 1.11 (9H, s), 7.35 (1H, s), 7.77 (1H, brs).

[Step 4] (1Z)-N-Hydroxy-2,2-dimethylpropanimidoyl chloride

To a solution of the compound (303 mg) obtained in the preceding step 3 in N,N-dimethylformamide (6 ml), N-chlorosuccinimide (401 mg) was added, and the mixture was stirred overnight at room temperature. The reaction solution was diluted with diethyl ether, washed with water and saturated saline in this order and then dried over anhydrous sodium sulfate. The solvent was distilled off under reduced pressure to obtain the title compound (473 mg).

$^1$H-NMR (CDCl$_3$) δ: 1.26 (9H, s), 7.52 (1H, s).

[Step 5] Ethyl 3-(tert-butyl)-5-(2,4,6-trichlorophenyl)-1,2-oxazole-4-carboxylate To a solution of the compound (278 mg) obtained in the preceding step 2 and the compound (407 mg) obtained in the preceding step 4 in N,N-dimethylformamide (5 ml), triethylamine (0.83 ml) was slowly added, and the mixture was stirred overnight at room temperature and then stirred at 50° C. for 6 hours. The reaction solution was diluted with ethyl acetate, washed with water and saturated saline in this order and then dried over anhydrous sodium sulfate. The solvent was distilled off under reduced pressure, and the residue obtained was purified by silica gel column chromatography (n-hexane/ethyl acetate) to obtain the title compound (406 mg).

$^1$H-NMR (CDCl$_3$) δ: 1.00 (3H, t, J=7.0 Hz), 1.52 (9H, s), 4.12 (3H, q, J=7.1 Hz), 7.45 (2H, s).

[Step 6] 3-(tert-Butyl)-5-(2,4,6-trichlorophenyl)-1,2-oxazole-4-carboxylic acid The title compound (211 mg) was obtained by the same method as in step 4 of Reference Example X-1 using the compound (406 mg) obtained in the preceding step 5.

$^1$H-NMR (CDCl$_3$) δ: 1.52 (9H, s), 7.45 (2H, s).

The following compound was obtained by the same method as in Reference Example X-75.

TABLE 26

| Reference Example No. | Name and structure | Instrumental data |
|---|---|---|
| X-76 | 3-[1-(tert-Butoxycarbonyl)-4-piperidyl]-5-(2,4,6-trichlorophenyl)-1,2-oxazole-4-carboxylic acid | $^1$H-NMR(CDCl$_3$)δ: 1.47(9H, s), 1.75-1.90(2H, brm), 2.03-2.13(2H, m), 2.81-3.02(2H, brm), 3.34-3.46(1H, m), 4.11-4.30(2H, brm), 7.46(2H, s). |

Reference Example E-1 tert-Butyl (E)-3-(1H-indol-4-yl)prop-2-enoate

[Formula 53]

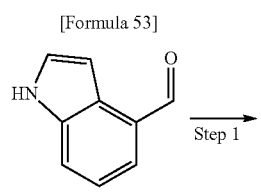

[Step 1]
To a solution of 1H-indole-4-carbaldehyde (30 g) in N,N-dimethylformamide (300 ml), tert-butyl diethylphosphonoacetate (53.4 ml) and potassium carbonate (60 g) were added, and the mixture was stirred at 80° C. for 9.5 hours. After cooling, water was added to the reaction solution, followed by extraction with ethyl acetate. The extract was washed with water and saturated saline in this order and then dried over anhydrous sodium sulfate. The solvent was distilled off under reduced pressure, and the residue obtained was purified by silica gel column chromatography (n-hexane/ethyl acetate). The eluted fraction was concentrated under reduced pressure. n-Hexane was added to the residue obtained, and the mixture was stirred at room temperature. Then, the suspension was collected by filtration to obtain the title compound (41.3 g).

$^1$H-NMR (CDCl$_3$) δ: 1.56 (9H, s), 6.55 (1H, d, J=16.3 Hz), 6.84 (1H, brs), 7.20 (1H, t, J=7.9 Hz), 7.32 (1H, t, J=3.0 Hz), 7.37 (1H, d, J=7.3 Hz), 7.43 (1H, d, J=7.9 Hz), 8.01 (1H, d, J=15.7 Hz), 8.32 (1H, brs).

The following compound was obtained by the same method as in Reference Example E-1.

TABLE 27

| Reference Example No. | Name and structure | Instrumental data |
|---|---|---|
| E-2 | tert-Butyl (E)-3-(1H-indazol-4-yl)prop-2-enoate | $^1$H-NMR(CDCl$_3$)δ: 1.57(9H, s), 6.61(1H, d, J = 16.3 Hz), 7.35-7.43(2H, m), 7.53(1H, d, J = 7.9 Hz), 7.93(1H, d, J = 15.7 Hz), 8.35(1H, s), 10.26(1H, br s). |

-continued

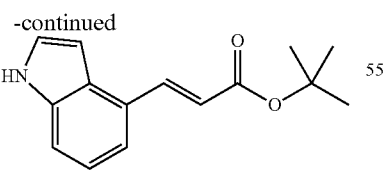

Reference Example E-3 tert-Butyl (E)-3-(3-fluoro-1H-indol-4-yl) prop-2-enoate

[Formula 54]

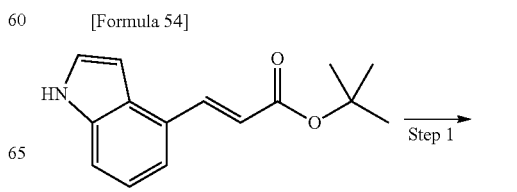

-continued

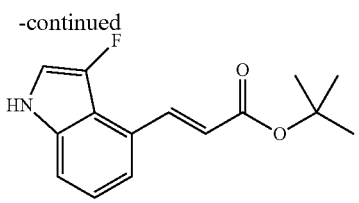

[Step 1]

To a mixed solution of the compound (1.60 g) obtained in step 1 of Reference Example E-1 in acetone (13 ml) and acetonitrile (20 ml), 1-chloromethyl-4-fluoro-1,4-diazoniabicyclo[2.2.2]octane bis(tetrafluoroborate) (2.70 g) was added, and the mixture was stirred at room temperature for 1 hour. The reaction solution was concentrated under reduced pressure, and the residue obtained was diluted with ethyl acetate, washed with a saturated aqueous solution of sodium bicarbonate, water (50 ml), and saturated saline (50 ml) in this order and then dried over anhydrous sodium sulfate. The solvent was distilled off under reduced pressure, and the residue obtained was purified by silica gel column chromatography (n-hexane/ethyl acetate) to obtain the title compound (74 mg).

¹H-NMR (CDCl₃) δ: 1.56 (9H, s), 6.51 (1H, dd, J=15.7, 1.8 Hz), 7.07 (1H, dd, J=2.7, 1.4 Hz), 7.21 (1H, dd, J=7.9, 3.9 Hz), 7.32 (1H, dd, J=8.2, 2.7 Hz), 7.44 (1H, d, J=7.3 Hz), 7.70 (1H, brs), 8.26 (1H, d, J=15.7 Hz).

MS (m/z): 260 (M−H)⁻.

Reference Example E-4 tert-Butyl (E)-3-(3-chloro-1H-indol-4-yl) prop-2-enoate

[Formula 55]

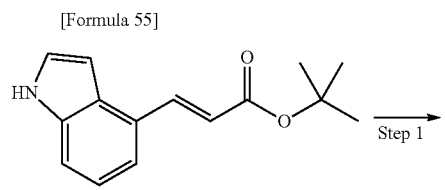

[Step 1]

To a solution of the compound (1.20 g) obtained in step 1 of Reference Example E-1 in N,N-dimethylformamide (20 ml), N-chlorosuccinimide (659 mg) was added, and the mixture was stirred at room temperature for 2 hours. The reaction solution was diluted with ethyl acetate, washed with water and saturated saline in this order and then dried over anhydrous magnesium sulfate. The solvent was distilled off under reduced pressure, and the residue obtained was purified by silica gel column chromatography (n-hexane/ethyl acetate) to obtain the title compound (1.25 g).

¹H-NMR (CDCl₃) δ: 1.56 (9H, s), 6.41 (1H, d, J=15.7 Hz), 7.20-7.25 (3H, m), 7.38 (1H, d, J=7.9 Hz), 8.21 (1H, brs), 8.90 (1H, d, J=15.7 Hz).

The following compound was obtained by the same method as in Reference Example E-4.

TABLE 28

| Reference Example No. | Name and structure | Instrumental data |
|---|---|---|
| E-5 | tert-Butyl (E)-3-(3-bromo-1H-indol-4-yl)prop-2-enoate | ¹H-NMR(CDCl₃)δ: 1.56(9H, s), 6.39(1H, d, J = 15.7 Hz), 7.20-7.31(2H, m), 7.40(1H, d, J = 8.5 Hz), 7.46(1H, d, J = 7.9 Hz), 8.32(1H, brs), 9.04(1H, d, J = 15.7 Hz). |

Reference Example E-6 tert-Butyl (E)-3-(3-formyl-1H-indol-4-yl) prop-2-enoate

[Formula 56]

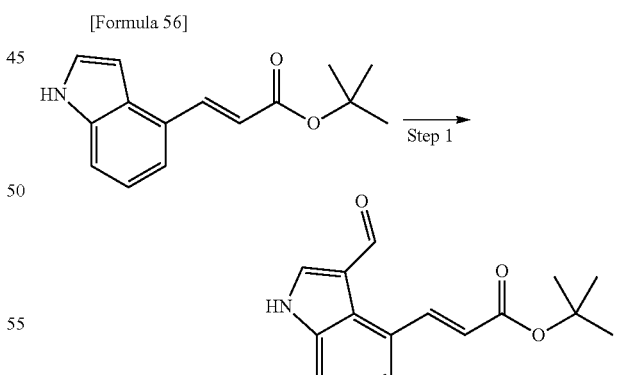

[Step 1]

To a solution of N,N-dimethylformamide (0.883 g) in 1,2-dichloroethane (65 ml), a solution of oxalyl chloride (1.3 ml) in 1,2-dichloroethane (7 ml) was added under ice cooling under a nitrogen atmosphere, and the mixture was stirred at the same temperature as above for 20 minutes. The compound (2.45 g) obtained in step 1 of Reference Example E-1 was added to the reaction solution, and the mixture was stirred at room temperature for 3.5 hours. A 10% aqueous sodium carbonate solution (50 ml) was added to the reaction solution under ice cooling, and the mixture was stirred at the same temperature as above for 2 hours. After separation into two layers, the aqueous layer was subjected to extraction with dichloromethane. The organic layers were combined, washed with saturated saline and then dried over anhydrous sodium sulfate. The solvent was distilled off under reduced pressure, and the residue obtained was purified by silica gel column chromatography (n-hexane/ethyl acetate) to obtain the title compound (1.99 g).

$^1$H-NMR (CDCl$_3$) δ: 1.59 (9H, s), 6.41 (1H, d, J=15.1 Hz), 7.32 (1H, dd, J=7.9, 3.9 Hz), 7.47 (1H, d, J=8.5 Hz), 7.61 (1H, d, J=7.9 Hz), 8.01 (1H, d, J=3.0 Hz), 9.21 (2H, d, J=16.3 Hz), 10.03 (1H, s).

MS (m/z): 270 (M−H)$^-$.

Reference Example E-7 tert-Butyl 2-(1H-indol-4-yl)cyclopropanecarboxylate

[Formula 57]

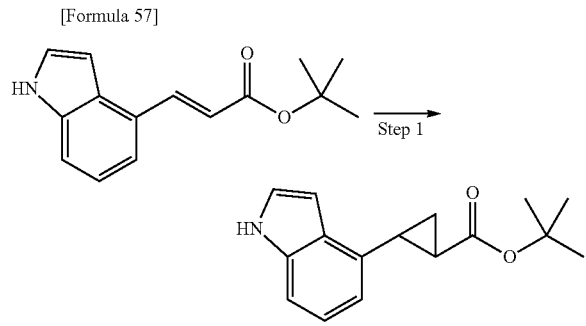

[Step 1]

Trimethylsulfoxonium iodide was dissolved in dimethyl sulfoxide (2 ml). To the solution, potassium tert-butoxide (138 mg) was added, and the mixture was stirred at room temperature for 1 hour. The compound (150 mg) obtained in step 1 of Reference Example E-1 was added to the reaction solution, and the mixture was stirred at room temperature for 17 hours. Saturated saline was added to the reaction solution, followed by extraction with ethyl acetate. The extract was washed with saturated saline and then dried over anhydrous sodium sulfate. The solvent was distilled off under reduced pressure, and the residue obtained was purified by silica gel column chromatography (n-hexane/ethyl acetate) to obtain the title compound (66.9 mg).

$^1$H-NMR (CDCl$_3$) δ: 1.37-1.43 (1H, m), 1.50 (9H, s), 1.56-1.62 (1H, m), 1.93-1.99 (1H, m), 2.75-2.81 (1H, m), 6.67-6.70 (1H, m), 6.73-6.77 (1H, m), 7.09-7.14 (1H, m), 7.22-7.25 (1H, m), 7.25-7.29 (1H, m), 8.23 (1H, br).

MS (ESI): 258 (M+H)$^+$.

Reference Example E-8 tert-Butyl (E)-3-(3-methyl-1H-indol-4-yl) prop-2-enoate

[Formula 58]

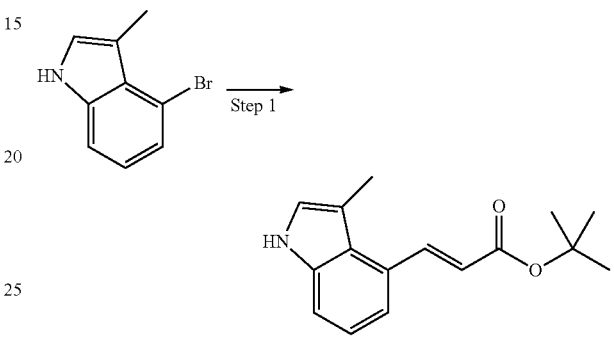

[Step 1]

To a solution of 4-bromo-3-methyl-1H-indole (15 g) in N,N-dimethylformamide (500 ml), N,N-di(propan-2-yl)ethylamine (18.7 ml), tris(2-methylphenyl)phosphine (2.2 g), palladium acetate (0.8 g), and tert-butyl acrylate (15.7 ml) were added, and the mixture was stirred at 140° C. for 8 hours under a nitrogen atmosphere. After cooling, water was added to the reaction solution, followed by extraction with ethyl acetate. The extract was washed with water and saturated saline in this order and then dried over anhydrous sodium sulfate. The solvent was distilled off under reduced pressure, and the residue obtained was purified by silica gel column chromatography (n-hexane/ethyl acetate). The eluted fraction was concentrated under reduced pressure. n-Hexane was added to the residue obtained, and the mixture was stirred at room temperature. Then, the suspension was collected by filtration to obtain the title compound (15.6 g).

$^1$H-NMR (CDCl$_3$) δ: 1.56 (9H, s), 2.56 (3H, s), 6.39 (1H, d, J=15.7 Hz), 7.03 (1H, s), 7.15 (1H, t, J=7.3 Hz), 7.35 (1H, d, J=8.5 Hz), 7.41 (1H, d, J=7.3 Hz), 7.99 (1H, brs), 8.49 (1H, d, J=15.7 Hz).

The following compounds were obtained by the same method as in Reference Example E-8.

TABLE 29

| Reference Example No. | Name and structure | Instrumental data |
|---|---|---|
| E-9 | tert-Butyl (E)-3-(7-fluoro-1H-indol-4-yl)prop-2-enoate | $^1$H-NMR(CDCl$_3$)δ: $^1$H-NMR(CDCl$_3$)δ: 1.56(9H, s), 6.48(1H, d, J = 16.3 Hz), 6.87-6.88(1H, m), 6.91(1H, dd, J = 10.9, 8.5 Hz), 7.28-7.29(1H, m), 7.34(1H, dd, J = 3.0, 1.5 Hz), 7.93 (1H, d, J = 16.3 Hz), 8.49(1H, brs). |

TABLE 29-continued

| Reference Example No. | Name and structure | Instrumental data |
|---|---|---|
| E-10 | tert-Butyl (E)-3-(1H-indol-4-yl)-2-methyl-prop-2-enoate | $^1$H-NMR(CDCl$_3$)δ: 1.58(9H, s), 2.08(3H, s), 6.62(1H, s), 7.14-7.31(3H, m), 7.38(1H, d, J = 7.9 Hz), 7.99(1H, s), 8.26(1H, brs). |
| E-11 | tert-Butyl (E)-3-(1H-pyrrolo[2,3-b]pyridin-4-yl)prop-2-enoate | $^1$H-NMR(CDCl$_3$)δ: 1.57(9H, s), 6.69(1H, d, J = 15.7 Hz), 6.75-6.78(1H, m), 7.22(1H, d, J = 5.4 Hz), 7.43-7.46(1H, m), 7.91(1H, d, J = 15.7 Hz), 8.34 (1H, d, J = 5.4 Hz), 10.05(1H, brs). MS(ESI): 245(M + H)$^+$. |
| E-12 | tert-Butyl (E)-3-(indolin-4-yl)prop-2-enoate | $^1$H-NMR(CDCl$_3$)δ: 1.53(9H, s), 3.16(1H, t, J = 8.5 Hz), 3.60(1H, t, J = 8.5 Hz), 6.29(1H, d, J = 15.7 Hz), 6.63(1H, d, J = 7.9 Hz), 6.91(1H, d, J = 7.3 Hz), 7.02(1H, dd, J = 7.9, 7.3 Hz), 7.62(1H, d, J = 15.7 Hz). MS(ESI): 246(M + H)$^+$. |

Reference Example E-13 tert-Butyl 3-(3-methyl-1H-indol-4-yl)propanoate

[Formula 59]

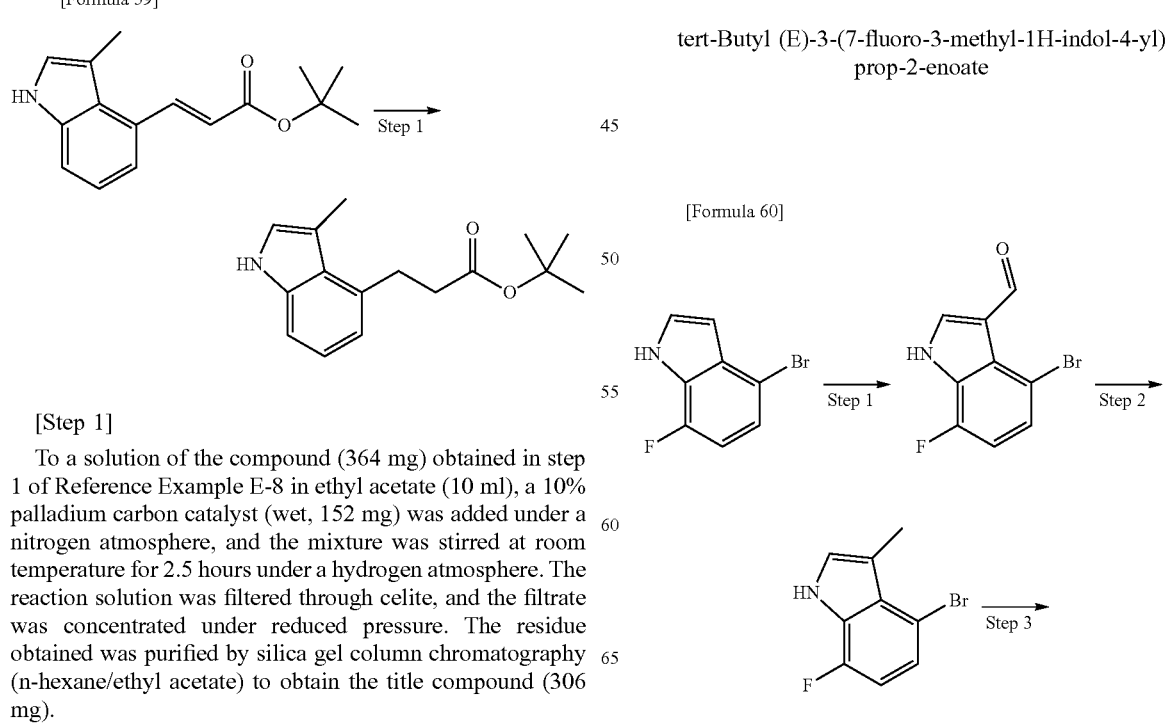

[Step 1]

To a solution of the compound (364 mg) obtained in step 1 of Reference Example E-8 in ethyl acetate (10 ml), a 10% palladium carbon catalyst (wet, 152 mg) was added under a nitrogen atmosphere, and the mixture was stirred at room temperature for 2.5 hours under a hydrogen atmosphere. The reaction solution was filtered through celite, and the filtrate was concentrated under reduced pressure. The residue obtained was purified by silica gel column chromatography (n-hexane/ethyl acetate) to obtain the title compound (306 mg).

$^1$H-NMR (CDCl$_3$) δ: 1.45 (9H, s), 2.51 (3H, d, J=1.2 Hz), 2.58-2.64 (2H, m), 3.31-3.37 (2H, m), 6.87 (1H, d, J=7.3 Hz), 6.94 (1H, q, J=1.2 Hz), 7.07 (1H, t, J=7.6 Hz), 7.20 (1H, d, J=7.9 Hz), 7.88 (1H, brs).

Reference Example E-14 tert-Butyl (E)-3-(7-fluoro-3-methyl-1H-indol-4-yl)prop-2-enoate

[Formula 60]

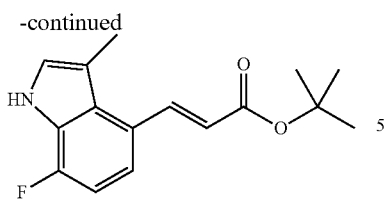

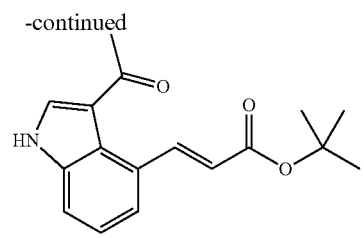

[Step 1]
4-Bromo-7-fluoro-1H-indole-3-carbaldehyde

The title compound (502 mg) was obtained by the same method as in step 1 of Reference Example E-6 using 4-bromo-7-fluoro-1H-indole (1.10 g).
$^1$H-NMR (CDCl$_3$) δ: 6.91 (1H, dd, J=10.0, 8.2 Hz), 7.40 (1H, dd, J=8.5, 4.2 Hz), 8.11 (1H, d, J=3.0 Hz), 9.10 (1H, brs), 10.92 (1H, s).
MS (m/z): 242 (M+H)$^+$.

[Step 2] 4-Bromo-7-fluoro-3-methyl-1H-indole

To a mixed solution of the compound (500 mg) obtained in the preceding step 1 in toluene (10 ml) and tetrahydrofuran (2 ml), sodium bis (2-methoxyethoxy)aluminum hydride (65% solution in toluene, 1.89 ml) was added under ice cooling under a nitrogen atmosphere, and the mixture was heated to reflux for 1 hour. A saturated aqueous solution of ammonium chloride was added to the reaction solution under ice cooling, followed by extraction with ethyl acetate. The extract was washed with saturated saline and then dried over anhydrous sodium sulfate. The solvent was distilled off under reduced pressure, and the residue obtained was purified by silica gel column chromatography (n-hexane/ethyl acetate) to obtain the title compound (357 mg).
$^1$H-NMR (CDCl$_3$) δ: 2.54 (3H, s), 6.73 (1H, dd, J=10.3, 8.5 Hz), 7.00-7.03 (1H, brm), 7.12 (1H, dd, J=8.5, 4.2 Hz), 8.12 (1H, brs).
MS (m/z): 228 (M+H)$^+$.

[Step 3] tert-Butyl (E)-3-(7-fluoro-3-methyl-1H-indol-4-yl) prop-2-enoate

The title compound (366 mg) was obtained by the same method as in step 1 of Reference Example E-8 using the compound (354 mg) obtained in the preceding step 2.
$^1$H-NMR (CDCl$_3$) δ: 1.55 (9H, s), 2.54 (3H, s), 6.33 (1H, d, J=15.7 Hz), 6.87 (1H, dd, J=10.6, 8.2 Hz), 7.05-7.05 (1H, brm), 7.33 (1H, dd, J=8.5, 4.8 Hz), 8.14 (1H, brs), 8.40 (1H, d, J=15.7 Hz).

Reference Example E-15 tert-Butyl (E)-3-(3-acetyl-1H-indol-4-yl) prop-2-enoate

[Formula 61]

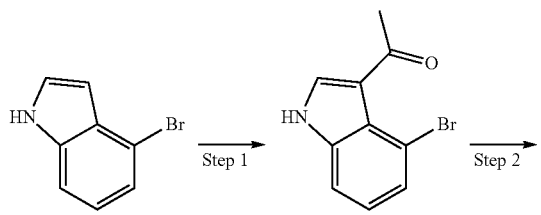

[Step 1] 1-(4-Bromo-1H-indol-3-yl)ethanone

To a solution of 4-bromo-1H-indole (1.96 g) in dichloromethane (20 ml), acetyl chloride (1.18 g) and tin tetrachloride (1.0 mol solution in dichloromethane, 15 ml) were added under ice cooling, and the mixture was stirred at room temperature for 1 hour. A saturated aqueous solution of sodium bicarbonate and celite were added to the reaction solution, and the mixture was stirred at room temperature for 30 minutes and then filtered. After separation into two layers, the organic layer was washed with saturated saline and then dried over anhydrous magnesium sulfate. The solvent was distilled off under reduced pressure, and the solid obtained was washed with dichloromethane/n-hexane to obtain the title compound (2.02 g).
$^1$H-NMR (CDCl$_3$) δ: 2.62 (3H, s), 7.11-7.14 (1H, m), 7.36-7.38 (1H, m), 7.48-7.51 (1H, m), 7.79-7.81 (1H, m), 8.63 (1H, brs).

[Step 2] tert-Butyl (E)-3-(3-acetyl-1H-indol-4-yl) prop-2-enoate

The title compound (2.02 g) was obtained by the same method as in step 1 of Reference Example E-8 using the compound (2.02 g) obtained in the preceding step 1.
$^1$H-NMR (CDCl$_3$) δ: 1.57 (9H, s), 2.58 (3H, s), 6.31 (1H, d, J=15.7 Hz), 7.29 (1H, d, J=7.9 Hz), 7.42 (1H, d, J=8.5 Hz), 7.55 (1H, d, J=7.9 Hz), 7.98-7.99 (1H, m), 8.83 (1H, s), 9.24 (1H, d, J=15.7 Hz).

Reference Example E-16 tert-Butyl (E)-3-(3-ethyl-1H-indol-4-yl) prop-2-enoate

[Formula 62]

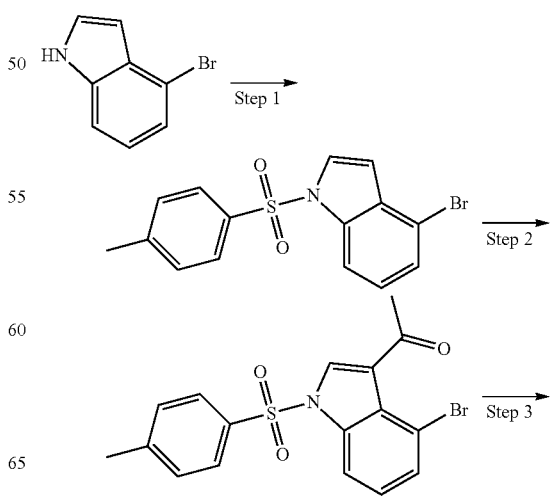

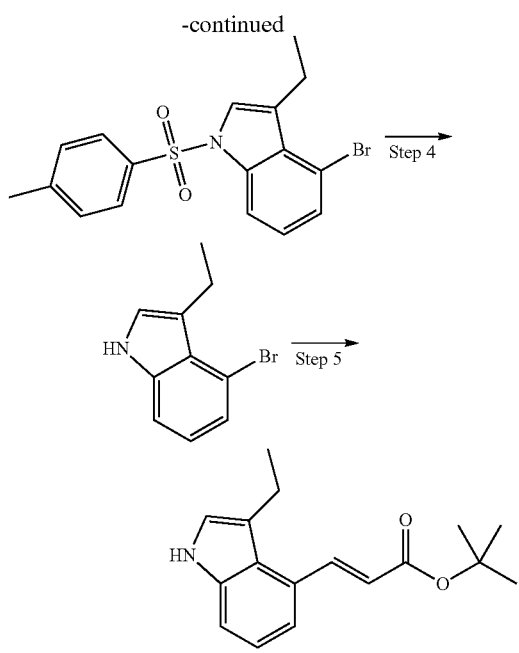

[Step 1] 4-Bromo-1-[(4-methylphenyl)sulfonyl]-1H-indole

To a solution of 4-bromo-1H-indole (6.18 g) in toluene (50 ml), a 50% aqueous sodium hydroxide solution (24.6 g) and p-toluenesulfonyl chloride (6.4 g) were added under ice cooling, and the mixture was stirred overnight at room temperature. Water was added to the reaction solution, which was then separated into two layers. The organic layer was washed with saturated saline and then dried over anhydrous magnesium sulfate. The solvent was distilled off under reduced pressure, and the solid obtained was washed with dichloromethane/n-hexane to obtain the title compound (9.33 g).
$^1$H-NMR (CDCl$_3$) δ: 2.35 (3H, s), 6.72 (1H, d, J=3.6 Hz), 7.16-7.18 (1H, m), 7.24 (2H, d, J=7.9 Hz), 7.39 (1H, d, J=7.9 Hz), 7.62 (1H, d, J=3.6 Hz), 7.76 (2H, d, J=7.9 Hz), 7.94 (1H, d, J=8.5 Hz).

[Step 2] 1-[4-Bromo-1-[(4-methylphenyl)sulfonyl]-1H-indol-3-yl]ethanone

To dichloromethane (60 ml), aluminum chloride (10.7 g) and acetic anhydride (5.44 g) were added under ice cooling. After confirmation that the aluminum chloride was dissolved, the compound (9.33 g) obtained in the preceding step 1 was added thereto, and the mixture was stirred at room temperature for 1 hour. The reaction solution was diluted with dichloromethane, washed with water, a saturated aqueous solution of sodium bicarbonate, and saturated saline in this order and then dried over anhydrous magnesium sulfate. The solvent was distilled off under reduced pressure, and the solid obtained was washed with dichloromethane/n-hexane to obtain the title compound (9.15 g).
$^1$H-NMR (CDCl$_3$) δ: 2.38 (3H, s), 2.64 (3H, s), 7.20-7.22 (1H, m), 7.28 (2H, d, J=8.5 Hz), 7.52 (1H, d, J=7.9 Hz), 7.79 (2H, d, J=8.5 Hz), 7.95 (1H, d, J=8.5 Hz), 8.04 (1H, s).

[Step 3] 4-Bromo-3-ethyl-1-[(4-methylphenyl)sulfonyl]-1H-indole

To a mixed solution of trifluoroacetic acid (20 ml) and dichloromethane (15 ml), the compound (8.01 g) obtained in the preceding step 2 and sodium borohydride (7.72 g) were added under ice cooling, and the mixture was stirred at room temperature for 4 hours. The reaction solution was diluted with dichloromethane, washed with water and saturated saline in this order and then dried over anhydrous magnesium sulfate. The solvent was distilled off under reduced pressure, and the residue obtained was purified by silica gel column chromatography (n-hexane/ethyl acetate/dichloromethane) to obtain the title compound (6.61 g).
$^1$H-NMR (CDCl$_3$) δ: 1.31 (3H, t, J=7.3 Hz), 2.35 (3H, s), 2.98 (2H, q, J=7.3 Hz), 7.09-7.11 (1H, m), 7.22 (2H, d, J=7.9 Hz), 7.36-7.37 (2H, m), 7.73 (2H, d, J=7.9 Hz), 7.94 (1H, d, J=9.1 Hz).

[Step 4] 4-Bromo-3-ethyl-1H-indole

A mixture of the compound (1.10 g) obtained in the preceding step 3, magnesium (0.29 g), ammonium chloride (83.8 mg), and methanol (20 ml) was stirred at room temperature for 2 hours. A saturated aqueous solution of ammonium chloride was added to the reaction solution, followed by extraction with ethyl acetate. The extract was washed with water and saturated saline in this order and then dried over anhydrous magnesium sulfate. The solvent was distilled off under reduced pressure, and the residue obtained was purified by silica gel column chromatography (n-hexane/ethyl acetate) to obtain the title compound (0.51 g).
$^1$H-NMR (CDCl$_3$) δ: 1.33 (3H, t, J=7.5 Hz), 3.07 (2H, q, J=7.5 Hz), 6.97-7.02 (2H, m), 7.26-7.29 (2H, m), 8.01 (1H, brs).

[Step 5] tert-Butyl (E)-3-(3-ethyl-1H-indol-4-yl)prop-2-enoate

The title compound (1.21 g) was obtained by the same method as in step 1 of Reference Example E-8 using the compound (1.23 g) obtained in the preceding step 4.
$^1$H-NMR (CDCl$_3$) δ: 1.37 (3H, t, J=7.5 Hz), 1.56 (9H, s), 3.00 (2H, q, J=7.5 Hz), 6.38 (1H, d, J=15.7 Hz), 7.05-7.06 (1H, m), 7.15-7.17 (1H, m), 7.35-7.40 (2H, m), 8.02 (1H, brs), 8.44 (1H, d, J=15.7 Hz).

Reference Example E-17 tert-Butyl (2E)-(3,4-dihydrobenzo[cd]indol-5(1H)-ylideneethanoate

[Formula 63]

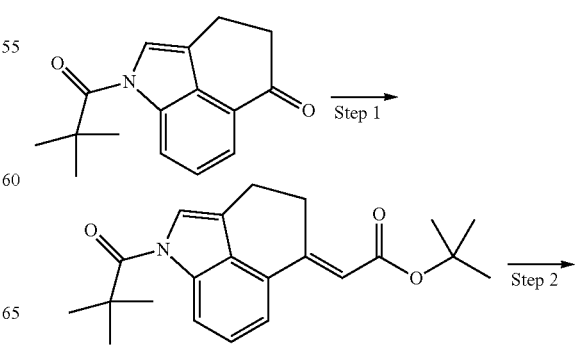

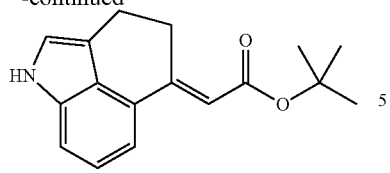

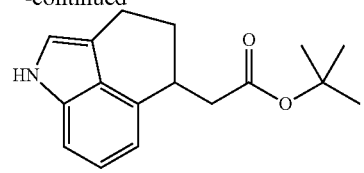

[Step 1] tert-Butyl (2E)-[1-(2,2-dimethylpropanoyl)-3,4-dihydrobenzo[cd]indol-5(1H)-ylideneethanoate To a solution of tert-butyl diethylphosphonoacetate (1.12 ml) in tetrahydrofuran (5 ml), sodium hydride (55% oil, 190 mg) was added under ice cooling, and the mixture was stirred for 30 minutes. A solution of 1-(2,2-dimethylpropanoyl)-3,4-dihydrobenzo[cd]indol-5(1H)-one [Tetrahedron Lett., 39, 8729-8732 (1998)] (1.01 g) in tetrahydrofuran (10 ml) was added to the reaction solution, and the mixture was stirred overnight at room temperature. The reaction solution was diluted with ethyl acetate, washed with water and saturated saline in this order and then dried over anhydrous sodium sulfate. The solvent was distilled off under reduced pressure, and the residue obtained was purified by silica gel column chromatography (n-hexane/ethyl acetate) to obtain the title compound (490 mg).
$^1$H-NMR (CDCl$_3$) δ: 1.52 (9H, s), 1.55 (9H, s), 2.95 (2H, t, J=6.7 Hz), 3.43 (2H, t, J=6.7 Hz), 6.44 (1H, s), 7.33 (1H, t, J=7.9 Hz), 7.43-7.48 (2H, m), 8.33 (1H, d, J=7.9 Hz).

[Step 2] tert-Butyl (2E)-(3,4-dihydro-benzo[cd]indol-5(1H)-ylideneethanoate

To a mixed solution of the compound (490 mg) obtained in the preceding step 1 in tetrahydrofuran (1 ml) and methanol (3 ml), a 1 N aqueous sodium hydroxide solution (3 ml) was added at room temperature, and the mixture was stirred at room temperature for 1 hour. The reaction solution was diluted with ethyl acetate, washed with 1 N hydrochloric acid, water, and saturated saline in this order and then dried over anhydrous sodium sulfate. The solvent was distilled off under reduced pressure, and the residue obtained was purified by silica gel column chromatography (n-hexane/ethyl acetate) to obtain the title compound (298 mg).
$^1$H-NMR (CDCl$_3$) δ: 1.55 (9H, s), 2.98-3.03 (2H, m), 3.43-3.49 (2H, m), 6.45 (1H, t, J=1.5 Hz), 6.94-6.95 (1H, m), 7.18 (1H, t, J=7.9 Hz), 7.28-7.33 (2H, m), 7.93 (1H, brs).

Reference Example E-18 tert-Butyl 1,3,4,5-tetrahydrobenzo[cd]indol-5-ylacetate

[Formula 64]

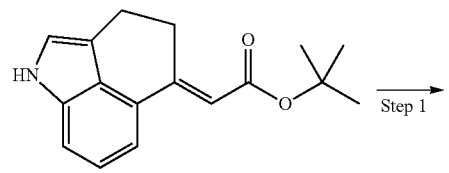

[Step 1]

The title compound (90 mg) was obtained by the same method as in step 1 of Reference Example E-13 using the compound (149 mg) obtained in step 2 of Reference Example E-17.
$^1$H-NMR (CDCl$_3$) δ: 1.49 (9H, s), 1.86-1.96 (1H, m), 2.08-2.21 (1H, m), 2.44 (1H, dd, J=14.8, 8.8 Hz), 2.79 (1H, dd, J=14.5, 6.0 Hz), 2.82-2.97 (2H, m), 3.47-3.58 (1H, m), 6.85-6.91 (2H, m), 7.12 (1H, t, J=7.6 Hz), 7.18 (1H, d, J=7.9 Hz), 7.86 (1H, brs).

Reference Example E-19 tert-Butyl (2E)-(6-fluoro-3,4-dihydro-1H-benzo[cd]indol-5(1H)-ylideneethanoate

[Formula 65]

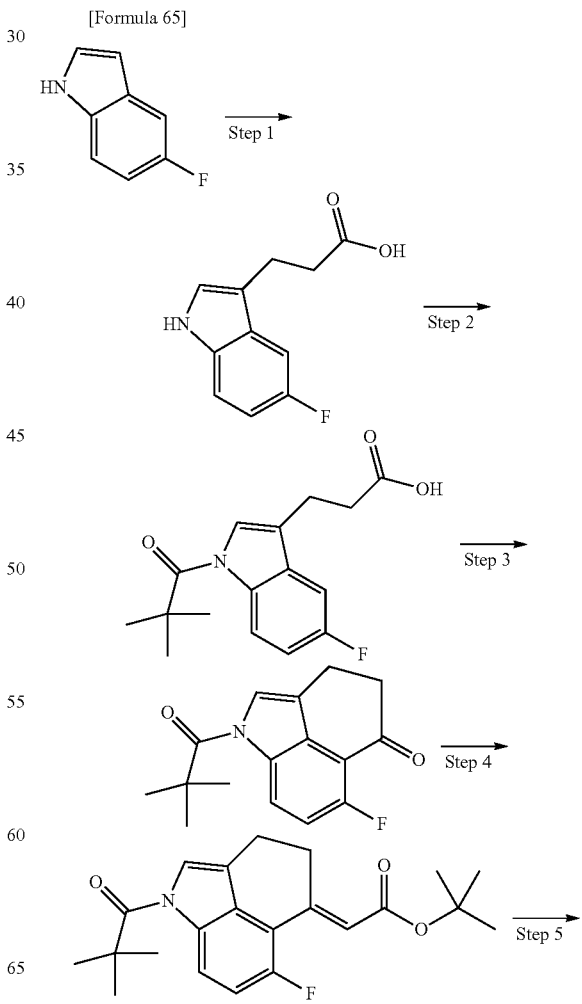

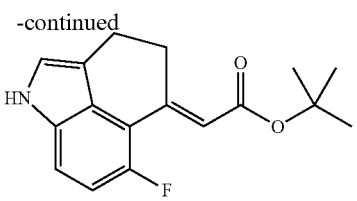

[Step 1] 3-(5-Fluoro-1H-indol-3-yl)propanoic acid

A mixture of 5-fluoro-1H-indole (2.03 g), acetic acid (15 ml) and acrylic acid (2.27 ml) was stirred at 90° C. for 3 days. The reaction solution was concentrated under reduced pressure. A 3 N aqueous sodium hydroxide solution was added to the residue obtained, and the mixture was stirred. Then, the insoluble matter was filtered off. The filtrate was washed with diethyl ether, and the aqueous layer obtained was rendered acidic by the addition of concentrated hydrochloric acid under ice cooling, followed by extraction with dichloromethane. The extract was dried over anhydrous magnesium sulfate. The solvent was distilled off under reduced pressure to obtain the title compound (2.37 g).

$^1$H-NMR (CDCl$_3$) δ: 2.76 (2H, t, J=7.6 Hz), 3.07 (2H, t, J=7.6 Hz), 6.90-6.99 (1H, m), 7.07 (1H, d, J=2.4 Hz), 7.22-7.28 (2H, m), 7.98 (1H, brs).

[Step 2] 3-[1-(2,2-Dimethylpropanoyl)-5-fluoro-1H-indol-3-yl]propanoic acid

To a solution of the compound (2.37 g) obtained in the preceding step 1 in tetrahydrofuran (57 ml), n-butyllithium (1.6 mol solution in n-hexane, 14.6 ml) was added at −78° C. under a current of nitrogen, and the mixture was stirred at the same temperature as above for 5 minutes. Pivaloyl chloride (1.51 ml) was added to the reaction solution, and the mixture was stirred at room temperature for 3 hours. A saturated aqueous solution of ammonium chloride was added to the reaction solution under ice cooling, followed by extraction with ethyl acetate. The extract was washed with saturated saline and then dried over anhydrous magnesium sulfate. The solvent was distilled off under reduced pressure to obtain a crude form of the title compound (3.21 g), which was used in the next reaction without being purified.

[Step 3] 1-(2,2-Dimethylpropanoyl)-6-fluoro-3,4-dihydrobenzo[cd]indol-5(1H)-one

To a solution of the compound (2.85 g) obtained in the preceding step 2 in dichloromethane (24.5 ml), thionyl chloride (2.86 ml) was added under ice cooling under a current of nitrogen, and the mixture was stirred at room temperature for 20 minutes. The reaction solution was concentrated under reduced pressure, and the residue obtained was dissolved in dichloromethane (24.5 ml) to prepare a solution of acid chloride.

To a solution of aluminum chloride (2.87 g) in dichloromethane (24.5 ml), chloroacetyl chloride (2.57 ml) was added dropwise under ice cooling under a current of nitrogen. Subsequently, the prepared acid chloride solution was added thereto, and the mixture was stirred at room temperature for 20 minutes and then heated to reflux for 2.5 hours. The reaction solution was added to ice, followed by extraction with dichloromethane. The extract was dried over anhydrous magnesium sulfate. The solvent was distilled off under reduced pressure, and the residue obtained was purified by silica gel column chromatography (n-hexane/ethyl acetate) to obtain the title compound (662 mg).

$^1$H-NMR (CDCl$_3$) δ: 1.53 (9H, s), 2.89 (2H, t, J=7.3 Hz), 3.20 (2H, q, J=4.8 Hz), 7.10 (1H, dd, J=10.9, 9.1 Hz), 7.63 (1H, s), 8.50 (1H, dd, J=8.8, 3.9 Hz).

[Step 4] tert-Butyl (2E)-[1-(2,2-dimethylpropanoyl)-6-fluoro-3,4-dihydro-1H-benzo[cd]indol-5(1H)-ylideneethanoate The title compound (192 mg) was obtained by the same method as in step 1 of Reference Example E-17 using the compound (662 mg) obtained in the preceding step 3.

$^1$H-NMR (CDCl$_3$) δ: 1.51 (9H, s), 1.54 (9H, s), 2.91 (2H, t, J=6.3 Hz), 3.39 (2H, t, J=6.7 Hz), 6.69 (1H, s), 7.06 (1H, dd, J=11.8, 8.8 Hz), 7.48 (1H, s), 8.25 (1H, dd, J=9.1, 3.6 Hz).

[Step 5] tert-Butyl (2E)-(6-fluoro-3,4-dihydro-1H-benzo[cd]indol-5(1H)-ylideneethanoate The title compound (146 mg) was obtained by the same method as in step 2 of Reference Example E-17 using the compound (192 mg) obtained in the preceding step 4.

$^1$H-NMR (CDCl$_3$) δ: 1.55 (9H, s), 2.95 (2H, t, J=6.7 Hz), 3.42 (2H, t, J=6.3 Hz), 6.70 (1H, s), 6.89-6.99 (2H, m), 7.19 (1H, dd, J=8.5, 3.0 Hz), 7.91 (1H, brs).

Reference Example E-20 tert-Butyl 6,7,8,9-tetrahydro-3H-benzo[e]indole-8-carboxylate

[Formula 66]

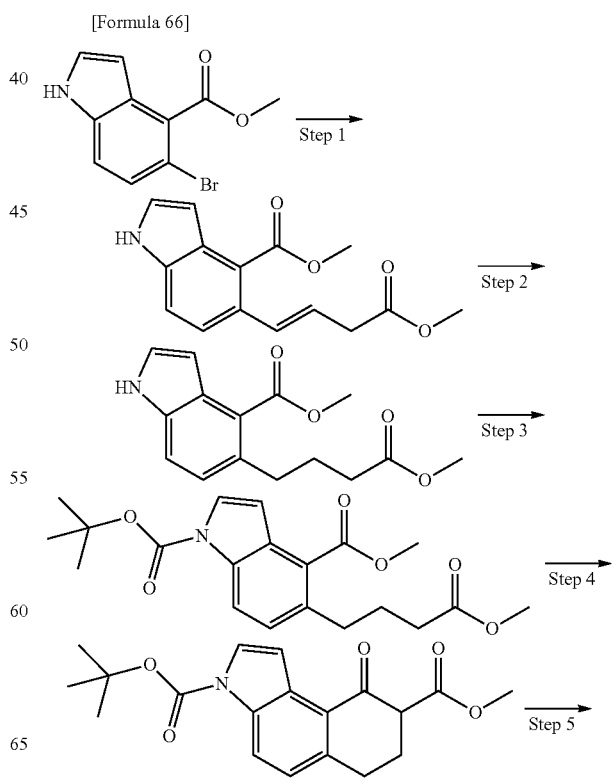

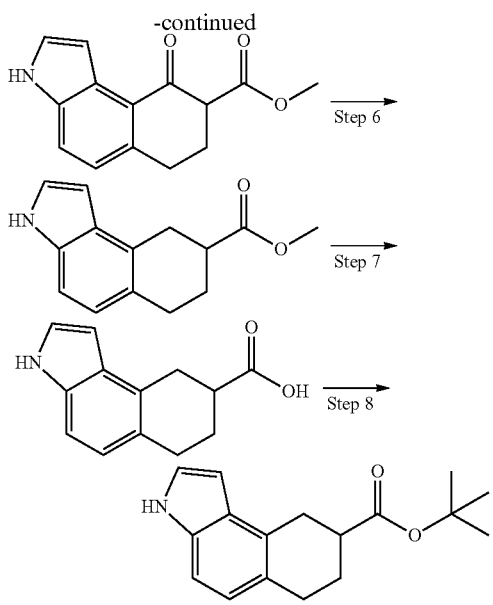

[Step 1] Methyl 5-[(1E)-4-methoxy-4-oxobut-1-en-1-yl]-1H-indole-4-carboxylate

To a solution of methyl 5-bromo-1H-indole-4-carboxylate (WO2004/063198) (1.21 g) in N,N-dimethylformamide (9.5 ml), N,N-di(propan-2-yl)ethylamine (2.49 ml), tris(2-methylphenyl)phosphine (580 mg), palladium acetate (214 mg), and methyl but-3-enoate (1.07 ml) were added, and the mixture was stirred at 140° C. for 1 hour under a nitrogen atmosphere using a microwave apparatus. The mixture was diluted with ethyl acetate, washed with water and saturated saline in this order and then dried over anhydrous sodium sulfate. The solvent was distilled off under reduced pressure, and the residue obtained was purified by silica gel column chromatography (n-hexane/ethyl acetate) to obtain the title compound (990 mg).
$^1$H-NMR (CDCl$_3$) δ: 3.32 (2H, dd, J=7.3, 1.8 Hz), 3.73 (3H, s), 4.00 (3H, s), 6.20 (1H, dt, J=15.7, 7.3 Hz), 6.83 (1H, t, J=2.7 Hz), 7.02-7.53 (4H, m), 8.29 (1H, brs).

[Step 2] Methyl 5-(4-methoxy-4-oxobutyl)-1H-indole-4-carboxylate

The title compound (850 mg) was obtained by the same method as in step 1 of Reference Example E-13 using the compound (990 mg) obtained in the preceding step 1.
$^1$H-NMR (CDCl$_3$) δ: 1.99 (2H, tt, J=7.9, 7.9 Hz), 2.38 (2H, t, J=7.6 Hz), 3.01 (2H, t, J=7.6 Hz), 3.66 (3H, s), 3.99 (3H, s), 6.81-6.84 (1H, m), 7.08 (1H, d, J=8.5 Hz), 7.28 (1H, t, J=2.4 Hz), 7.44 (1H, d, J=8.5 Hz), 8.23 (1H, brs).

[Step 3] 1-tert-Butyl 4-methyl 5-(4-methoxy-4-oxobutyl)indole-1,4-dicarboxylate

To a solution of the compound (850 mg) obtained in the preceding step 2 in dichloromethane (15 ml), triethylamine (0.86 ml), 4-dimethylaminopyridine (38 mg), and di-tert-butyl dicarbonate (809 mg) were added under ice cooling, and the mixture was stirred at room temperature for 3 days. The reaction solution was concentrated under reduced pressure, and the residue obtained was purified by silica gel column chromatography (n-hexane/ethyl acetate) to obtain the title compound (1.00 g).
$^1$H-NMR (CDCl$_3$) δ: 1.67 (9H, s), 1.93-2.02 (2H, m), 2.37 (2H, t, J=7.6 Hz), 2.98 (2H, t, J=7.6 Hz), 3.67 (3H, s), 3.98 (3H, s), 6.84 (1H, d, J=3.6 Hz), 7.19 (1H, d, J=9.1 Hz), 7.62 (1H, d, J=3.6 Hz), 8.20 (1H, d, J=8.5 Hz).

[Step 4] 3-tert-Butyl 8-methyl 9-oxo-6,7,8,9-tetrahydro-3H-benzo[e]indole-3,8-dicarboxylate To a solution of lithium di(propan-2-yl)amide (1.09 mol solution in tetrahydrofuran, 7.33 ml), a solution of the compound (1.00 g) obtained in the preceding step 3 in tetrahydrofuran (5 ml) was added dropwise at −78° C., and the mixture was stirred for 2 hours. The reaction solution was poured into a mixed solution of ethyl acetate and 1 N hydrochloric acid and vigorously stirred, and separated into two layers. The organic layer was washed with saturated saline and then dried over anhydrous sodium sulfate. The solvent was distilled off under reduced pressure, and the residue obtained was purified by silica gel column chromatography (n-hexane/ethyl acetate) to obtain the title compound (809 mg).

[Step 5] Methyl 9-oxo-6,7,8,9-tetrahydro-3H-benzo[e]indole-8-carboxylate

To a solution of the compound (809 mg) obtained in the preceding step 4 in dichloromethane (7.9 ml), trifluoroacetic acid (7.9 ml) was added under ice cooling, and the mixture was stirred at room temperature for 1 hour. The reaction solution was concentrated under reduced pressure to obtain the title compound (695 mg).
$^1$H-NMR (CDCl$_3$) δ: 2.38-2.48 (1H, m), 2.52-2.64 (1H, m), 3.06-3.24 (2H, m), 3.74 (1H, dd, J=10.3, 4.8 Hz), 3.82 (3H, s), 7.23-7.28 (1H, m), 7.65 (1H, d, J=3.6 Hz), 7.75 (1H, d, J=3.6 Hz), 8.36 (1H, d, J=8.5 Hz).

[Step 6] Methyl 6,7,8,9-tetrahydro-3H-benzo[e]indole-8-carboxylate

The compound (547 mg) obtained in the preceding step 5 was dissolved by the addition of ethyl acetate (5 ml), methanol (10 ml), dichloromethane (3 ml), and acetic acid (0.13 ml), and then, a 5% palladium carbon catalyst (wet, 547 mg) was added to the solution under a nitrogen atmosphere. The mixture was stirred at 50° C. for 7 hours under a hydrogen atmosphere, then purged with nitrogen and filtered through celite. The filtrate was concentrated under reduced pressure, and the residue obtained was purified by silica gel column chromatography (n-hexane/ethyl acetate) to obtain the title compound (111 mg).
$^1$H-NMR (CDCl$_3$) δ: 1.86-1.98 (1H, m), 2.24-2.33 (1H, m), 2.85 (1H, tdd, J=11.2, 5.5, 2.9 Hz), 2.92-2.99 (2H, m), 3.15 (1H, dd, J=16.6, 11.2 Hz), 3.31 (1H, dd, J=16.9, 5.4 Hz), 3.76 (3H, s), 6.53 (1H, t, J=2.4 Hz), 6.94 (1H, d, J=8.5 Hz), 7.17-7.22 (2H, m), 8.13 (1H, brs).

[Step 7] 6,7,8,9-Tetrahydro-3H-benzo[e]indole-8-carboxylic acid

To a mixed solution of the compound (111 mg) obtained in the preceding step 6 in tetrahydrofuran (1 ml) and methanol (1 ml), a 1 N aqueous sodium hydroxide solution (1 ml) was added at room temperature, and the mixture was stirred at 50° C. for 1 hour. The reaction solution was concentrated under reduced pressure, and ethyl acetate and 1 N hydrochloric acid were added to the residue obtained, which was then separated into two layers. The organic layer was washed with saturated saline and then dried over anhydrous sodium sulfate. The solvent was distilled off under reduced pressure to obtain the title compound (104 mg).

¹H-NMR (CDCl₃) δ: 1.90-2.02 (1H, m), 2.29-2.38 (1H, m), 2.91 (1H, tdd, J=10.9, 5.5, 2.9 Hz), 2.95-3.02 (2H, m), 3.18 (1H, dd, J=16.9, 10.3 Hz), 3.34 (1H, dd, J=16.9, 5.4 Hz), 6.53 (1H, t, J=2.4 Hz), 6.95 (1H, d, J=8.5 Hz), 7.18-7.23 (2H, m), 8.14 (1H, brs).

[Step 8] tert-Butyl 6,7,8,9-tetrahydro-3H-benzo[e]indole-8-carboxylate

To a suspension of the compound (104 mg) obtained in the preceding step 7 in toluene (5 ml), N,N-dimethylformamide di-tert-butylacetal (1.2 ml) was added at 70° C., and the mixture was stirred at 90° C. for 45 minutes. After cooling, the reaction solution was diluted with ethyl acetate, washed with water and saturated saline in this order and then dried over anhydrous sodium sulfate. The solvent was distilled off under reduced pressure, and the residue obtained was purified by silica gel column chromatography (n-hexane/ethyl acetate) to obtain the title compound (82 mg).

¹H-NMR (CDCl₃) δ: 1.50 (9H, s), 1.80-1.93 (1H, m), 2.20-2.28 (1H, m), 2.72 (1H, tdd, J=11.2, 5.4, 2.8 Hz), 2.90-2.97 (2H, m), 3.10 (1H, dd, J=16.6, 10.6 Hz), 3.24 (1H, dd, J=16.9, 5.4 Hz), 6.53 (1H, t, J=2.4 Hz), 6.93 (1H, d, J=8.5 Hz), 7.16-7.21 (2H, m), 8.12 (1H, brs).

Example 1

(2E)-3-(1-{[5-(3-Methyloxetan-3-yl)-3-(2,4,6-trichlorophenyl)-1,2-oxazol-4-yl]carbonyl}-1H-indol-4-yl)prop-2-enoic acid

[Formula 67]

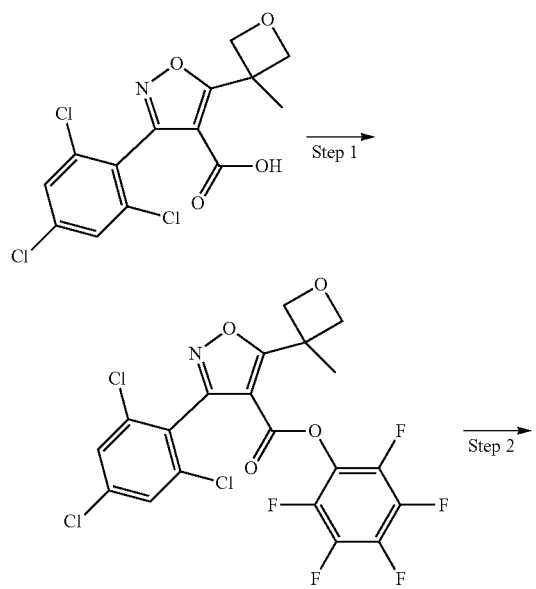

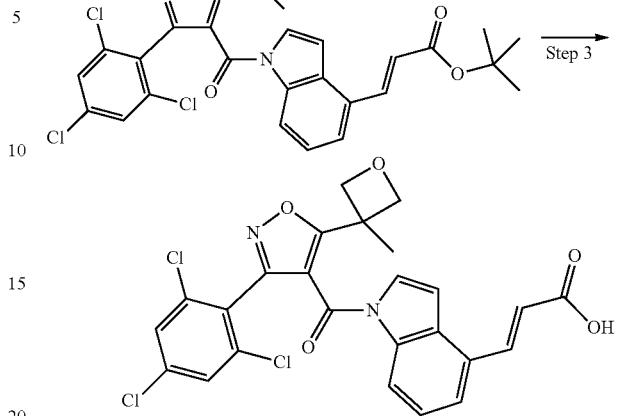

[Step 1] Pentafluorophenyl 5-(3-methyloxetan-3-yl)-3-(2,4,6-trichlorophenyl)-1,2-oxazole-4-carboxylate To a solution of the compound (10.2 g) obtained in Reference Example X-11 in dichloromethane (100 ml), N,N-di(propan-2-yl)amine (7.6 ml) and pentafluorophenyl trifluoroacetate (7.3 ml) were added dropwise in this order under ice cooling, and the mixture was stirred overnight at room temperature. The reaction solution was concentrated under reduced pressure, and the residue obtained was purified by silica gel column chromatography (n-hexane/dichloromethane) to obtain the title compound (11.4 g).

¹H-NMR (CDCl₃) δ: 1.92 (3H, s), 4.70 (2H, d, J=6.7 Hz), 5.21 (2H, d, J=6.7 Hz), 7.46 (2H, s).

[Step 2] tert-Butyl (2E)-3-(1-{[5-(3-methyloxetan-3-yl)-3-(2,4,6-trichlorophenyl)-1,2-oxazol-4-yl]carbonyl}-1H-indol-4-yl)prop-2-enoate To a solution of the compound (4.98 g) obtained in Reference Example E-1 in N,N-dimethylformamide (60 ml), sodium hydride (55% oil, 936 mg) was slowly added under ice cooling, and the mixture was stirred at room temperature for 45 minutes. A solution of the compound (10.3 g) obtained in the preceding step 1 in N,N-dimethylformamide (50 ml) was added to the reaction solution under ice cooling, and the mixture was stirred at room temperature for 30 minutes. Water was added to the reaction solution under ice cooling, followed by extraction with ethyl acetate. The extract was washed with water and saturated saline in this order and then dried over anhydrous sodium sulfate. The solvent was distilled off under reduced pressure, and the residue obtained was purified by silica gel column chromatography (n-hexane/ethyl acetate) to obtain the title compound (11.9 g).

¹H-NMR (CDCl₃) δ: 1.55 (9H, s), 1.92 (3H, s), 4.60 (2H, d, J=6.7 Hz), 5.12 (2H, d, J=6.7 Hz), 6.45 (1H, d, J=16.3 Hz), 6.71 (1H, d, J=3.6 Hz), 7.13 (1H, d, J=4.2 Hz), 7.31 (2H, s), 7.36 (1H, t, J=7.9 Hz), 7.53 (1H, d, J=7.3 Hz), 7.85 (1H, d, J=16.3 Hz), 8.29 (1H, d, J=8.5 Hz).

[Step 3] (2E)-3-(1-{[5-(3-Methyloxetan-3-yl)-3-(2,4,6-trichlorophenyl)-1,2-oxazol-4-yl]carbonyl}-1H-indol-4-yl)prop-2-enoic acid To a solution of the compound (11.9 g) obtained in the preceding step 2 in tetrahydrofuran (20 ml), formic acid (120 ml) was added, and the mixture was stirred at room temperature for 2 hours. The reaction solution was diluted with dichloromethane, washed with water and saturated saline in this order and then dried over anhydrous sodium sulfate. The solvent was distilled off under reduced pressure, and the residue obtained was purified by silica gel column chromatography (dichloromethane/methanol). The eluted fraction was concentrated under reduced pressure, and a n-hexane/dichloromethane mixed solution was added to the residue obtained. The resulting solid was collected by filtration and dried to obtain the title compound (7.61 g).

$^1$H-NMR (CDCl$_3$) δ: 1.93 (3H, s), 4.62 (2H, d, J=6.7 Hz), 5.13 (2H, d, J=6.7 Hz), 6.55 (1H, d, J=15.7 Hz), 6.74 (1H, d, J=4.2 Hz), 7.17 (1H, d, J=4.2 Hz), 7.32 (2H, s), 7.40 (1H, t, J=7.3 Hz), 7.59 (1H, d, J=7.3 Hz), 8.05 (1H, d, J=15.7 Hz), 8.34 (1H, d, J=7.9 Hz).

MS (m/z): 531 (M+H)$^+$.

The following compounds were obtained by the same method as in Example 1 using the compounds obtained in the Reference Examples.

TABLE 30

| Example No. | Reference Example No. | Name and structure | Instrumental data |
|---|---|---|---|
| 2 | X-11 E-8 | (2E)-3-(3-Methyl-1-{[5-(3-methyloxetan-3-yl)-3-(2,4,6-trichlorophenyl)-1,2-oxazol-4-yl]carbonyl}-1H-indol-4-yl)prop-2-enoic acid | $^1$H-NMR(CDCl$_3$) δ: 1.93(3H, s), 2.32 (3H, s), 4.63(2H, d, J = 6.0 Hz), 5.13 (2H, d, J = 6.0 Hz), 6.45 (1H, d, J = 15.7 Hz), 6.90 (1H, s), 7.31 (2H, s), 7.36 1H, t, J = 7.9 Hz), 7.57 (1H, d, J = 7.9 Hz), 8.35 (1H, d, J = 8.5 Hz), 8.42 (1H, d, J = 15.7 Hz). MS (m/z): 545 (M + H)$^+$. |

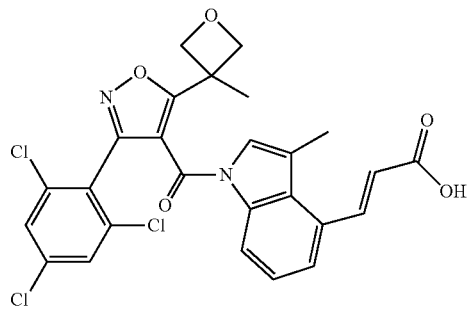 [SMILES: Cc1cn(C(=O)c2c(-c3c(Cl)cc(Cl)cc3Cl)noc2C2(C)COC2)c2cccc(/C=C/C(=O)O)c12]

| 3 | X-69 E-1 | (2E)-3-(1-{[5-(3-Methoxyoxetan-3-yl)-3-(2,4,6-trichlorophenyl)-1,2-oxazol-4-yl]carbonyl}-1H-indol-4-yl)prop-2-enoic acid | $^1$H-NMR(CDCl$_3$) δ: 3.27(3H, s), 4.90 (2H, d, J = 7.9 Hz), 5.14(2H, d, J = 7.9 Hz), 6.57(1H, d, J = 16.3 Hz), 6.83(1H d, J = 4.2 Hz), 7.16(1H, d, J = 4.2 Hz), 7.38(2H, s), 7.39(1H, t, J = 7.9 Hz), 7.60(1H, d, J = 7.9 Hz), 8.09(1H, d, J = 15.7 Hz), 8.38(1H, d, J = 7.9 Hz). MS (m/z): 547 (M + H)$^+$. |

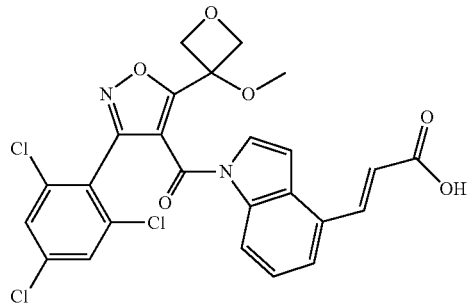 [SMILES: COC1(c2onc(-c3c(Cl)cc(Cl)cc3Cl)c2C(=O)n2ccc3c(/C=C/C(=O)O)cccc32)COC1]

TABLE 30-continued

| Example No. | Reference Example No. | Name and structure | Instrumental data |
|---|---|---|---|
| 4 | X-69 E-8 | (2E)-3-(1-{[5-(3-Methoxyoxetan-3-yl)-3-(2,4,6-trichlorophenyl)-1,2-oxazol-4-yl]carbonyl}-3-methyl-1H-indol-4-yl)prop-2-enoic acid 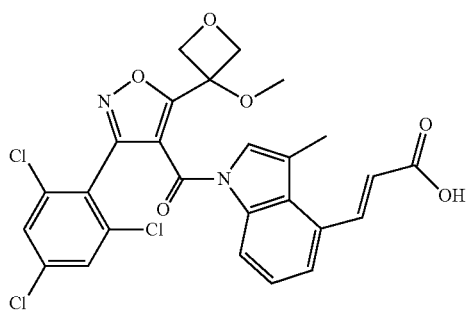 [SMILES: COC1(c2onc(-c3c(Cl)cc(Cl)cc3Cl)c2C(=O)n2cc(C)c3c(/C=C/C(=O)O)cccc32)COC1] | $^1$H-NMR(CDCl$_3$) δ: 2.38(3H, s), 3.28 (3H, s), 4.90(2H, d, J = 7.9 Hz), 5.14 (2H, d, J = 7.9 Hz), 6.46(1H, d, J = 15.7 Hz), 6.88(1H, s), 7.33-7.39(3H, m), 7.58(1H, d, J = 7.3 Hz), 8.39(1H, d, J = 7.9 Hz), 8.46(1H, d, J = 15.7 Hz). MS (m/z): 561 (M + H)$^+$. |

TABLE 31

| Example No. | Reference Example No. | Name and structure | Instrumental data |
|---|---|---|---|
| 5 | X-13 E-1 | (2E)-3-(1-{[3-(2,6-Dichlorophenyl)-5-(3-ethyloxetan-3-yl)-1,2-oxazol-4-yl]carbonyl}-1H-indol-4-yl)prop-2-enoic acid 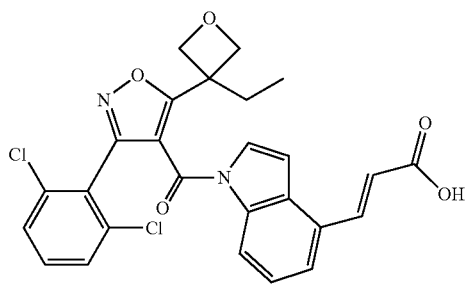 [SMILES: CCC1(c2onc(-c3c(Cl)cccc3Cl)c2C(=O)n2ccc3c(/C=C/C(=O)O)cccc32)COC1] | $^1$H-NMR(CDCl$_3$) δ: 1.00(3H, t, J = 7.3 Hz), 2.35(2H, q, J = 7.3 Hz), 4.68 (2H, d, J = 6.7 Hz), 5.12(2H, d, J = 6.7 Hz), 6.54(1H, d, J = 16.3 Hz), 6.70(1H, d, J = 3.6 Hz), 7.17(1H, d, J = 3.6 Hz), 7.30 (2H, s), 7.39(1H, t, J = 8.2 Hz), 7.57(1H, d, J = 7.3 Hz), 8.03(1H, d, J = 15.7 Hz), 8.32(1H, d, J = 7.9 Hz). MS (m/z): 545 (M + H)$^+$. |
| 6 | X-70 E-1 | (2E)-3-(1-{[5-(3-Fluorooxetan-3-yl)-3-(2,4,6-trichlorophenyl)-1,2-oxazol-4-yl]carbonyl}-1H-indol-4-yl)prop-2-enoic acid 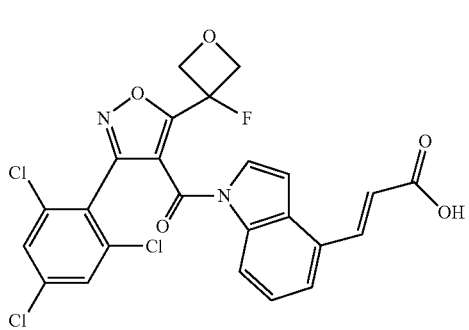 | $^1$H-NMR(CDCl$_3$) δ: 5.04(2H, dd, J = 22.4, 9.1 Hz), 5.25(2H, dd, J = 23.6, 9.1 Hz), 6.57(1H, d, J = 15.7 Hz), 6.85 (1H, d, J = 3.6 Hz), 7.17(1H, d, J = 3.6 Hz), 7.37-7.43(3H, m), 7.61(1H, d, J = 7.9 Hz), 8.09(1H, d, J = 15.7 Hz), 8.37(1H, d, J = 8.5 Hz). MS (m/z): 535 (M + H)$^+$. |

TABLE 31-continued

| 7 | X-71 E-1 | (2E)-3-(1-{[3-(2,6-Dichlorophenyl)-5-(2-hydroxypropan-2-yl)-1,2-oxazol-4-yl]carbonyl}-1H-indol-4-yl)prop-2-enoic acid | $^1$H-NMR(CDCl$_3$) δ: 1.80(6H, s), 3.55 (1H, brs), 6.52(1H, d, J = 16.3 Hz), 6.66(1H, d, J = 4.2 Hz), 7.18-7.30(4H, m), 7.38(1H, t, J = 7.9 Hz), 7.56(1H, d, J = 7.9 Hz), 8.01(1H, d, J = 16.3 Hz), 8.39(1H, d, J = 8.5 Hz). MS (m/z): 485 (M + H)$^+$. |

TABLE 32

| 8 | X-11 E-17 | (2E)-[1-{[5-(3-Methyloxetan-3-yl)-3-(2,4,6-trichlorophenyl)-1,2-oxazol-4-yl]carbonyl}-3,4-dihydrobenzo[cd]indol-5(1H)-ylidene]ethanoic acid | $^1$H-NMR(CDCl$_3$) δ: 1.92(3H, s), 2.76 (2H, t, J = 6.7 Hz), 3.37(2H, t, J = 6.7 Hz), 4.62(2H, d, J = 6.7 Hz), 5.13(2H, d, J = 6.7 Hz), 6.53(1H, s), 6.81(1H, s), 7.31(2H, s), 7.37(1H, t, J = 7.9 Hz), 7.50(1H, d, J = 7.9 Hz), 8.11(1H, d, J = 7.9 Hz). MS (m/z): 557 (M + H)$^+$. |
| 9 | X-11 E-11 | (2E)-3-(1-{[5-(3-Methyloxetan-3-yl)-3-(2,4,6-trichlorophenyl)-1,2-oxazol-4-yl]carbonyl}-1H-pyrrolo[2,3-b]pyridin-4-yl)prop-2-enoic acid | $^1$H-NMR(CDCl$_3$) δ: 1.78(3H, s), 4.52 2H, d, J = 6.0 Hz), 5.01(2H, d, J = 6.0 Hz), 6.81(1H, d, J = 15.7 Hz), 7.13 (1H, d, J = 4.2 Hz), 7.54(2H, s), 7.58 (1H, d, J = 4.8 Hz), 7.78(1H, d, J = 15.7 Hz), 7.90(1H, d, J = 4.2 Hz), 8.25(1H, d, J = 4.8 Hz), 12.86(1H, brs). MS (m/z): 532 (M + H)$^+$. |

Example 10

(2E)-3-(3-Methyl-1-{[5-(1-methylcyclobutyl)-3-(2,4,6-trichlorophenyl)-1,2-oxazol-4-yl]carbonyl}-1H-indol-4-yl)prop-2-enoic acid

[Formula 68]

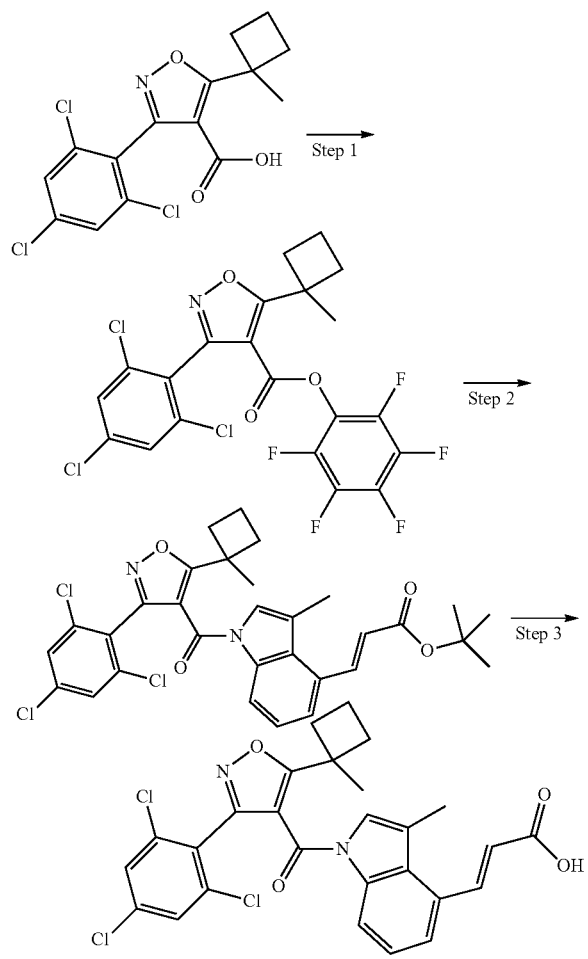

[Step 1] Pentafluorophenyl 5-(1-methylcyclobutyl)-3-(2,4,6-trichlorophenyl)-1,2-oxazole-4-carboxylate The title compound (0.123 g) was obtained by the same method as in step 1 of Example 1 using the compound (0.109 g) obtained in Reference Example X-14.
$^1$H-NMR (CDCl$_3$) δ: 1.72 (3H, s), 1.92-2.01 (1H, m), 2.14-2.30 (3H, m), 2.72-2.82 (2H, m), 7.44 (2H, s).
MS (m/z): 526 (M+H)$^+$.

[Step 2] tert-Butyl (2E)-3-(3-methyl-1-{[5-(1-methylcyclobutyl)-3-(2,4,6-trichlorophenyl)-1,2-oxazol-4-yl]carbonyl}-1H-indol-4-yl)prop-2-enoate The title compound (0.103 g) was obtained by the same method as in step 2 of Example 1 using the compound (0.123 g) obtained in the preceding step 1 and the compound (0.054 g) obtained in Reference Example E-8.
$^1$H-NMR (CDCl$_3$) δ: 1.54 (9H, s), 1.67 (3H, s), 1.88-2.22 (4H, m), 2.38 (3H, s), 2.56-2.63 (2H, m), 6.36 (1H, d, J=15.7 Hz), 6.95 (1H, s), 7.29-7.33 (3H, m), 7.52 (1H, d, J=7.9 Hz), 8.28 (1H, d, J=15.7 Hz), 8.37 (1H, d, J=8.5 Hz).
MS (m/z): 599 (M+H)$^+$.

[Step 3] (2E)-3-(3-Methyl-1-{[5-(1-methylcyclobutyl)-3-(2,4,6-trichlorophenyl)-1,2-oxazol-4-yl]carbonyl}-1H-indol-4-yl)prop-2-enoic acid To a solution of the compound (0.100 g) obtained in the preceding step 2 in dichloromethane (5 ml), trifluoroacetic acid (1 ml) was added under ice cooling, and the mixture was stirred overnight at room temperature. The reaction solution was concentrated under reduced pressure, and ethyl acetate and water were added to the residue obtained, which was then separated into two layers. The organic layer was washed with water and then dried over anhydrous sodium sulfate. The solvent was distilled off under reduced pressure to obtain the title compound (0.072 g).
$^1$H-NMR (CDCl$_3$) δ: 1.68 (3H, s), 1.88-2.17 (4H, m), 2.39 (3H, s), 2.56-2.64 (2H, m), 6.46 (1H, d, J=15.7 Hz), 6.98 (1H, s), 7.32 (2H, s), 7.35 (1H, t, J=7.9 Hz), 7.58 (1H, d, J=7.9 Hz), 8.41 (1H, d, J=7.9 Hz), 8.48 (1H, d, J=15.7 Hz).
MS (m/z): 543 (M+H)$^+$.

The following compounds were obtained by the same method as in Example 1 using the compounds obtained in the Reference Examples.

TABLE 33

| Example No. | Reference Example No. | Name and structure | Instrumental data |
|---|---|---|---|
| 11 | X-21<br>E-8 | (2E)-3-(1-{[3-(3,5-Dichloropyridin-2-yl)-5-(2-fluoropropan-2-yl)-1,2-oxazol-4-yl]carbonyl}-3-methyl-1H-indol-4-yl)prop-2-enoic acid | $^1$H-NMR(CDCl$_3$) δ: 1.90(6H, d, J = 21.8 Hz), 2.41(3H, d, J = 1.2 Hz), 6.45 1H, d, J = 15.7 Hz), 6.98 (1H, s), 7.35 (1H, t, J = 7.9 Hz), 7.57 (1H, d, J = 7.9 Hz), 8.42-8.53 (4H, m).<br>MS (m/z): 502 (M + H)$^+$. |

TABLE 33-continued

| Example No. | Reference Example No. | Name and structure | Instrumental data |
|---|---|---|---|
| 12 | X-15<br>E-17 | (2E)-[1-{[5-(1-Methoxycyclobutyl)-3-(2,4,6-trichlorophenyl)-1,2-oxazol-4-yl]carbonyl}-3,4-dihydrobenzo[cd]indol-5(1H)-ylidene]ethanoic acid | $^1$H-NMR(CDCl$_3$) δ: 1.97-2.08(2H, m), 2.41-2.48(2H, m), 2.65-2.72(2H, m), 2.87(2H, t, J = 6.7 Hz), 3.15(3H, s), 3.43 (2H, t, J = 6.7 Hz), 6.52(1H, s), 6.91(1H, s), 7.35(1H, t, J = 7.9 Hz), 7.38(2H, s), 7.50(1H, d, J = 7.9 Hz), 8.18(1H, d, J = 7.9 Hz).<br>MS (m/z): 571 (M + H)$^+$. |
| 13 | X-20<br>E-17 | (2E)-[1-{[5-(2-Fluoropropan-2-yl)-3-(2,4,6-trichlorophenyl)-1,2-oxazol-4-yl]carbonyl}-3,4-dihydrobenzop[cd]indol-5(1H)-ylidene]ethanoic acid | $^1$H-NMR(CDCl$_3$) δ: 1.87(6H, d, J = 21.8 Hz), 2.87 (2H, t, J = 6.3 Hz), 3.42 (2H, t, J = 6.3 Hz), 6.53(1H, s), 6.95 (1H, s), 7.33-7.39(3H, m), 7.51(1H, d, J = 7.3 Hz), 8.19(1H, d, J = 7.3 Hz).<br>MS (m/z): 547 (M + H)$^+$. |

TABLE 34

| Example No. | Reference Example No. | Name and structure | Instrumental data |
|---|---|---|---|
| 14 | X-16<br>E-8 | (2E)-3-(1-{[3-(2,4-Dichloro-6-fluorophenyl)-5-(1-methoxycyclobutyl)-1,2-oxazol-4-yl]carbonyl}-3-methyl-1H-indol-4-yl)prop-2-enoic acid | $^1$H-NMR(CDCl$_3$) δ: 1.98-2.06(2H, m), 2.41-2.50(2H, m), 2.42(3H, s), 2.61-2.72(2H, m), 3.13(3H, s), 6.46(1H, d, J = 15.7 Hz), 6.94(1H, s), 7.09(1H, dd, J = 8.5, 1.8 Hz), 7.26-7.28(1H, m), 7.34(1H, t, J = 7.9 Hz), 7.58(1H, d, J = 7.9 Hz), 8.43(1H, d, J = 7.9 Hz), 8.50(1H, d, J = 15.7 Hz).<br>MS (m/z): 543 (M + H)$^+$. |

TABLE 34-continued

| | | | |
|---|---|---|---|
| 15 | X-16<br>E-17 | (2E)-[1-{[3-(2,4-Dichloro-6-fluorophenyl)-5-(1-methoxycyclobutyl)-1,2-oxazol-4-yl]carbonyl}-3,4-dihydrobenzo[cd]indol-5(1H)-ylidene]ethanoic acid | $^1$H-NMR(CDCl$_3$) δ: 1.98-2.05(2H, m), 2.41-2.49(2H, m), 2.64-2.72(2H, m), 2.87(2H, t, J = 7.0 Hz), 3.15(3H, s), 3.43(2H, t, J = 7.0 Hz), 6.53(1H, s), 6.87(1H, s), 7.08(1H, dd, J = 9.1, 1.8 Hz), 7.25-7.27(1H, m), 7.35(1H, t, J = 7.9 Hz), 7.51(1H, d, J = 7.9 Hz), 8.14(1H, d, J = 7.9 Hz).<br>MS (m/z): 555 (M + H)$^+$. |
| 16 | X-23<br>E-17 | (2E)-[1-{[3-(2,4-Dichloro-6-fluorophenyl)-5-(2-fluoropropan-2-yl)-1,2-oxazol-4-yl]carbonyl}-3,4-dihydrobenzo[cd]indol-5(1H)-ylidene]ethanoic acid | $^1$H-NMR(CDCl$_3$) δ: 1.87(6H, d, J = 21.2 Hz), 2.81-2.90(2H, m), 3.37-3.46(2H, m), 6.53(1H, s), 6.89(1H, s), 7.02-7.08(1H, m), 7.32-7.39(1H, m), 7.48-7.53(1H, m), 8.13(1H, brs).<br>MS (m/z): 529 (M − H)$^−$. |

TABLE 35

| | | | |
|---|---|---|---|
| 17 | X-48<br>E-8 | (2E)-3-(1-{[3-(2,4-Dichloro-3-fluorophenyl-5-(2-fluoropropan-2-yl)-1,2-oxazol-4-yl]carbonyl}-3-methyl-1H-indol-4-yl)prop-2-enoic acid | $^1$H-NMR(CDCl$_3$) δ: 1.86(6H, d, J = 21.2 Hz), 2.42(3H, s), 6.45(1H, d, J = 15.7 Hz), 6.95(1H, s), 7.23-7.28(1H, m), 7.33-7.39(2H, m), 7.58(1H, d, J = 7.9 Hz), 8.37-8.44(1H, m), 8.48(1H, d, J = 15.7 Hz).<br>MS (m/z): 519 (M + H)$^+$. |

| # | | Name | NMR / MS |
|---|---|---|---|
| 18 | X-20 E-20 | 3-{[5-(2-Fluoropropan-2-yl)-3-(2,4,6-trichlorophenyl)-1,2-oxazol-4-yl]carbonyl}-6,7,8,9-tetrahydro-3H-Benzo[e]indole-8-carboxylic acid | $^1$H-NMR(CDCl$_3$) δ: 1.85(6H, d, J = 21.8 Hz), 1.85-2.00(1H, m), 2.27-2.35(1H, m), 2.83-3.03(3H, m), 3.11(1H, dd, J = 16.9, 10.3 Hz), 3.24(1H, dd, J = 16.6, 5.7 Hz), 6.57(1H, d, J = 4.2 Hz), 7.08(1H, d, J = 8.5 Hz), 7.17(1H, d, J = 4.2 Hz), 7.35(2H, s), 8.13(1H, d, J = 8.5 Hz). MS (m/z): 549 (M + H)$^+$. |
| 19 | X-51 E-17 | (2E)-[1-{[5-(3,3-Difluoro-1-methylcyclobutyl)-3-(2,4,6-trichlorophenyl)-1,2-oxazol-4-yl]carbonyl}-3,4- | $^1$H-NMR(CDCl$_3$) δ: 1.76(3H, s), 2.73-2.82(4H, m), 3.17-3.28(2H, m), 3.38(2H, t, J = 6.7 Hz), 6.53(1H, s), 6.83(1H, s), 7.31(2H, s), 7.38(1H, t, J = 7.9 Hz), 7.51(1H, d, J = 7.9 Hz), 8.14(1H, d, J = 7.9 Hz). MS (m/z): 591 (M + H)$^+$. |

TABLE 36

| # | | Name | NMR / MS |
|---|---|---|---|
| 20 | X-48 E-17 | (2E)-[1-{[3-(2,4-Dichloro-3-fluorophenyl)-5-(2-fluoropropan-2-yl)-1,2-oxazol-4-yl]carbonyl}-3,4-dihydrobenzo[cd]indol-5(1H)-ylidene]ethanoic acid | $^1$H-NMR(CDCl$_3$) δ: 1.86(6H, d, J = 21.3 Hz), 2.81-2.97(2H, m), 3.43(2H, t, J = 6.7 Hz), 6.53(1H, s), 6.82-6.98(1H, m), 7.25-7.31(1H, m), 7.32-7.42(2H, m), 7.51(1H, d, J = 7.9 Hz), 8.04-8.33(1H, brm). MS (m/z): 531 (M + H)$^+$. |

Example 21

(2E)-3-(1-{[5-(2-Fluoropropan-2-yl)-3-(2,4,6-trichlorophenyl)-1,2-oxazol-4-yl]carbonyl}-3-methyl-1H-indol-4-yl)prop-2-enoic acid

[Formula 69]

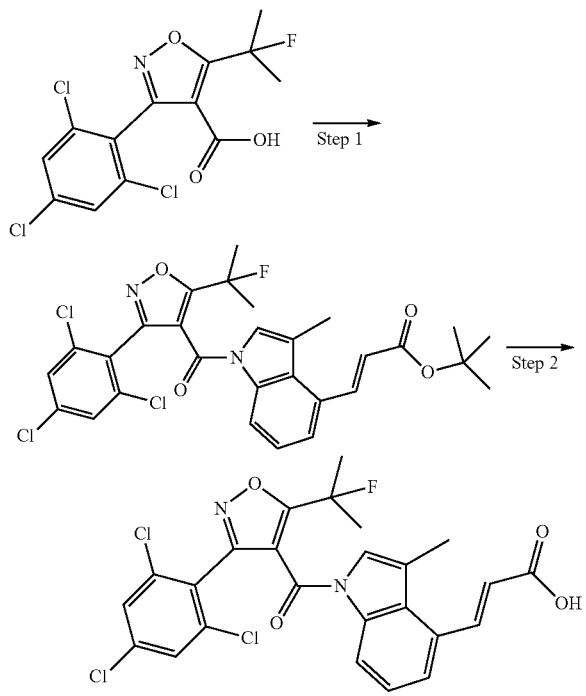

[Step 1] tert-Butyl (2E)-3-(1-{[5-(2-fluoropropan-2-yl)-3-(2,4,6-trichlorophenyl)-1,2-oxazol-4-yl]carbonyl}-3-methyl-1H-indol-4-yl)prop-2-enoate To a solution of the compound (200 mg) obtained in Reference Example X-20 and N,N-dimethylformamide (10 µl) in dichloromethane (6 ml), oxalyl chloride (216 mg) was added, and the mixture was stirred at room temperature for 30 minutes. The reaction solution was concentrated under reduced pressure to obtain acid chloride.

To a solution of the compound (218 mg) obtained in Reference Example E-8, N,N-di(propan-2-yl)ethylamine (0.19 ml), and 4-dimethylaminopyridine (7.0 mg) in dichloromethane (3 ml), a solution of the acid chloride in dichloromethane (3 ml) was added dropwise under ice cooling, and the mixture was stirred overnight at room temperature. The reaction solution was poured into a mixed solution of n-hexane, ethyl acetate, and water and separated into two layers. The organic layer was washed with water and saturated saline in this order and then dried over anhydrous sodium sulfate. The solvent was distilled off under reduced pressure, and the residue obtained was purified by silica gel column chromatography (n-hexane/ethyl acetate) to obtain the title compound (171 mg).

$^1$H-NMR (CDCl$_3$) δ: 1.54 (9H, s), 1.88 (6H, d, J=21.8 Hz), 2.41 (3H, s), 6.36 (1H, d, J=15.7 Hz), 6.98 (1H, s), 7.31 (1H, dd, J=8.2, 4.1 Hz), 7.35 (2H, s), 7.53 (1H, d, J=7.9 Hz), 8.30 (1H, d, J=15.7 Hz), 8.41 (1H, d, J=7.9 Hz).

MS (m/z): 591 (M+H)$^+$.

[Step 2] (2E)-3-(1-{[5-(2-Fluoropropan-2-yl)-3-(2,4,6-trichlorophenyl)-1,2-oxazol-4-yl]carbonyl}-3-methyl-1H-indol-4-yl)prop-2-enoic acid The title compound (110 mg) was obtained by the same method as in step 3 of Example 10 using the compound (170 mg) obtained in the preceding step 1.

$^1$H-NMR (CDCl$_3$) δ: 1.88 (6H, d, J=21.8 Hz), 2.42 (3H, d, J=1.2 Hz), 6.45 (1H, d, J=15.7 Hz), 7.02 (1H, s), 7.35 (3H, t, J=7.9 Hz), 7.58 (1H, d, J=7.3 Hz), 8.48 (2H, dd, J=13.0, 6.5 Hz).

MS (m/z): 535 (M+H)$^+$.

The following compounds were obtained by the same method as in Example 21 using the compounds obtained in the Reference Examples.

TABLE 37

| Example No. | Reference Example No. | Name and structure | Instrumental data |
| --- | --- | --- | --- |
| 22 | X-5 E-1 | (2E)-3-(1-{[5-(tert-Butyl)-3-(2,4,6-trichlorophenyl)-1,2-oxazol-4-yl]carbonyl}-1H-indol-4-yl)prop-2-enoic acid | $^1$H-NMR(CDCl$_3$) δ: 1.44(9H, s), 6.56 (1H, d, J = 16.3 Hz), 6.83(1H, d, J = 4.2 Hz), 7.30(1H, d, J = 3.6 Hz), 7.32(2H, s), 7.39(1H, t, J = 7.9 Hz), 7.59 (1H, d, J = 7.3 Hz), 8.08(1H, d, J = 15.7 Hz), 8.45(1H, d, J = 8.5 Hz). MS (m/z): 517 (M + H)$^+$. |

TABLE 37-continued

| Example No. | Reference Example No. | Name and structure | Instrumental data |
|---|---|---|---|
| 23 | X-1<br>E-1 | (2E)-3-(1-{[3-(2,6-Dichlorophenyl)-5-(propan-2-yl)-1,2-oxazol-4-yl]carbonyl}-1H-indol-4-yl)prop-2-enoic acid<br>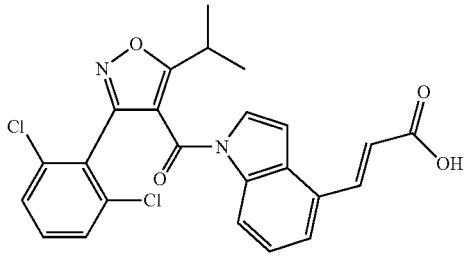 [SMILES: CC(C)c1onc(-c2c(Cl)cccc2Cl)c1C(=O)n1ccc2c(/C=C/C(=O)O)cccc21] | $^1$H-NMR(CDCl$_3$) δ: 1.34(6H, d, J = 6.7 Hz), 3.29-3.36(1H, m), 6.63(1H, d, J = 16.3 Hz), 7.04(1H, d, J = 3.6 Hz), 7.38(1H, t, J = 7.9 Hz), 7.47-7.52(1H, m), 7.55-7.60(3H, m), 7.73(1H, d, J = 7.9 Hz), 7.88(1H, d, J = 15.7 Hz), 8.21(1H, d, J = 8.5 Hz), 12.55 (1H, brs). |
| 24 | X-4<br>E-1 | (2E)-3-(1-{[5-(tert-Butyl)-3-(2,6-dichlorophenyl)-1,2-oxazol-4-yl]carbonyl}-1H-indol-4-yl)prop-2-enoic acid<br>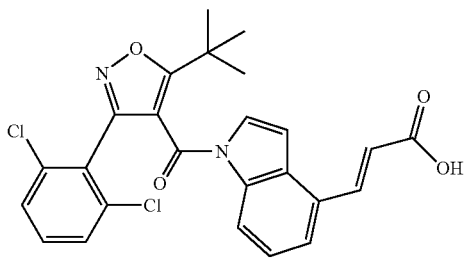 [SMILES: CC(C)(C)c1onc(-c2c(Cl)cccc2Cl)c1C(=O)n1ccc2c(/C=C/C(=O)O)cccc21] | $^1$H-NMR(CDCl$_3$) δ: 1.37(9H, s), 6.62 1H, d, J = 16.3 Hz), 7.05(1H, d, J = 3.6 Hz), 7.37-7.54(5H, m), 7.74(1H, d, J = 7.3 Hz), 7.87(1H, d, J = 16.3 Hz), 8.25(1H, d, J = 7.9 Hz), 12.51(1H, brs). |

TABLE 38

| Example No. | Reference Example No. | Name and structure | Instrumental data |
|---|---|---|---|
| 25 | X-1<br>E-8 | (2E)-3-(1-{[3-(2,6-Dichlorophenyl)-5-(propan-2-yl)-1,2-oxazol-4-yl]carbonyl}-3-methyl-1H-indol-4-yl)prop-2-enoic acid<br>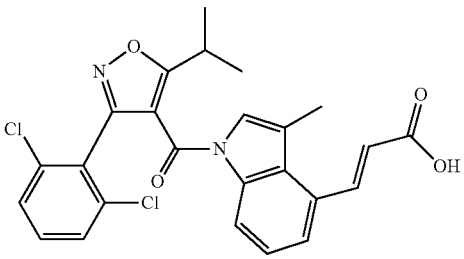 [SMILES: Cc1cn(C(=O)c2c(-c3c(Cl)cccc3Cl)noc2C(C)C)c2cccc(/C=C/C(=O)O)c12] | $^1$H-NMR(DMSO-d$_6$) δ: 1.35(6H, d, J = 6.6 Hz), 2.32(3H, d, J = 1.2 Hz), 3.35(1H, m), 6.50(1H, d, J = 15.7 Hz), 7.34-7.38(2H, m), 7.48(1H, m), 7.56(2H, m), 7.69(1H, d, J = 7.9 Hz), 8.23(2H, dd, J = 11.8, 3.9 Hz), 12.49(1H, s).<br>MS (m/z): 483 (M + H)$^+$. |

TABLE 38-continued

| 26 | X-2 E-1 | (2E)-3-(1-{[5-(Propan-2-yl)-3-(2,4,6-Trichlorophenyl)-1,2-oxazol-4-yl]carbonyl}-1H-indol-4-yl)prop-2-enoic acid | $^1$H-NMR(CDCl$_3$) δ: 1.44(6H, d, J = 7.3 Hz), 3.29-3.41(1H, m), 6.57(1H, d, J = 16.3 Hz), 6.82(1H, d, J = 4.2 Hz), 7.28(1H, d, J = 4.2 Hz), 7.35(2H, s), 7.40(1H, t, J = 7.9 Hz), 7.59(1H, d, J = 7.3 Hz), 8.09 (1H, d, J = 16.3 Hz), 8.38(1H, d, J = 8.5 Hz). MS (m/z): 503 (M + H)$^+$. |

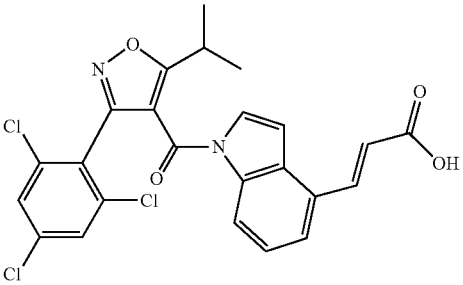

| 27 | X-18 E-1 | (2E)-3-(1-{[3-(2,6-Dichlorophenyl)-5-(2-methoxypropan-2-yl)-1,2-oxazol-4-yl]carbonyl}-1H-indol-4-yl)prop-2-enoic acid | $^1$H-NMR(CDCl$_3$) δ: 1.67(6H, s), 3.09 3H, s), 6.56(1H, d, J = 15.7 Hz), 6.82 (1H, d, J = 3.6 Hz), 7.24-7.40(5H, m), 7.57(1H, d, J = 7.9 Hz), 8.08(1H, d, J = 15.7 Hz), 8.47(1H, d, J = 8.5 Hz). MS (m/z): 499 (M + H)$^+$. |

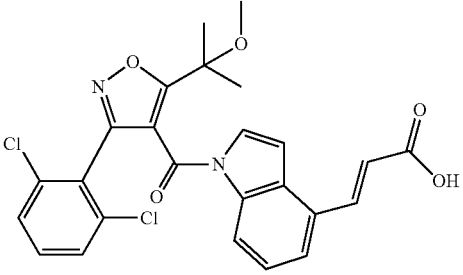 [SMILES: COC(C)(C)c1onc(-c2c(Cl)cccc2Cl)c1C(=O)n1ccc2c(/C=C/C(=O)O)cccc21]

TABLE 39

| 28 | X-3 E-1 | (2E)-3-(1-{[3-(2,6-Dichloro-3-fluorophenyl)-5-(propan-2-yl)-1,2-oxazol-4-yl]carbonyl}-1H-indol-4-yl)prop-2-enoic acid | $^1$H-NMR(CDCl$_3$) δ: 1.45(3H, d, J = 7.0 Hz), 1.46(3H, d, J = 7.0 Hz), 3.31-3.43(1H, m), 6.56(1H, d, J = 16.0 Hz), 6.81(1H, d, J = 3.9 Hz), 7.14(1H, t, J = 8.6 Hz), 7.25-7.31(2H, m), 7.39(1H, t, J = 8.0 Hz), 7.59(1H, d, J = 7.4 Hz), 8.08 (1H, d, J = 16.0 Hz), 8.38(1H, d, J = 8.2 Hz). MS (m/z): 487 (M + H)$^+$. |

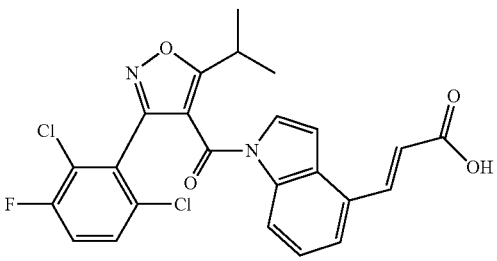 [SMILES: CC(C)c1onc(-c2c(Cl)ccc(F)c2Cl)c1C(=O)n1ccc2c(/C=C/C(=O)O)cccc21]

TABLE 39-continued

| 29 | X-2 E-8 | (2E)-3-(1-{[5-(Propan-2-yl)-3-(2,4,6-trichlorophenyl)-1,2-oxazol-4-yl]carbonyl}-3-methyl-1H-indol-4-yl)prop-2-enoic acid | ¹H-NMR(CDCl₃) δ: 1.44(6H, d, J = 7.3 Hz), 2.39(3H, s), 3.32-3.44(1H, m), 6.46(1H, d, J = 15.7 Hz), 6.99(1H, s), 7.34(2H, s), 7.36(1H, t, J = 7.9 Hz), 7.58(1H, d, J = 7.9 Hz), 8.40(1H, d, J = 7.9 Hz), 8.47(1H, d, J = 15.7 Hz). MS (m/z): 517 (M + H)⁺. |
|---|---|---|---|
| 30 | X-3 E-8 | (2E)-3-(1-{[3-(2,6-Dichloro-3-fluorophenyl)-5-(propan-2-yl)-1,2-oxazol-4-yl]carbonyl}-3-methyl-1H-indol-4-yl)prop-2-enoic acid | ¹H-NMR(CDCl₃) δ: 1.45(6H, d, J = 6.7 Hz), 2.36(3H, s), 3.34-3.47(1H, m), 6.45(1H, d, J = 15.7 Hz), 6.99(1H, s), 7.12(1H, t, J = 8.5 Hz), 7.21-7.31(1H, m), 7.35(1H, t, J = 7.9 Hz), 7.56(1H, d, J = 7.9 Hz), 8.39(1H, d, J = 7.3 Hz), 8.45(1H, d, J = 15.7 Hz). MS (m/z): 501 (M + H)⁺. |

TABLE 40

| 31 | X-68 E-1 | (2E)-3-(1-{[5-(2-Methoxypropan-2-yl)-3-(2,4,6-trichlorophenyl)-1,2-oxazol-4-yl]carbonyl}-1H-indol-4-yl)prop-2-enoic acid | ¹H-NMR(CDCl₃) δ: 1.66(6H, s), 3.07 (3H, s), 6.57(1H, d, J = 16.3 Hz), 6.84 (1H, d, J = 3.6 Hz), 7.30-7.41(4H, m), 7.58(1H, d, J = 7.9 Hz), 8.10(1H, d, J = 16.3 Hz), 8.47 (1H, d, J = 7.9 Hz). MS (m/z): 533(M + H)⁺. |
|---|---|---|---|

TABLE 40-continued

| 32 | X-5 E-12 | (2E)-3-(1-{[5-(tert-Butyl)-3-(2,4,6-trichlorophenyl)-1,2-oxazol-4-yl]carbonyl}-2,3-dihydro-1H-indol-4-yl)prop-2-enoic acid | ¹H-NMR(CDCl₃) δ: 1.47(9H, s), 3.03-3.29(2H, brm), 3.87-4.11(2H, brm), 6.39(1H, d, J = 15.7 Hz), 7.21-7.35(3H, m), 7.40(1H, s), 7.74(1H, d, J = 15.7 Hz), 8.15-8.25(1H, m). MS (m/z): 519 (M + H)⁺. |

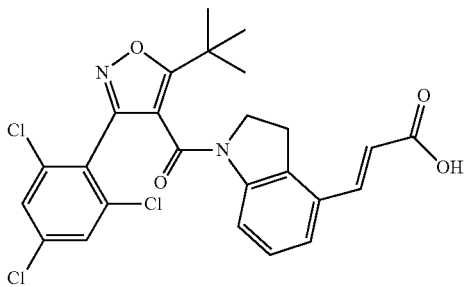 [SMILES: CC(C)(C)c1onc(-c2c(Cl)cc(Cl)cc2Cl)c1C(=O)N1CCc2c(/C=C/C(=O)O)cccc21]

| 33 | X-5 E-8 | (2E)-3-(1-{[5-(tert-Butyl)-3-(2,4,6-trichlorophenyl)-1,2-oxazol-4-yl]carbonyl}-3-methyl-1H-indol-4-yl)prop-2-enoic acid | ¹H-NMR(CDCl₃) δ: 1.45(9H, s), 2.39 (3H, s), 6.45(1H, d, J = 15.7 Hz), 7.00 (1H, s), 7.28-7.33(2H, m), 7.36(1H, t, J = 7.9 Hz), 7.57(1H, d, J = 7.3 Hz), 8.46(1H, d, J = 15.7 Hz), 8.46(1H, d, J = 7.9 Hz). MS (m/z): 531 (M + H)⁺. |

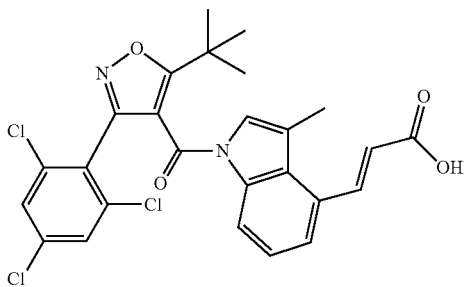 [SMILES: Cc1cn(C(=O)c2c(-c3c(Cl)cc(Cl)cc3Cl)noc2C(C)(C)C)c2cccc(/C=C/C(=O)O)c12]

| 34 | X-75 E-1 | (2E)-3-(1-{[3-(tert-Butyl)-5-(2,4,6-trichlorophenyl)-1,2-oxazol-4-yl]carbonyl}-1H-indol-4-yl)prop-2-enoic acid | ¹H-NMR(CDCl₃) δ: 1.47(9H, s), 6.55 (1H, d, J = 16.3 Hz), 6.76(1H, d, J = 3.6 Hz), 7.25-7.29(1H, m), 7.29-7.35(2H, m), 7.41(1H, t, J = 7.9 Hz), 7.59(1H, d, J = 7.9 Hz), 8.06(1H, d, J = 16.3 Hz), 8.51(1H, d, J = 7.9 Hz). MS (m/z): 517 (M + H)⁺. |

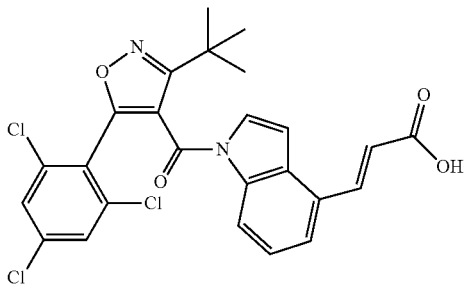 [SMILES: CC(C)(C)c1noc(-c2c(Cl)cc(Cl)cc2Cl)c1C(=O)n1ccc2c(/C=C/C(=O)O)cccc21]

TABLE 41

| | | | |
|---|---|---|---|
| 35 | X-6<br>E-1 | (2E)-3-(1-{[5-(tert-Butyl)-3-(2,4-dichloro-6-fluorophenyl)-1,2-oxazol-4-yl]carbonyl}-1H-indol-4-yl)prop-2-enoic acid | $^1$H-NMR(CDCl$_3$) δ: 1.45(9H, s), 6.56 (1H, d, J = 16.3 Hz), 6.81(1H, d, J = 3.6 Hz), 7.01(1H, ddd, J = 8.9, 2.0, 1.0 Hz), 7.20-7.21(2H, m), 7.40(1H, dd, J = 8.2, 4.1 Hz), 7.59(1H, d, J = 7.3 Hz), 8.08(1H, d, J = 16.3 Hz), 8.42(1H, d, J = 7.9 Hz).<br>MS (m/z): 501 (M + H)$^+$. |
| 36 | X-20<br>E-1 | (2E)-3-(1-{[5-(2-Fluoropropan-2-yl)-3-(2,4,6-trichlorophenyl)-1,2-oxazol-4-yl]carbonyl}-1H-indol-4-yl)prop-2-enoic acid | $^1$H-NMR(CDCl$_3$) δ: 1.88(6H, d, J = 21.8 Hz), 6.57(1H, d, J = 16.3 Hz), 6.86 (1H, d, J = 3.6 Hz), 7.32(1H, d, J = 4.2 Hz), 7.38-7.40(3H, m), 7.59(1H, d, J = 7.3 Hz), 8.10(1H, d, J = 15.7 Hz), 8.45(1H, d, J = 8.5 Hz).<br>MS (m/z): 519 (M − H)$^-$. |
| 37 | X-17<br>E-1 | (2E)-3-(1-{[5-(1-Methylcyclopropyl)-3-(2,4,6-trichlorophenyl)-1,2-oxazol-4-yl]carbonyl}-1H-indol-4-yl)prop-2-enoic acid | $^1$H-NMR(CDCl$_3$) δ: 0.92-0.96(2H, m), 1.30(3H, s), 1.44(2H, dd, J = 6.7, 3.3 Hz), 6.59(1H, d, J = 16.3 Hz), 6.90(1H, d, J = 3.6 Hz), 7.36-7.42(3H, m), 7.61(1H, d, J = 7.9 Hz), 8.13(1H, d, J = 15.7 Hz), 8.44(1H, d, J = 8.5 Hz).<br>MS (m/z): 513 (M − H)$^-$. |

TABLE 42

| 38 | X-7 E-1 | (2E)-3-(1-{[5-(tert-Butyl)-3-(2,6-dichloro-4-methylphenyl)-1,2-oxazol-4-yl]carbonyl}-1H-indol-4-yl)prop-2-enoic acid | ¹H-NMR(CDCl₃) δ: 1.44(9H, s), 2.26 (3H, s), 6.55(1H, d, J = 16.3 Hz), 6.79 (1H, d, J = 4.2 Hz), 7.10(2H, s), 7.34 (1H, d, J = 4.2 Hz), 7.38(1H, dd, J = 8.2, 4.1 Hz), 7.58(1H, d, J = 7.3 Hz), 8.08 (1H, d, J = 15.7 Hz), 8.47(1H, d, J = 8.5 Hz). MS (m/z): 497 (M + H)⁺. |
| --- | --- | --- | --- |
| 39 | X-8 E-1 | (2E)-3-(1-{[3-(2-Bromo-6-chlorophenyl)-5-(tert-butyl)-1,2-oxazol-4-yl]carbonyl}-1H-indol-4-yl)prop-2-enoic acid | ¹H-NMR(CDCl₃) δ: 1.45(9H, s), 6.55 (1H, d, J = 16.3 Hz), 6.80(1H, d, J = 3.6 Hz), 7.15(1H, dd, J = 7.9, 3.9 Hz), 7.30-7.41(3H, m), 7.48(1H, d, J = 8.5 Hz), 7.58(1H, d, J = 7.3 Hz), 8.08(1H, d, J = 16.3 Hz), 8.46(1H, d, J = 8.5 Hz). MS (m/z): 527 (M + H)⁺. |
| 40 | X-5 E-3 | (2E)-3-(1-{[5-(tert-Butyl)-3-(2,4,6-trichlorophenyl)-1,2-oxazol-4-yl]carbonyl}-3-fluoro-1H-indol-4-yl)prop-2-enoic acid | ¹H-NMR(CDCl₃) δ: 1.45(9H, s), 6.56 1H, dd, J = 16.0, 2.1 Hz), 7.10(1H, d, J = 2.4 Hz), 7.35(2H, brs), 7.44(1H, dd, J = 8.2, 4.1 Hz), 7.67(1H, d, J = 7.9 Hz), 8.32(1H, t, J = 16.3 Hz), 8.46 (1H, dd, J = 8.5, 1.8 Hz). MS (m/z): 535 (M + H)⁺. |

TABLE 43

| 41 | X-9 E-1 | (2E)-3-(1-{[5-(tert-Butyl)-3-(2,4-dichloro-6-methylphenyl)-1,2-oxazol-4-yl]carbonyl}-1H-indol-4-yl)prop-2-enoic acid | ¹H-NMR(CDCl₃) δ: 1.40(9H, s), 2.28 (3H, s), 6.56(1H, d, J = 16.3 Hz), 6.84-6.88(1H, brm), 7.17(2H, d, J = 24.2 Hz), 7.28-7.42(2H, m), 7.59(1H, d, J = 7.3 Hz), 8.09(1H, d, J = 15.7 Hz), 8.43(1H, d, J = 8.5 Hz). MS (m/z): 497 (M + H)⁺. |
| --- | --- | --- | --- |

TABLE 43-continued

| 42 | X-36 E-1 | (2E)-3-(1-{[5-(1-Methoxy-2-methylpropan-2-yl)-3-(2,4,6-trichlorophenyl)-1,2-oxazol-4-yl]carbonyl}-1H-indol-4-yl)prop-2-enoic acid | ¹H-NMR(CDCl₃) δ: 1.46(6H, s), 3.01 (3H, s), 3.40-3.58(2H, brm), 6.55(1H, d, J = 16.3 Hz), 6.77(1H, d, J = 3.6 Hz), 7.29(2H, s), 7.33-7.39(2H, m), 7.57(1H, d, J = 7.3 Hz), 8.07(1H, d, J = 16.3 Hz), 8.45(1H, d, J = 7.9 Hz). MS (m/z): 547 (M + H)⁺. |
| --- | --- | --- | --- |
| 43 | X-17 E-8 | (2E)-3-(3-Methyl-1-{[5-(1-methylcyclopropyl)-3-(2,4,6-trichlorophenyl)-1,2-oxazol-4-yl]carbonyl}-1H-indol-4-yl)prop-2-enoic acid | ¹H-NMR(CDCl₃) δ: 0.92-0.97(2H, m), 1.33(3H, s), 1.42-1.46(2H, m), 2.45(3H, s), 6.47(1H, d, J = 15.7 Hz), 7.10(1H, s), 7.35-7.37(3H, m), 7.59(1H, d, J = 7.3 Hz), 8.44(1H, d, J = 8.5 Hz), 8.51(1H, d, J = 15.7 Hz). MS (m/z): 527(M − H)⁻. |

TABLE 44

| 44 | X-35 E-1 | (2E)-3-(1-{[5-(1-Methoxycyclopropyl)-3-(2,4,6-trichlorophenyl)-1,2-oxazol-4-yl]carbonyl}-1H-indol-4-yl)prop-2-enoic acid | ¹H-NMR(CDCl₃) δ: 1.38(2H, dd, J = 8.2, 5.7 Hz), 1.53(2H, dd, J = 7.9, 5.4 Hz), 3.19(3H, s), 6.57(1H, d, J = 16.3 Hz), 6.91(1H, d, J = 3.6 Hz), 7.36 (1H, dd, J = 8.2, 4.1 Hz), 7.41 (2H, s), 7.45(1H, d, J = 3.6 Hz), 7.58(1H, d, J = 7.3 Hz), 8.11(1H, d, J = 16.3 Hz), 8.43 (1H, d, J = 8.5 Hz). MS (m/z): 529(M − H)⁻. |
| --- | --- | --- | --- |

TABLE 44-continued

| 45 | X-20 E-3 | (2E)-3-(3-Fluoro-1-{[5-(2-fluoropropan-2-yl)-3-(2,4,6-trichlorophenyl)-1,2-oxazol-4-yl]carbonyl}-1H-indol-4-yl)prop-2-enoic acid | $^1$H-NMR(CDCl$_3$) δ: 1.88(6H, d, J = 21.8 Hz), 6.55(1H, dd, J = 16.0, 2.1 Hz), 7.11(1H, d, J = 2.4 Hz), 7.39(2H, s), 7.42(1H, dd, J = 8.2, 4.1 Hz), 7.66 (1H, d, J = 7.9 Hz), 8.32(1H, d, J = 15.7 Hz), 8.45(1H, d, J = 8.5 Hz). MS (m/z): 537 (M − H)$^−$. |
| 46 | X-23 E-1 | (2E)-3-(1-{[3-(2,4-Dichloro-6-fluorophenyl)-5-(2-fluoropropan-2-yl)-1,2-oxazol-4-yl]carbonyl}-1H-indol-4-yl)prop-2-enoic acid | $^1$H-NMR(CDCl$_3$) δ: 1.88(6H, d, J = 21.8 Hz), 6.57(1H, d, J = 16.3 Hz), 6.85 (1H, d, J = 4.2 Hz), 7.07(1H, dd, J = 9.1, 1.8 Hz), 7.25(1H, d, J = 4.2 Hz), 7.39 (1H, dd, J = 8.2, 4.1 Hz), 7.60 (1H, d, J = 7.9 Hz), 8.11(1H, d, J = 15.7 Hz), 8.43(1H, d, J = 7.9 Hz). MS (m/z): 503 (M − H)$^−$. |

TABLE 45

| 47 | X-23 E-8 | (2E)-3-(1-{[3-(2,4-Dichloro-6-fluorophenyl)-5-(2-fluoropropan-2-yl)-1,2-oxazol-4-yl]carbonyl}-3-methyl-1H-indol-4-yl)prop-2-enoic acid | $^1$H-NMR(CDCl$_3$)δ: 1.88(6H, d, J = 21.8 Hz), 2.41(3H, s), 6.46(1H, d, J = 15.7 Hz), 6.95(1H, s), 7.06(1H, dd, J = 8.8, 2.1 Hz), 7.25-7.27(1H, m), 7.36(1H, dd, J = 7.9, 3.9 Hz), 7.58(1H, d, J = 7.3 Hz), 8.44(1 H, d, J = 8.5 Hz), 8.50(1H, d, J = 15.7 Hz). MS(m/z): 517(M − H)$^−$. |

TABLE 45-continued

| 48 | X-5 E-9 | (2E)-3-(1-{[5-(tert-Butyl)-3-(2,4,6-trichlorophenyl)-1,2-oxazole-4-carbonyl]-7-fluoroindol-4-yl}prop-2-enoic acid | ¹H-NMR(CDCl₃)δ: 1.54(9H, s), 6.47(1H, d, J = 15.7 Hz), 6.75-6.77(1H, brm), 7.05(1H, dd, J = 11.5, 8.5 Hz), 7.18(2H, s), 7.37(1H, d, J = 3.6 Hz), 7.50(1H, dd, J = 8.5, 4.2 Hz), 7.98(1H, d, J = 16.3 Hz). MS(m/z): 533(M − H)⁻. |

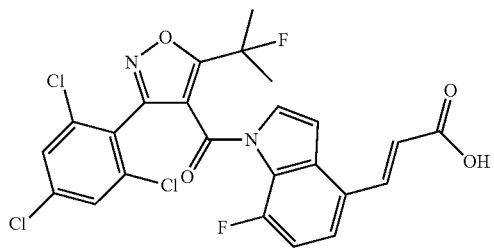 [SMILES: CC(C)(F)c1onc(-c2c(Cl)cc(Cl)cc2Cl)c1C(=O)n1ccc2c(/C=C/C(=O)O)ccc(F)c21]

| 49 | X-26 E-8 | (2E)-3-(1-{[3-(2,6-Dichloro-4-fluorophenyl)-5-(2-fluoropropan-2-yl)-1,2-oxazol-4-yl]carbonyl}-3-methyl-1H-indol-4-yl)prop-2-enoic acid | ¹H-NMR(CDCl₃)δ: 1.88(6H, d, J = 21.2 Hz), 2.41(3H, s), 6.45(1H, d, J = 15.7 Hz), 7.02(1H, s), 7.11(2H, d, J = 7.9 Hz), 7.35(1H, dd, J = 7.9, 3.9 Hz), 7.58(1H, d, J = 7.9 Hz), 8.43-8.52(2H, m). MS(m/z): 517(M − H)⁻. |

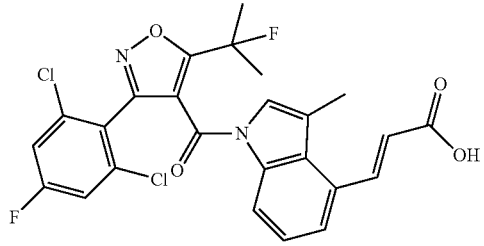

TABLE 46

| 50 | X-20 E-14 | (2E)-3-(7-Fluoro-1-{[5-(2-fluoropropan-2-yl)-3-(2,4,6-trichlorophenyl)-1,2-oxazol-4-yl]carbonyl}-3-methyl-1H-indol-4-yl)prop-2-enoic acid | ¹H-NMR(DMSO-d₆)δ: 1.87(6H, d, J = 22.4 Hz), 2.34(3H, s), 6.46(1H, d, J = 15.7 Hz), 7.18(1H, dd, J = 11.2, 8.8 Hz), 7.54(1H, s), 7.69(1H, dd, J = 8.5, 4.2 Hz), 7.77(2H, s), 8.18(1H, d, J = 15.7 Hz), 12.48(1H, s). MS(m/z): 551(M − H)⁻. |

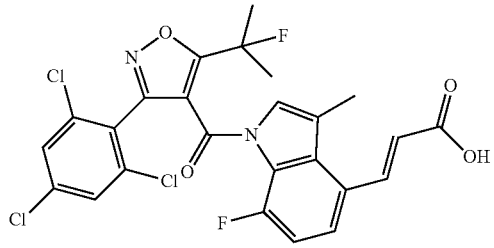 [SMILES: Cc1cn(C(=O)c2c(-c3c(Cl)cc(Cl)cc3Cl)noc2C(C)(C)F)c2c(F)ccc(/C=C/C(=O)O)c12]

| 51 | X-52 E-8 | (2E)-3-(1-{[5-(1,1-Difluoroethyl)-3-(2,4,6-trichlorophenyl)-1,2-oxazol-4-yl]carbonyl}-3-methyl-1H-indol-4-yl)prop-2-enoic acid | ¹H-NMR(CDCl₃)δ: 2.16(3H, t, J = 18.7 Hz), 2.43(3H, s), 6.46(1H, d, J = 15.7 Hz), 7.03(1H, s), 7.35(1H, d, J = 7.9 Hz), 7.39(2H, s), 7.59(1H, d, J = 7.9 Hz), 8.45(1H, d, J = 7.9 Hz), 8.50(1H, d, J = 15.7 Hz). MS(m/z): 539(M + H)⁺. |

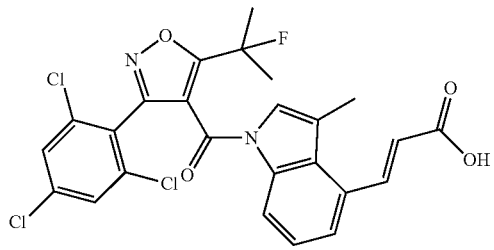

TABLE 46-continued

| | | | |
|---|---|---|---|
| 52 | X-27<br>E-8 | (2E)-3-(1-{[3-(2-Chloro-6-fluorophenyl)-5-(2-fluoropropan-2-yl)-1,2-oxazol-4-yl]carbonyl}-3-methyl-1H-indol-4-yl)prop-2-enoic acid | $^1$H-NMR(CDCl$_3$)δ: 1.89(6H, d, J = 21.8 Hz), 2.39(3H, s), 6.44(1H, d, J = 15.7 Hz), 6.95-7.03(2H, m), 7.21(1H, d, J = 8.5 Hz), 7.28-7.37(2H, m), 7.56(1H, d, J = 7.9 Hz), 8.43-8.51(2H, m). MS(m/z): 485(M + H)$^+$. |

TABLE 47

| | | | |
|---|---|---|---|
| 53 | X-19<br>E-8 | (2E)-3-(1-{[3-(2,6-Dichlorophenyl)-5-(2-fluoropropan-2-yl)-1,2-oxazol-4-yl]carbonyl}-3-methyl-1H-indol-4-yl)prop-2-enoic acid | $^1$H-NMR(CDCl$_3$)δ: 1.89(6H, d, J = 21.8 Hz), 2.39(3H, s), 6.44(1H, d, J = 15.7 Hz), 7.06(1H, s), 7.23-7.37(4H, m), 7.56(1H, d, J = 7.9 Hz), 8.44-8.50(2H, m). MS(m/z): 501(M + H)$^+$. |
| 54 | X-28<br>E-8 | (2E)-3-(1-{[3-(4-Chloro-2,6-difluorophenyl)-5-(2-fluoropropan-2-yl)-1,2-oxazol-4-yl]carbonyl}-3-methyl-1H-indol-4-yl)prop-2-enoic acid | $^1$H-NMR(CDCl$_3$)δ: 1.85(6H, d, J = 21.8 Hz), 2.43(3H, s), 6.46(1H, d, J = 15.7 Hz), 6.94-7.00(3H, m), 7.37(1H, dd, J = 7.9, 3.9 Hz), 7.59(1H, d, J = 7.3 Hz), 8.40-8.45(1H, brm), 8.51(1H, d, J = 15.7 Hz). MS(m/z): 503(M + H)$^+$. |
| 55 | X-30<br>E-8 | (2E)-3-(1-{[3-(4-Chloro-2,6-dimethylphenyl)-5-(2-fluoropropan-2-yl)-1,2-oxazol-4-yl]carbonyl}-3-methyl-1H-indol-4-yl)prop-2-enoic acid | $^1$H-NMR(CDCl$_3$)δ: 1.85(6H, d, J = 21.2 Hz), 2.20(6H, s), 2.43(3H, s), 6.45 (1H, d, J = 15.7 Hz), 6.90(1H, s), 7.03 (2H, s), 7.34(1H, dd, J = 7.9, 3.9 Hz), 7.57(1H, d, J = 7.9 Hz), 8.44(1H, d, J = 8.5 Hz), 8.49(1H, d, J = 15.7 Hz). MS(m/z): 493(M − H)$^-$. |

TABLE 48

| 56 | X-24 E-8 | (2E)-3-(1-{[3-(2,6-Dichloro-4-methylphenyl)-5-(2-fluoropropan-2-yl)-1,2-oxazol-4-yl]carbonyl}-3-methyl-1H-indol-4-yl)prop-2-enoic acid | 1H-NMR(CDCl$_3$)δ: 1.88(6H, d, J = 21.8 Hz), 2.28(3H, s), 2.40(3H, s), 6.44 (1H, d, J = 15.7 Hz), 7.06(1H, s), 7.13 (2H, s), 7.34(1H, dd, J = 7.9, 3.9 Hz), 7.56(1H, d, J = 7.3 Hz), 8.45-8.50(2H, m). MS(m/z): 515(M + H)$^+$. |
| --- | --- | --- | --- |
| 57 | X-35 E-8 | (2E)-3-(1-{[5-(1-Methoxycyclopropyl)-3-(2,4,6-trichlorophenyl)-1,2-oxazol-4-yl]carbonyl}-3-methyl-1H-indol-4-yl)prop-2-enoic acid | $^1$H-NMR(CDCl$_3$)δ: 1.37(2H, dd, J = 7.9, 5.4 Hz), 1.52(2H, dd, J = 7.9, 5.4 Hz), 2.47(3H, s), 3.20(3H, s), 6.46(1 H, d, J = 15.7 Hz), 7.16(1H, s), 7.33 (1H, dd, J = 7.9, 3.9 Hz), 7.40(2H, s), 7.58(1H, d, J = 7.3 Hz), 8.44(1H, d, J = 7.9 Hz), 8.52(1H, d, J = 15.7 Hz). MS(m/z): 545(M + H)$^+$. |
| 58 | X-31 E-8 | (2E)-3-(1-{[3-(2,4-Dichloro-6-methoxyphenyl)-5-(2-fluoropropan-2-yl)-1,2-oxazol-4-yl]carbonyl}-3-methyl-1H-indol-4-yl)prop-2-enoic acid | $^1$H-NMR(CDCl$_3$)δ: 1.88(6H, d, J = 21.8 Hz), 2.39(3H, d, J = 1.2 Hz), 3.58(3 H, s), 6.45(1H, d, J = 15.7 Hz), 6.66 (1H, d, J = 1.8 Hz), 6.97(1H, s), 7.08 (1H, d, J = 1.8 Hz), 7.34(1H, dd, J = 7.9, 3.9 Hz), 7.57(1H, d, J = 7.9 Hz), 8.43-8.51(2H, m). MS(m/z): 531(M + H)$^+$. |

TABLE 49

| 59 | X-25 E-8 | (2E)-3-(1-{[3-(2,4-Dichloro-6-methylphenyl)-5-(2-fluoropropan-2-yl)-1,2-oxazol-4-yl]carbonyl}-3-methyl-1H-indol-4-yl)prop-2-enoic acid | $^1$H-NMR(CDCl$_3$)δ: 1.79-1.92(6H, m), 2.30(3H, s), 2.43(3H, s), 6.45(1H, d, J = 15.7 Hz), 7.04(1H, s), 7.17(1H, d, J = 1.8 Hz), 7.23(1H, d, J = 1.8 Hz), 7.34(1H, dd, J = 8.2, 4.1 Hz), 7.57(1H, d, J = 7.9 Hz), 8.44(1 H, d, J = 8.5 Hz), 8.50(1H, d, J = 15.7 Hz). MS(m/z): 513(M − H)$^-$. |
| --- | --- | --- | --- |

TABLE 49-continued

| 60 | X-29 E-8 | (2E)-3-(1-{[5-(2-Fluoropropan-2-yl)-3-(2,4,6-trimethylphenyl)-1,2-oxazol-4-yl]carbonyl}-3-methyl-1H-indol-4-yl)prop-2-enoic acid | ¹H-NMR(CDCl₃)δ: 1.85(6H, d, J = 21.8 Hz), 2.19(6H, s), 2.22(3H, s), 2.42 (3H, s), 6.44(1H, d, J = 15.7 Hz), 6.83 (2H, s), 6.92(1H, s), 7.29-7.35(1H, m), 7.56(1H, d, J = 7.9 Hz), 8.43-8.52(2H, m). MS(m/z): 475(M + H)⁺. |
| 61 | X-53 E-8 | (2E)-3-(3-Methyl-1-{[3-(2,4,6-trichlorophenyl)-5-(trifluoromethyl)-1,2-oxazol-4-yl]carbonyl}-1H-indol-4-yl)prop-2-enoic acid | ¹H-NMR(CDCl₃)δ: 2.43(3H, s), 6.47 (1H, d, J = 15.7 Hz), 6.93(1H, s), 7.36-7.42(3H, m), 7.61(1H, d, J = 7.9 Hz), 8.44(1H, d, J = 7.9 Hz), 8.48(1H, d, J = 15.7 Hz). MS(m/z): 540(M − H)⁻. |

TABLE 50

| 62 | X-22 E-8 | (2E)-3-(1-{[3-(2,4-Dichlorophenyl)-5-(2-fluoropropan-2-yl)-1,2-oxazol-4-yl]carbonyl}-3-methyl-1H-indol-4-yl)prop-2-enoic acid | ¹H-NMR(CDCl₃)δ: 1.86(6H, d, J = 21.2 Hz), 2.40(3H, s), 6.45(1H, d, J = 15.7 Hz) , 6.95(1H, s), 7.24-7.45(5H, m), 7.58(1H, d, J = 7.9 Hz), 8.40-8.52(2H, m). MS(m/z): 501(M + H)⁺. |
| 63 | X-32 E-8 | (2E)-3-(1-{[3-(2,4-Dichloro-5-fluorophenyl)-5-(2-fluoropropan-2-yl)-1,2-oxazol-4-yl]carbonyl}-3-methyl-1H-indol-4-yl)prop-2-enoic acid | ¹H-NMR(CDCl₃)δ: 1.86(3H, d, J = 21.8 Hz), 2.42(3H, s), 6.46(1H, d, J = 15.7 Hz), 6.96(1H, s), 7.34-7.38(2H, m), 7.44(1H, d, J = 7.1 Hz), 7.59(1H, d, J = 7.9 Hz), 8.40-8.51(2H, m). MS(m/z): 517(M − H)⁻. |

TABLE 50-continued

| 64 | X-20 E-15 | (2E)-3-(3-Acetyl-1-{[5-(2-fluoropropan-2-yl)-3-(2,4,6-trichlorophenyl)-1,2-oxazol-4-yl]carbonyl}-1H-indol-4-yl)prop-2-enoic acid | $^1$H-NMR(CDCl$_3$)δ: 1.91(6H, d, J = 21.8 Hz), 2.53 (3H, s), 6.33 (1H, dd, J = 15.7, 1.2 Hz), 7.38(1H, s), 7.45(1H, t, J = 7.9 Hz), 7.64(1H, d, J = 7.3 Hz), 7.86 (1H, s), 8.45(1H, d, J = 8.5 Hz), 8.97 (1H, d, J = 15.7 Hz). MS(m/z): 561(M − H)$^-$. |
|---|---|---|---|

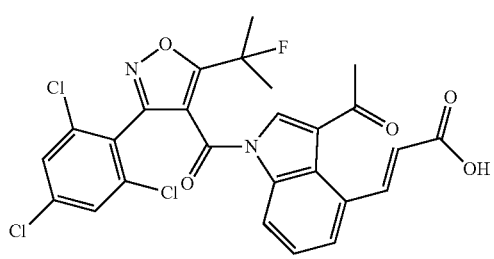

TABLE 51

| 65 | X-20 E-16 | (2E)-3-(3-Ethyl-1-{[5-(2-fluoropropan-2-yl)-3-(2,4,6-trichlorophenyl)-1,2-oxazol-4-yl]carbonyl}-1H-indol-4-yl)prop-2-enoic acid | $^1$H-NMR(CDCl$_3$)δ: 1.27(3H, t, J = 7.3 Hz), 1.88(6H, d, J = 21.8 Hz), 2.86(2 H, q, J = 7.3 Hz), 6.44(1H, d, J = 15.7 Hz), 7.00(1H, s), 7.33-7.38(3H, m), 7.57(1H, d, J = 7.3 Hz), 8.43-8.49(2H, m). MS(m/z): 547(M − H)$^-$. |
|---|---|---|---|

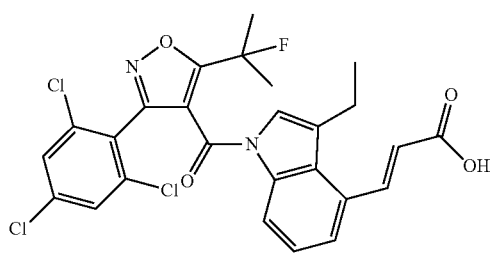 [SMILES: Cc1cn(C(=O)c2c(-c3c(Cl)cc(Cl)cc3Cl)noc2C(C)(C)F)c2cccc(/C=C/C(=O)O)c12]

| 66 | X-20 E-4 | (2E)-3-(3-Chloro-1-{[5-(2-fluoropropan-2-yl)-3-(2,4,6-trichlorophenyl)-1,2-oxazol-4-yl]carbonyl}-1H-indol-4-yl)prop-2-enoic acid | $^1$H-NMR(CDCl$_3$)δ: 1.89(6H, d, J = 21.8 Hz), 6.46(1H, d, J = 15.7 Hz), 7.29 (1H, s), 7.38(2H, s), 7.42(1H, t, J = 8.2 Hz), 7.63(1H, d, J = 7.9 Hz), 8.47(1 H, d, J = 8.5 Hz), 8.94(1H, d, J = 15.7 Hz). MS(m/z): 553(M − H)$^-$. |
|---|---|---|---|

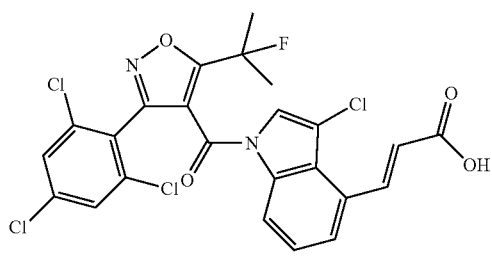 [SMILES: CC(C)(F)c1onc(-c2c(Cl)cc(Cl)cc2Cl)c1C(=O)n1cc(Cl)c2c(/C=C/C(=O)O)cccc21]

| 67 | X-20 E-19 | (2E)-[6-Fluoro-1-{[5-(2-fluoropropan-2-yl)-3-(2,4,6-trichlorophenyl)-1,2-oxazol-4-yl]carbonyl}-3,4-dihydrobenzo[cd]indol-5(1H)-ylidene]ethanoic acid | $^1$H-NMR(CDCl$_3$)δ: 1.88(6H, d, J = 21.8 Hz), 2.84(2H, t, J = 6.3 Hz), 3.34-3.45(2H, m), 6.80(1H, s), 6.97(1H, s), 7.08(1H, dd, J = 12.1, 8.5 Hz), 7.37 (2H, s), 8.13(1H, t, J = 4.5 Hz), 10.84 (1H, brs). |
|---|---|---|---|

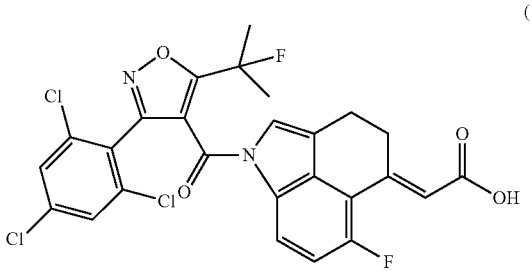

TABLE 52

| 68 | X-49 E-8 | (2E)-3-(1-{[3-(4-Bromo-2,6-dichlorophenyl)-5-(2-fluoropropan-2-yl)-1,2-oxazol-4-yl]carbonyl}-3-methyl-1H-indol-4-yl)prop-2-enoic acid | $^1$H-NMR(CDCl$_3$)δ: 1.88(6H, d, J = 22.4 Hz), 2.42(3H, s), 6.45(1H, d, J = 15.7 Hz), 7.02(1H, s), 7.36(1H, dd, J = 7.9, 3.9 Hz), 7.51(2H, s), 7.58(1H, d, J = 6.7 Hz), 8.43-8.52(2H, m). MS(m/z): 577(M − H)$^-$. |
|---|---|---|---|

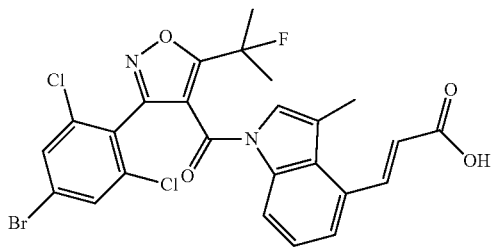

| 69 | X-22 E-17 | (2E)-[1-{[3-(2,4-Dichlorophenyl)-5-(2-fluoropropan-2-yl)-1,2-oxazol-4-yl]carbonyl}-3,4-dihydrobenzo[cd]indol-5(1H)-ylidene]ethanoic acid | $^1$H-NMR(CDCl$_3$)δ: 1.86(6H, d, J = 21.8 Hz), 2.83-2.89(2H, m), 3.39-3.45(2H, m), 6.53(1H, s), 7.24-7.39(5H, m), 7.44(1H, d, J = 7.9 Hz), 7.51(1H, d, J = 7.9 Hz). MS(m/z): 513(M + H)$^+$. |
|---|---|---|---|

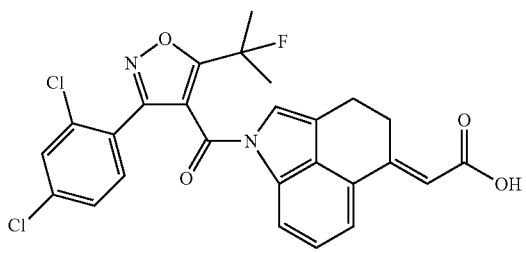 [SMILES: CC(C)(F)c1onc(-c2ccc(Cl)cc2Cl)c1C(=O)n1cc2c3c(cccc31)/C(=C/C(=O)O)CC2]

TABLE 53

| 70 | X-74 E-8 | (2E)-3-(1-{[3-(2,6-Dichloro-4-cyclopropylphenyl)-5-(2-fluoropropan-2-yl)-1,2-oxazol-4-yl]carbonyl}-3-methyl-1H-indol-4-yl)prop-2-enoic acid | $^1$H-NMR(CDCl$_3$)δ: 0.67(2H, dt, J = 5.8, 4.5 Hz), 1.02(2H, dt, J = 7.4, 5.5 Hz), 1.76-1.83(1H, m), 1.88(6H, d, J = 21.9 Hz), 2.40(3H, s), 6.45(1H, d, J = 15.8 Hz), 6.98(2H, s), 7.04(1H, s), 7.34(1H, dd, J = 7.9, 3.9 Hz), 7.57(1H, d, J = 7.9 Hz), 8.46-8.51(2H, m). MS(m/z): 539(M − H)$^-$. |
|---|---|---|---|

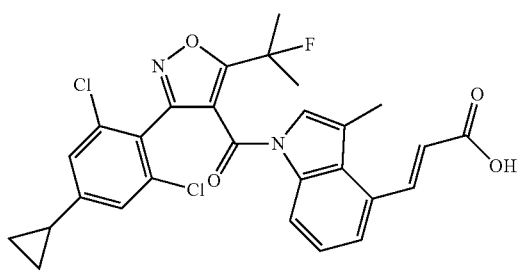 [SMILES: Cc1cn(C(=O)c2c(-c3c(Cl)cc(C4CC4)cc3Cl)noc2C(C)(C)F)c2cccc(/C=C/C(=O)O)c12]

Example 71

(2E)-3-(3-Cyclopropyl-1-{[5-(2-fluoropropan-2-yl)-3-(2,4,6-trichlorophenyl)-1,2-oxazol-4-yl]carbonyl}-3-methyl-1H-indol-4-yl)prop-2-enoic acid

[Formula 70]

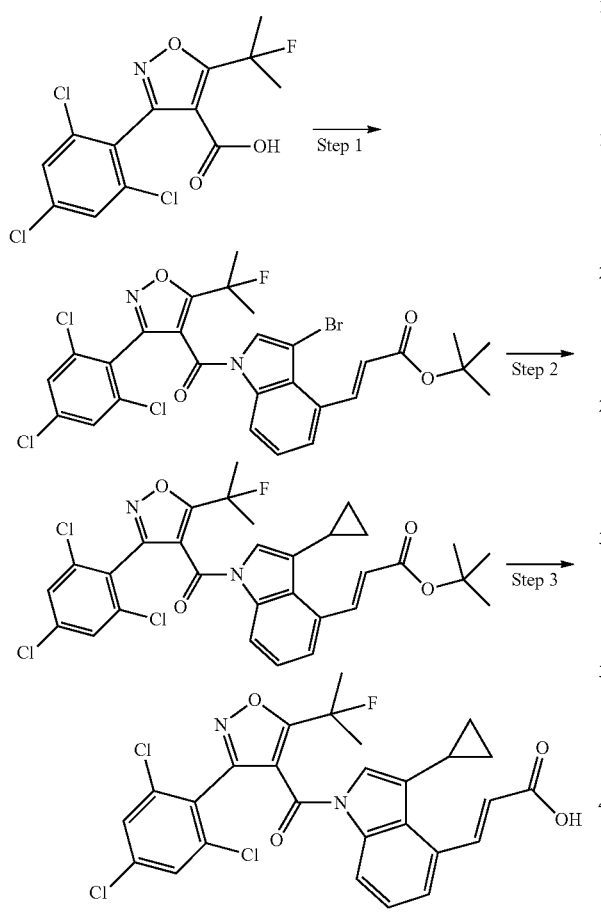

[Step 1]tert-Butyl (2E)-3-(3-bromo-1-{[5-(2-fluoropropan-2-yl)-3-(2,4,6-trichlorophenyl)-1,2-oxazol-4-yl]carbonyl}-1H-indol-4-yl)prop-2-enoate The title compound (3.27 g) was obtained by the same method as in step 1 of Example 21 using the compound (2.08 g) obtained in Reference Example X-20 and the compound (1.90 g) obtained in Reference Example E-5.

$^1$H-NMR (CDCl$_3$) δ: 1.55 (9H, s), 1.89 (6H, d, J=21.8 Hz), 6.36 (1H, d, J=15.7 Hz), 7.29-7.41 (4H, m), 7.57 (1H, d,J=7.3 Hz), 8.43 (1H, d, J=8.5 Hz), 8.88 (1H, d, J=15.7 Hz).

[Step 2] tert-Butyl (2E)-3-(3-cyclopropyl-1-{[5-(2-fluoropropan-2-yl)-3-(2,4,6-trichlorophenyl)-1,2-oxazol-4-yl]carbonyl}-3-methyl-1H-indol-4-yl)prop-2-enoate The compound (1.50 g) obtained in the preceding step 1, cyclopropylboronic acid (0.216 g), tripotassium phosphate (1.45 g), tricyclohexylphosphine (0.128 g), and palladium acetate (51.3 mg) were suspended in toluene (30 ml) and water (0.1 ml), and the mixture was stirred at 90° C. for 2 hours under a nitrogen atmosphere. After being allowed to cool, the reaction solution was diluted with ethyl acetate, washed with water and saturated saline in this order and then dried over anhydrous magnesium sulfate. The solvent was distilled off under reduced pressure, and the residue obtained was purified by silica gel column chromatography (n-hexane/ethyl acetate) to obtain the title compound (863.9 mg), $^1$H-NMR (CDCl$_3$) δ: 0.54-0.59 (2H, m), 1.01 (2H, dd, J=8.2, 1.5 Hz), 1.54 (9H, s), 1.87 (6H, d, J=21.2 Hz),1.88-1.99 (0H, m), 6.38 (1H, d, J=15.7 Hz), 6.87 (1H, s), 7.29-7.36 (3H, m), 7.56 (1H, d, J=7.9 Hz), 8.40 (1H, d, J=8.5 Hz), 8.74 (1H, d, J=15.7 Hz).

[Step 3](2E)-3-(3-Cyclopropyl-1-{[5-(2-fluoropropan-2-yl)-3-(2,4,6-trichlorophenyl)-1,2-oxazol-4-yl]carbonyl}-3-methyl-1H-indol-4-yl)prop-2-enoic acid The title compound (547.0 mg) was obtained by the same method as in step 3 of Example 10 using the compound (863.9 mg) obtained in the preceding step 2.

$^1$H-NMR (CDCl$_3$) δ: 0.55-0.60 (2H, m), 1.01-1.05 (2H, m), 1.87 (6H, d, J=21.8 Hz), 1.88-1.97 (7H, m), 6.46 (1H, d,J=15.7 Hz), 6.91 (1H, s), 7.33-7.38 (3H, m), 7.61 (1H,d, J=7.9 Hz), 8.44 (1H, d, J=8.5 Hz), 8.97 (1H, d,J=15.7 Hz).

MS (m/z): 559 (M−H)$^-$.

Example 72

(2E)-3-(1-{[5-(tert-Butyl)-3-(2,4,6-trichlorophenyl)-1,2-oxazol-4-yl]carbonyl}-3-(difluoromethyl)-1H-indol-4-yl)prop-2-enoic acid

[Formula 71]

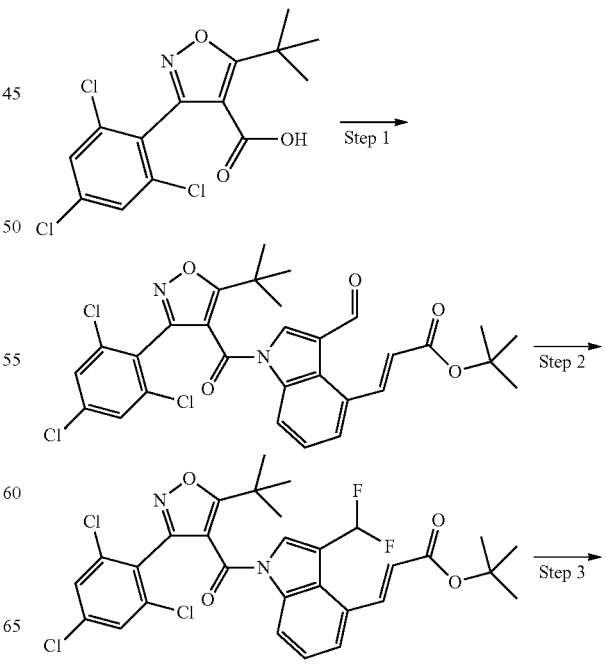

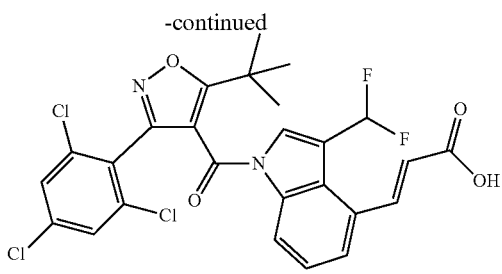

[Step 1] tert-Butyl (2E)-3-(1-{[5-(tert-butyl)-3-(2,4,6-trichlorophenyl)-1,2-oxazol-4-yl]carbonyl}-3-formyl-1H-indol-4-yl)prop-2-enoate The title compound (1.95 g) was obtained by the same method as in step 1 of Example 21 using the compound (1.20 g) obtained in Reference Example X-5 and the compound (0.93 g) obtained in Reference Example E-6.

$^1$H-NMR (CDCl$_3$) δ: 1.50 (9H, s), 1.58 (9H, s), 6.37 (1H, d, J=16.3 Hz), 7.27-7.28 (2H, m), 7.46 (1H, dd, J=8.2, 4.1 Hz), 7.68 (1H, d, J=7.3 Hz), 7.90 (1H, s), 8.41 (1H, d, J=8.5 Hz), 8.88 (1H, d, J=16.3 Hz), 9.96 (1H, s).

MS (m/z): 545 (M+H)$^+$.

[Step 2] tert-Butyl (2E)-3-(1-{[5-(tert-butyl)-3-(2,4,6-trichlorophenyl)-1,2-oxazol-4-yl]carbonyl}-3-(difluoromethyl)-1H-indol-4-yl)prop-2-enoate To a solution of the compound (300 mg) obtained in the preceding step 1 in dichloromethane (5 ml), diethylamino sulfur trifluoride (0.36 ml) was added under ice cooling under a nitrogen atmosphere, and the mixture was stirred at the same temperature as above for 4 hours and then stirred overnight at room temperature. The reaction solution was poured into a mixed solution of ethyl acetate and a saturated aqueous solution of sodium bicarbonate and separated into two layers. The organic layer was washed with water and saturated saline in this order and then dried over anhydrous sodium sulfate. The solvent was distilled off under reduced pressure, and the residue obtained was purified by silica gel column chromatography (n-hexane/ethyl acetate) to obtain the title compound (282 mg).

$^1$H-NMR (CDCl$_3$) δ: 1.47 (9H, s), 1.55 (9H, s), 6.37 (1H, d, J=15.1 Hz), 6.89 (1H, t, J=55.0 Hz), 7.28-7.31 (2H, m), 7.43 (1H, dd, J=7.9, 3.9 Hz), 7.49 (1H, dd, J=1.8, 0.9 Hz), 7.58 (1H, d, J=7.3 Hz), 8.06 (1H, d, J=15.7 Hz), 8.43 (1H, d, J=7.3 Hz).

MS (m/z): 623 (M+H)$^+$.

[Step 3] (2E)-3-(1-{[5-(tert-Butyl)-3-(2,4,6-trichlorophenyl)-1,2-oxazol-4-yl]carbonyl}-3-(difluoromethyl)-1H-indol-4-yl)prop-2-enoic acid The title compound (93 mg) was obtained by the same method as in step 3 of Example 10 using the compound (280 mg) obtained in the preceding step 2.

$^1$H-NMR (CDCl$_3$) δ: 1.48 (9H, s), 6.47 (1H, d, J=15.7 Hz), 6.89 (1H, t, J=55.0 Hz), 7.30 (2H, s), 7.47 (1H, dd, J=7.9, 3.9 Hz), 7.51 (1H, dd, J=2.1, 1.1 Hz), 7.64 (1H, d, J=7.9 Hz), 8.27 (1H, d, J=15.7 Hz), 8.48 (1H, d, J=7.9 Hz).

MS (m/z): 567 (M+H)$^+$.

Example 73

(2E)-3-(1-{[5-(6-Ethenylpyridin-3-yl)-3-(2,4,6-trichlorophenyl)-1,2-oxazol-4-yl]carbonyl}-1H-indol-4-yl)prop-2-enoic acid

[Formula 72]

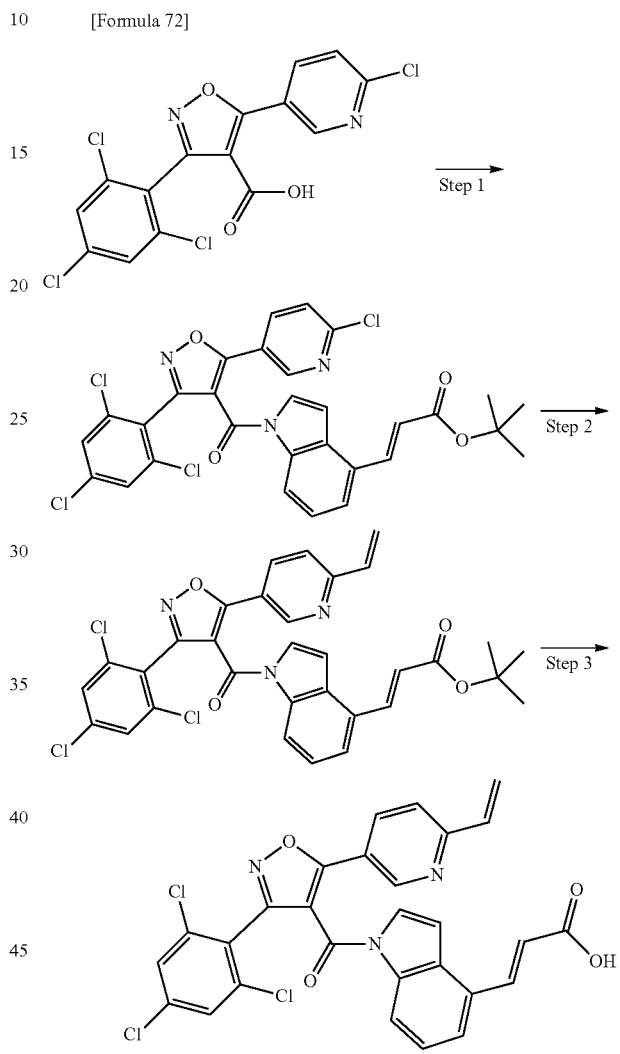

[Step 1] tert-Butyl (2E)-3-(1-{[5-(6-chloropyridin-3-yl)-3-(2,4,6-trichlorophenyl)-1,2-oxazol-4-yl]carbonyl}-1H-indol-4-yl)prop-2-enoate The title compound (518 mg) was obtained by the same method as in step 1 of Example 21 using the compound (464 mg) obtained in Reference Example X-54 and the compound (0.31 g) obtained in Reference Example E-1.

$^1$H-NMR (CDCl$_3$) δ: 1.54 (9H, s), 6.46 (1H, d, J=15.7 Hz), 6.71-6.76 (1H, m), 7.14 (1H, d, J=4.2 Hz), 7.38-7.40 (4H, m), 7.56 (1H, d, J=7.9 Hz), 7.85 (1H, d, J=15.7 Hz), 8.00 (1H, dd, J=8.5, 1.8 Hz), 8.39 (1H, d, J=7.9 Hz), 8.77 (1H, d, J=2.4 Hz).

MS (m/z): 628 (M+H)$^+$.

[Step 2] tert-Butyl (2E)-3-(1-{[5-(6-ethenylpyridin-3-yl)-3-(2,4,6-trichlorophenyl)-1,2-oxazol-4-yl]carbonyl}-1H-indol-4-yl)prop-2-enoate To a suspension of the compound (250 mg) obtained in the preceding step 1, potassium vinyl trifluoroborate (84 mg), and N,N-di(propan-2-yl)ethylamine (0.14 ml) in (propan-2-yl) alcohol (3 ml) and water (0.6 ml), [1,1'-bis(diphenylphosphino)ferrocene]palladium(II) dichloride-dichloromethane adduct was added, and the mixture was stirred at 120° C. for 1 hour using a microwave apparatus. After cooling, the reaction solution was poured into a mixed solution of ethyl acetate and water and separated into two layers. The organic layer was washed with water and saturated saline in this order and then dried over anhydrous sodium sulfate. The solvent was distilled off under reduced pressure, and the residue obtained was purified by silica gel column chromatography (n-hexane/ethyl acetate) to obtain the title compound (50 mg).

$^1$H-NMR (CDCl$_3$) δ: 1.56 (9H, s), 5.61 (1H, d, J=10.9 Hz), 6.30 (1H, d, J=17.5 Hz), 6.46 (1H, d, J=16.3 Hz), 6.72 (1H, d, J=4.2 Hz), 6.79 (1H, dd, J=17.2, 10.6 Hz), 7.17 (1H, d, J=3.6 Hz), 7.37 (2H, dd, J=15.1, 7.9 Hz), 7.41 (2H, s), 7.56 (1H, d, J=7.9 Hz), 7.85 (1H, d, J=15.7 Hz), 7.94 (1H, dd, J=8.5, 2.4 Hz), 8.42 (1H, d, J=8.5 Hz), 8.92 (1H, d, J=2.4 Hz).

MS (m/z): 620 (M+H)$^+$.

[Step 3] (2E)-3-(1-{[5-(6-Ethenylpyridin-3-yl)-3-(2,4,6-trichlorophenyl)-1,2-oxazol-4-yl]carbonyl}-1H-indol-4-yl)prop-2-enoic acid The title compound (5.5 mg) was obtained by the same method as in step 3 of Example 10 using the compound (49 mg) obtained in the preceding step 2.

$^1$H-NMR (CDCl$_3$) δ: 5.62 (1H, d, J=10.9 Hz), 6.30 (1H, d, J=17.5 Hz), 6.51 (1H, d, J=15.7 Hz), 6.75-6.82 (2H, m), 7.20 (1H, d, J=3.6 Hz), 7.39-7.42 (4H, m), 7.60 (1H, d, J=7.3 Hz), 7.99-8.02 (2H, m), 8.47 (1H, d, J=7.9 Hz), 8.90 (1H, s).

MS (m/z): 564 (M+H)$^+$.

Example 74

(2E)-3-(1-{[5-(1-Methoxycyclobutyl)-3-(2,4,6-trichlorophenyl)-1,2-oxazol-4-yl]carbonyl}-1H-indol-4-yl)prop-2-enoic acid

[Formula 73]

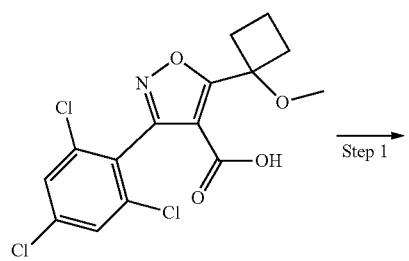

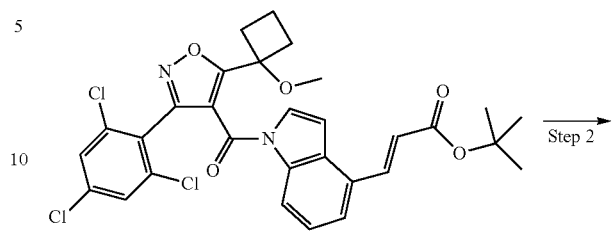

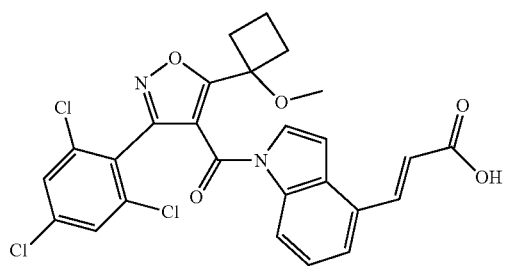

[Step 1] tert-Butyl (2E)-3-(1-{[5-(1-methoxycyclobutyl)-3-(2,4,6-trichlorophenyl)-1,2-oxazol-4-yl]carbonyl}-1H-indol-4-yl)prop-2-enoate The title compound (316 mg) was obtained by the same method as in step 1 of Example 21 using the compound (0.316 g) obtained in Reference Example X-15 and the compound (0.204 g) obtained in Reference Example E-1. The compound obtained was directly used in the next reaction.

[Step 2] (2E)-3-(1-{[5-(1-Methoxycyclobutyl)-3-(2,4,6-trichlorophenyl)-1,2-oxazol-4-yl]carbonyl}-1H-indol-4-yl)prop-2-enoic acid The title compound (0.147 g) was obtained by the same method as in step 3 of Example 1 using the compound (316 mg) obtained in the preceding step 1.

$^1$H-NMR (CDCl$_3$) δ: 1.97-2.10 (2H, m), 2.42-2.50 (2H, m), 2.65-2.72 (2H, m), 3.13 (3H, s), 6.57 (1H, d, J=15.7 Hz), 6.86 (1H, d, J=4.2 Hz), 7.28 (1H, d, J=4.2 Hz), 7.35-7.39 (3H, m), 7.58 (1H, d, J=7.3 Hz), 8.11 (1H, d, J=15.7 Hz), 8.44 (1H, d, J=8.5 Hz).

The following compounds were obtained by the same method as in Example 74 using the compounds obtained in the Reference Examples.

TABLE 54

| Example No. | Reference Example No. | Name and structure | Instrumental data |
|---|---|---|---|
| 75 | X-10<br>E-1 | (2E)-3-(1-{[3-(2,6-Dichlorophenyl)-5-(3-methyloxetan-3-yl)-1,2-oxazol-4-yl]carbonyl}-1H-indol-4-yl)prop-2-enoic acid | $^1$H-NMR(CDCl$_3$)δ: 1.95(3H, s), 4.64 (2H, d, J = 6.3 Hz), 5.15(2H, d, J = 6.3 Hz), 6.52(1H, d, J = 16.3 Hz), 6.65(1H, d, J = 4.1 Hz), 7.18-7.30(4H, m), 7.38(1H, t, J = 7.9 Hz), 7.55(1H, d, J = 7.7 Hz), 8.01(1H, d, J = 15.9 Hz), 8.34(1H, d, J = 8.2 Hz).<br>MS(m/z): 497(M + H)$^+$. |
| 76 | X-67<br>E-1 | (2E)-3-(1-{[3-(2,6-Dichlorophenyl)-5-(3-methoxyoxetan-3-yl)-1,2-oxazol-4-yl]carbonyl}-1H-indol-4-yl)prop-2-enoic acid | $^1$H-NMR(CDCl$_3$)δ: 3.28(3H, s), 4.90 (2H, d, J = 7.9 Hz), 5.16(2H, d, J = 7.9 Hz), 6.55(1H, d, J = 16.3 Hz), 6.77(1H, d, J = 3.6 Hz), 7.19(1H, d, J = 4.2 Hz), 7.25-7.40(4H, m), 7.57(1H, d, J = 7.9 Hz), 8.06(1H, d, J = 15.7 Hz), 8.38(1H, d, J = 8.5 Hz).<br>MS(m/z): 513(M + H)$^+$. |
| 77 | X-72<br>E-1 | (2E)-3-(1-{[3-(2,6-Dichlorophenyl)-5-(2-methyloxetan-2-yl)-1,2-oxazol-4-yl]carbonyl}-1H-indol-4-yl)prop-2-enoic acid | $^1$H-NMR(CDCl$_3$)δ: 1.94(3H, s), 2.78-2.89(1H, m), 3.09-3.18(1H, m), 4.45-4.56(2H, m), 6.54(1H, d, J = 15.7 Hz), 6.80(1H, d, J = 4.2 Hz), 7.24-7.39(5H, m), 7.55(1H, d, J = 7.9 Hz), 8.07(1H, d, J = 15.7 Hz), 8.46(1H, d, J = 7.9 Hz).<br>MS(m/z): 497(M + H)$^+$. |

TABLE 55

| 78 | X-12 E-8 | (2E)-3-(1-{[3-(2,4-Dichlorophenyl)-5-(3-methyloxetan-3-yl)-1,2-oxazol-4-yl]carbonyl}-3-methyl-1H-indol-4-yl)prop-2-enoic acid | $^1$H-NMR(CDCl$_3$)δ: 1.91(3H, s), 2.26 (3H, s), 4.59(2H, d, J = 6.7 Hz), 5.10 (2H, d, J = 6.7 Hz), 6.45(1H, d, J = 15.7 Hz), 6.71-6.73(1H, m), 7.27-7.31(2H, m), 7.37(1H, t, J = 7.9 Hz), 7.47(1H, d, J = 7.9 Hz), 7.58(1H, d, J = 7.9 Hz), 8.34-8.37(1H, m), 8.42(1H, d, J = 15.7 Hz). MS(m/z): 512(M + H)$^+$. |
|---|---|---|---|
| 79 | X-15 E-8 | (2E)-3-(1-{[5-(1-Methoxycyclobutyl)-3-(2,4,6-trichlorophenyl)-1,2-oxazol-4-yl]carbonyl}-3-methyl-1H-indol-4-yl)prop-2-enoic acid | $^1$H-NMR(CDCl$_3$)δ: 1.99-2.09(2H, m), 2.41-2.50(2H, m), 2.42(3H, s), 2.66-2.73(2H, m), 3.14(3H, s), 6.45(1H, d, J = 15.7 Hz), 6.99(1H, s), 7.34(1H, t, J = 7.9 Hz), 7.38(2H, s), 7.58(1H, d, J = 7.9 Hz), 8.45(1H, d, J = 7.9 Hz), 8.51(1H, d, J = 15.7 Hz). MS(m/z): 559(M + H)$^+$. |

TABLE 56

| 80 | X-34 E-8 | (2E)-3-(1-{[5-[1-(Methoxymethyl)cyclobutyl]-3-(2,4,6-trichlorophenyl)-1,2-oxazol-4-yl]carbonyl}-3-methyl-1H-indol-4-yl)prop-2-enoic acid | $^1$H-NMR(CDCl$_3$)δ: 1.99-2.23(4H, m), 2.37(3H, s), 2.59-2.67(2H, m), 3.17(3H, s), 3.83(2H, s), 6.44(1H, d, J = 15.7 Hz), 7.11(1H, s), 7.28-7.35(3H, m), 7.55(1H, d, J = 7.3 Hz), 8.43(1H, d, J = 8.5 Hz), 8.48(1H, d, J = 15.7 Hz). MS(m/z): 573(M + H)$^+$. |
|---|---|---|---|

Example 81

(2E)-3-(1-{[5-[1-(Dimethylamino)cyclobutyl]-3-(2,4,6-trichlorophenyl)-1,2-oxazol-4-yl]carbonyl}-3-methyl-1H-indol-4-yl)prop-2-enoic acid

[Formula 74]

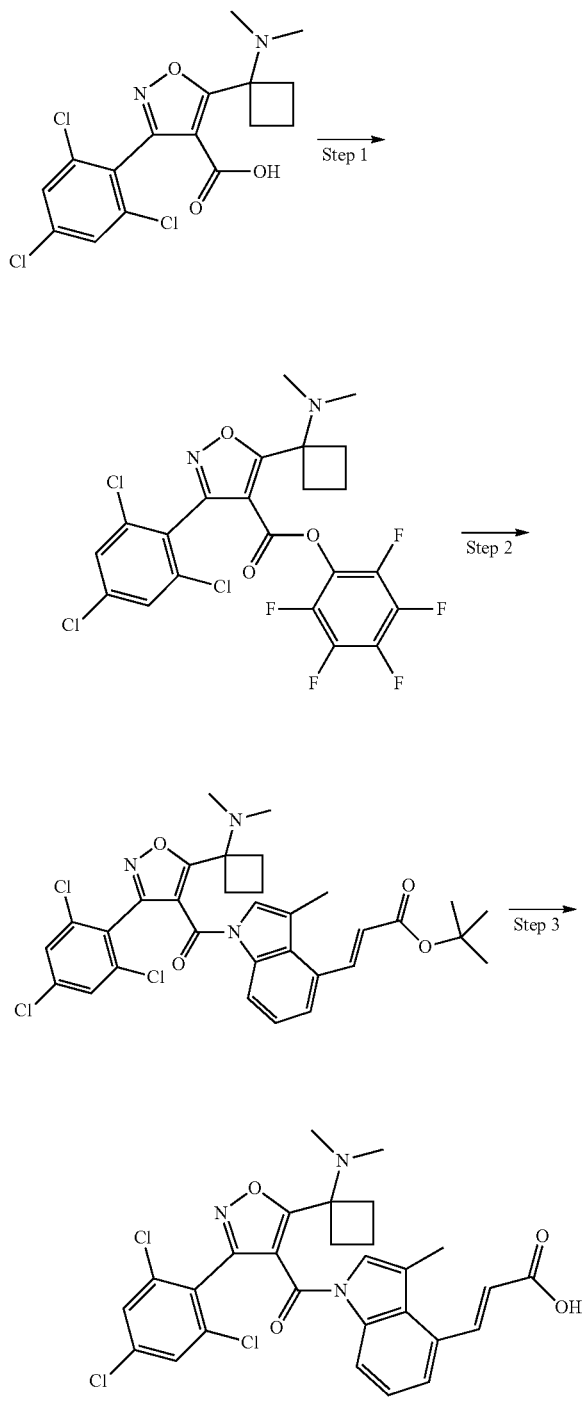

[Step 1] Pentafluorophenyl 5-[1-(dimethylamino)cyclobutyl]-3-(2,4,6-trichlorophenyl)-1,2-oxazole-4-carboxylate The title compound (0.061 g) was obtained by the same method as in step 1 of Example 1 using the compound (0.050 g) obtained in Reference Example X-60.

$^1$H-NMR (CDCl$_3$) δ: 1.85-1.94 (1H, m), 2.04-2.18 (1H, m), 2.21 (6H, s), 2.45-2.53 (2H, m), 2.74-2.82 (2H, m), 7.45 (2H, s).

[Step 2] tert-Butyl (2E)-3-(1-{[5-[1-(dimethylamino)cyclobutyl]-3-(2,4,6-trichlorophenyl)-1,2-oxazol-4-yl]carbonyl}-3-methyl-1H-indol-4-yl)prop-2-enoate The title compound (0.283 g) was obtained by the same method as in step 2 of Example 1 using the compound (416 mg) obtained in the preceding step 1 and the compound (0.174 g) obtained in Reference Example E-8.

$^1$H-NMR (CDCl$_3$) δ: 1.54 (9H, s), 1.83-1.95 (2H, m), 2.20 (6H, s), 2.38 (3H, s), 2.40-2.47 (2H, m), 2.51-2.61 (2H, m), 6.36 (1H, d, J=15.7 Hz), 7.00 (1H, s), 7.27-7.33 (3H, m), 7.52 (1H, d, J=7.3 Hz), 8.28 (1H, d, J=15.7 Hz), 8.39 (1H, d, J=7.9 Hz).

[Step 3] (2E)-3-(1-{[5-[1-(Dimethylamino)cyclobutyl]-3-(2,4,6-trichlorophenyl)-1,2-oxazol-4-yl]carbonyl}-3-methyl-1H-indol-4-yl)prop-2-enoic acid To a solution of the compound (0.283 g) obtained in the preceding step 2 in dichloromethane (3 ml), a solution of 4 N hydrochloric acid in 1,4-dioxane (1 ml) was added, and the mixture was stirred at room temperature for 1.5 hours. A solution of 4 N hydrochloric acid in 1,4-dioxane (3 ml) was further added to the reaction solution, and the mixture was stirred for another 1 hour. The reaction solution was concentrated under reduced pressure, and water and dichloromethane were added to the residue obtained. After separation into two layers, the organic layer was dried over anhydrous sodium sulfate. The solvent was distilled off under reduced pressure, and the residue obtained was purified by silica gel column chromatography (n-hexane/ethyl acetate). The eluted fraction was concentrated under reduced pressure, and a n-hexane/diethyl ether mixed solution was added to the residue obtained. The resulting solid was collected by filtration and dried to obtain the title compound (0.161 g).

$^1$H-NMR (CDCl$_3$) δ: 1.84-1.97 (2H, m), 2.21 (6H, s), 2.38 (3H, s), 2.40-2.48 (2H, m), 2.52-2.61 (2H, m), 6.45 (1H, d, J=15.7 Hz), 7.02 (1H, s), 7.31-7.36 (3H, m), 7.56 (1H, d, J=7.9 Hz), 8.42-8.47 (2H, m).

MS (m/z): 572 (M+H)$^+$.

The following compound was obtained by the same method as in Example 81 using the compound obtained in the Reference Example.

TABLE 57

| Example No. | Reference Example No. | Name and structure | Instrumental data |
|---|---|---|---|
| 82 | X-66 E-8 | (2E)-3-(1-{[5-[1-(Dimethylamino)cyclopropyl]-3-(2,4,6-trichlorophenyl)-1,2-oxazol-4-yl]carbonyl}-3-methyl-1H-indol-4-yl)prop-2-enoic acid | $^1$H-NMR(CDCl$_3$)δ: 1.19-1.30(4H, m), 2.26(6H, s), 2.39(3H, s), 6.45(1H, d, J = 15.7 Hz), 7.01(1H, s), 7.33(2H, s), 7.35(1H, t, J = 7.9 Hz), 7.57(1H, d, J = 7.9 Hz), 8.44-8.50(2H, m). MS(m/z): 558(M + H)$^+$. |

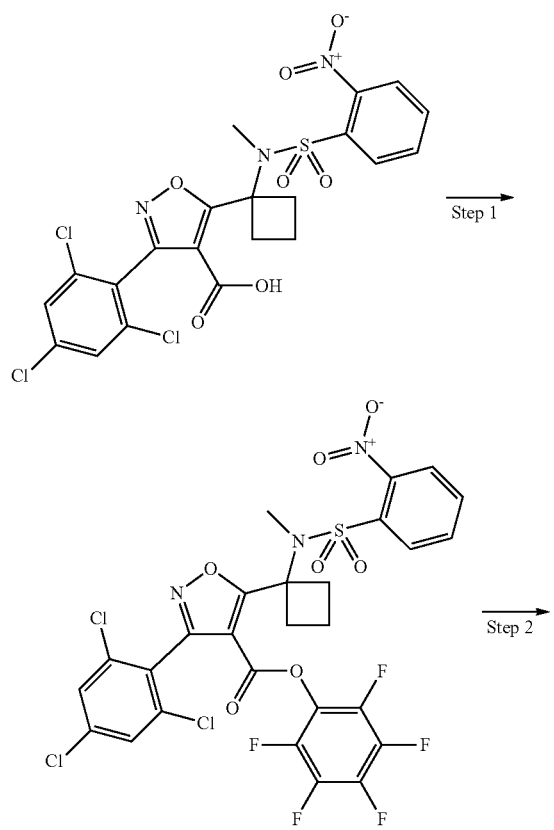

Example 83

(2E)-3-(3-Methyl-1-{[5-[1-(methylamino)cyclobutyl]-3-(2,4,6-trichlorophenyl)-1,2-oxazol-4-yl]carbonyl}-1H-indol-4-yl)prop-2-enoic acid

[Formula 75]

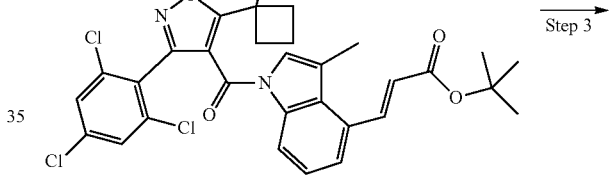

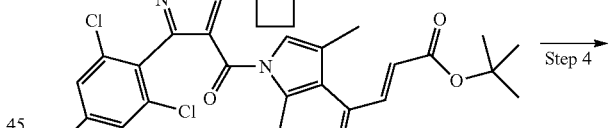

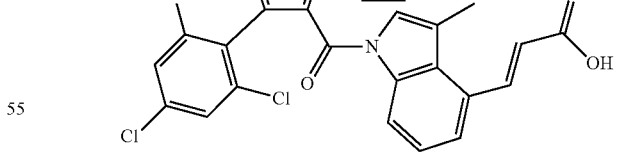

[Step 1] Pentafluorophenyl 5-(1-{methyl[(2-nitrophenyl)sulfonyl]amino}cyclobutyl)-3-(2,4,6-trichlorophenyl)-1,2-oxazole-4-carboxylate The title compound (0.454 g) was obtained by the same method as in step 1 of Example 1 using the compound obtained in Reference Example X-62.

¹H-NMR (CDCl₃) δ: 1.79-1.91 (1H, m), 1.94-2.03 (1H, m), 2.86-3.01 (4H, m), 3.09 (3H, s), 7.46 (2H, s), 7.59-7.72 (3H, m), 7.90 (1H, dd, J=7.9, 1.2 Hz).

[Step 2] tert-Butyl (2E)-3-(3-methyl-1-{[5-(1-{methyl[(2-nitrophenyl)sulfonyl]amino}cyclobutyl)-3-(2,4,6-trichlorophenyl)-1,2-oxazol-4-yl]carbonyl}-1H-indol-4-yl)prop-2-enoate The title compound (0.386 g) was obtained by the same method as in step 2 of Example 1 using the compound (0.447 g) obtained in the preceding step 1 and the compound (0.158 g) obtained in Reference Example E-8.

¹H-NMR (CDCl₃) δ: 1.54 (9H, s), 1.83-2.01 (2H, m), 2.34 (3H, d, J=1.2 Hz), 2.63-2.72 (2H, m), 2.80-2.87 (2H, m), 3.05 (3H, s), 6.35 (1H, d, J=15.7 Hz), 7.04 (1H, d, J=1.2 Hz), 7.26-7.32 (3H, m), 7.51 (1H, d, J=7.3 Hz), 7.60-7.71 (3H, m), 7.96-7.99 (1H, m), 8.26 (1H, d, J=15.7 Hz), 8.37 (1H, d, J=8.5 Hz).

MS (m/z): 799 (M+H)⁺.

[Step 3] tert-Butyl (2E)-3-[3-methyl-1-({5-[1-(methylamino)cyclobutyl]-3-(2,4,6-trichlorophenyl)-1,2-oxazol-4-yl}carbonyl)-1H-indol-4-yl]prop-2-enoate To a solution of the compound (0.376 g) obtained in the preceding step 2 in acetonitrile (10 ml), 4-bromobenzenethiol (0.192 g) and potassium carbonate (0.281 g) were added under ice cooling, and the mixture was stirred at the same temperature as above for 1 hour and at room temperature for 3 hours. Ethyl acetate and water were added under ice cooling to the reaction solution, which was then separated into two layers. The organic layer was washed with saturated saline and then dried over anhydrous sodium sulfate. The solvent was distilled off under reduced pressure, and the residue obtained was purified by silica gel column chromatography (n-hexane/ethyl acetate) to obtain the title compound (0.244 g).

¹H-NMR (CDCl₃) δ: 1.54 (9H, s), 1.97-2.28 (4H, m), 2.25 (3H, s), 2.34 (3H, d, J=1.2 Hz), 2.60-2.67 (2H, m), 6.36 (1H, d, J=15.7 Hz), 6.93 (1H, d, J=1.2 Hz), 7.29-7.33 (3H, m), 7.52 (1H, d, J=7.9 Hz), 8.26 (1H, d, J=15.7 Hz), 8.35 (1H, d, J=8.5 Hz).

MS (m/z): 614 (M+H)⁺.

[Step 4] (2E)-3-[3-Methyl-1-({5-[1-(methylamino)cyclobutyl]-3-(2,4,6-trichlorophenyl)-1,2-oxazol-4-yl}carbonyl)-1H-indol-4-yl]prop-2-enoic acid The title compound (0.085 g) was obtained by the same method as in step 3 of Example 10 using the compound (0.100 g) obtained in the preceding step 3.

¹H-NMR (CDCl₃) δ: 1.99-2.39 (4H, m), 2.30 (3H, s), 2.33 (3H, s), 2.62-2.70 (2H, m), 6.43 (1H, d, J=15.7 Hz), 6.94 (1H, s), 7.31 (2H, s), 7.35 (1H, t, J=7.9 Hz), 7.55 (1H, d, J=7.9 Hz), 8.37-8.43 (2H, m).

MS (ESI): 558 (M+H)⁺.

The following compounds were obtained by the same method as in Example 83 using the compounds obtained in the Reference Examples.

TABLE 58

| Example No. | Reference Example No. | Name and structure | Instrumental data |
| --- | --- | --- | --- |
| 84 | X-63 E-8 | (2E)-3-[3-Methyl-1-({5-[2-(methylamino)propan-2-yl]-3-(2,4,6-trichlorophenyl)-1,2-oxazol-4-yl]carbonyl}-1H-indol-4-yl)prop-2-enoic acid | ¹H-NMR(DMSO-d₆) δ: 1.45(6H, brs), 2.07(3H, s), 2.34 (3H, s), 6.49(1H, d, J = 15.7 Hz), 7.25 (1H, s), 7.35(1H, t, J = 8.0 Hz), 7.68 (1H, d, J = 8.0 Hz), 7.80(2H, s), 8.24 (1H, d, J = 15.7 Hz), 8.27(1H, d, J = 8.0 Hz). MS(m/z): 546(M + H)⁺. |

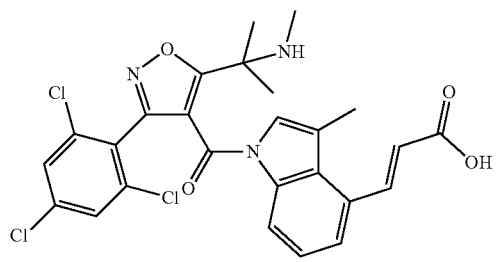 [SMILES: CNC(C)(C)c1onc(-c2c(Cl)cc(Cl)cc2Cl)c1C(=O)n1cc(C)c2c(/C=C/C(=O)O)cccc21]

TABLE 58-continued

| Example No. | Reference Example No. | Name and structure | Instrumental data |
|---|---|---|---|
| 85 | X-63<br>E-17 | (2E)-[1-({5-[2-(Methylamino)propan-2-yl]-3-(2,4,6-trichlorophenyl)-1,2-oxazol-4-yl}carbonyl)-3,4-dihydrobenzo[cd]indol-5(1H)-ylidene]ethanoic acid | $^1$H-NMR(CDCl$_3$)δ: 1.60(6H, brs), 2.30 (3H, s), 2.77(2H, t, J = 6.7 Hz), 3.31-3.39(2H, m), 6.50(1H, s), 6.88(1H, s), 7.29(2H, brs), 7.37(1H, t, J = 7.9 Hz), 7.49(1H, d, J = 7.9 Hz), 8.17(1H, d, J = 7.9 Hz). |

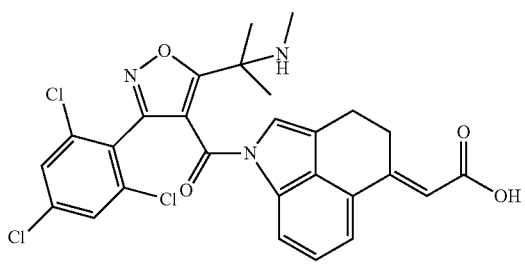 [SMILES: CNC(C)(C)c1onc(-c2c(Cl)cc(Cl)cc2Cl)c1C(=O)n1cc2c3c(cccc31)/C(=C/C(=O)O)CC2]

TABLE 59

| 86 | X-64<br>E-17 | (2E)-[1-({5-[1-(Methylamino)cyclopropyl]-3-(2,4,6-trichlorophenyl)-1,2-oxazol-4-yl}carbonyl)-3,4-dihydrobenzo[cd]indol-5(1H)-ylidene]ethanoic acid | $^1$H-NMR(CDCl$_3$)δ: 1.24-1.30(2H, m), 1.49-1.52(2H, m), 2.33(3H, s), 2.83(2H, t, J = 6.4 Hz), 3.40(2H, t, J = 6.4 Hz), 6.53 (1H, s), 6.97(1H, s), 7.32(2H, s), 7.38(1H, t, J = 7.9 Hz), 7.51(1H, d, J = 7.9 Hz), 8.16(1H, d, J = 7.9 Hz). MS(m/z): 556(M + H)$^+$. |
|---|---|---|---|

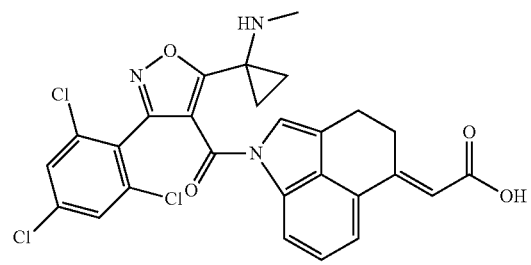 [SMILES: CNC1(c2onc(-c3c(Cl)cc(Cl)cc3Cl)c2C(=O)n2cc3c4c(cccc42)/C(=C/C(=O)O)CC3)CC1]

Example 87

(2E)-3-(1-{[5-{1-[Acryloyl(methyl)amino]cyclobutyl}-3-(2,4,6-trichlorophenyl)-1,2-oxazol-4-yl]carbonyl}-3-methyl-1H-indol-4-yl)prop-2-enoic acid

[Formula 76]

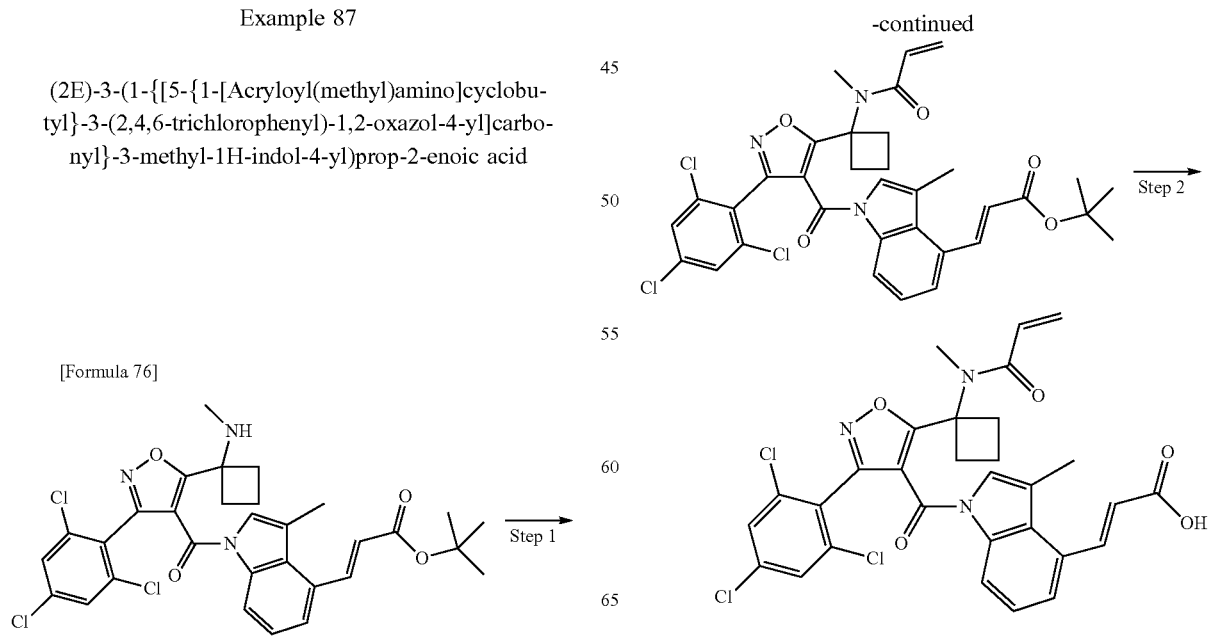

[Step 1] tert-Butyl (2E)-3-(1-{[5-{1-[acryloyl(methyl)amino]cyclobutyl}-3-(2,4,6-trichlorophenyl)-1,2-oxazol-4-yl]carbonyl}-3-methyl-1H-indol-4-yl)prop-2-enoate To a solution of the compound (0.133 g) obtained in step 3 of Example 83 in dichloromethane (3 ml), triethylamine (0.090 ml) and acryloyl chloride (0.035 ml) were added, and the mixture was stirred at room temperature for 1 hour. Dichloromethane and water were added to the reaction solution, which was then separated into two layers. Then, the organic layer was dried over anhydrous sodium sulfate. The solvent was distilled off under reduced pressure to obtain the title compound, which was directly used in the next reaction.
MS(m/z):668(M+H)$^+$.

[Step 2] (2E)-3-(1-{[5-{1-[Acryloyl(methyl)amino]cyclobutyl}-3-(2,4,6-trichlorophenyl)-1,2-oxazol-4-yl]carbonyl}-3-methyl-1H-indol-4-yl)prop-2-enoic acid The title compound (0.112 g) was obtained by the same method as in step 3 of Example 10 using the compound obtained in the preceding step 1.
$^1$H-NMR (CDCl$_3$) δ: 1.94-2.02 (1H, m), 2.32-2.42 (1H, m), 2.34 (3H, s), 2.53-3.09 (4H, m), 3.04 (3H, s), 5.32 (1H, d, J=10.3 Hz), 5.83 (1H, d, J=16.9 Hz), 6.16 (1H, dd, J=16.9, 10.3 Hz), 6.41 (1H, d, J=15.7 Hz), 6.95 (1H, s), 7.26-7.32 (3H, m), 7.53 (1H, d, J=7.9 Hz), 8.40 (1H, d, J=7.9 Hz), 8.44 (1H, d, J=15.7 Hz).
MS (m/z): 612 (M+H)$^1$.

Example 88

(2E)-3-(1-{[5-{1-[(Dimethylamino)methyl]cyclobutyl}-3-(2,4,6-trichlorophenyl)-1,2-oxazol-4-yl]carbonyl}-3-methyl-1H-indol-4-yl)prop-2-enoic acid

[Formula 77]

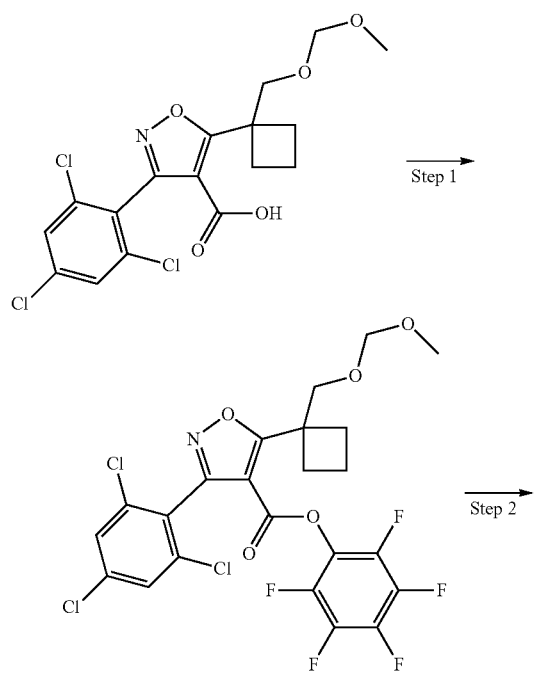

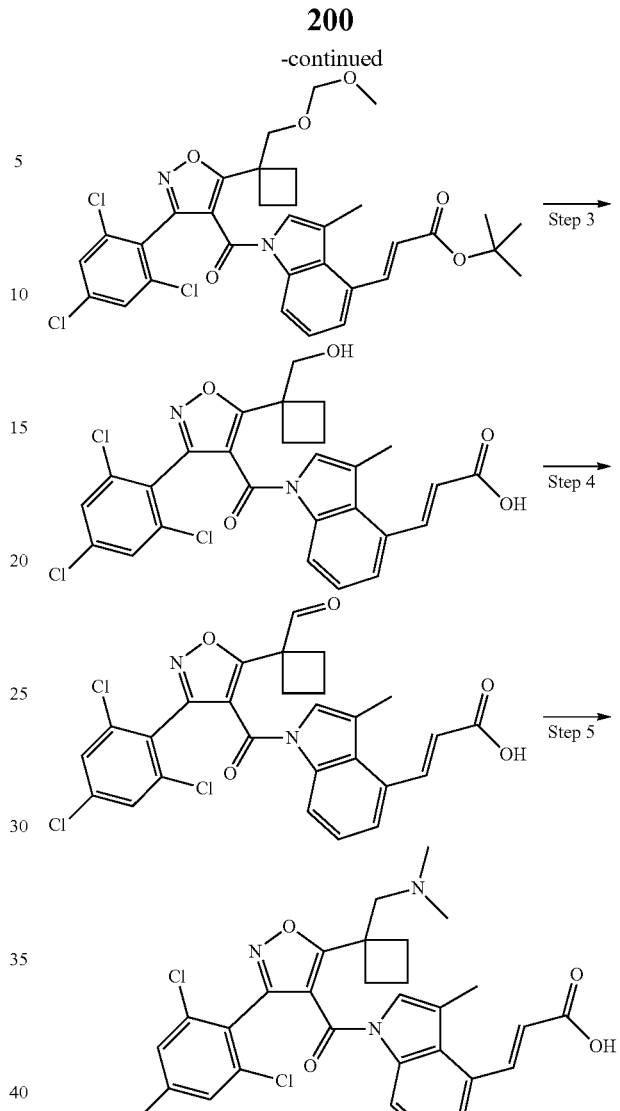

[Step 1] Pentafluorophenyl 5-{1-[(methoxymethoxy)methyl]cyclobutyl}-3-(2,4,6-trichlorophenyl)-1,2-oxazole-4-carboxylate The title compound (2.34 g) was obtained by the same method as in step 1 of Example 1 using the compound (2.04 g) obtained in Reference Example X-33.
$^1$H-NMR (CDCl$_3$) δ: 1.98-2.11 (1H, m), 2.14-2.22 (1H, m), 2.41-2.48 (2H, m), 2.73-2.83 (2H, m), 3.24 (3H, s), 4.03 (2H, s), 4.59 (2H, s), 7.44 (2H, s).
MS (m/z): 586 (M+H)$^+$.

[Step 2] tert-Butyl (2E)-3-(1-{[5-{1-[(methoxymethoxy)methyl]cyclobutyl}-3-(2,4,6-trichlorophenyl)-1,2-oxazol-4-yl]carbonyl}-3-methyl-1H-indol-4-yl)prop-2-enoate The title compound (2.00 g) was obtained by the same method as in step 2 of Example 1 using the compound (2.34 g) obtained in the preceding step 1 and the compound (1.03 g) obtained in Reference Example E-8.
$^1$H-NMR (CDCl$_3$) δ: 1.54 (9H, s), 1.95-2.24 (4H, m), 2.36 (3H, s), 2.59-2.66 (2H, m), 3.23 (3H, s), 4.01 (2H, s), 4.50

(2H, s), 6.36 (1H, d, J=15.7 Hz), 7.09 (1H, d, J=1.2 Hz), 7.28-7.32 (1H, m), 7.31 (2H, s), 7.52 (1H, d, J=7.9 Hz), 8.28 (1H, d, J=15.7 Hz), 8.38 (1H, d, J=8.5 Hz).

MS (m/z): 659 (M+H)⁺.

[Step 3] (2E)-3-[1-({5-[1-(Hydroxymethyl)cyclobutyl]-3-(2,4,6-trichlorophenyl)-1,2-oxazol-4-yl}carbonyl)-3-methyl-1H-indol-4-yl]prop-2-enoic acid To a solution of the compound (1.47 g) obtained in the preceding step 2 in dichloromethane (10 ml), trifluoroacetic acid (2 ml) was added, and the mixture was stirred at room temperature for 1.5 hours. Trifluoroacetic acid (1 ml) was further added to the reaction solution, and the mixture was stirred for 30 minutes. Then, trifluoroacetic acid (2 ml) was further added thereto, and the mixture was stirred for 30 minutes. Dichloromethane and water were added to the reaction solution, which was then separated into two layers. The organic layer was washed with water and saturated saline in this order and then dried over anhydrous sodium sulfate. The solvent was distilled off under reduced pressure, and n-hexane was added to the residue obtained. The resulting solid was collected by filtration to obtain the title compound (1.32 g).

MS(m/z):559(M+H)¹.

[Step 4] (2E)-3-(1-{[5-(1-Formylcyclobutyl)-3-(2,4,6-trichlorophenyl)-1,2-oxazol-4-yl]carbonyl}-3-methyl-1H-indol-4-yl)prop-2-enoic acid To a solution of the compound (0.60 g) obtained in the preceding step 3 in dichloromethane (5 ml), Dess-Martin periodic acid (0.909 g) was added, and the mixture was stirred at room temperature for 2 hours. Water and dichloromethane were added to the reaction solution, which was then separated into two layers. The organic layer was washed with water, an aqueous sodium thiosulfate solution, and saturated saline in this order and then dried over anhydrous sodium sulfate. The solvent was distilled off under reduced pressure, and diethyl ether and n-hexane were added to the residue obtained. The resulting solid was collected by filtration to obtain the title compound (0.460 g).

MS(m/z):557(M+H)⁺.

[Step 5] (2E)-3-(1-{[5-{1-[(Dimethylamino)methyl]cyclobutyl}-3-(2,4,6-trichlorophenyl)-1,2-oxazol-4-yl]carbonyl}-3-methyl-1H-indol-4-yl)prop-2-enoic acid To a suspension of the compound (0.160 g) obtained in the preceding step 4 in 1,2-dichloroethane (3 ml), dimethylamine (2.0 mol solution in tetrahydrofuran, 0.57 ml) and sodium triacetoxyborohydride (0.304 g) were added, and the mixture was stirred at room temperature for 2 hours. Dichloromethane and water were added to the reaction solution, which was then separated into two layers. The aqueous layer was subjected to extraction with dichloromethane. The organic layers were combined, washed with water and then dried over anhydrous sodium sulfate. The solvent was distilled off under reduced pressure, and the residue obtained was purified by silica gel column chromatography (n-hexane/ethyl acetate) and then purified by preparative thin-layer chromatography (ethyl acetate). n-Hexane was added to the residue obtained, and the resulting solid was collected by filtration to obtain the title compound (0.028 g).

¹H-NMR (CDCl₃) δ: 2.01 (6H, s), 2.05-2.30 (4H, m), 2.35 (3H, d, J=1.2 Hz), 2.69-2.76 (2H, m), 2.89 (2H, s), 6.40 (1H, d, J=15.7 Hz), 7.04 (1H, d, J=1.2 Hz), 7.27 (2H, s), 7.31 (1H, t, J=7.9 Hz), 7.52 (1H, d, J=7.9 Hz), 8.39-8.45 (2H, m).

MS (m/z): 586 (M+H)¹.

Example 89

(2E)-3-(1-{[5-[1-(Dimethylcarbamoyl)cyclobutyl]-3-(2,4,6-trichlorophenyl)-1,2-oxazol-4-yl]carbonyl}-3-methyl-1H-indol-4-yl)prop-2-enoic acid

[Formula 78]

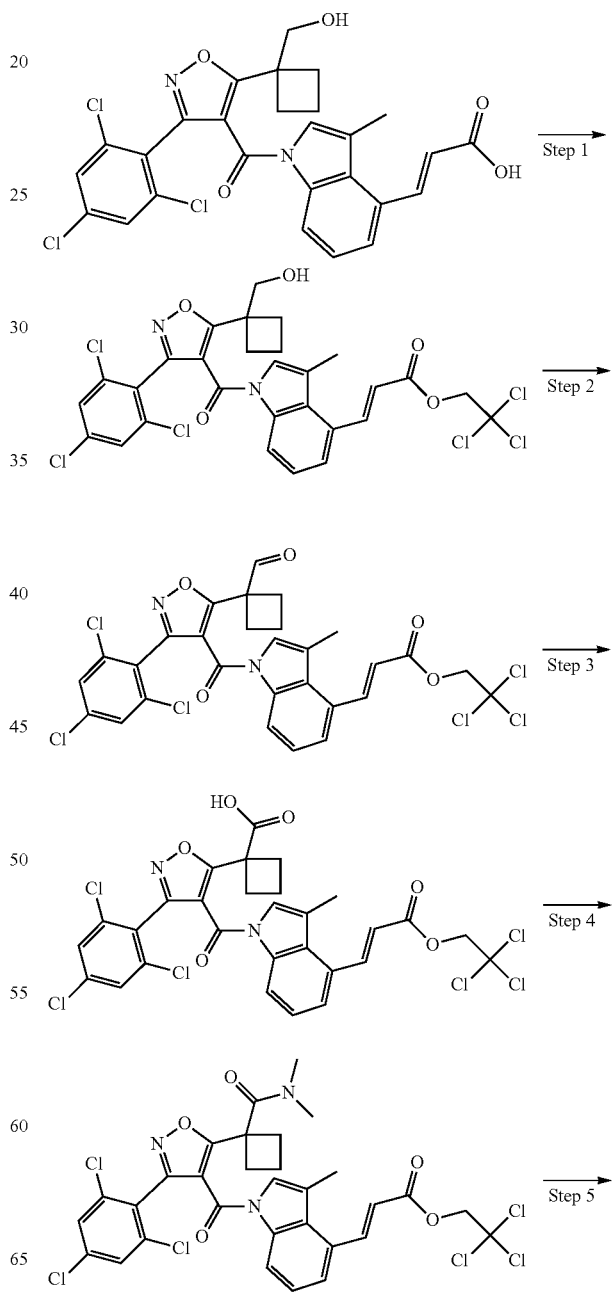

-continued

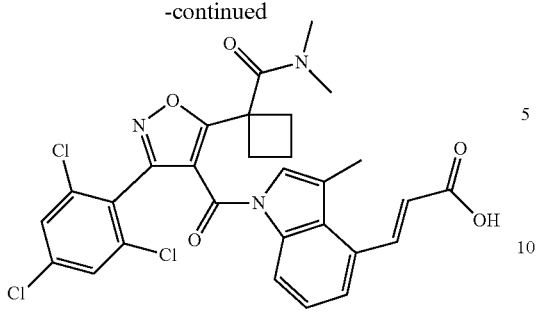

[Step 1] 2,2,2-Trichloroethyl (2E)-3-[1-({5-[1-(hydroxymethyl)cyclobutyl]-3-(2,4,6-trichlorophenyl)-1,2-oxazol-4-yl}carbonyl)-3-methyl-1H-indol-4-yl)prop-2-enoate To a solution of the compound (0.398 g) obtained in step 3 of Example 88 in 2,2,2-trichloroethanol (3.5 ml), 1-ethyl-3-(3-dimethylaminopropyl)-carbodiimide hydrochloride (0.204 g) and 1-hydroxybenzotriazole monohydrate (0.035 g) were added, and the mixture was stirred at room temperature for 1 hour and then stirred at 70° C. for 1.5 hours. Ethyl acetate and water were added to the reaction solution, which was then separated into two layers. The organic layer was washed with saturated saline and then dried over anhydrous sodium sulfate. The solvent was distilled off under reduced pressure, and the residue obtained was purified by silica gel column chromatography (n-hexane/ethyl acetate) to obtain the title compound (0.262 g).

$^1$H-NMR (CDCl$_3$) δ: 1.97-2.06 (1H, m), 2.11-2.23 (1H, m), 2.27-2.34 (2H, m), 2.32 (3H, d, J=1.2 Hz), 2.51-2.59 (2H, m), 4.11 (2H, d, J=5.4 Hz), 4.88 (2H, s), 6.52 (1H, d, J=15.7 Hz), 7.01 (1H, d, J=1.2 Hz), 7.29 (2H, s), 7.36 (1H, t, J=7.9 Hz), 7.59 (1H, d, J=7.9 Hz), 8.40 (1H, d, J=7.9 Hz), 8.51 (1H, d, J=15.7 Hz).

MS (m/z): 689 (M+H)$^+$.

[Step 2] 2,2,2-Trichloroethyl (2E)-3-(1-{[5-(1-formylcyclobutyl)-3-(2,4,6-trichlorophenyl)-1,2-oxazol-4-yl]carbonyl}-3-methyl-1H-indol-4-yl)prop-2-enoate The title compound (0.261 g) was obtained by the same method as in step 4 of Example 88 using the compound (0.262 g) obtained in the preceding step 1.

MS(m/z):687(M+H)$^+$.

[Step 3] 1-[4-({3-Methyl-4-[(1E)-3-oxo-3-(2,2,2-trichloroethoxy)prop-1-en-1-yl]indole-1-carbonyl}-3-(2,4,6-trichlorophenyl)-1,2-oxazol-5-yl)cyclobutanecarboxylic acid To the compound (0.261 g) obtained in the preceding step 2, tert-butanol (3 ml), acetonitrile (5 ml), water (1 ml), sodium dihydrogen phosphate dihydrate (0.065 g), 2-methyl-2-butene (0.18 ml), and sodium chlorite (0.077 g) were added, and the reaction was stirred at room temperature for 1.5 hours. The reaction solution was rendered weakly acidic by the addition of 1 N hydrochloric acid, followed by extraction with dichloromethane. The extract was washed with saturated saline and then dried over anhydrous sodium sulfate. The solvent was distilled off under reduced pressure to obtain the title compound (0.198 g).

$^1$H-NMR (CDCl$_3$) δ: 1.99-2.38 (2H, m), 2.33 (3H, s), 2.73-2.79 (4H, m), 4.87 (2H, s), 6.51 (1H, d, J=15.7 Hz), 7.00 (1H, s), 7.29-7.33 (3H, m), 7.57 (1H, d, J=7.9 Hz), 8.35 (1H, d, J=7.9 Hz), 8.52 (1H, d, J=15.7 Hz).

MS (m/z): 703 (M+H)$^+$.

[Step 4] 2,2,2-Trichloroethyl (1-{[5-[1-(dimethylcarbamoyl)cyclobutyl]-3-(2,4,6-trichlorophenyl)-1,2-oxazol-4-yl]carbonyl}-3-methyl-1H-indol-4-yl)prop-2-enoate To a solution of the compound (0.064 g) obtained in the preceding step 3 and O-(7-azabenzotriazol-1-yl)-N,N,N',N'-tetramethyluronium hexafluorophosphate (0.045 g) in N,N-dimethylformamide (1 ml), dimethylamine (2.0 mol solution in tetrahydrofuran, 0.091 ml) was added, and the mixture was stirred at room temperature for 1 hour. Ethyl acetate and saturated saline were added to the reaction solution, which was then separated into two layers. The aqueous layer was subjected to extraction with ethyl acetate. The organic layers were combined, washed with saturated saline and then dried over anhydrous sodium sulfate. The solvent was distilled off under reduced pressure, and the residue obtained was purified by silica gel column chromatography (n-hexane/ethyl acetate) to obtain the title compound (0.068 g).

$^1$H-NMR (CDCl$_3$) δ: 2.03-2.24 (2H, m), 2.43 (3H, s), 2.61 (3H, s), 2.65 (3H, s), 2.82-2.92 (4H, m), 4.88 (2H, s), 6.51 (1H, d, J=15.7 Hz), 6.79 (1H, d, J=1.2 Hz), 7.30 (1H, t, J=7.9 Hz), 7.37 (2H, s), 7.58 (1H, d, J=7.9 Hz), 8.36 (1H, d, J=7.9 Hz), 8.58 (1H, d, J=15.7 Hz).

MS (m/z): 730 (M+H)$^+$.

[Step 5] (2E)-3-(1-{[5-[1-(Dimethylcarbamoyl)cyclobutyl]-3-(2,4,6-trichlorophenyl)-1,2-oxazol-4-yl]carbonyl}-3-methyl-1H-indol-4-yl)prop-2-enoic acid To a solution of the compound (0.054 g) obtained in the preceding step 4 in tetrahydrofuran (2 ml), water (0.2 ml), indium (0.127 g), and formic acid (0.08 ml) were added, and the mixture was stirred at 100° C. for 1 hour using a microwave apparatus. Indium (0.085 g) was further added to the reaction solution, and the mixture was stirred at 100° C. for 30 minutes using a microwave apparatus. The inorganic matter was filtered off, and water and ethyl acetate were added to the filtrate, which was then separated into two layers. The organic layer was washed with saturated saline and then dried over anhydrous sodium sulfate. The solvent was distilled off under reduced pressure, and the residue obtained was purified by silica gel column chromatography (dichloromethane/methanol) and then purified by preparative thin-layer chromatography (dichloromethane/methanol) to obtain the title compound (0.009 g).

$^1$H-NMR (CDCl$_3$) δ: 2.03-2.14 (1H, m), 2.17-2.28 (1H, m), 2.43 (3H, s), 2.62 (3H, s), 2.67 (3H, s), 2.83-2.96 (4H, m), 6.36 (1H, d, J=15.7 Hz), 6.78 (1H, s), 7.29 (1H, t, J=8.0 Hz), 7.38 (2H, s), 7.54 (1H, d, J=8.0 Hz), 8.34 (1H, d, J=8.0 Hz), 8.44 (1H, d, J=15.7 Hz).

MS (m/z): 600 (M+H)$^+$.

Example 90

(2E)-3-(1-{[5-(1-Aminocyclobutyl)-3-(2,4,6-trichlorophenyl)-1,2-oxazol-4-yl]carbonyl}-3-methyl-1H-indol-4-yl)prop-2-enoic acid

[Formula 79]

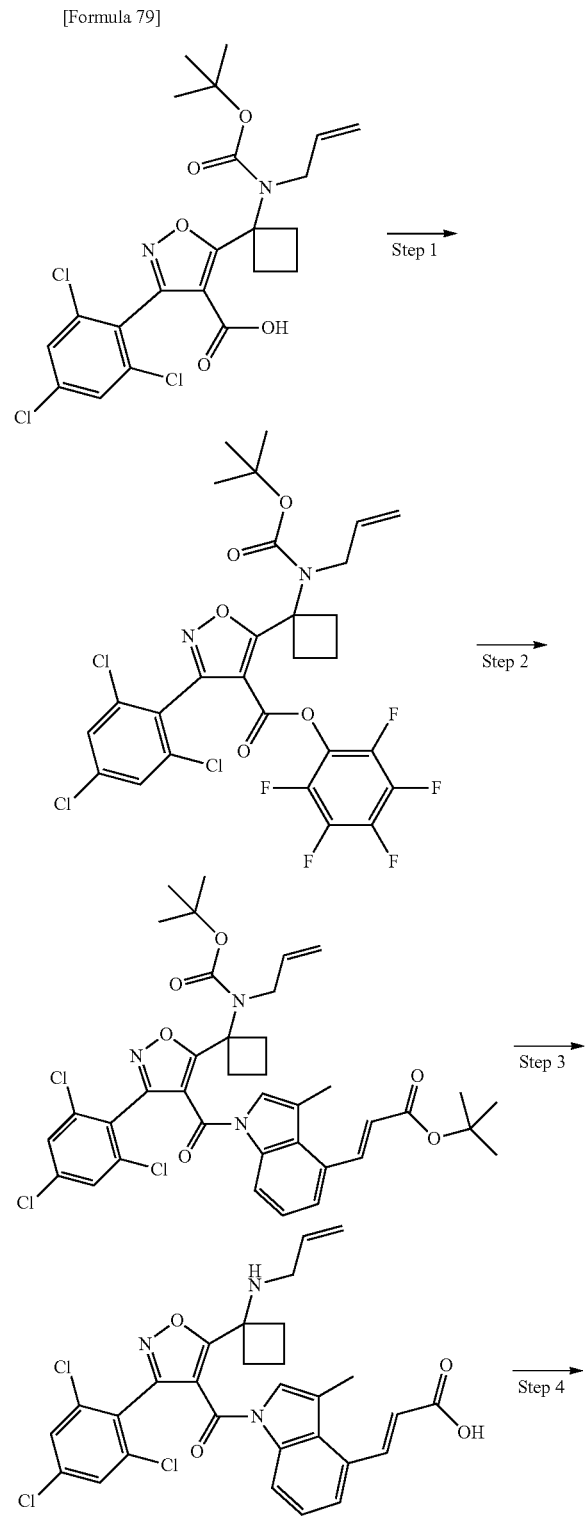

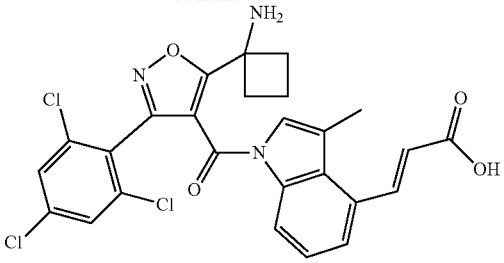 [SMILES: Cc1cn(C(=O)c2c(-c3c(Cl)cc(Cl)cc3Cl)noc2C2(N)CCC2)c2cccc(/C=C/C(=O)O)c12]

[Step 1] Pentafluorophenyl 5-{1-[(tert-butoxycarbonyl)(prop-2-en-1-yl)amino]cyclobutyl}-3-(2,4,6-trichlorophenyl)-1,2-oxazole-4-carboxylate The title compound (1.01 g) was obtained by the same method as in step 1 of Example 1 using the compound obtained in Reference Example X-65.

$^{1}$H-NMR (CDCl$_{3}$) δ: 1.36 (9H, s), 1.91-2.06 (2H, m), 2.69-2.78 (2H, m), 2.88-2.96 (2H, m), 4.07-4.13 (2H, m), 5.19-5.28 (2H, m), 5.92-6.02 (1H, m), 7.45 (2H, s).

[Step 2] tert-Butyl (2E)-3-(1-{[5-{1-[(tert-butoxycarbonyl)(prop-2-en-1-yl)amino]cyclobutyl}-3-(2,4,6-trichlorophenyl)-1,2-oxazol-4-yl]carbonyl}-3-methyl-1H-indol-4-yl)prop-2-enoate The title compound (0.899 g) was obtained by the same method as in step 2 of Example 1 using the compound (1.01 g) obtained in the preceding step 1 and the compound (0.389 g) obtained in Reference Example E-8.

$^{1}$H-NMR (CDCl$_{3}$) δ: 1.28 (9H, brs), 1.54 (9H, s), 1.89-1.99 (1H, m), 2.12-2.27 (1H, m), 2.31 (3H, d, J=1.2 Hz), 2.60-2.79 (2H, m), 2.81-2.99 (2H, m), 3.60-3.74 (2H, m), 5.11-5.18 (2H, m), 5.79-5.89 (1H, m), 6.35 (1H, d, J=15.7 Hz), 6.91 (1H, brs), 7.26-7.32 (3H, m), 7.51 (1H, d, J=7.9 Hz), 8.25 (1H, d, J=15.7 Hz), 8.39 (1H, d, J=7.9 Hz).
MS (m/z): 740 (M+H)$^{+}$.

[Step 3] (2E)-3-[3-Methyl-1-({5-[1-(prop-2-en-1-yl)cyclobutyl]-3-(2,4,6-trichlorophenyl)-1,2-oxazol-4-yl}carbonyl)-1H-indol-4-yl]prop-2-enoic acid To a solution of the compound (0.40 g) obtained in the preceding step 2 in dichloromethane (2 ml), 4 N hydrochloric acid-1,4-dioxane (4 ml) was added, and the mixture was stirred at room temperature for 2.5 hours. The reaction solution was concentrated under reduced pressure. Trifluoroacetic acid (3 ml) was added to the residue obtained, and the mixture was stirred at room temperature for 1 hour. The reaction solution was concentrated under reduced pressure, and dichloromethane and water were added to the residue obtained, which was then separated into two layers. The organic layer was washed with water and then dried over anhydrous sodium sulfate. The solvent was distilled off under reduced pressure, and diethyl ether and n-hexane were added to the residue obtained. The resulting solid was collected by filtration to obtain the title compound (0.281 g).

¹H-NMR (CDCl₃) δ: 1.99-2.10 (1H, m), 2.12-2.22 (1H, m), 2.27-2.36 (2H, m), 2.35 (3H, s), 2.63-2.70 (2H, m), 3.11 (2H, d, J=6.0 Hz), 4.93-4.97 (1H, m), 5.00-5.06 (1H, m), 5.69-5.79 (1H, m), 6.45 (1H, d, J=15.7 Hz), 6.95 (1H, d, J=1.2 Hz), 7.32-7.37 (3H, m), 7.57 (1H, d, J=7.9 Hz), 8.40 (1H, d, J=7.9 Hz), 8.46 (1H, d, J=15.7 Hz).

MS (m/z): 584 (M+H)⁺.

[Step 4] (2E)-3-(1-{[5-(1-Aminocyclobutyl)-3-(2,4,6-trichlorophenyl)-1,2-oxazol-4-yl]carbonyl}-3-methyl-1H-indol-4-yl)prop-2-enoic acid To the compound (0.237 g) obtained in the preceding step 3, 3-diphenylphosphanylpropyl(diphenyl)phosphane (0.084 g), and bis[(2,2,2-trifluoroacetyl)oxy]palladium (0.067 g), acetonitrile (2 ml) and water (0.2 ml) were added, and the mixture was stirred at 110° C. for 1 hour under a nitrogen atmosphere using a microwave apparatus. The insoluble matter was filtered off, and then, the filtrate was concentrated under reduced pressure, and the residue obtained was purified by silica gel column chromatography (dichloromethane/methanol) and then purified by preparative thin-layer chromatography (dichloromethane/methanol). Dichloromethane was added to the residue obtained. The resulting solid was collected by filtration to obtain the title compound (0.020 g).

¹H-NMR (DMSO-d₆) δ: 1.84-1.92 (1H, m), 2.01-2.10 (3H, m), 2.35 (3H, s), 2.65-2.70 (2H, m), 6.50 (1H, d, J=15.7 Hz), 7.29 (1H, s), 7.33 (1H, t, J=7.9 Hz), 7.68 (1H, d, J=7.9 Hz), 7.83 (2H, s), 8.23-8.28 (2H, m).

MS (m/z): 544 (M+H)⁺.

Example 91

(2E)-3-[1-({5-[2-(Dimethylamino)propan-2-yl]-3-(2,4,6-trichlorophenyl)-1,2-oxazol-4-yl}carbonyl)-3-methyl-1H-indol-4-yl]prop-2-enoic acid

[Formula 80]

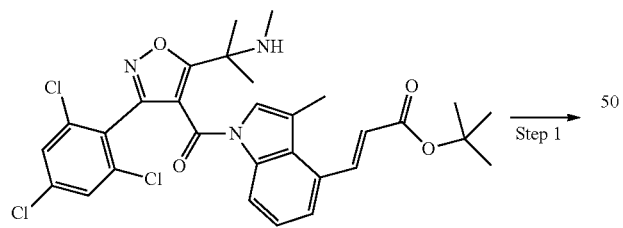

Step 1

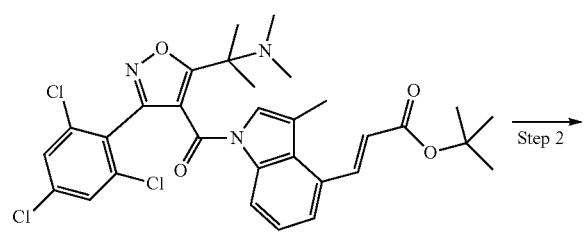

Step 2

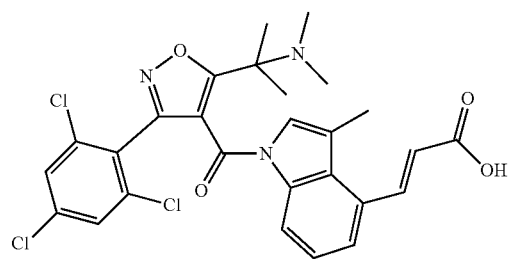

[Step 1] tert-Butyl (2E)-3-[1-({5-[2-(dimethylamino)propan-2-yl]-3-(2,4,6-trichlorophenyl)-1,2-oxazol-4-yl}carbonyl)-3-methyl-1H-indol-4-yl]prop-2-enoate To a solution of the compound (0.220 g) obtained in step 3 of Example 84 in 1,2-dichloroethane (3 ml), formaldehyde (37% aqueous solution, 0.136 ml) and sodium triacetoxyborohydride (0.387 g) were added, and the mixture was stirred at room temperature for 1 hour. Water and dichloromethane were added to the reaction solution, which was then separated into two layers. Then, the organic layer was dried over anhydrous sodium sulfate. The solvent was distilled off under reduced pressure to obtain the title compound (0.199 g).

¹H-NMR (CDCl₃) δ: 1.49 (6H, brs), 1.54 (9H, s), 2.14 (6H, s), 2.41 (3H, d, J=1.2 Hz), 6.36 (1H, d, J=15.7 Hz), 7.01 (1H, s), 7.30 (1H, t, J=7.9 Hz), 7.34 (2H, s), 7.52 (1H, d, J=7.9 Hz), 8.31 (1H, d, J=15.7 Hz), 8.43 (1H, d, J=7.9 Hz).

MS (m/z): 616 (M+H)⁺.

[Step 2] (2E)-3-[1-({5-[2-(Dimethylamino)propan-2-yl]-3-(2,4,6-trichlorophenyl)-1,2-oxazol-4-yl}carbonyl)-3-methyl-1H-indol-4-yl]prop-2-enoic acid The title compound (0.127 g) was obtained by the same method as in step 3 of Example 10 using the compound (0.199 g) obtained in the preceding step 1.

¹H-NMR (CDCl₃) δ: 1.51 (6H, brs), 2.15 (6H, s), 2.41 (3H, s), 6.42 (1H, d, J=15.7 Hz), 7.03 (1H, s), 7.31-7.35 (3H, m), 7.56 (1H, d, J=7.9 Hz), 8.46-8.50 (2H, m).

MS (m/z): 516 (M+H)¹.

The following compound was obtained by the same method as in Example 91 using the compound obtained in step 3 of Example 86.

TABLE 60

| Example No. | Name and structure | Instrumental data |
| --- | --- | --- |
| 92 | (2E)-[1-({5-[1-(Dimethylamino)cyclopropyl]-3-(2,4,6-trichlorophenyl)-1,2-oxazol-4-yl}carbonyl)-3,4-dihydrobenzo[cd]indol-5(1H)-ylidene]ethanoic acid | $^1$H-NMR(CDCl$_3$) δ: 1.19-1.30(4H, m), 2.25(6H, s), 2.84 (2H, t, J = 6.4 Hz), 3.40(2H, t, J = 6.4 Hz), 6.53(1H, s), 6.94(1H, s), 7.33 (2H, s), 7.36(1H, t, J = 7.9 Hz), 7.50(1H, d, J = 7.9 Hz), 8.17(1H, d, J = 7.9 Hz). MS(m/z): 570(M + H)$^+$. |

Example 93

(2E)-3-(1-{[5-(1-Cyanocyclobutyl)-3-(2,4,6-trichlorophenyl)-1,2-oxazol-4-yl]carbonyl}-3-methyl-1H-indol-4-yl)prop-2-enoic acid

[Formula 81]

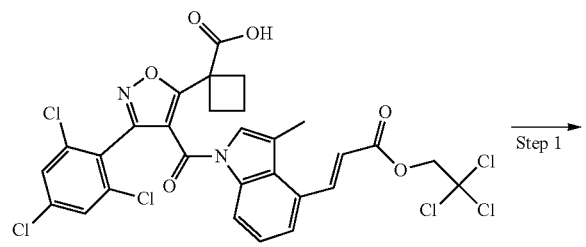

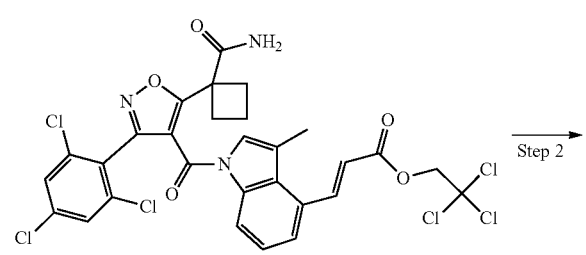

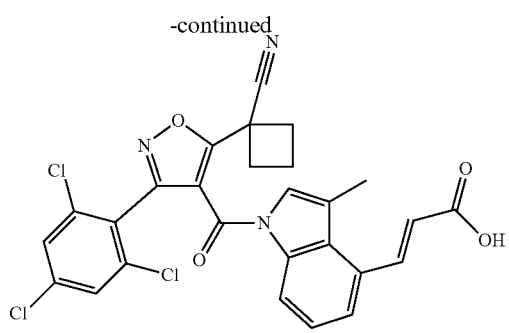

[Step 1] 2,2,2-Trichloroethyl(2E)-3-(1-{[5-(1-carbamoylcyclobutyl)-3-(2,4,6-trichlorophenyl)-1,2-oxazol-4-yl]carbonyl}-3-methyl-1H-indol-4-yl)prop-2-enoate To a solution of the compound (0.067 g) obtained in step 3 of Example 89 and O-(7-azabenzotriazol-1-yl)-N,N,N',N'-tetramethyluronium hexafluorophosphate (0.047 g) in N,N-dimethylformamide (1 ml), N,N-di(propan-2-yl)ethylamine (0.049 ml) was added, and the mixture was stirred at room temperature for 5 minutes. Then, ammonium chloride (0.008 g) was added thereto, and the mixture was stirred overnight at room temperature. Water and ethyl acetate were added to the reaction solution, which was then separated into two layers. The aqueous layer was subjected to extraction with ethyl acetate. The organic layers were combined, washed with saturated saline and then dried over anhydrous sodium sulfate. The solvent was distilled off under reduced pressure, and the residue obtained was purified by silica gel column chromatography (n-hexane/ethyl acetate) to obtain the title compound (0.034 g).

$^1$H-NMR (CDCl$_3$) δ: 1.90-2.00 (1H, m), 2.17-2.25 (1H, m), 2.33 (3H, d, J=1.2 Hz), 2.55-2.63 (2H, m), 2.90-3.00 (2H, m), 4.88 (2H, s), 5.73 (1H, brs), 6.53 (1H, d, J=15.7 Hz), 6.98 (1H, d, J=1.2 Hz), 7.30 (2H, s), 7.38 (1H, t, J=7.9 Hz), 7.59-7.64 (2H, m), 8.39 (1H, d, J=7.9 Hz), 8.50 (1H, d, J=15.7 Hz).

[Step 2] 2,2,2-Trichloroethyl(2E)-3-(1-{[5-(1-cyanocyclobutyl)-3-(2,4,6-trichlorophenyl)-1,2-oxazol-4-yl]carbonyl}-3-methyl-1H-indol-4-yl)prop-2-enoate To a solution of the compound (0.290 g) obtained in the preceding step 1 in pyridine (1 ml), trifluoroacetic anhydride (0.172 ml) was added, and the mixture was stirred at room temperature for 1 hour. The reaction solution was concentrated under reduced pressure, and then, the residue obtained was diluted with ethyl acetate, washed with 1 N aqueous hydrochloric acid solution-saturated saline (1:1) and saturated aqueous solution of sodium bicarbonate-saturated saline (1:1) in this order and then dried over anhydrous sodium sulfate. The solvent was distilled off under reduced pressure to obtain the title compound (0.308 g).

$^1$H-NMR (CDCl$_3$) δ: 2.15-2.25 (1H, m), 2.41 (3H, s), 2.44-2.53 (1H, m), 2.75-2.82 (2H, m), 2.92-2.99 (2H, m), 4.88 (2H, s), 6.53 (1H, d, J=15.7 Hz), 6.95 (1H, s), 7.35-7.39 (3H, m), 7.61 (1H, d, J=7.9 Hz), 8.41 (1H, d, J=7.9 Hz), 8.55 (1H, d, J=15.7 Hz).

MS (m/z): 684 (M+H)$^+$.

[Step 3] (2E)-3-(1-{[5-(1-Cyanocyclobutyl)-3-(2,4,6-trichlorophenyl)-1,2-oxazol-4-yl]carbonyl}-3-methyl-1H-indol-4-yl)prop-2-enoic acid The title compound (0.131 g) was obtained by the same method as in step 5 of Example 89 using the compound (0.289 g) obtained in the preceding step 2.

$^1$H-NMR (CDCl$_3$) δ: 2.15-2.25 (1H, m), 2.41 (3H, d, J=1.2 Hz), 2.43-2.53 (1H, m), 2.76-2.83 (2H, m), 2.92-2.99 (2H, m), 6.46 (1H, d, J=15.7 Hz), 6.95 (1H, d, J=1.2 Hz), 7.35-7.39 (3H, m), 7.59 (1H, d, J=8.0 Hz), 8.41 (1H, d, J=8.0 Hz), 8.48 (1H, d, J=15.7 Hz).

Example 94

(2E)-[1-{[5-(1-Acryloylpiperidin-4-yl)-3-(2,4,6-trichlorophenyl)-1,2-oxazol-4-yl]carbonyl}-3,4-dihydrobenzo[cd]indol-5(1H)-ylidene]ethanoic acid

[Formula 82]

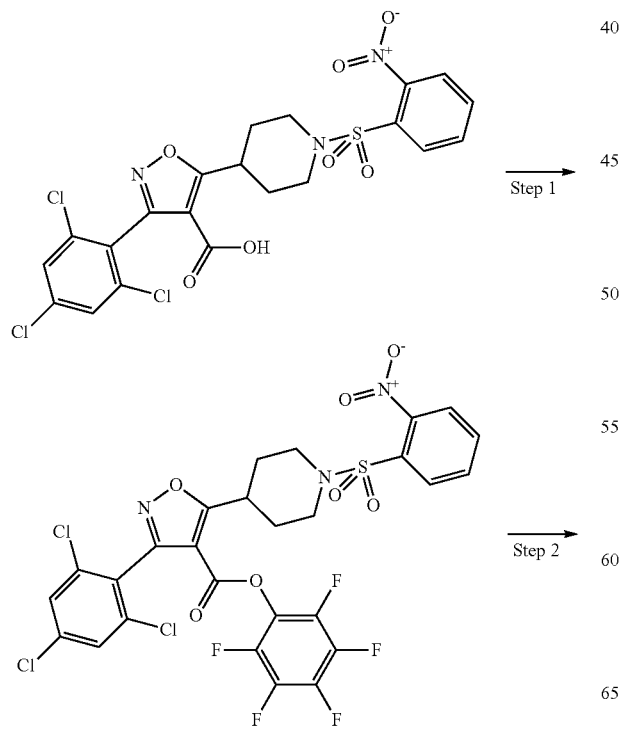

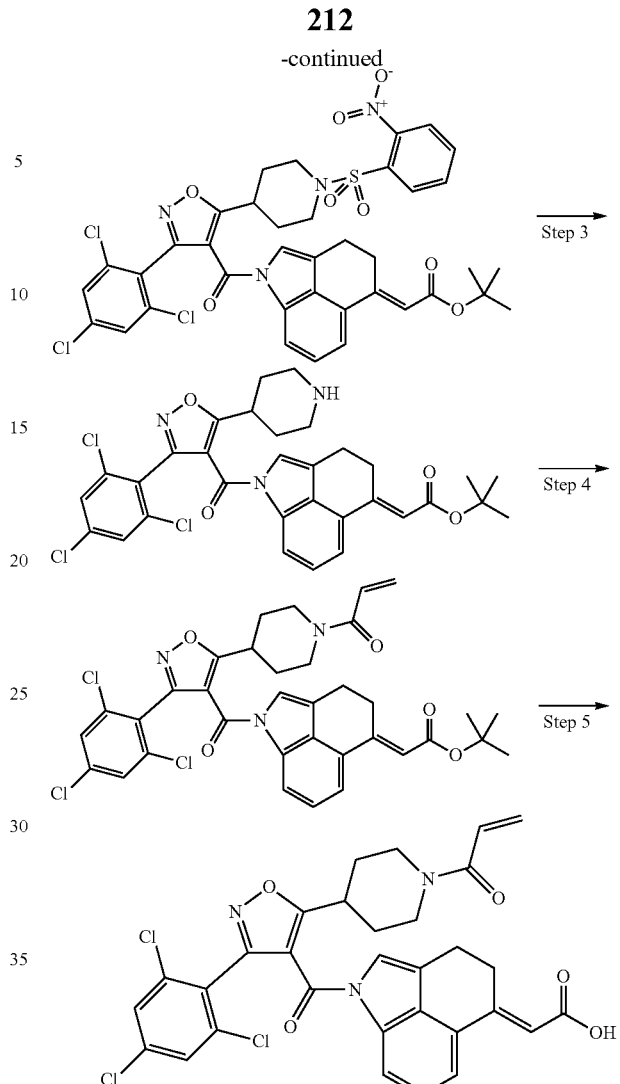

[Step 1] Pentafluorophenyl 5-{1-[(2-nitrophenyl)sulfonyl]piperidin-4-yl}-3-(2,4,6-trichlorophenyl)-1,2-oxazole-4-carboxylate To a solution of the compound (20.0 g) obtained in Reference Example X-38 in dichloromethane (200 ml), N,N-di(propan-2-yl)ethylamine (9.1 ml) and pentafluorophenyl trifluoroacetate (8.0 ml) were added under ice cooling, and the mixture was stirred overnight at room temperature. The reaction solution was concentrated under reduced pressure, and the residue obtained was purified by silica gel column chromatography (n-hexane/ethyl acetate) to obtain the title compound (24.7 g).

$^1$H-NMR (CDCl$_3$) δ: 2.07-2.24 (4H, m), 2.93-3.08 (2H, m), 3.61-3.73 (1H, m), 4.00-4.08 (2H, m), 7.44 (2H, s), 7.68-7.63 (1H, m), 7.69-7.76 (2H, m), 8.02-8.06 (1H, m).

[Step 2] tert-Butyl (2E)-[1-{[5-{1-[(2-nitrophenyl)sulfonyl]piperidin-4-yl}-3-(2,4,6-trichlorophenyl)-1,2-oxazol-4-yl]carbonyl}-3,4-dihydrobenzo[cd]indol-5(1H)-ylidene]ethanoate To a solution of the compound (5.22 g) obtained in Reference Example E-17 in N,N-dimethylformamide (97 ml), sodium hydride (55% oil, 846 mg) was slowly added under ice cooling, and the mixture was stirred at room temperature for 30 minutes. The compound (14.1 g) obtained in the preceding step 1 was added to the reaction solution under ice cooling, and the mixture was stirred at room temperature for 10 minutes. The reaction solution was diluted with ethyl acetate under ice cooling, and ice water was added thereto. After separation into two layers, the organic layer was washed with water and saturated saline in this order and then dried over anhydrous sodium sulfate. The solvent was distilled off under reduced pressure, and the residue obtained was purified by silica gel column chromatography (n-hexane/ethyl acetate) to obtain the title compound (11.5 g).

$^1$H-NMR (CDCl$_3$) δ: 1.53 (9H, s), 2.75 (2H, t, J=6.7 Hz), 2.86-2.97 (4H, m), 2.88-2.95 (2H, m), 3.20-3.35 (3H, m), 3.94-4.02 (2H, m), 6.41 (1H, s), 6.78 (1H, s), 7.30-7.36 (3H, m), 7.46 (1H, d, J=7.9 Hz), 7.60-7.65 (1H, m), 7.66-7.76 (2H, m), 8.00 (1H, dd, J=7.6, 2.1 Hz), 8.06 (1H, d, J=8.5 Hz).

[Step 3] tert-Butyl (2E)-[1-{[5-(piperidin-4-yl)-3-(2,4,6-trichlorophenyl)-1,2-oxazol-4-yl]carbonyl}-3,4-dihydrobenzo[cd]indol-5(1H)-ylidene]ethanoate To a solution of the compound (14.2 g) obtained in the preceding step 2 in acetonitrile (175 ml), 4-bromobenzenethiol (6.61 g) and potassium carbonate (9.67 g) were added under ice cooling, and the mixture was stirred at room temperature for 7 hours. The reaction solution was diluted with ethyl acetate under ice cooling, and ice water was added thereto. After separation into two layers, the organic layer was washed with water and saturated saline in this order and then dried over anhydrous sodium sulfate. The solvent was distilled off under reduced pressure, and the residue obtained was purified by silica gel column chromatography (dichloromethane/methanol) to obtain the title compound (8.66 g).

$^1$H-NMR (CDCl$_3$) δ: 1.54 (9H, s), 1.91-2.17 (4H, m), 2.71 (2H, td, J=11.8, 3.2 Hz), 2.78 (2H, t, J=6.7 Hz), 3.18-3.31 (3H, m), 3.34 (2H, t, J=6.7 Hz), 6.42 (1H, s), 6.84 (1H, s), 7.31-7.37 (3H, m), 7.47 (1H, d, J=7.3 Hz), 8.10 (1H, d, J=7.9 Hz).

[Step 4] tert-Butyl (2E)-[1-{[5-(1-acryloylpiperidin-4-yl)-3-(2,4,6-trichlorophenyl)-1,2-oxazol-4-yl]carbonyl}-3,4-dihydrobenzo[cd]indol-5(1H)-ylidene] ethanoate To a solution of the compound (6.13 g) obtained in the preceding step 3 in dichloromethane (98 ml), triethylamine (2.7 ml) and acryloyl chloride (0.95 ml) were added under ice cooling, and the mixture was stirred at 0° C. for 20 minutes. Ice water was added to the reaction solution, followed by extraction with chloroform. The extract was washed with saturated saline and then dried over anhydrous sodium sulfate. The solvent was distilled off under reduced pressure, and the residue obtained was purified by silica gel column chromatography (n-hexane/ethyl acetate) to obtain the title compound (5.93 g).

$^1$H-NMR (CDCl$_3$) δ: 1.54 (9H, s), 2.00 (2H, ddd, J=24.6, 11.9, 3.8 Hz), 2.08-2.16 (2H, m), 2.72-2.84 (3H, m), 3.12-3.25 (1H, m), 3.34 (2H, t, J=6.7 Hz), 3.42 (1H, tt, J=11.5, 4.2 Hz), 4.07-4.18 (1H, m), 4.70-4.81 (1H, m), 5.71 (1H, dd, J=10.9, 1.8 Hz), 6.30 (1H, dd, J=16.3, 1.8 Hz), 6.42 (1H, s), 6.59 (1H, dd, J=16.9, 10.3 Hz), 6.81 (1H, s), 7.32 (2H, s), 7.35 (1H, t, J=7.9 Hz), 7.47 (1H, d, J=7.3 Hz), 8.10 (1H, d, J=7.9 Hz).

[Step 5] (2E)-[1-{[5-(1-Acryloylpiperidin-4-yl)-3-(2,4,6-trichlorophenyl)-1,2-oxazol-4-yl]carbonyl}-3,4-dihydrobenzo[cd]indol-5(1H)-ylidene]ethanoic acid The title compound (5.28 g) was obtained by the same method as in step 3 of Example 10 using the compound (6.36 g) obtained in the preceding step 4.

$^1$H-NMR (CDCl$_3$) δ: 2.02 (2H, ddd, J=25.1, 11.8, 3.9 Hz), 2.09-2.20 (2H, m), 2.75-2.89 (3H, m), 3.16-3.28 (1H, brm), 3.38 (2H, t, J=6.3 Hz), 3.44 (1H, tt, J=12.1, 3.6 Hz), 4.07-4.19 (1H, m), 4.71-4.81 (1H, m), 5.75 (1H, dd, J=10.9, 1.8 Hz), 6.30 (1H, dd, J=16.9, 1.8 Hz), 6.54 (1H, s), 6.59 (1H, dd, J=16.6, 10.6 Hz), 6.84 (1H, s), 7.32 (2H, s), 7.39 (1H, t, J=7.9 Hz), 7.52 (1H, d, J=7.9 Hz), 8.14 (1H, d, J=7.9 Hz).

MS (m/z): 624 (M+H)$^+$.

The following compounds were obtained by the same method as in Example 94 using the compounds obtained in the Reference Examples.

TABLE 61

| Example | Reference Example | Structure and name | Instrumental data |
|---|---|---|---|
| 95 | X-46 E-1 | (2E)-3-(1-{[5-(1-Acryloylazetidin-3-yl)-3-(2,4,6-trichlorophenyl)-1,2-oxazol-4-yl]carbonyl}-1H-indol-4-yl)prop-2-enoic acid 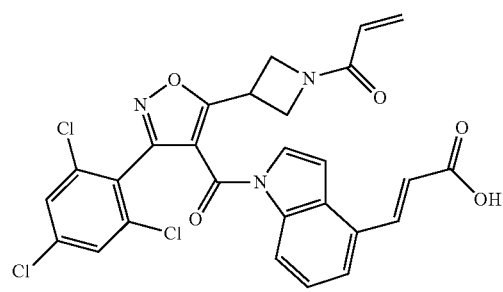 | $^1$H-NMR(CDCl$_3$)δ: 4.20-4.29(1H, m), 4.45-4.56(2H, m), 4.59-4.69(2H, m), 5.76(1H, dd, J = 10.6, 1.5 Hz), 6.20 (1H, dd, J = 16.9, 10.3 Hz), 6.40(1H, dd, J = 16.9, 1.2 Hz), 6.56(1H, d, J = 16.3 Hz), 6.81(1H, d, J = 3.6 Hz), 7.16(1H, d, J = 3.6 Hz), 7.36-7.43(3H, m), 7.60(1H, d, J = 7.3 Hz), 8.06(1H, d, J = 16.3 Hz), 8.31(1H, d, J = 7.9 Hz). MS(m/z): 570(M + H)$^+$. |

TABLE 61-continued

| Example | Reference Example | Structure and name | Instrumental data |
|---|---|---|---|
| 96 | X-45<br>E-1 | (2E)-3-(1-{[5-(3-Acryloylpiperidin-3-yl)-3-(2,4,6-trichlorophenyl)-1,2-oxazol-4-yl]carbonyl}-1H-indol-4-yl)prop-2-enoic acid | $^1$H-NMR(CDCl$_3$)δ: 1.53-1.71(1H, m), 1.84-2.45(2H, m), 2.82-2.98(1H, m), 3.19-3.38(2H, m), 3.46-3.59(1H, m), 3.95-4.37(1H, m), 4.51-4.92(1H, m), 5.30(1H, s), 5.60-5.79(1H, m), 6.21-6.31(1H, m), 6.47-6.62(2H, m), 6.77(1H, d, J = 3.6 Hz), 7.16-7.46(4H, m), 7.51-7.62(1H, m), 7.98-8.08(1H, m), 8.37(1H, d, J = 8.5 Hz).<br>MS(m/z): 598(M + H)$^+$. |
| 97 | X-73<br>E-1 | (2E)-3-(1-{[5-(1-Acryloyl-3-methoxyazetidin-3-yl)-3-(2,4,6-trichlorophenyl)-1,2-oxazol-4-yl]carbonyl}-1H-indol-4-yl)prop-2-enoic acid | $^1$H-NMR(CDCl$_3$)δ: 3.25(3H, s), 4.39(1H, d, J = 11.5 Hz), 4.50(1H, d, J = 9.7 Hz), 4.66(1H, d, J = 11.5 Hz), 4.79(1H, d, J = 9.7 Hz), 5.78(1H, t, J = 6.0 Hz), 6.21(1H, dd, J = 16.9, 10.3 Hz), 6.41(1H, dd, J = 17.2, 1.5 Hz), 6.56(1H, d, J = 15.7 Hz), 6.83(1H, d, J = 4.2 Hz), 7.16(1H, d, J = 3.6 Hz), 7.35-7.45(3H, m), 7.60(1H, d, J = 7.3 Hz), 8.07(1H, d, J = 15.7 Hz), 8.39(1H, d, J = 8.5 Hz).<br>MS(m/z): 600(M + H)$^+$. |

TABLE 62

| | | | |
|---|---|---|---|
| 98 | X-55<br>E-1 | (2E)-3-(1-{[5-(1-Acryloyl-3-methylazetidin-3-yl)-3-(2,4,6-trichlorophenyl)-1,2-oxazol-4-yl]carbonyl}-1H-indol-4-yl)prop-2-enoic acid | $^1$H-NMR(CDCl$_3$)δ: 1.89(3H, s), 4.18(1H, d, J = 10.3 Hz), 4.30(1H, d, J = 9.1 Hz), 4.59(1H, d, J = 10.3 Hz), 4.74(1H, d, J = 9.1 Hz), 5.75(1H, dd, J = 10.3, 1.2 Hz), 6.17(1H, dd, J = 16.9, 10.9 Hz), 6.38(1H, dd, J = 16.9, 1.2 Hz), 6.53(1H, d, J = 16.3 Hz), 6.72(1H, d, J = 3.6 Hz), 7.15(1H, d, J = 3.6 Hz), 7.29-7.33(2H, m), 7.41(1H, t, J = 7.9 Hz), 7.58(1H, d, J = 7.9 Hz), 8.02(1H, d, J = 15.7 Hz), 8.35(1H, d, J = 8.5 Hz).<br>MS(m/z): 584(M + H)$^+$. |

TABLE 62-continued

| 99 | X-38 E-1 | (2E)-3-(1-{[5-(1-Acryloylpiperidin-4-yl)-3-(2,4,6-trichlorophenyl)-1,2-oxazol-4-yl]carbonyl}-1H-indol-4-yl)prop-2-enoic acid 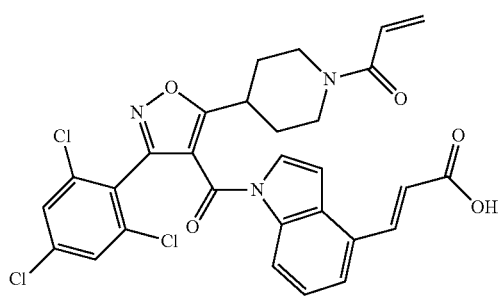 | $^1$H-NMR(CDCl$_3$)δ: 2.02(2H, ddd, J = 25.1, 12.1, 3.9 Hz), 2.10-2.20(2H, m), 2.75-2.87(1H, m), 3.15-3.27(1H, m), 3.42(1H, tt, J = 11.5, 3.6 Hz), 4.12-4.16(1H, m), 4.73-4.83(1H, m), 5.76(1H, dd, J = 10.6, 1.5 Hz), 6.31(1H, dd, J = 16.6, 1.5 Hz), 6.56(1H, d, J = 16.3 Hz), 6.59(1H, dd, J = 16.9, 10.9 Hz), 6.77(1H, d, J = 3.6 Hz), 7.20(1H, d, J = 4.2 Hz), 7.33(2H, s), 7.42(1H, t, J = 8.2 Hz), 7.60(1H, d, J = 7.9 Hz), 8.07(1H, d, J = 16.3 Hz), 8.38(1H, d, J = 7.9 Hz). MS(API): 598(M + H)$^+$. |

TABLE 63

| 100 | X-38 E-1 | (2E)-3-[1-({5-[1-(Prop-2-ynoyl)piperidin-4-yl]-3-(2,4,6-trichlorophenyl)-1,2-oxazol-4-yl}carbonyl)-1H-indol-4-yl]prop-2-enoic acid 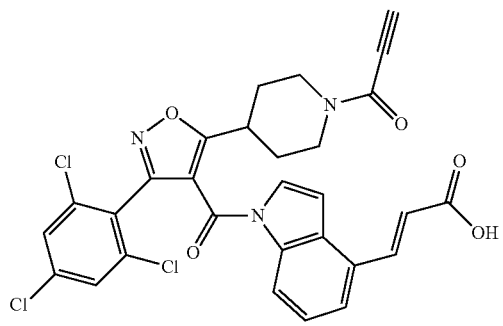 | $^1$H-NMR(CDCl$_3$)δ: 1.97-2.20(4H, m), 2.82(1H, t, J = 11.2 Hz), 3.16(1H, s), 3.25(1H, dd, J = 18.4, 7.6 Hz), 3.43(1H, t, J = 11.5 Hz), 4.53(1H, d, J = 13.9 Hz), 4.68(1H, d, J = 13.3 Hz), 6.56(1H, d, J = 16.3 Hz), 6.77(1H, d, J = 3.6 Hz), 7.19(1H, d, J = 3.6 Hz), 7.33(2H, s), 7.42(1H, t, J = 7.9 Hz), 7.60(1H, d, J = 7.3 Hz), 8.07(1H, d, J = 16.3 Hz), 8.38(1H, d, J = 8.5 Hz). MS(m/z): 596(M + H)$^+$. |
| 101 | X-46 E-1 | (2E)-3-[1-({5-[1-(Prop-2-ynoyl)azetidin-3-yl]-3-(2,4,6-trichlorophenyl)-1,2-oxazol-4-yl}carbonyl)-1H-indol-4-yl]prop-2-enoic acid 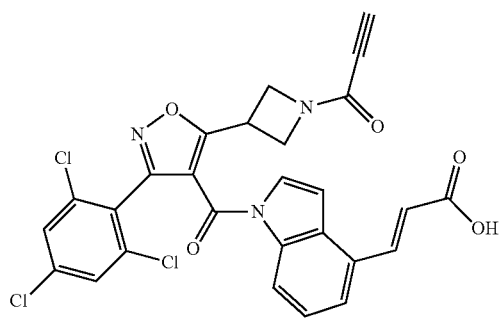 | $^1$H-NMR(CDCl$_3$)δ: 3.05(1H, s), 3.38-3.47(1H, m), 4.27(1H, q, J = 7.5 Hz), 4.42-4.51(2H, m), 4.60-4.68(2H, m), 6.56(1H, d, J = 16.3 Hz), 6.82(1H, d, J = 3.6 Hz), 7.14(1H, d, J = 3.6 Hz), 7.36-7.43(3H, m), 7.60(1H, d, J = 7.9 Hz), 8.06(1H, d, J = 15.7 Hz), 8.30(1H, d, J = 7.9 Hz). MS(m/z): 570(M + H)$^+$. |

TABLE 63-continued

| 102 | X-37 E-1 | (2E)-3-(1-{[5-(1-Acryloylpiperidin-4-yl)-3-(2,6-dichlorophenyl)-1,2-oxazol-4-yl]carbonyl}-1H-indol-4-yl)prop-2-enoic acid 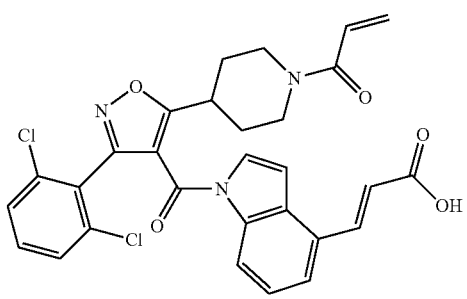 | $^1$H-NMR(CDCl$_3$)δ: 1.94-2.06(2H, m), 2.09-2.17(2H, m), 2.71-2.84(1H, m), 3.11-3.24(1H, m), 3.43(1H, tt, J = 10.6, 4.3 Hz), 4.06-4.18(1H, m), 4.70-4.82(1H, m), 5.71(1H, dd, J = 10.6, 1.6 Hz), 6.29(1H, dd, J = 16.8, 1.6 Hz), 6.51(1H, d, J = 15.7 Hz), 6.58(1H, dd, J = 16.8, 10.6 Hz), 6.67(1H, d, J = 3.9 Hz), 7.16-7.30(4H, m), 7.37(1H, t, J = 8.0 Hz), 7.55(1H, d, J = 7.4 Hz), 8.00(1H, d, J = 16.0 Hz), 8.36(1H, d, J = 7.8 Hz). MS(m/z): 564(M + H)$^+$. |

TABLE 64

| 103 | X-38 E-1 | (2E)-3-[1-({5-[1-(Ethenylsulfonyl)piperidin-4-yl]-3-(2,4,6-trichlorophenyl)-1,2-oxazol-4-yl}-carbonyl)-1H-indol-4-yl]prop-2-enoic acid 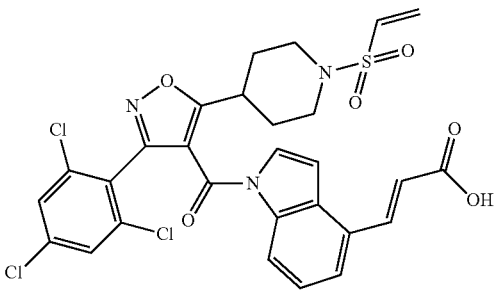 | $^1$H-NMR(CDCl$_3$)δ: 2.10-2.24(4H, m), 2.72-2.79(2H, m), 3.20-3.28(1H, m), 3.87(2H, d, J = 12.7 Hz), 6.05(1H, d, J = 9.7 Hz), 6.26(1H, d, J = 16.3 Hz), 6.44(1H, dd, J = 16.3, 9.7 Hz), 6.56(1H, d, J = 15.7 Hz), 6.77(1H, d, J = 3.6 Hz), 7.19(1H, d, J = 3.6 Hz), 7.33(2H, s), 7.41(1H, t, J = 8.2 Hz), 7.60(1H, d, J = 7.9 Hz), 8.07(1H, d, J = 15.7 Hz), 8.37(1H, d, J = 8.5 Hz). MS(m/z): 634(M + H)$^+$. |
| 104 | X-38 E-8 | (2E)-3-(1-{[5-(1-Acryloylpiperidin-4-yl)-3-(2,4,6-trichlorophenyl)-1,2-oxazol-4-yl]carbonyl}-3-methyl-1H-indol-4-yl)prop-2-enoic acid 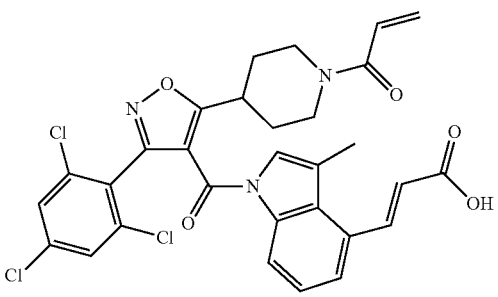 | $^1$H-NMR(CDCl$_3$)δ: 1.92-2.08(2H, m), 2.08-2.19(2H, m), 2.33(3H, s), 2.72-2.86(1H, m), 3.13-3.26(1H, m), 3.39-3.50(1H, m), 4.08-4.19(1H, m), 4.73-4.83(1H, m), 5.73(1H, dd, J = 10.9, 1.8 Hz), 6.31(1H, dd, J = 16.9, 1.8 Hz), 6.46(1H, d, J = 15.7 Hz), 6.60(1H, dd, J = 16.9, 10.9 Hz), 6.92(1H, s), 7.32(2H, s), 7.38(1H, t, J = 7.9 Hz), 7.58(1H, d, J = 7.9 Hz), 8.34-8.51(2H, m). MS(m/z): 612(M + H)$^+$. |

TABLE 64-continued

| 105 | X-38 E-7 | 2-(1-{[5-(1-Acryloylpiperidin-4-yl)-3-(2,4,6-trichlorophenyl)-1,2-oxazol-4-yl]carbonyl}-1H-indol-4-yl)cyclopropane carboxylic acid | $^1$H-NMR(CDCl$_3$)δ: 1.46-1.53(1H, m), 1.70-1.76(1H, m), 1.94-2.07(2H, m), 2.09-2.39(3H, m), 2.73-2.86(2H, m), 3.13-3.26(1H, m), 3.34-3.43(1H, m), 4.06-4.19(1H, m), 4.70-4.80(1H, m), 5.75(1H, dd, J = 10.6, 1.2 Hz), 6.30(1H, dd, J = 16.9, 1.2 Hz), 6.58(1H, dd, J = 16.9, 10.3 Hz), 6.67(1H, d, J = 4.2 Hz), 6.95(1H, d, J = 7.9 Hz), 7.13(1H, d, J = 3.6 Hz), 7.30(1H, t, J = 7.9 Hz), 7.34(2H, s), 8.19(1H, d, J = 8.5 Hz). MS(m/z): 612(M + H)$^+$. |

TABLE 65

| 106 | X-40 E-8 | (2E)-3-(1-{[5-(1-Acryloylpiperidin-4-yl)-3-(2,4,-dichlorophenyl)-1,2-oxazol-4-yl]carbonyl}-3-methyl-1H-indol-4-yl)prop-2-enoic acid | $^1$H-NMR(CDCl$_3$)δ: 1.95-2.07(2H, m), 2.07-2.18(2H, m), 2.29(3H, d, J = 1.2 Hz), 2.76-2.92(1H, m), 3.15-3.60(2H, m), 4.08-4.20(1H, m), 4.71-4.84(1H, m), 5.78(1H, dd, J = 10.6, 1.5 Hz), 6.31(1H, dd, J = 16.9, 1.8 Hz), 6.46(1H, d, J = 15.7 Hz), 6.59(1H, dd, J = 16.9, 10.9 Hz), 6.76-6.77(1H, m), 7.28-7.33(2H, m), 7.39(1H, t, J = 8.2 Hz), 7.47-7.53(1H, m), 7.60(1H, d, J = 7.3 Hz), 8.39(1H, d, J = 7.9 Hz), 8.46(1H, d, J = 15.7 Hz). MS(m/z): 578(M + H)$^+$. |
| 107 | X-41 E-8 | (2E)-3-(1-{[5-(1-Acryloylpiperidin-4-yl)-3-(2,4-dichloro-6-fluorophenyl)-1,2-oxazol-4-yl]carbonyl}-1H-indol-4-yl)prop-2-enoic acid | $^1$H-NMR(CDCl$_3$)δ: 1.93-2.07(2H, m), 2.07-2.19(2H, m), 2.33(3H, s), 2.71-2.87(1H, m), 3.12-3.26(1H, m), 3.36-3.61(1H, m), 4.07-4.20(1H, m), 4.72-4.83(1H, m), 5.72(1H, d, J = 10.3 Hz), 6.31(1H, d, J = 16.3 Hz), 6.46(1H, d, J = 15.7 Hz), 6.60(1H, dd, J = 16.6, 10.6 Hz), 6.84(1H, s), 6.99-7.05(1H, m), 7.20(1H, s), 7.38(1H, t, J = 8.2 Hz), 7.58(1H, d, J = 8.5 Hz), 8.37(1H, d, J = 8.5 Hz), 8.42(1H, d, J = 15.7 Hz). MS(m/z): 596(M + H)$^+$. |

TABLE 66

| | | | |
|---|---|---|---|
| 108 | X-37<br>E-8 | (2E)-3-(1-{[5-(1-Acryloylpiperidin-4-yl)-3-(2,6-dichlorophenyl)-1,2-oxazol-4-yl]carbonyl}-3-methyl-1H-indol-4-yl)prop-2-enoic acid<br>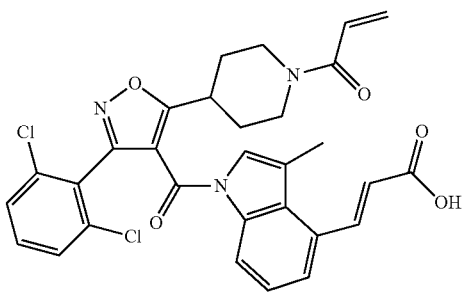 | $^1$H-NMR(CDCl$_3$)δ: 1.93-2.10(2H, m), 2.11-2.22(2H, m), 2.29(3H, s), 2.75-2.88(1H, m), 3.16-3.28(1H, m), 3.45-3.55(1H, m), 4.10-4.20(1H, m), 4.74-4.83(1H, m), 5.73(1H, dd, J = 10.9, 1.8 Hz), 6.31 (1H, dd, J = 16.3, 1.8 Hz), 6.44(1H, d, J = 15.7 Hz), 6.61(1H, dd, J = 16.6, 10.6 Hz), 6.94(1H, s), 7.18-7.30(3H, m), 7.36(1H, t, J = 8.2 Hz), 7.56(1H, d, J = 7.9 Hz), 8.37-8.44(2H, m).<br>MS(m/z): 578(M + H)$^+$. |
| 109 | X-39<br>E-1 | (2E)-3-(1-{[5-(1-Acryloylpiperidin-4-yl)-3-(2,4,6-trimethylphenyl)-1,2-oxazol-4-yl]carbonyl}-1H-indol-4-yl)prop-2-enoic acid<br>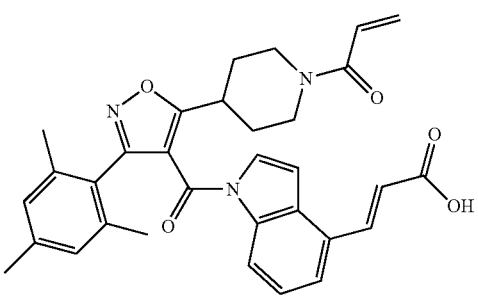 | $^1$H-NMR(CDCl$_3$)δ: 1.93-2.13(4H, m), 2.17(6H, s), 2.21(3H, s), 2.71-2.82(1H, brm), 3.11-3.22(1H, brm), 3.26-3.35(1H, m), 4.07-4.16(1H, m), 4.70-4.80(1H, m), 5.72(1H, dd, J = 10.9, 1.8 Hz), 6.30 (1H, dd, J = 16.3, 1.8 Hz), 6.52-6.62(2H, m), 6.73(1H, d, J = 3.6 Hz), 6.81(2H, s), 7.08(1H, d, J = 3.6 Hz), 7.39(1H, t, J = 7.9 Hz), 7.58(1H, d, J = 7.9 Hz), 8.06(1H, d, J = 15.7 Hz), 8.42(1H, d, J = 7.9 Hz). |
| 110 | X-43<br>E-1 | (2E)-3-(1-{[5-(1-Acryloylpiperidin-4-yl)-3-(4-chloro-2,6-dimethylphenyl)-1,2-oxazol-4-yl]carbonyl}-1H-indol-4-yl)prop-2-enoic acid<br>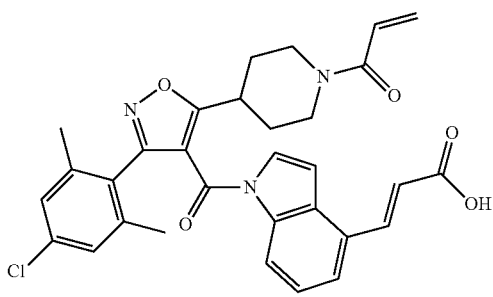 | $^1$H-NMR(CDCl$_3$)δ: 1.93-2.13(4H, m), 2.19(6H, s), 2.70-2.81(1H, brm), 3.11-3.21(1H, brm), 3.23-3.33(1H, m), 4.07-4.16(1H, m), 4.70-4.80(1H, m), 5.72(1H, dd, J = 10.9, 1.8 Hz), 6.30 (1H, dd, J = 16.3, 1.8 Hz), 6.53-6.62(2H, m), 6.80(1H, d, J = 3.6 Hz), 7.02(2H, s), 7.08(1H, d, J = 3.6 Hz), 7.41(1H, t, J = 7.9 Hz), 7.60(1H, d, J = 7.9 Hz), 8.07(1H, d, J = 15.7 Hz), 8.40(1H, d, J = 7.9 Hz). |

TABLE 67

| | | | |
|---|---|---|---|
| 111 | X-56 E-1 | (2E)-3-(1-{[5-(1-Acryloyl-4-methylpiperidin-4-yl)-3-(2,4,6-trichlorophenyl)-1,2-oxazol-4-yl]carbonyl}-1H-indol-4-yl)prop-2-enoic acid | ¹H-NMR(CDCl₃)δ: 1.55(3H, s), 1.72-1.80(2H, m), 2.26-2.36(2H, brm), 3.35-3.50(2H, brm), 3.67-3.75(1H, brm), 3.92-4.01(1H, brm), 5.68(1H, d, J = 10.3 Hz), 6.27 (1H, d, J = 16.9 Hz), 6.49-6.59(2H, m), 6.81(1H, d, J = 3.6 Hz), 7.23(1H, d, J = 3.6 Hz), 7.32(2H, brs), 7.41(1H, dd, J = 8.2, 4.1 Hz), 7.60(1H, d, J = 7.9 Hz), 8.06(1H, d, J = 16.3 Hz), 8.43(1H, d, J = 7.9 Hz). MS(m/z): 612(M + H)⁺. |
| 112 | X-42 E-8 | (2E)-3-(1-{[5-(1-Acryloylpiperidin-4-yl)-3-(2,6-dichloro-4-fluorophenyl)-1,2-oxazol-4-yl]carbonyl}-3-methyl-1H-indol-4-yl)prop-2-enoic acid | ¹H-NMR(CDCl₃)δ: 1.92-2.24(4H, m), 2.33(3H, s), 2.74-2.87(1H, m), 3.14-3.28(1H, m), 3.41-3.51(1H, m), 4.09-4.20(1H, m), 4.73-4.83(1H, m), 5.74(1H, dd, J = 10.6, 1.5 Hz), 6.31 (1H, dd, J = 16.9, 1.8 Hz), 6.46(1H, d, J = 15.7 Hz), 6.60(1H, dd, J = 16.6, 10.6 Hz), 6.92(1H, d, J = 1.2 Hz), 7.04-7.10(2H, m), 7.38(1H, t, J = 8.2 Hz), 7.58(1H, d, J = 7.9 Hz), 8.39(1H, d, J = 7.9 Hz), 8.43(1H, d, J = 15.7 Hz). MS(m/z): 596(M + H)⁺. |

TABLE 68

| | | | |
|---|---|---|---|
| 113 | X-56 E-8 | (2E)-3-(1-{[5-(1-Acryloyl-4-methylpiperidin-4-yl)-3-(2,4,6-trichlorophenyl)-1,2-oxazol-4-yl]carbonyl}-3-methyl-1H-indol-4-yl)prop-2-enoic acid | ¹H-NMR(CDCl₃)δ: 1.56(3H, s), 1.73-1.81(2H, m), 2.29-2.39(5H, brm), 3.34-3.51(2H, brm), 3.66-3.78(1H, brm), 3.94-4.04(1H, brm), 5.68(1H, d, J = 10.3 Hz), 6.27 (1H, d, J = 16.3 Hz), 6.45(1H, d, J = 15.7 Hz), 6.49-6.59(1H, m), 6.94(1H, s), 7.24-7.42(3H, m), 7.58(1H, d, J = 7.3 Hz), 8.41-8.48(2H, m). MS(m/z): 626(M + H)⁺. |

TABLE 68-continued

| 114 | X-39<br>E-8 | (2E)-3-(1-{[5-(1-Acryloylpiperidin-4-yl)-3-(2,4,6-trimethylphenyl)-1,2-oxazol-4-yl]carbonyl}-3-methyl-1H-indol-4-yl)prop-2-enoic acid | $^1$H-NMR(CDCl$_3$)δ: 1.92-2.04(2H, m), 2.06-2.14(2H, m), 2.17(6H, s), 2.21(3H, s), 2.30(3H, s), 2.74-2.84(1H, m), 3.13-3.24(1H, m), 3.30-3.39(1H, m), 4.04-4.18(1H, m), 4.70-4.80(1H, m), 5.71(1H, dd, J = 10.3, 1.8 Hz), 6.30 (1H, dd, J = 16.9, 1.8 Hz), 6.45(1H, d, J = 15.7 Hz), 6.59(1H, dd, J = 16.9, 10.9 Hz), 6.76(1H, s), 6.80(2H, s), 7.35(1H, t, J = 7.9 Hz), 7.57(1H, d, J = 7.9 Hz), 8.46-8.46(2H, m). |

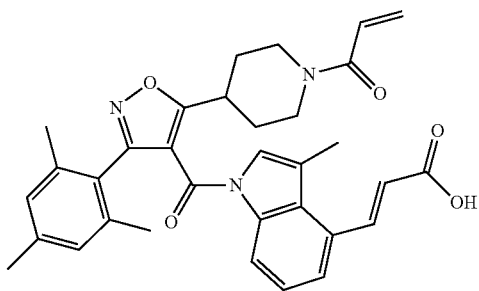

| 115 | X-38<br>E-13 | 3-(1-{[5-(1-Acryloylpiperidin-4-yl)-3-(2,4,6-trichlorophenyl)-1,2-oxazol-4-yl]carbonyl}-3-methyl-1H-indol-4-yl)propanoic acid | $^1$H-NMR(CDCl$_3$)δ: 1.91-2.06(2H, m), 2.08-2.21(2H, m), 2.29(3H, d, J = 1.2 Hz), 2.69(2H, t, J = 7.9 Hz), 2.76-2.89(1H, m), 3.17-3.28(1H, m), 3.29(2H, t, J = 7.9 Hz), 3.39-3.49(1H, m), 4.07-4.18(1H, m), 4.70-4.79(1H, m), 5.77(1H, dd, J = 10.9, 1.8 Hz), 6.30 (1H, dd, J = 16.9, 1.2 Hz), 6.59(1H, dd, J = 16.6, 10.6 Hz), 6.82(1H, d, J = 1.2 Hz), 7.10(1H, d, J = 7.3 Hz), 7.25-7.33(3H, m), 8.21(1H, d, J = 8.5 Hz).<br>MS(m/z): 614(M + H)$^+$. |

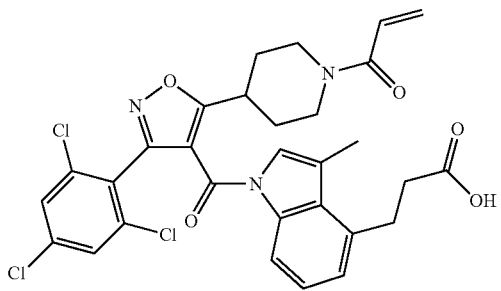

TABLE 69

| 118 | X-38<br>E-10 | (2E)-3-(1-{[5-(1-Acryloylpiperidin-4-yl)-3-(2,4,6-trichlorophenyl)-1,2-oxazol-4-yl]carbonyl}-1H-indol-4-yl)-2-methylprop-2-enoic acid | $^1$H-NMR(CDCl$_3$)δ: 1.95-2.04(2H, m), 2.07(3H, s), 2.10-2.22(2H, m), 2.75-2.87(1H, m), 3.15-3.27(1H, m), 3.38-3.48(1H, m), 4.07-4.18(1H, m), 4.71-4.82(1H, m), 5.76(1H, dd, J = 10.6, 1.5 Hz), 6.26-6.36(1H, m), 6.51-6.64(2H, m), 7.12-7.16(1H, m), 7.30-7.45(4H, m), 8.01(1H, s), 8.30(1H, d, J = 7.9 Hz).<br>MS(m/z): 612(M + H)$^+$. |

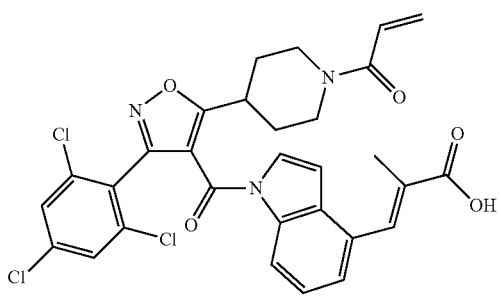

TABLE 69-continued

| 117 | X-59 E-8 | (2E)-3-(1-{[5-(1-Acryloyl-4-methoxypiperidin-4-yl)-3-(2,4,6-trichlorophenyl)-1,2-oxazol-4-yl]carbonyl}-3-methyl-1H-indol-4-yl)prop-2-enoic acid | $^1$H-NMR(CDCl$_3$)δ: 1.98-2.46(4H, m), 2.39(3H, s), 3.03-3.16(1H, m), 3.24(3H, s), 3.42-3.58(1H, m), 3.80-3.91(1H, m), 4.43-4.54(1H, m), 5.72(1H, d, J = 10.3 Hz), 6.29(1H, dd, J = 16.6, 1.5 Hz), 6.45(1H, d, J = 15.7 Hz), 6.57 (1H, dd, J = 16.9, 10.9 Hz), 6.95(1H, d, J = 1.2 Hz), 7.31-7.41(3H, m), 7.59(1H, d, J = 7.9 Hz), 8.43-8.51(2H, m). MS(m/z): 642(M + H)$^+$. |
|---|---|---|---|

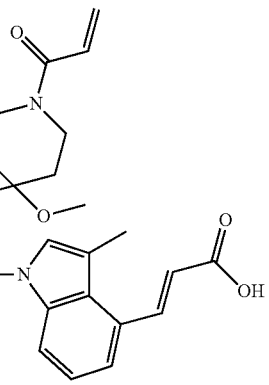

| 118 | X-38 E-2 | (2E)-3-(1-{[5-(1-Acryloylpiperidin-4-yl)-3-(2,4,6-trichlorophenyl)-1,2-oxazol-4-yl]carbonyl}-1H-indazol-4-yl)prop-2-enoic acid | $^1$H-NMR(CDCl$_3$)δ: 1.93-2.14(2H, m), 2.15-2.24(2H, m), 2.75-2.88(1H, m), 3.15-3.29(1H, m), 3.49-3.61(1H, m), 4.10-4.23(1H, m), 4.75-4.84(1H, m), 5.74(1H, dd, J = 10.3, 1.8 Hz), 6.32 (1H, dd, J = 16.9, 1.8 Hz), 6.62(1H, d, J = 16.3 Hz), 6.62(1H, dd, J = 16.9, 10.3 Hz), 7.33(2H, s), 7.60-7.67(2H, m), 8.03(1H, d, J = 16.3 Hz), 8.14(1H, s), 8.47(1H, dd, J = 6.0, 3.0 Hz). MS(m/z): 599(M + H)$^+$. |
|---|---|---|---|

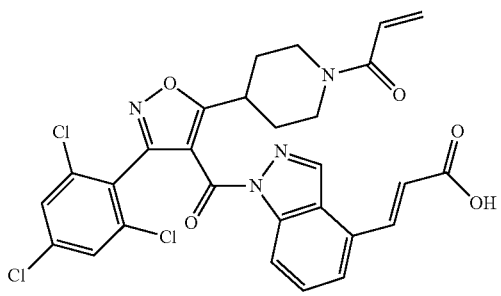

TABLE 70

| 119 | X-38 E-8 | (2E)-3-(1-{[5-{1-[(2E)-But-2-enoyl]piperidin-4-yl}-3-(2,4,6-trichlorophenyl)-1,2-oxazol-4-yl]carbonyl}-3-methyl-1H-indol-4-yl)prop-2-enoic acid | $^1$H-NMR(CDCl$_3$)δ: 1.90(3H, dd, J = 7.0, 1.5 Hz), 1.93-2.06(2H, m), 2.08-2.16(2H, m), 2.33(3H, s), 2.70-2.84(1H, m), 3.10-3.23(1H, m), 3.37-3.48(1H, m), 4.05-4.22(1H, m), 4.68-4.83(1H, m), 6.29(1H, dq, J = 15.1, 1.8 Hz), 6.46 (1H, d, J = 15.7 Hz), 6.85-6.95(2H, m), 7.32(2H, s), 7.38(1H, t, J = 7.9 Hz), 7.58(1H, d, J = 7.9 Hz), 8.39(1H, d, J = 7.3 Hz), 8.43(1H, d, J = 15.7 Hz). MS(m/z): 626(M + H)$^+$. |
|---|---|---|---|

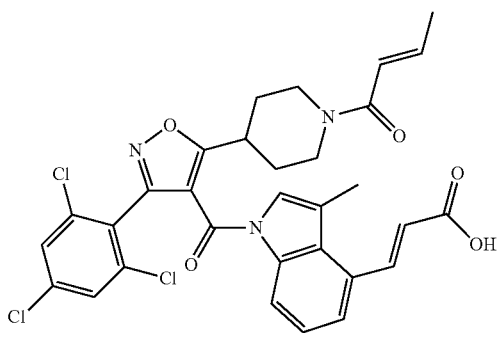

TABLE 70-continued

| | | | | |
|---|---|---|---|---|
| 120 | X-58 E-1 | (2E)-3-[1-({5-[1-Acryloyl-4-(methoxymethyl)piperidin-4-yl]-3-(2,4,6-trichlorophenyl)-1,2-oxazol-4-yl}carbonyl)-1H-indol-4-yl]prop-2-enoic acid | | $^1$H-NMR(CDCl$_3$)δ: 1.74-1.84(2H, m), 2.37-2.50(2H, m), 3.09(3H, s), 3.24-3.35(1H, brm), 3.37-3.67(3H, brm), 3.76-3.88(1H, brm), 4.16-4.29(1H, brm), 5.70(1H, dd, J = 10.3, 1.8 Hz), 6.29(1H, dd, J = 16.6, 2.1 Hz), 6.53-6.60(2H, m), 6.76(1H, d, J = 4.2 Hz), 7.27-7.34(3H, m), 7.39(1H, dd, J = 7.9, 3.9 Hz), 7.58 (1H, d, J = 7.9 Hz), 8.05(1H, d, J = 15.7 Hz), 8.43 (1H, d, J = 8.5 Hz). MS(m/z): 642(M + H)$^+$. |

TABLE 71

| | | | | |
|---|---|---|---|---|
| 121 | X-44 E-8 | (2E)-3-(1-{[5-(1-Acryloylpiperidin-4-yl)-3-(2,4-dichloro-5-fluorophenyl)-1,2-oxazol-4-yl]carbonyl}-3-methyl-1H-indol-4-yl)prop-2-enoic acid | | $^1$H-NMR(CDCl$_3$)δ: 1.94-2.06(2H, m), 2.06-2.19(2H, m), 2.34(3H, s), 2.75-2.86(1H, m), 3.02-3.27(1H, m), 3.32-3.42(1H, m), 4.07-4.19(1H, m), 4.70-4.82(1H, m), 5.77(1H, dd, J = 10.9, 1.2 Hz), 6.31 (1H, dd, J = 16.9, 1.8 Hz), 6.47(1H, d, J = 15.7 Hz), 6.59(1H, dd, J = 16.9, 10.3 Hz), 6.81(1H, s), 7.34-7.43(3H, m), 7.60(1H, d, J = 7.3 Hz), 8.38(1H, d, J = 7.9 Hz), 8.46(1H, d, J = 15.7 Hz). MS(m/z): 596(M + H)$^+$. |
| 122 | X-43 E-8 | (2E)-3-(1-{[5-(1-Acryloylpiperidin-4-yl)-3-(4-chloro-2,6-dimethylphenyl)-1,2-oxazol-4-yl]carbonyl}-3-methyl-1H-indol-4-yl)prop-2-enoic acid | | $^1$H-NMR(CDCl$_3$)δ: 1.91-2.04(2H, m), 2.06-2.14(2H, m), 2.19(6H, s), 2.34(3H, s), 2.73-2.83(1H, m), 3.10-3.24(1H, m), 3.27-3.38(1H, m), 4.04-4.18(1H, m), 4.69-4.79(1H, m), 5.72(1H, dd, J = 10.3, 1.8 Hz), 6.30 (1H, dd, J = 16.9, 1.8 Hz), 6.45(1H, d, J = 15.7 Hz), 6.58(1H, dd, J = 16.9, 10.9 Hz), 6.75(1H, d, J = 1.2 Hz), 7.00(2H, s), 7.37(1H, t, J = 7.9 Hz), 7.58(1H, d, J = 7.9 Hz), 8.38-8.47(2H, m). |

TABLE 72

| | | | |
|---|---|---|---|
| 123 | X-47<br>E-8 | (2E)-3-(1-{[5-(1-Acryloyl-4-hydroxypiperidin-4-yl)-3-(2,4,6-trichlorophenyl)-1,2-oxazol-4-yl]carbonyl}-3-methyl-1H-indol-4-yl)prop-2-enoic acid | ¹H-NMR(CDCl₃)δ: 1.30-1.32(1H, m), 2.03-2.39(4H, m), 2.28(3H, s), 3.19-3.32(1H, m), 3.59-3.73(1H, m), 3.89-4.02(1H, m), 4.51-4.67(1H, m), 5.74(1H, d, J = 10.3 Hz), 6.32(1H, d, J = 16.9 Hz), 6.45(1H, d, J = 15.7 Hz), 6.63(1H, dd, J = 16.6, 10.6 Hz), 6.87(1H, s), 7.25-7.32(2H, m), 7.38(1H, t, J = 7.9 Hz), 7.58(1H, d, J = 7.3 Hz), 8.34-8.44(2H, m).<br>MS(m/z): 628(M + H)⁺. |

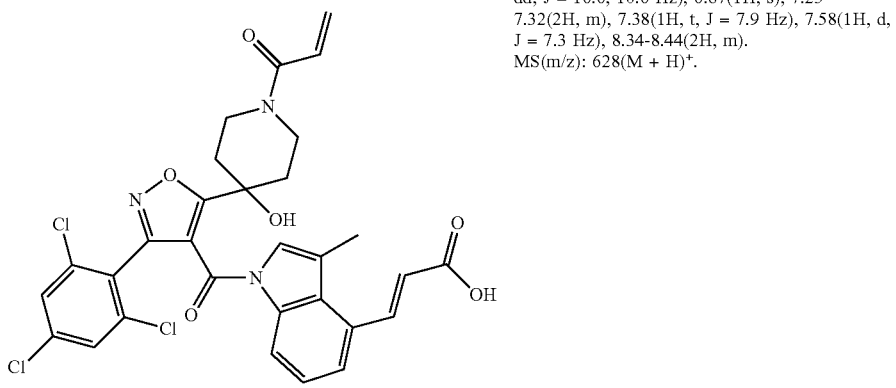

| | | | |
|---|---|---|---|
| 124 | X-57<br>E-8 | (2E)-3-(1-{[5-(3-Acryloyl-3-azabicyclo[3.1.0]hex-6-yl)-3-(2,4,6-trichlorophenyl)-1,2-oxazol-4-yl]carbonyl}-3-methyl-1H-indol-4-yl)prop-2-enoic acid | ¹H-NMR(CDCl₃)δ: 2.05(1H, dd, J = 8.2, 3.9 Hz), 2.40(3H, s), 2.56-2.66(2H, m), 3.69(1H, dd, J = 13.0, 3.9 Hz), 3.79-3.87(2H, m), 4.01(1H, d, J = 13.3 Hz), 5.71(1H, dd, J = 9.4, 2.7 Hz), 6.23-6.38(2H, m), 6.45(1H, d, J = 15.7 Hz), 7.07(1H, s), 7.33-7.39(3H, m), 7.58(1H, d, J = 7.9 Hz), 8.34(1H, d, J = 7.9 Hz), 8.45(1H, d, J = 15.7 Hz).<br>MS(m/z): 610(M + H)⁺. |

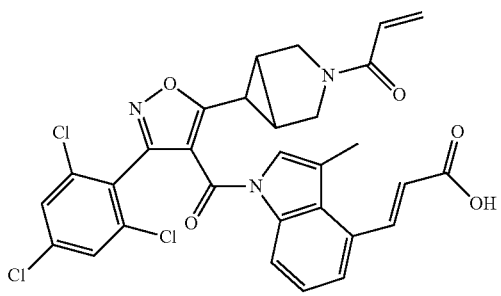

TABLE 73

| | | | |
|---|---|---|---|
| 125 | X-38<br>E-18 | (1-{[5-(1-Acryloylpiperidin-4-yl)-3-(2,4,6-trichlorophenyl)-1,2-oxazol-4-yl]carbonyl}1,3,4,5-tetrahydrobenzo[cd]indol-5-yl)acetic acid | ¹H-NMR(CDCl₃)δ: 1.84-2.18(6H, m), 2.45-2.92(5H, m), 3.13-3.27(1H, m), 3.41(1H, tt, J = 11.5, 3.8 Hz), 3.46-3.54(1H, m), 4.05-4.18(1H, m), 4.68-4.80(1H, m), 5.73(1H, dd, J = 10.6, 1.5 Hz), 6.30(1H, dd, J = 16.9, 1.8 Hz), 6.58(1H, dd, J = 16.9, 10.9 Hz), 6.76(1H, s), 7.13(1H, d, J = 7.3 Hz), 7.28-7.34(3H, m), 7.98(1H, d, J = 7.9 Hz).<br>MS(m/z): 626(M + H)⁺. |

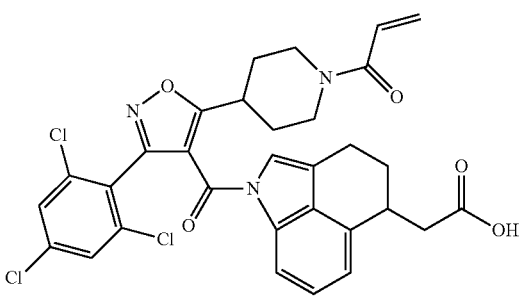

TABLE 73-continued

| 126 | X-61 E-8 | (2E)-3-[1-({5-[1-Acryloyl-4-(dimethylamino)piperidin-4-yl]-3-(2,4,6-trichlorophenyl)-1,2-oxazol-4-yl}carbonyl)-3-methyl-1H-indol-4-yl]prop-2-enoic acid | $^1$H-NMR(CDCl$_3$)δ: 2.29-2.65(2H, m), 2.34(3H, s), 2.69-2.94(2H, m), 2.84(6H, s), 3.88-4.25(2H, m), 4.33-4.71(2H, m), 5.71(1H, brs), 6.28(1H, d, J = 16.3 Hz), 6.39-6.58(1H, m), 6.44(1H, d, J = 15.7 Hz), 6.82(1H, s), 7.18-7.31(1H, m), 7.38-7.46(2H, m), 7.60(1H, d, J = 7.3 Hz), 8.35-8.44(2H, m). MS(m/z): 655(M + H)$^+$. |

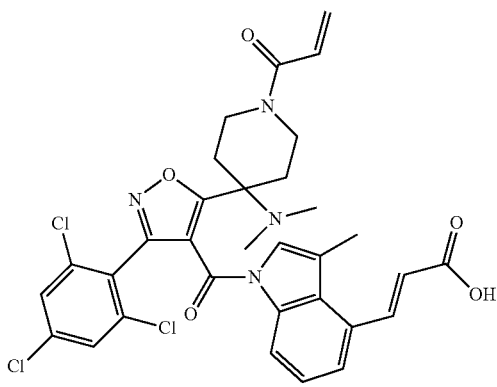

| 127 | X-41 E-17 | (2E)-[1-{[5-(1-Acryloylpiperidin-4-yl)-3-(2,4-dichloro-6-fluorophenyl)-1,2-oxazol-4-yl]carbonyl}-3,4-dihydrobenzo[cd]indol-5(1H)-ylidene]ethanoic acid | $^1$H-NMR(CDCl$_3$)δ: 1.93-2.06(2H, m), 2.08-2.18(2H, m), 2.77-2.86(1H, m), 2.78(2H, t, J = 6.7 Hz), 3.14-3.27(1H, m), 3.37-3.48(1H, m), 3.37(2H, t, J = 6.7 Hz), 4.07-4.18(1H, m), 4.72-4.82(1H, m), 5.73(1H, d, J = 10.3 Hz), 6.30(1H, d, J = 16.3 Hz), 6.53(1H, s), 6.59(1H, dd, J = 16.9, 10.3 Hz), 6.77(1H, s), 7.02(1H, d, J = 8.5 Hz), 7.19(1H, s), 7.38(1H, t, J = 7.9 Hz), 7.51(1H, d, J = 7.9 Hz), 8.09(1H, d, J = 8.5 Hz). MS(m/z): 608(M + H)$^+$. |

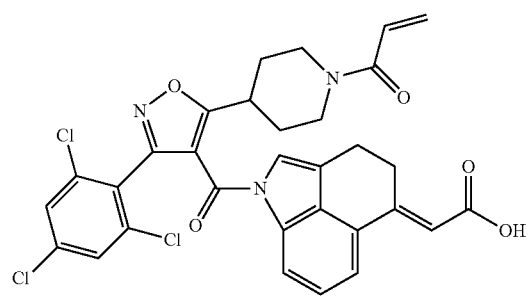

TABLE 74

| 128 | X-44 E-17 | (2E)-[1-{[5-(1-Acryloylpiperidin-4-yl)-3-(2,4-dichloro-5-fluorophenyl)-1,2-oxazol-4-yl]carbonyl}-3,4-dihydrobenzo[cd]indol-5(1H)-ylidene]ethanoic acid | $^1$H-NMR(CDCl$_3$)δ: 1.91-2.04(2H, m), 2.04-2.13(2H, m), 2.71-2.82(1H, m), 2.80(2H, t, J = 6.7 Hz), 3.11-3.25(1H, m), 3.30-3.43(1H, m), 3.39(2H, t, J = 6.7 Hz), 4.05-4.18(1H, m), 4.69-4.81(1H, m), 5.73(1H, dd, J = 10.3, 1.8 Hz), 6.30(1H, dd, J = 16.9, 1.8 Hz), 6.54(1H, s), 6.58(1H, dd, J = 16.9, 10.3 Hz), 6.77(1H, s), 7.34-7.43(3H, m), 7.53(1H, d, J = 7.9 Hz), 8.09(1H, d, J = 7.9 Hz). MS(m/z): 608(M + H)$^+$. |

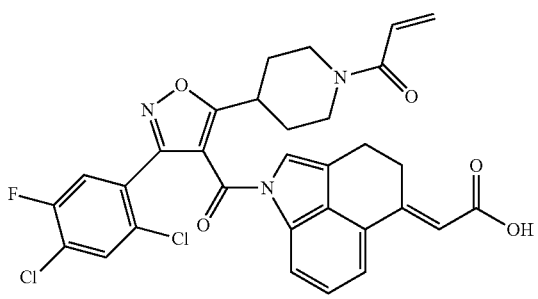

TABLE 74-continued

| | | | |
|---|---|---|---|
| 129 | X-50<br>E-8 | (2E)-3-(1-{[5-(1-Acryloylpiperidin-4-yl)-3-(2,4-dichloro-3-fluorophenyl)-1,2-oxazol-4-yl]carbonyl}-3-methyl-1H-indol-4-yl)prop-2-enoic acid | $^1$H-NMR(CDCl$_3$)δ: 1.92-2.19(4H, m), 2.32(3H, s), 2.72-2.89(1H, m), 3.13-3.26(1H, m), 3.31-3.42(1H, m), 4.06-4.20(1H, m), 4.69-4.83(1H, m), 5.75(1H, dd, J = 10.6, 1.5 Hz), 6.31(1H, dd, J = 16.9, 1.8 Hz), 6.47(1H, d, J = 15.7 Hz), 6.59(1H, dd, J = 16.6, 10.6 Hz), 6.80 (1H, s), 7.24-7.43(3H, m), 7.59(1H, d, J = 7.3 Hz), 8.37(1H, d, J = 8.5 Hz), 8.45(1H, d, J = 15.7 Hz).<br>MS(m/z): 596(M + H)$^+$. |

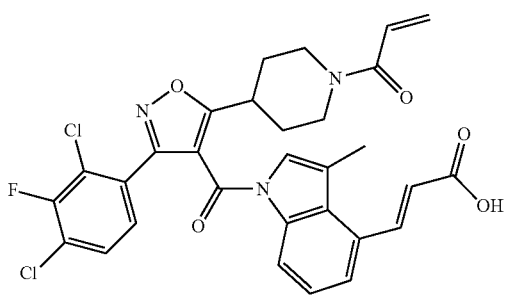

TABLE 75

| | | | |
|---|---|---|---|
| 130 | X-50<br>E-17 | (2E)-[1-{[5-(1-Acryloylpiperidin-4-yl)-3-(2,4-dichloro-3-fluorophenyl)-1,2-oxazol-4-yl]carbonyl}-3,4-dihydrobenzo[cd]indol-5(1H)-ylidene]ethanoic acid | $^1$H-NMR(CDCl$_3$)δ: 1.98 (2H, ddd, J = 24.8, 12.1, 3.9 Hz), 2.04-2.15(2H, m), 2.70-2.86(1H, m), 2.79(2H, t, J = 6.3 Hz), 3.11-3.24(1H, m), 3.30-3.43(1H, m), 3.39(2H, t, J = 6.3 Hz), 4.03-4.19 (1H, m), 4.69-4.83(1H, m), 5.73(1H, dd, J = 10.3, 1.8 Hz), 6.30(1H, dd, J = 16.9, 1.8 Hz), 6.54(1H, s), 6.58 (1H, dd, J = 16.6, 10.6 Hz), 6.77(1H, s), 7.30(1H, dd, J = 8.5, 1.2 Hz), 7.36 (1H, dd, J = 8.5, 6.7 Hz), 7.38(1H, t, J = 7.9 Hz), 7.52(1H, d, J = 7.9 Hz), 8.07(1H, d, J = 7.9 Hz).<br>MS(m/z): 608(M + H)$^+$. |

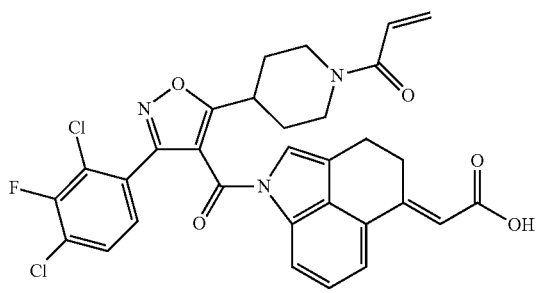 [SMILES: C=CC(=O)N1CCC(c2onc(-c3ccc(Cl)c(F)c3Cl)c2C(=O)n2cc3c4c(cccc42)/C(=C/C(=O)O)CC3)CC1]

| | | | |
|---|---|---|---|
| 131 | X-40<br>E-17 | (2E)-[1-{[5-(1-Acryloylpiperidin-4-yl)-3-(2,4-dichlorophenyl)-1,2-oxazol-4-yl]carbonyl}-3,4-dihydrobenzo[cd]indol-5(1H)-ylidene]ethanoic acid | $^1$H-NMR(CDCl$_3$)δ: 1.98 (2H, ddd, J = 24.8, 12.1, 3.9 Hz), 2.05-2.15(2H, m), 2.72-2.85(3H, m), 3.12-3.25(1H, brm), 3.34-3.44(3H, m), 4.02-4.18(1H, m), 4.69-4.81(1H, m), 5.73(1H, dd, J = 10.3, 1.8 Hz), 6.30(1H, dd, J = 16.9, 1.8 Hz), 6.53(1H, s), 6.59(1H, dd, J = 16.9, 10.9 Hz), 6.73(1H, s), 7.27-7.32(2H, m), 7.38 (1H, t, J = 7.9 Hz), 7.47-7.54(2H, m), 8.10(1H, d, J = 7.9 Hz).<br>MS (m/z): 590(M + H)$^+$. |

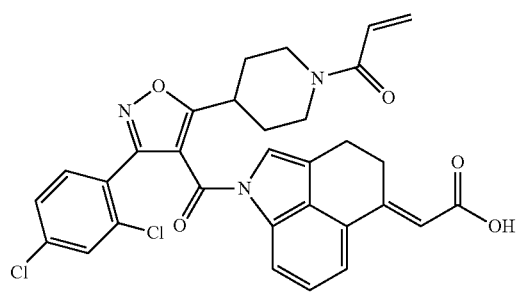 [SMILES: C=CC(=O)N1CCC(c2onc(-c3ccc(Cl)cc3Cl)c2C(=O)n2cc3c4c(cccc42)/C(=C/C(=O)O)CC3)CC1]

Example 132

(2E)-3-(1-{[3-(1-Acryloylpiperidin-4-yl)-5-(2,4,6-trichlorophenyl)-1,2-oxazol-4-yl]carbonyl}-1H-indol-4-yl)prop-2-enoic acid

[Formula 83]

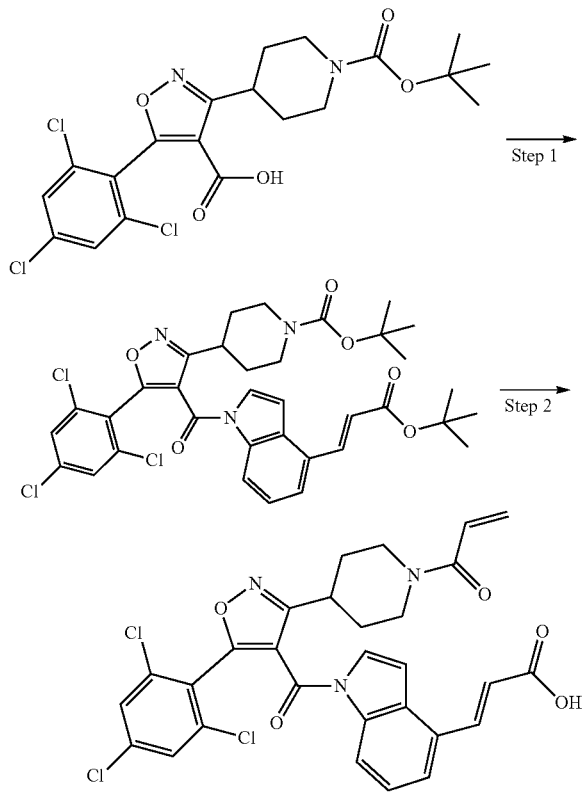

[Step 1] tert-Butyl 4-[4-({4-[(1E)-3-tert-butoxy-3-oxoprop-1-en-1-yl]-1H-indol-1-yl}carbonyl)-5-(2,4,6-trichlorophenyl)-1,2-oxazol-3-yl]piperidine-1-carboxylate To a solution of the compound (160 mg) obtained in Reference Example X-76 in dichloromethane (2 ml), 1-chloro-N,N,2-trimethyl-1-propenylamine (0.054 ml) was added dropwise under ice cooling, and the mixture was stirred at room temperature for 1 hour. 1-Chloro-N,N,2-trimethyl-1-propenylamine (0.054 ml) was further added to the reaction solution under ice cooling, and the mixture was stirred at room temperature for 45 minutes. The reaction solution was added to a solution of the compound (0.082 mg) obtained in Reference Example E-1, N,N-di(propan-2-yl)ethylamine (0.16 ml), and 4-dimethylaminopyridine (4 mg) in dichloromethane (1 ml), and the mixture was stirred overnight at room temperature. The reaction solution was diluted with ethyl acetate, washed with water and saturated saline in this order and then dried over anhydrous sodium sulfate. The solvent was distilled off under reduced pressure, and the residue obtained was purified by silica gel column chromatography (n-hexane/ethyl acetate) to obtain the title compound (93 mg).

$^1$H-NMR (CDCl$_3$) δ: 1.46 (9H, s), 1.55 (9H, s), 1.80-1.93 (2H, m), 2.01-2.10 (2H, m), 2.77-2.91 (2H, m), 3.15-3.25 (1H, m), 4.07-4.24 (2H, m), 6.46 (1H, d, J=15.7 Hz), 6.71 (1H, d, J=4.2 Hz), 7.14 (1H, d, J=4.2 Hz), 7.31-7.45 (3H, m), 7.54 (1H, d, J=7.9 Hz), 7.85 (1H, d, J=15.7 Hz), 8.37 (1H, d, J=8.5 Hz).

[Step 2] (2E)-3-(1-{[3-(1-Acryloylpiperidin-4-yl)-5-(2,4,6-trichlorophenyl)-1,2-oxazol-4-yl]carbonyl}-1H-indol-4-yl)prop-2-enoic acid To a solution of the compound (93 mg) obtained in the preceding step 1 in dichloromethane (1 ml), trifluoroacetic acid (2 ml) was added at room temperature, and the mixture was stirred at room temperature for 1 hour. The reaction solution was concentrated under reduced pressure. Dichloromethane (2 ml) and a saturated aqueous solution of sodium bicarbonate (1 ml) were added to the residue obtained under ice cooling, and acryloyl chloride (0.01 ml) was added thereto with vigorous stirring. The mixture was stirred at room temperature for 10 minutes, then acryloyl chloride (0.01 ml) was further added thereto, and the resulting mixture was stirred for 10 minutes. The reaction solution was cooled in ice and rendered acidic with 1 N hydrochloric acid, followed by extraction with dichloromethane. The extract was washed with water and saturated saline in this order and then dried over anhydrous sodium sulfate. The solvent was distilled off under reduced pressure, and the residue obtained was purified by silica gel column chromatography (dichloromethane/methanol) and preparative thin-layer chromatography (dichloromethane/methanol) to obtain the title compound (26 mg).

$^1$H-NMR (CDCl$_3$) δ: 1.82-2.06 (2H, m), 2.09-2.26 (2H, m), 2.80-2.93 (1H, m), 3.16-3.30 (1H, m), 3.29-3.40 (1H, m), 4.03-4.17 (1H, m), 4.62-4.74 (1H, m), 5.70 (1H, dd, J=10.3, 1.8 Hz), 6.28 (1H, dd, J=16.9, 1.8 Hz), 6.55 (1H, d, J=15.7 Hz), 6.59 (1H, dd, J=16.9, 10.3 Hz), 6.73 (1H, d, J=3.6 Hz), 7.17 (1H, d, J=3.6 Hz), 7.34 (2H, s), 7.42 (1H, t, J=7.9 Hz), 7.59 (1H, d, J=7.3 Hz), 8.04 (1H, d, J=16.3 Hz), 8.41 (1H, d, J=8.5 Hz).

MS (m/z): 598 (M+H)$^+$.

Example 133

(2E)-3-(1-{[3-(2,6-Dichlorophenyl)-5-(dimethylamino)-1,2-oxazol-4-yl]carbonyl}-1H-indol-4-yl)prop-2-enoic acid

[Formula 84]

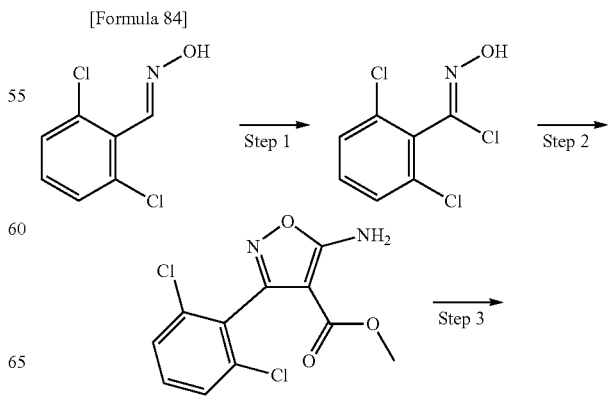

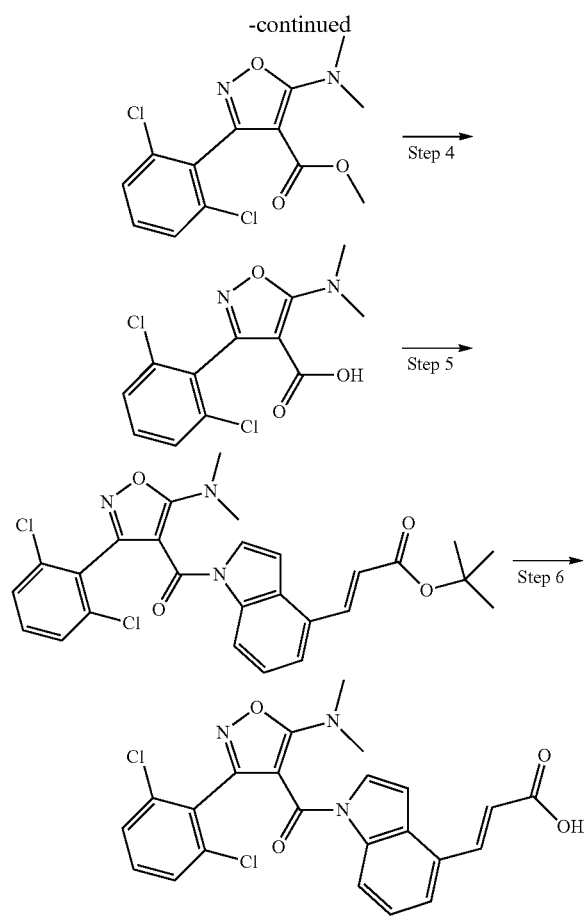

[Step 1]
(1Z)-2,6-Dichloro-N-hydroxybenzenecarboximidoyl chloride 2,6-Dichlorobenzaldoxime (5.0 g) was dissolved in N,N-dimethylformamide (75 ml). To the solution, N-chlorosuccinimide (3.69 g) was added at room temperature under a nitrogen atmosphere. The mixture was stirred for 5 hours, and then, water was added thereto, followed by extraction with diethyl ether. The extract was washed with saturated saline and then dried over anhydrous sodium sulfate. The solvent was distilled off under reduced pressure to obtain the title compound (6.13 g).
$^1$H-NMR (CDCl$_3$) δ: 7.30-7.41 (3H, m), 9.03 (1H, brs).

[Step 2] Methyl 5-amino-3-(2,6-dichlorophenyl)-1,2-oxazole-4-carboxylate

To a solution of ethyl cyanoacetate (0.25 ml) in tetrahydrofuran (3 ml), a solution of sodium methoxide (28% solution in methanol, 0.46 ml) in methanol (6 ml) was added dropwise under ice cooling under a nitrogen atmosphere, and the mixture was stirred at room temperature for 1 hour. A solution of the compound (0.50 g) obtained in the preceding step 1 in tetrahydrofuran (1 ml) was added dropwise to the reaction solution under ice cooling, and the mixture was stirred overnight at room temperature. The reaction solution was concentrated under reduced pressure, and the residue obtained was diluted with diethyl ether, washed with water and saturated saline in this order and then dried over anhydrous sodium sulfate. The solvent was distilled off under reduced pressure, and the residue obtained was purified by silica gel column chromatography (n-hexane/ethyl acetate) to obtain the title compound (0.40 g).
$^1$H-NMR (CDCl$_3$) δ: 3.62 (3H, s), 6.08 (2H, brs), 7.30-7.41 (3H, m).

[Step 3] Methyl 3-(2,6-dichlorophenyl)-5-(dimethylamino)-1,2-oxazole-4-carboxylate To a solution of the compound (0.10 g) obtained in the preceding step 2 in N,N-dimethylformamide (2 ml), potassium carbonate (0.24 g) and methyl iodide (0.49 g) were added under ice cooling, and the mixture was stirred at 50° C. for 3.5 hours. The reaction solution was allowed to cool, and then, water was added to the reaction solution, followed by extraction with ethyl acetate. The extract was washed with saturated saline and then dried over anhydrous sodium sulfate. The solvent was distilled off under reduced pressure, and the residue obtained was purified by silica gel column chromatography (n-hexane/ethyl acetate) to obtain the title compound (0.085 g).
$^1$H-NMR (CDCl$_3$) δ: 3.30 (6H, s), 3.47 (3H, s), 7.27-7.39 (3H, m).

[Step 4] 3-(2,6-Dichlorophenyl)-5-(dimethylamino)-1,2-oxazole-4-carboxylic acid

To a solution of the compound (0.51 g) obtained in the preceding step 3 in methanol (10 ml), a 1 N aqueous sodium hydroxide solution (10 ml) was added at room temperature, and the mixture was stirred at 50° C. for 8 hours. After being allowed to cool, the reaction solution was concentrated under reduced pressure, and ethyl acetate was added to the residue obtained, which was then separated into two layers. The aqueous layer was neutralized by the addition of 1 N hydrochloric acid under ice cooling, followed by extraction with ethyl acetate. The extract was washed with saturated saline and then dried over anhydrous sodium sulfate. The solvent was distilled off under reduced pressure to obtain the title compound (0.36 g).
$^1$H-NMR (CDCl$_3$) δ: 3.29 (6H, s), 7.26-7.37 (3H, m).

[Step 5] tert-Butyl (2E)-3-(1-{[3-(2,6-dichlorophenyl)-5-(dimethylamino)-1,2-oxazol-4-yl]carbonyl}-1H-indol-4-yl)prop-2-enoate To a solution of the compound (0.10 g) obtained in the preceding step 4 in benzene (3 ml), thionyl chloride (0.12 ml) and N,N-dimethylformamide (0.01 ml) were added under a nitrogen atmosphere, and the mixture was heated to reflux for 3 hours. After being allowed to cool, the reaction solution was concentrated under reduced pressure, and the residue obtained was dissolved in N,N-dimethylformamide (3 ml).
To a solution of the compound (0.08 g) obtained in Reference Example E-1 in N,N-dimethylformamide (3 ml), sodium hydride (55% oil, 0.014 g) was added under ice cooling under a nitrogen atmosphere, and the mixture was stirred at room temperature for 2 hours. The acid chloride solution was added to the reaction solution under ice cooling, and the mixture was stirred at room temperature for 16 hours. Water was added to the reaction solution, followed by extraction with ethyl acetate. The extract was washed with saturated saline and then dried over anhydrous sodium sulfate. The solvent was distilled off under reduced pressure, and the residue obtained was purified by silica gel column chromatography (n-hexane/ethyl acetate) to obtain the title compound (0.165 g).

$^1$H-NMR (CDCl$_3$) δ: 1.55 (9H, s), 3.16 (6H, s), 6.42 (1H, d, J=15.7 Hz), 6.56 (1H, d, J=4.2 Hz), 7.08-7.21 (3H, m), 7.30 (1H, d, J=7.9 Hz), 7.34 (1H, d, J=3.6 Hz), 7.45 (1H, d =7.3 Hz), 7.84 (1H, d, J=16.3 Hz), 8.21 (1H, d, J=8.5 Hz).

[Step 6] (2E)-3-(1-{[3-(2,6-Dichlorophenyl)-5-(dimethylamino)-1,2-oxazol-4-yl]carbonyl}-1H-indol-4-yl)prop-2-enoic acid To a solution of the compound (0.16 g) obtained in the preceding step 5 in dichloromethane (7 ml), trifluoroacetic acid (1 ml) was added under ice cooling, and the mixture was stirred at room temperature for 18 hours. The reaction solution was diluted with dichloromethane, washed with water and then dried over anhydrous sodium sulfate. The solvent was distilled off under reduced pressure, and the residue obtained was purified by silica gel column chromatography (dichloromethane/methanol) to obtain the title compound (0.083 g).

$^1$H-NMR (DMSO-d6) δ: 3.04 (6H, s), 6.58 (1H, d, J=15.7 Hz), 6.81 (1H, d, J=3.6 Hz), 7.30-7.44 (4H, m), 7.54 (1H, d, J=3.6 Hz), 7.64 (1H, d, J=7.9 Hz), 7.83 (1H, d, J=15.7 Hz), 8.09 (1H, d, J=8.5 Hz), 12.46 (1H, brs).

The following compounds were obtained by the same method as in Example 133 using the compound obtained in step 2 of Example 133 as a starting material.

TABLE 76

| Example No. | Name and structure | Instrumental data |
| --- | --- | --- |
| 134 | (2E)-3-(1-{[3-(2,6-Dichlorophenyl)-5-(diethylamino)-1,2-oxazol-4-yl]carbonyl}-1H-indol-4-yl)prop-2-enoic acid | $^1$H-NMR(DMSO-d$_6$)δ: 1.16(6H, t, J = 7.0 Hz), 3.45-3.54(4H, m), 6.56(1H, d, J = 16.3 Hz), 6.77(1H, d, J = 3.6 Hz), 7.28-7.41(4H, m), 7.45(1H, d, J = 3.6 Hz), 7.62(1H, d, J = 7.9 Hz), 7.79(1H, d, J = 15.7 Hz), 8.07(1H, d, J = 8.5 Hz). MS(m/z): 498(M + H)$^+$. |
| 135 | (2E)-3-(1-{[3-(2,6-Dichlorophenyl)-5-(pyrrolidin-1-yl)-1,2-oxazol-4-yl]carbonyl}-1H-indol-4-yl)prop-2-enoic acid | $^1$H-NMR(DMSO-d$_6$)δ: 1.90-1.96(4H, brm), 3.40-3.53(4H, brm), 6.56(1H, d, J = 15.7 Hz), 6.75(1H, d, J = 3.6 Hz), 7.29-7.44(4H, m), 7.47(1H, d, J = 3.6 Hz), 7.62(1H, d, J = 7.9 Hz), 7.81 (1H, d, J = 16.3 Hz), 8.08(1H, d, J = 8.5 Hz), 12.44(1H, s). MS(m/z): 496(M + H)$^+$. |
| 136 | (2E)-3-(1-{[3-(2,6-Dichlorophenyl)-5-(morpholin-4-yl)-1,2-oxazol-4-yl]carbonyl}-1H-indol-4-yl)prop-2-enoic acid | $^1$H-NMR(DMSO-d$_6$)δ: 3.41-3.46(4H, m), 3.62-3.67(4H, m), 6.58(1H, d, J = 15.7 Hz), 6.87 (1H, d, J = 4.2 Hz), 7.30-7.45 (5H, m), 7.59(1H, d, J = 4.2 Hz), 7.65(1H, d, J = 7.9 Hz), 7.84(1H, d, J = 15.7 Hz), 8.08(1H, d, J = 8.5 Hz). MS(m/z): 512(M + H)$^+$. |

Example 137

(2E)-3-(1-{[3-(2,6-Dichlorophenyl)-5-(cis-2,6-dimethylpiperidin-1-yl)-1,2-oxazol-4-yl]carbonyl}-1H-indol-4-yl)prop-2-enoic acid

[Formula 85]

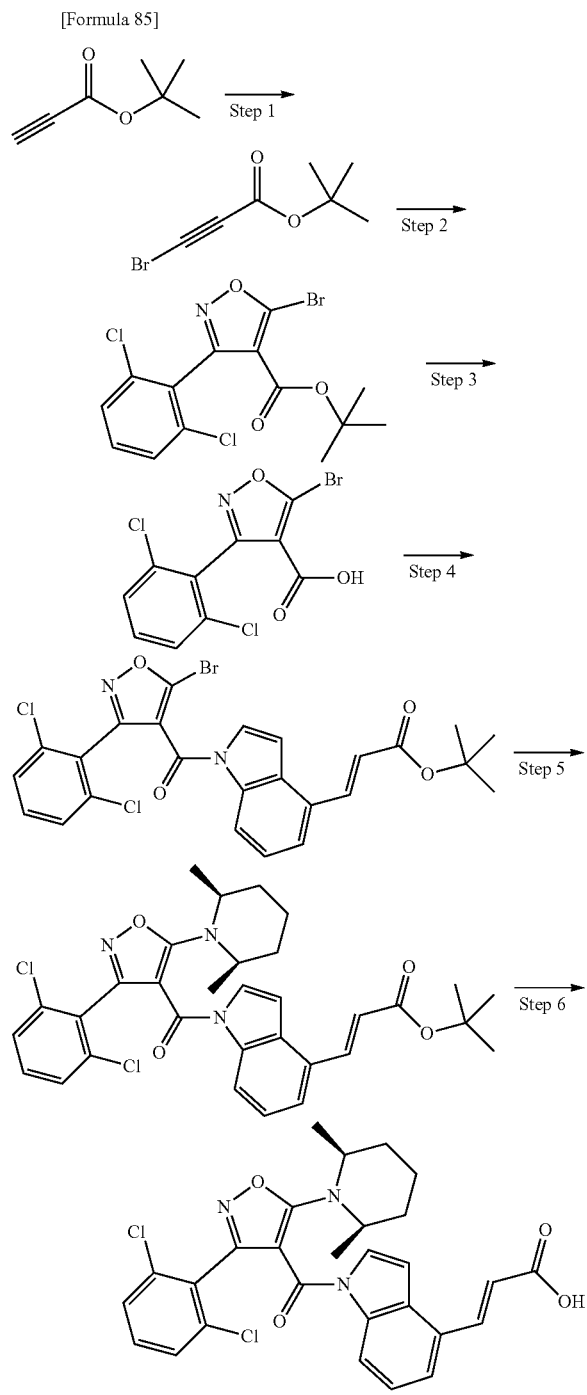

[Step 1] tert-Butyl 3-bromoprop-2-ynoate

To a solution of tert-butyl 2-propynoate (50.0 g) in acetone (500 ml), silver nitrate (6.73 g) was added, and the mixture was stirred at room temperature for 1 hour. While the reaction solution was cooled in a water bath, N-bromosuccinimide (79.2 g) was added thereto, and the mixture was stirred at room temperature for 18 hours. The reaction solution was filtered through celite, and the filtrate was concentrated under reduced pressure. A diethyl ether/n-pentane (1:4) mixed solvent was added to the residue obtained, and the deposited insoluble matter was filtered through celite. The filtrate was concentrated under reduced pressure to obtain the title compound (81.3 g), which was used in the next reaction without being purified.

[Step 2] tert-Butyl 5-bromo-3-(2,6-dichlorophenyl)-1,2-oxazole-4-carboxylate

The compound (81.3 g) obtained in the preceding step 1 and the compound (44.5 g) obtained in step 1 of Example 4 were dissolved in ethyl acetate (480 ml). To the solution, water (60 ml) was added, and the mixture was stirred. Sodium bicarbonate (50.0 g) was added thereto under ice cooling, and the mixture was stirred at room temperature for 17 hours. The reaction solution was filtered through celite, and the filtrate was concentrated under reduced pressure. The residue obtained was dissolved in ethyl acetate, and the solution was washed with water and saturated saline in this order and then dried over anhydrous sodium sulfate. The solvent was distilled off under reduced pressure, and ethyl acetate/n-hexane was added to the residue obtained. The resulting solid was collected by filtration to obtain the title compound (34.7 g). Also, the filtrate was concentrated under reduced pressure, and then, n-hexane was added to the residue obtained. The resulting solid was collected by filtration to further obtain the title compound (15.7 g).

$^1$H-NMR (CDCl$_3$) δ: 1.27 (9H, s), 7.34-7.44 (3H, m).

[Step 3] 5-Bromo-3-(2,6-dichlorophenyl)-1,2-oxazole-4-carboxylic acid

To a solution of the compound (15.7 g) obtained in the preceding step 2 in dichloromethane (50 ml), trifluoroacetic acid (10 ml) was added under ice cooling, and the mixture was stirred at room temperature for 24 hours. The reaction solution was diluted with dichloromethane, washed with water and then dried over anhydrous sodium sulfate. The solvent was distilled off under reduced pressure, and n-hexane was added to the residue obtained. The resulting solid was collected by filtration to obtain the title compound (9.95 g).

$^1$H-NMR (CDCl$_3$) δ: 7.36-7.45 (3H, m).

[Step 4] tert-Butyl (2E)-3-[1-[5-bromo-3-(2,6-dichlorophenyl)-1,2-oxazol-4-yl]carbonyl}-1H-indol-4-yl)prop-2-enoate To a suspension of the compound (9.0 g) obtained in the preceding step 3 in dichloromethane (180 ml), N,N-dimethylformamide (0.1 ml) was added, and the mixture was stirred. Oxalyl chloride (2.5 ml) was added thereto under ice cooling, and the mixture was stirred at 30° C. for 3 hours.

To a suspension of the compound (6.5 g) obtained in Reference Example E-1 in N,N-dimethylformamide (180 ml), sodium hydride (55% oil, 1.3 g) was added under ice cooling, and the mixture was stirred at room temperature for 2 hours. The reaction solution was cooled in ice and added dropwise to the acid chloride solution over 30 minutes under ice cooling using a cannula. While heated to room temperature, the mixture was stirred for 17 hours, and then, water was added thereto, followed by extraction with ethyl acetate. The extract was washed with saturated saline and then dried over anhydrous sodium sulfate. The solvent was distilled off under reduced pressure, and the residue obtained was purified by silica gel column chromatography (n-hexane/ethyl acetate) to obtain the title compound (6.14 g).

$^1$H-NMR (CDCl$_3$) δ: 1.57 (9H, s), 6.48 (1H, d, J=16.3 Hz), 6.87-6.88 (1H, m), 7.33-7.39 (5H, m), 7.55 (1H, d, J=7.3 Hz), 7.91 (1H, d, J=16.3 Hz), 8.33 (1H, d, J=8.5 Hz).

[Step 5] tert-Butyl (2E)-3-(1-{[3-(2,6-dichlorophenyl)-5-(cis-2,6-dimethylpiperidin-1-yl)-1,2-oxazol-4-yl]carbonyl}-1H-indol-4-yl)prop-2-enoate To a solution of the compound (50 mg) obtained in the preceding step 4 in N,N-dimethylformamide (1 ml), cis-2,6-dimethylpiperidine (0.024 ml) was added, and the mixture was stirred at 80° C. for 7 hours. The reaction solution was concentrated under reduced pressure, and the residue obtained was purified by silica gel column chromatography (n-hexane/ethyl acetate) to obtain the title compound (16.1 mg).

$^1$H-NMR (CDCl$_3$) δ: 1.36 (6H, d, J=7.3 Hz), 1.56-1.60 (12H, m), 1.75-1.90 (3H, m), 4.27-4.31 (2H, m), 6.42 (1H, d, J=16.3 Hz), 6.57 (1H, d, J=3.6 Hz), 7.04-7.14 (3H, m), 7.29 (1H, d, J=7.9 Hz), 7.37 (1H, d, J=3.6 Hz), 7.44 (1H, d, J=7.9 Hz), 7.84 (1H, d, J=16.3 Hz), 8.19 (1H, d, J=8.5 Hz).

MS (m/z): 594 (M+H)$^1$.

[Step 6] (2E)-3-(1-{[3-(2,6-Dichlorophenyl)-5-(cis-2,6-dimethylpiperidin-1-yl)-1,2-oxazol-4-yl]carbonyl}-1H-indol-4-yl)prop-2-enoic acid To a solution of the compound (16.1 mg) obtained in the preceding step 5 in dichloromethane (2 ml), trifluoroacetic acid (0.3 ml) was added under ice cooling, and the mixture was stirred overnight at room temperature. The reaction solution was diluted with dichloromethane, washed with water and then dried over anhydrous sodium sulfate. The solvent was distilled off under reduced pressure, and the residue obtained was purified by preparative thin-layer chromatography (chloroform/methanol) to obtain the title compound (12.2 mg).

$^1$H-NMR (DMSO-d$_6$) δ: 1.27 (6H, d, J=6.7 Hz), 1.42-1.86 (6H, m), 4.05-4.13 (2H, m), 6.58 (1H, d, J=16.3 Hz), 6.88 (1H, d, J=3.6 Hz), 7.30-7.44 (4H, m), 7.57 (1H, d, J=4.2 Hz), 7.64 (1H, d, J=7.3 Hz), 7.83 (1H, d, J=16.3 Hz), 8.08 (1H, d, J=8.5 Hz).

MS (m/z): 538 (M+H)$^+$.

The following compound was obtained by the same method as in Example 137.

TABLE 77

| Example No. | Name and structure | Instrumental data |
|---|---|---|
| 138 | (2E)-3-(1-{[5-(Dimethylamino)-3-(2,4,6-trichlorophenyl)-1,2-oxazol-4-yl]carbonyl}-1H-indol-4-yl)prop-2-enoic acid | $^1$H-NMR(DMSO-d$_6$)δ: 3.03(6H, s), 6.59(1H, d, J = 15.7 Hz), 6.86(1H, d, J = 3.6 Hz), 7.33 (1H, t, J = 8.2 Hz), 7.55(1H, d, J = 3.6 Hz), 7.61-7.73(3H, m), 7.86(1H, d, J = 16.3 Hz), 8.07(1H, d, J = 8.5 Hz), 12.45 (1H, brs). MS(m/z): 504(M + H)$^+$. |

Example 139

(2E)-3-[1-({5-[(3R)-3-(Aminomethyl)pyrrolidin-1-yl]-3-(2,6-dichlorophenyl)-1,2-oxazol-4-yl}carbonyl)-1H-indol-4-yl]prop-2-enoic acid

[Formula 86]

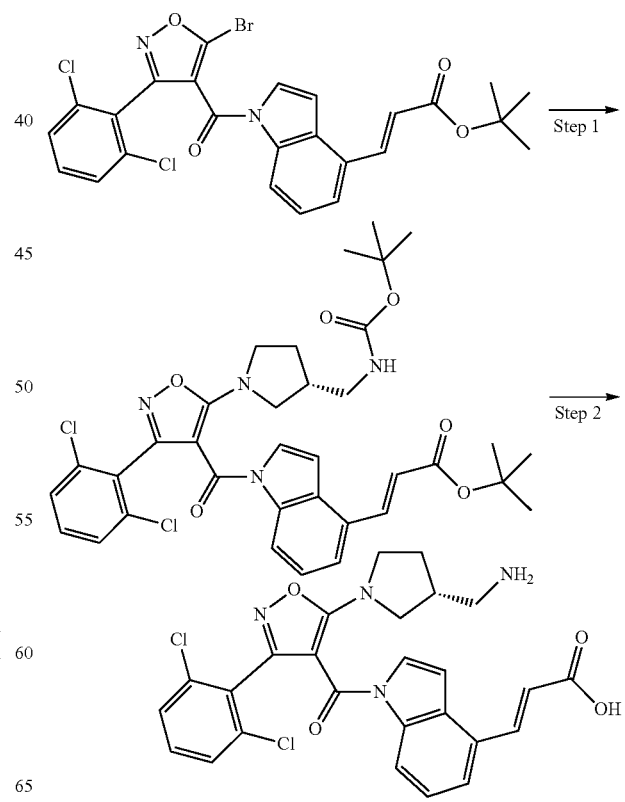

249

[Step 1] tert-Butyl (2E)-3-[1-({5-[(3R)-3-{[(tert-butoxycarbonyl)amino]methyl}pyrrolidin-1-yl]-3-(2,6-dichlorophenyl)-1,2-oxazol-4-yl}carbonyl)-1H-indol-4-yl]prop-2-enoate

To a solution of the compound (50 mg) obtained in step 4 of Example 137 and (S)-3-N-butoxycarbonylaminomethylpyrrolidine hydrochloride (35.6 mg) in N,N-dimethylformamide (1 ml), triethylamine (0.037 ml) was added, and the mixture was stirred overnight at room temperature. The reaction solution was concentrated under reduced pressure, and the residue obtained was purified by silica gel column chromatography (chloroform/methanol) to obtain the title compound (60.5 mg).

$^1$H-NMR (CDCl$_3$) δ: 1.42 (9H, s), 1.55 (9H, s), 1.74-1.87 (1H, m), 2.10-2.21 (1H, m), 2.51-2.64 (1H, m), 3.12-3.32 (2H, m), 3.34-3.81 (3H, m), 4.62-4.72 (1H, m), 6.42 (1H, d, J=15.7 Hz), 6.51 (1H, d, J=3.6 Hz), 7.06-7.21 (3H, m), 7.28-7.33 (2H, m), 7.44 (1H, d, J=7.3 Hz), 7.83 (1H, d, J=15.7 Hz), 8.20 (1H, d, J=8.5 Hz).

MS (m/z): 681 (M+H)$^+$.

[Step 2] (2E)-3-[1-({5-[(3R)-3-(Aminomethyl)pyrrolidin-1-yl]-3-(2,6-dichlorophenyl)-1,2-oxazol-4-yl}carbonyl)-1H-indol-4-yl]prop-2-enoic acid

To a solution of the compound (60.5 mg) obtained in the preceding step 1 in dichloromethane (3 ml), trifluoroacetic acid (0.5 ml) was added under ice cooling, and the mixture was stirred at room temperature for 8 hours. The reaction solution was concentrated under reduced pressure, then diluted with dichloromethane and rendered weakly basic by the addition of triethylamine under ice cooling. The reaction solution was concentrated under reduced pressure, and the residue obtained was purified by preparative thin-layer column chromatography (chloroform/methanol/water) to obtain the title compound (15.5 mg).

$^1$H-NMR (DMSO-d$_6$) δ: 1.20-1.31 (2H, m), 1.73-1.85 (1H, m), 2.04-2.16 (1H, m), 2.63-2.72 (3H, m), 2.83-2.91 (2H, m), 3.39-3.76 (3H, m), 6.56 (1H, d, J=15.7z), 6.73 (1H, d, J=3.6z), 7.30-7.35 (3H, m), 7.45 (2H, d, J=3.6z), 7.62 (1H, d, J=7.3z), 7.79 (1H, d, J=16.3z), 8.09 (1H, d, J=8.5z).

MS (m/z525 (M+H)$^+$.

The following compound was obtained by the same method as in Example 139.

250

Example 141

(2E)-3-[1-({5-[(2R)-4-Acryloyl-2-methylpiperazin-1-yl]-3-(2,6-dichlorophenyl)-1,2-oxazol-4-yl}carbonyl)-1H-indol-4-yl]prop-2-enoic acid

[Formula 87]

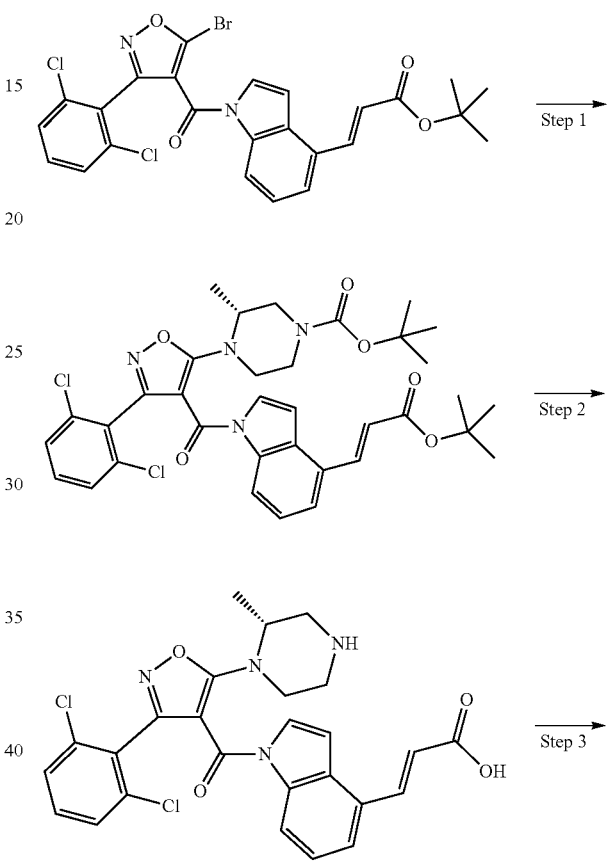

TABLE 78

| Example No. | Name and structure | Instrumental data |
|---|---|---|
| 140 | (2E)-3[1-({5-[(3S)-3-(Aminomethyl)pyrrolidin-1-yl]-3-(2,6-dichlorophenyl)-1,2-oxazol-4-yl}carbonyl)-1H-indol-4-yl]prop-2-enoic acid | $^1$H-NMR(DMSO-d$_6$)δ: 1.76-1.86 (1H, m), 2.07-2.17(1H, m), 2.55-2.64(1H, m), 2.84-2.99(3H, m), 3.44-3.80(3H, m), 6.56(1H, d, J = 16.3 Hz), 6.71-6.75(1H, m), 7.25-7.52(7H, m), 7.62(1H, d, J = 7.3 Hz), 7.80(1H, d, J = 15.7 Hz), 8.09 (1H, d, J = 27.9 Hz). MS(m/z): 525(M + H)$^+$. |

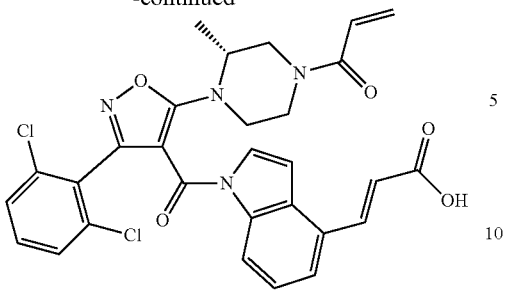

[Step 1] tert-Butyl (3R)-4-[4-({4-[(1E)-3-tert-butoxy-3-oxoprop-1-en-1-yl]-1H-indol-1-yl}carbonyl]-3-(2,6-dichlorophenyl)-1,2-oxazol-5-yl]-3-methyl-piperazine-1-carboxylate To a solution of the compound (150 mg) obtained in step 4 of Example 137 in N,N-dimethylformamide (3 ml), (3R)-1-tert-butoxycarbonyl-3-methylpiperazine (107 mg) was added, and the mixture was stirred overnight at room temperature. The reaction solution was concentrated under reduced pressure, and the residue obtained was purified by silica gel column chromatography (n-hexane/ethyl acetate) to obtain the title compound (137 mg).

$^1$H-NMR (CDCl$_3$) δ: 1.32-1.37 (3H, m), 1.45-1.48 (9H, m), 1.54-1.57 (9H, m), 2.95-3.31 (2H, m), 3.37-3.66 (2H, m), 3.85-4.35 (3H, m), 6.42-6.46 (1H, m), 6.59 (1H, s), 7.10-7.22 (3H, m), 7.28-7.35 (2H, m), 7.45-7.49 (1H, m), 7.84 (1H, d, J=18.7 Hz), 8.20 (1H, d, J=8.5 Hz).

MS (m/z): 681 (M+H)$^+$.

[Step 2] (2E)-3-[1-({3-(2,6-Dichlorophenyl)-5-[(2R)-2-methylpiperazin-1-yl]-1,2-oxazol-4-yl}carbonyl)-1H-indol-4-yl]prop-2-enoic acid To a solution of the compound (137 mg) obtained in the preceding step 1 in dichloromethane (5 ml), trifluoroacetic acid (1 ml) was added under ice cooling, and the mixture was stirred overnight at room temperature. The reaction solution was concentrated under reduced pressure, then diluted with dichloromethane and rendered weakly basic by the addition of triethylamine under ice cooling. The reaction solution was concentrated under reduced pressure to obtain the title compound, which was used in the next reaction without being purified.

[Step 3] (2E)-3-[1-({5-[(2R)-4-Acryloyl-2-methyl-piperazin-1-yl]-3-(2,6-dichlorophenyl)-1,2-oxazol-4-yl}carbonyl)-1H-indol-4-yl]prop-2-enoic acid The compound obtained in the preceding step 2 was suspended in dichloromethane (16 ml). To the suspension, a saturated aqueous solution of sodium bicarbonate (8 ml) and acryloyl chloride (0.034 ml) were added under ice cooling, and the mixture was stirred at room temperature for 5 hours. Acryloyl chloride (0.034 ml) was further added to the reaction solution under ice cooling, and the mixture was stirred overnight at room temperature. The reaction solution was rendered acidic by the addition of 1 N hydrochloric acid under ice cooling, followed by extraction with dichloromethane. The extract was dried over anhydrous sodium sulfate. The solvent was distilled off under reduced pressure, and the residue obtained was purified by silica gel column chromatography (dichloromethane/methanol) to obtain the title compound (86.4 mg).

$^1$H-NMR (DMSO-d$_6$) δ: 1.19 (3H, d, J=6.7 Hz), 2.87-3.11 (1H, m), 3.46-3.61 (2H, m), 3.94-4.30 (4H, m), 5.70 (1H, d, J=10.9 Hz), 6.11-6.21 (1H, m), 6.59 (1H, d, J=16.3 Hz), 6.71-6.83 (1H, m), 6.86 (1H, s), 7.31-7.47 (4H, m), 7.59 (1H, s), 7.66 (1H, d, J=7.9 Hz), 7.84 (1H, d, J=16.3 Hz), 8.10 (1H, d, J=8.5 Hz), 12.48 (1H, s).

MS (m/z): 579 (M+H)$^+$.

The following compounds were obtained by the same method as in Example 141.

TABLE 79

| Example No. | Name and structure | Instrumental data |
|---|---|---|
| 142 | (2E)-3-(1-{[5-(4-Acryloylpiperazin-1-yl)-3-(2,6-dichlorophenyl)-1,2-oxazol-4-yl]carbonyl}-1H-indol-4-yl)prop-2-enoic acid | $^1$H-NMR(DMSO-d$_6$)δ: 3.46-3.57(4H, m), 3.60-3.74(4H, m), 5.69(1H, dd, J = 2.4, 10.3 Hz), 6.12(1H, dd, J = 2.1, 16.6 Hz), 6.58(1H, d, J = 15.7 Hz), 6.77 (1H, dd, J = 10.3, 16.9 Hz), 6.85(1H, d, J = 3.6 Hz), 7.33 (1H, t, J = 7.9 Hz), 7.36-7.46 (3H, m), 7.60(1H, d, J = 3.6 Hz), 7.65(1H, d, J = 7.3 Hz), 7.84(1H, d, J = 15.7 Hz), 8.10(1H, d, J = 7.9 Hz). MS(m/z): 565(M + H)$^+$. |

TABLE 79-continued

| Example No. | Name and structure | Instrumental data |
|---|---|---|
| 143 | (2E)-3-(1-{[5-(4-Acryloylpiperazin-1-yl)-3-(2,4,6-trichlorophenyl)-1,2-oxazol-4-yl]carbonyl}-1H-indol-4-yl)prop-2-enoic acid 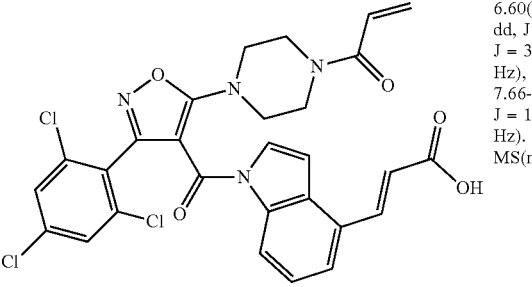 | 1H-NMR(DMSO-d$_6$)δ: 3.45-3.54 (4H, m), 3.60-3.70(4H, m), 5.69 (1H, dd, J = 2.4, 10.3 Hz), 6.12 (1H, dd, J = 2.4, 16.3 Hz), 6.60(1H, d, J = 16.3 Hz), 6.76(1H, dd, J = 10.6, 16.6 Hz), 6.91(1H, d, J = 3.6 Hz), 7.34 (1H, t, J = 8.2 Hz), 7.62(1H, d, J = 3.6 Hz), 7.66-7.71(3H, m), 7.87(1H, d, J = 16.3 Hz), 8.09(1H, d, J = 7.9 Hz). MS(m/z): 601(M + H)$^+$. |
| 144 | (2E)-3-(1-{[5-(4-Acryloyl-cis-2,6-dimethylpiperazin-1-yl)-3-(2,6-dichlorophenyl)-1,2-oxazol-4-yl]carbonyl}-1H-indol-4-yl)prop-2-enoic acid 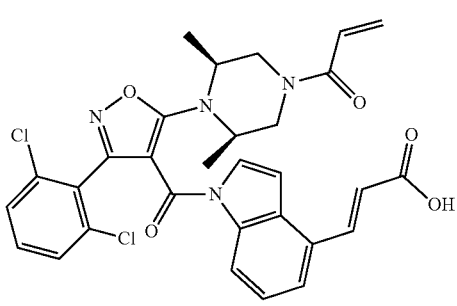 [SMILES: C=CC(=O)N1C[C@@H](C)N(c2onc(-c3c(Cl)cccc3Cl)c2C(=O)n2ccc3c(/C=C/C(=O)O)cccc32)[C@@H](C)C1] | $^1$H-NMR1.23(6H, m), 3.04-3.11 (1H, m), 3.42-3.52(1H, m), 3.98-4.34(4H, m), 5.74(1H, dd, J = 2.1, 10.6 Hz), 6.21(1H, dd, J = 2.1, 16.6 Hz), 6.57(1H, d, J = 16.3 Hz), 6.85 (2H, dd, J = 11.2, 16.0 Hz), 7.33 (2H, t, J = 7.9 Hz), 7.37-7.42(2H, m), 7.58(1H, d, J = 3.6 Hz), 7.63 (1H, d, J = 7.9 Hz), 7.79(1H, d, J = 16.3 Hz), 8.09(1H, d, J = 7.9 Hz). MS(m/z): 593(M + H)$^+$. |

TABLE 80

| | | |
|---|---|---|
| 145 | (2E)-3-[1-({5-[(2S)-4-Acryloyl-2-methylpiperazin-1-yl]-3-(2,6-dichlorophenyl)-1,2-oxazol-4-yl}carbonyl)-1H-indol-4-yl]prop-2-enoic acid 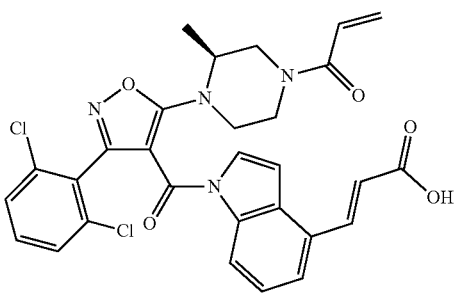 [SMILES: C=CC(=O)N1CCN(c2onc(-c3c(Cl)cccc3Cl)c2C(=O)n2ccc3c(/C=C/C(=O)O)cccc32)[C@@H](C)C1] | $^1$H-NMR(DMSO-d$_6$)δ: 1.19(3H, d, J = 6.7 Hz), 2.84-3.16(1H, m), 3.26-3.62(2H, m), 3.94-4.27(4H, m), 5.70(1H, d, J = 11.5 Hz), 6.15(1H, dd, J = 7.6, 16.0 Hz), 6.59(1H, d, J = 16.3 Hz), 6.72-6.84(1H, m), 6.85-6.88(1H, m), 7.31-7.46(4H, m), 7.57-7.60(1H, m), 7.66(1H, d, J = 7.9 Hz), 7.84(1H, d, J = 15.7 Hz), 8.10(1H, d, J = 8.5 Hz), 12.48(1H, s). MS(m/z): 579(M + H)$^+$. |

TABLE 80-continued

| 146 | (2E)-3-[1-({5-[(2R)-4-Acryloyl-2-methylpiperazin-1-yl]-3-(2,4,6-trichlorophenyl)-1,2-oxazol-4-yl}carbonyl)-1H-indol-4-yl]prop-2-enoic acid 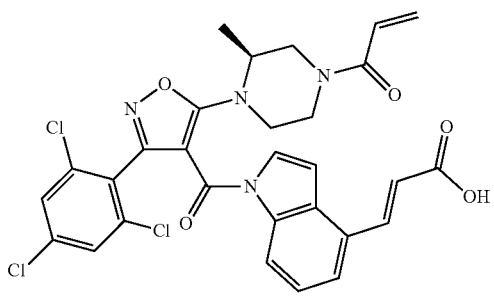 [SMILES: C=CC(=O)N1CCN(c2onc(-c3c(Cl)cc(Cl)cc3Cl)c2C(=O)n2ccc3c(/C=C/C(=O)O)cccc32)[C@@H](C)C1] | ¹H-NMR(CDCl₃)δ: 0.89(1H, t, J = 6.3 Hz), 1.34(3H, d, J = 6.3 Hz), 3.42-4.15(4H, m), 4.32-4.65(2H, m), 5.77 (1H, d, J = 10.3 Hz), 6.37(1H, d, J = 16.9 Hz), 6.46-6.60(2H, m), 6.70(1H, s), 7.23(2H, s), 7.33-7.42(2H, m), 7.55(1H, d, J = 7.3 Hz), 8.06(1H, d, J = 14.5 Hz), 8.24(1H, d, J = 8.5 Hz). |
|---|---|---|
| 147 | (2E)-3-(1-{[5-[7-Acryloyl-4,7-diazaspiro[2.5]oct-4-yl]-3-(2,6-dichlorophenyl)-1,2-oxazol-4-yl]carbonyl}-1H-indol-4-yl)prop-2-enoic acid 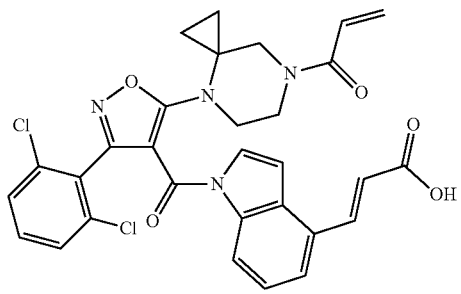 [SMILES: C=CC(=O)N1CCN(c2onc(-c3c(Cl)cccc3Cl)c2C(=O)n2ccc3c(/C=C/C(=O)O)cccc32)C2(CC2)C1] | ¹H-NMR(DMSO-d₆)δ: 0.82-0.92 (2H, m), 1.01-1.09(2H, m), 3.36-3.58 (4H, m), 3.68-3.78(2H, m), 5.67 (1H, d, J = 10.3 Hz), 6.07-6.17 (1H, m), 6.60(1H, d, J = 16.3 Hz), 6.67-6.81(1H, m), 6.90-6.96 (1H, m), 7.34(1H, t, J = 7.9 Hz), 7.39-7.52(3H, m), 7.62-7.71 (2H, m), 7.87(1H, d, J = 16.3 Hz), 8.07(1H, d, J = 8.5 Hz), 12.48(1H, s). MS(m/z): 591(M + H)⁺. |

TABLE 81

| 148 | (2E)-3-[1-({5-[(3R)-4-Acryloyl-3-methylpiperazin-1-yl]3-(2,4,6-trichlorophenyl)-1,2-oxazol-4-yl}carbonyl)-1H-indol-4-yl]prop-2-enoic acid 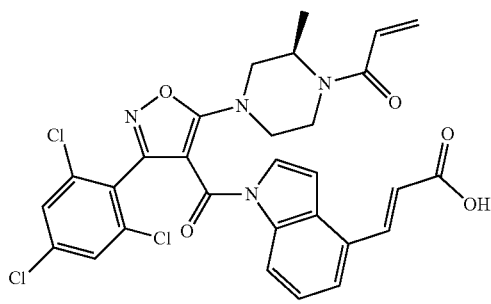 [SMILES: C=CC(=O)N1CCN(c2onc(-c3c(Cl)cc(Cl)cc3Cl)c2C(=O)n2ccc3c(/C=C/C(=O)O)cccc32)C[C@H]1C] | ¹H-NMR(CDCl₃)δ: 0.88(1H, t, J = 6.3 Hz), 1.25-1.31(2H, m), 1.37(3H, d, J = 6.3 Hz), 3.19-3.54(2H, m), 3.77-3.90(2H, m), 5.75(1H, d, J = 10.3 Hz), 6.34(1H, d, J = 16.9 Hz), 6.48-6.57 (2H, m), 6.67-6.71(1H, m), 7.18-7.30 (2H, m), 7.32-7.41(2H, m), 7.55 (1H, d, J = 7.9 Hz), 8.06(1H, d, J = 15.7 Hz), 8.24(1H, d, J = 7.9 Hz). |
|---|---|---|

TABLE 81-continued

| | | |
|---|---|---|
| 149 | (2E)-3-[1-({3-(2,6-Dichlorophenyl)-5-[4-(ethenylsulfonyl)piperazin-1-yl]-1,2-oxazol-4-yl}carbonyl)-1H-indol-4-yl]prop-2-enoic acid | $^1$H-NMR(DMSO-d$_6$)δ: 3.10-3.16 (4H, m), 3.52-3.61(4H, m), 6.12(1H, d, J = 16.9 Hz), 6.22(1H, d, J = 10.3 Hz), 6.59(1H, d, J = 15.7 Hz), 6.82-6.89(2H, m), 7.29-7.47(4H, m), 7.57 (1H, d, J = 3.6 Hz), 7.66(1H, d, J = 7.9 Hz), 7.84(1H, d, J = 15.7 Hz), 8.07(1H, d, J = 8.5 Hz). MS(m/z): 601(M + H)$^+$. |
| 150 | (2E)-3-(1-{[5-[7-Acryloyl-4,7-diazaspiro[2.5]oct-4-yl]-3-(2,4,6-trichlorophenyl)-1,2-oxazol-4-yl]carbonyl}-1H-indol-4-yl)prop-2-enoic acid | $^1$H-NMR(CDCl$_3$)δ: 0.86-0.93(2H, m), 1.01-1.13(2H, m), 1.23-1.30 (2H, m), 3.53-3.76(4H, m), 5.73 (1H, d, J = 10.3 Hz), 6.27-6.50(2H, m), 6.55(1H, d, J = 15.7 Hz), 6.73 (1H, brs), 7.22-7.38(4H, m), 7.56 (1H, d, J = 7.3 Hz), 8.07(1H, d, J = 16.3 Hz), 8.22(1H, d, J = 8.5 Hz). |

TABLE 82

| | | |
|---|---|---|
| 151 | (2E)-3-(1-{[5-(4-Acryloyl-cis-2,6-dimethylpiperazin-1-yl)-3-(2,4,6-trichlorophenyl)-1,2-oxazol-4-yl]carbonyl}-1H-indol-4-yl)prop-2-enoic acid | $^1$H-NMR(CDCl$_3$)δ: 0.88(1H, t, J = 7.0 Hz), 1.26(1H, t, J = 7.3 Hz), 1.38(6H, d, J = 6.7 Hz), 3.09-3.19(1H, m), 3.53-3.87(1H, m), 4.26-4.56(2H, m), 5.78-5.82 (1H, m), 6.42(1H, dd, J = 16.9, 1.8 Hz), 6.50-6.62(2H, m), 6.66(1H, d, J = 3.6 Hz), 7.18 (2H, s), 7.32-7.38(2H, m), 7.54 (1H, d, J = 7.9 Hz), 8.04(1H, d, J = 15.7 Hz), 8.23(1H, d, J = 8.5 Hz). |

TABLE 82-continued

| | | |
|---|---|---|
| 152 | (2E)-3-[1-({5-[(2R,5R)-4-Acryloyl-2,5-dimethylpiperazin-1-yl]-3-(2,4,6-trichlorophenyl)-1,2-oxazol-4-yl}carbonyl)-1H-indol-4-yl]prop-2-enoic acid<br />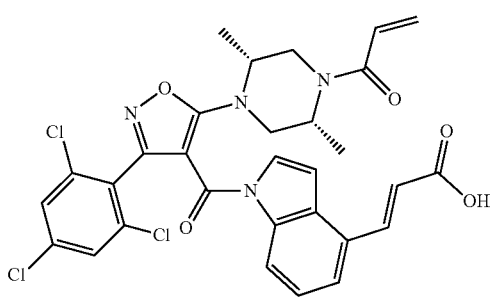 [SMILES: C=CC(=O)N1C[C@@H](C)N(c2onc(-c3c(Cl)cc(Cl)cc3Cl)c2C(=O)n2ccc3c(/C=C/C(=O)O)cccc32)C[C@H]1C] | $^1$H-NMR(CDCl$_3$)δ: 1.19(3H, d, J = 6.0 Hz), 1.24-1.28(2H, m), 1.33 (3H, d, J = 6.0 Hz), 3.21(1H, dd, J = 14.5, 10.3 Hz), 3.92-4.02(1H, m), 4.22-4.30(1H, m), 4.50-4.60 (1H, m), 5.79(1H, d, J = 10.9 Hz), 6.42-6.57(3H, m), 6.61(1H, d, J = 3.6 Hz), 7.17(2H, s), 7.30-7.37 (2H, m), 7.52(1H, d, J = 7.3 Hz), 8.03(1H, d, J = 15.7 Hz), 8.21 (1H, d, J = 8.5 Hz). |
| 153 | (2E)-3-(1-{[5-(4-Acryloyl-2,2-dimethylpiperazin-1-yl)-3-(2,6-dichlorophenyl)-1,2-oxazol-4-yl]carbonyl}-1H-indol-4-yl)prop-2-enoic acid<br />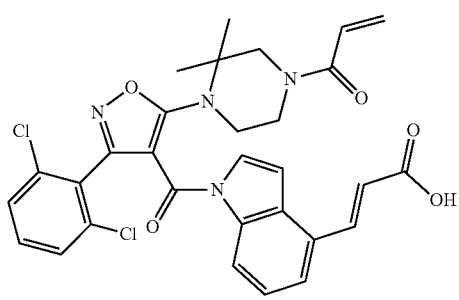 [SMILES: C=CC(=O)N1CCN(c2onc(-c3c(Cl)cccc3Cl)c2C(=O)n2ccc3c(/C=C/C(=O)O)cccc32)C(C)(C)C1] | $^1$H-NMR(DMSO-d$_6$)δ: 1.43-1.46 (6H, m), 3.35-3.41(3H, m), 3.51-3.57(1H, m), 3.62-3.66(2H, m), 5.68-5.73(1H, m), 6.13-6.19(1H, m), 6.56-6.92(3H, m), 7.34(1H, t, J = 8.2 Hz), 7.39-7.49(4H, m), 7.67(1H, d, J = 7.3 Hz), 7.85(1H, d, J = 16.3 Hz), 8.09(1H, d, J = 7.9 Hz), 12.48 (1H, s).<br />MS(m/z): 593(M + H)$^+$. |

TABLE 83

| | | |
|---|---|---|
| 154 | (2E)-3-[1-({5-[(2R)-4-Acryloyl-2-cyclopropylpiperazin-1-yl]-3-(2,6-dichlorophenyl)-1,2-oxazol-4-yl}carbonyl)-1H-indol-4-yl]prop-2-enoic acid<br />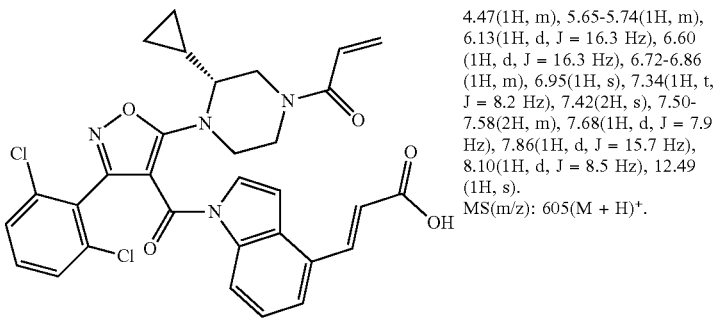 | $^1$H-NMR(DMSO-d$_6$)δ: 0.28-0.40(2H, m), 0.43-0.51(1H, m), 0.55-0.66(1H, m), 1.24-1.28(4H, m), 2.85-3.03(1H, m), 3.46-3.63 (1H, m), 4.02-4.15(1H, m), 4.33-4.47(1H, m), 5.65-5.74(1H, m), 6.13(1H, d, J = 16.3 Hz), 6.60 (1H, d, J = 16.3 Hz), 6.72-6.86 (1H, m), 6.95(1H, s), 7.34(1H, t, J = 8.2 Hz), 7.42(2H, s), 7.50-7.58(2H, m), 7.68(1H, d, J = 7.9 Hz), 7.86(1H, d, J = 15.7 Hz), 8.10(1H, d, J = 8.5 Hz), 12.49 (1H, s).<br />MS(m/z): 605(M + H)$^+$. |

TABLE 83-continued

| 155 | (2E)-3-[1-({5-[(6R)7-Acryloyl-6-methyl-4,7-diazaspiro[2.5]oct-4-yl]-3-(2,6-dichlorophenyl)-1,2-oxazol-4-yl}carbonyl)-1H-indol-4-yl]prop-2-enoic acid | ¹H-NMR(DMSO-d₆)δ: 0.60-1.45 (7H, m), 3.26-3.75(4H, m), 4.29-4.86(1H, m), 5.67(1H, d, J = 10.9 Hz), 6.12(1H, d, J = 16.3 Hz), 6.59(1H, d, J = 15.7 Hz), 6.66-6.79(1H, m), 6.82-7.01(1H, m), 7.24-7.47(3H, m), 7.49-7.61(2H, m), 9.59-9.62(1H, m), 7.85 (1H, d, J = 16.3 Hz), 8.10(1H, d, J = 7.9 Hz), 12.48(1H, s). MS(m/z): 605(M + H)⁺. |
|---|---|---|

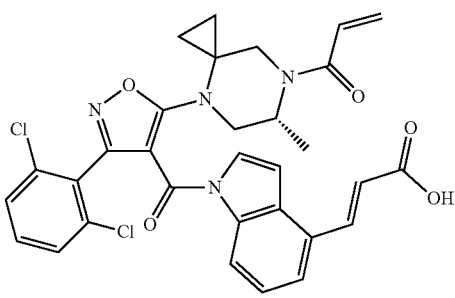 [SMILES: C=CC(=O)N1CC2(CC2)N(c2onc(-c3c(Cl)cccc3Cl)c2C(=O)n2ccc3c(/C=C/C(=O)O)cccc32)C[C@H]1C]

| 156 | (2E)-3-[1-({5-[(6R)7-Acryloyl-6-methyl-4,7-diazaspiro[2.5]oct-4-yl]-3-(2-chloro-6-fluorophenyl)-1,2-oxazol-4-yl}carbonyl)-1H-indol-4-yl]prop-2-enoic acid | ¹H-NMR(CDCl₃)δ: 1.25-1.34 (9H, m), 3.61(1H, d, J = 13.9 Hz), 3.83-3.94(1H, m), 4.47-4.55(1H, m), 5.72(1H, d, J = 10.3 Hz), 6.29-6.62(4H, m), 6.83-7.21(4H, m), 7.34(1H, t, J = 7.9 Hz), 7.52 (1H, d, J = 7.3 Hz), 8.01(1H, d, J = 15.7 Hz), 8.25(1H, d, J = 7.9 Hz). |
|---|---|---|

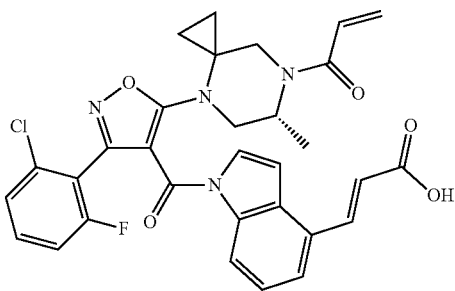 [SMILES: C=CC(=O)N1CC2(CC2)N(c2onc(-c3c(F)cccc3Cl)c2C(=O)n2ccc3c(/C=C/C(=O)O)cccc32)C[C@H]1C]

TABLE 84

| 157 | (2E)-3-(1-{[5-(4-Acryloyl-2,2-dimethylpiperazin-1-yl)-3-(2-chloro-6-fluorophenyl)-1,2-oxazol-4-yl]carbonyl}-1H-indol-4-yl)prop-2-enoic acid | ¹H-NMR(CDCl₃)δ: 1.60(6H, d, J = 13.9 Hz), 3.37-3.49(2H, m), 3.53-3.64(3H, m), 3.75(1H, s), 5.76(1H, d, J = 11.5 Hz), 6.33-6.55(3H, m), 6.68(1H, brs), 6.87-6.95(1H, m), 7.08-7.15(1H, m), 7.20-7.25(1H, m), 7.28-7.39(2H, m), 7.53 (1H, d, J = 7.9 Hz), 8.04(1H, d, J = 15.7 Hz), 8.23(1H, d, J = 7.9 Hz). |
|---|---|---|

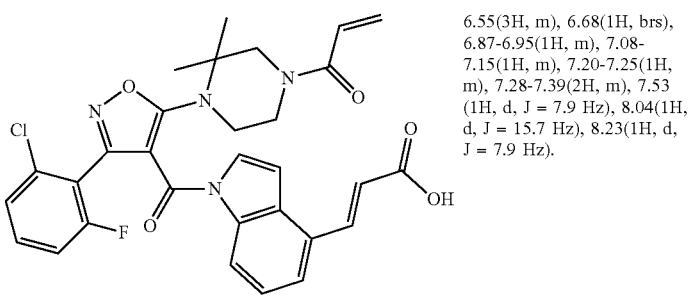

TABLE 84-continued

| 158 | (2E)-3-[1-({5-[(6R)7-Acryloyl-6-methyl-4,7-diazaspiro[2.5]oct-4-yl]-3-(2-chloro-6-methoxyphenyl)-1,2-oxazol-4-yl}carbonyl)-1H-indol-4-yl]prop-2-enoic acid | $^{1}$H-NMR(CDCl$_3$)δ: 0.80-1.02(4H, m), 1.31-1.40(3H, m), 2.98-3.11(1H, m), 3.45-3.70(5H, m), 3.92-4.00(2H, m), 5.72(1H, d, J = 9.1 Hz), 6.27-6.58 (4H, m), 6.89-6.98(1H, m), 7.07-7.15(1H, m), 7.24-7.28(2H, m), 7.29-7.36(1H, m), 7.51(1H, d, J = 7.9 Hz), 8.01(1H, d, J = 15.7 Hz), 8.30(1H, d, J = 8.5 Hz). |
|---|---|---|
| 159 | (2E)-3-[1-({5-[(5R)7-Acryloyl-5-methyl-4,7-diazaspiro[2.5]oct-4-yl]-3-(2,6-dichlorophenyl)-1,2-oxazol-4-yl}carbonyl)-1H-indol-4-yl]prop-2-enoic acid | $^{1}$H-NMR(DMSO-d$_6$)δ: 0.85(3H, d, J = 6.7 Hz), 1.04-1.13(4H, m), 1.21-1.31(4H, m), 3.21-3.32(1H, m), 3.51-4.24(4H, m), 5.65-5.73(1H, m), 6.15(1H, dd, J = 2.1, 16.6 Hz), 6.60 (1H, d, J = 15.7 Hz), 6.66-6.83 (1H, m), 6.93(1H, brs), 7.32-7.45 (3H, m), 7.59-7.69(3H, m), 7.86 (1H, d, J = 16.3 Hz), 8.06(1H, d, J = 7.9 Hz), 12.48(1H, brs). MS(m/z): 605(M + H)$^+$. |

TABLE 85

| 160 | (2E)-3-[1-({5-[(6R)7-Acryloyl-6-ethyl-4,7-diazaspiro[2.5]oct-4-yl]-3-(2-chloro-6-fluorophenyl)-1,2-oxazol-4-yl}carbonyl)-1H-indol-4-yl]prop-2-enoic acid | $^{1}$H-NMR(CDCl$_3$)δ: 0.71-1.09(6H, m), 1.24-1.30(2H, m), 1.64-1.71(1H, m), 3.56(1H, d, J = 13.3 Hz), 3.79-4.03 (2H, m), 4.17-4.43(1H, m), 5.72 (1H, brs), 6.26-6.66(4H, m), 6.87 (1H, brs), 7.03-7.21(2H, m), 7.24-7.28(1H, m), 7.34(1H, t, J = 7.9 Hz), 7.52(1H, d, J = 7.9 Hz), 8.02(1H, d, J = 15.7Hz), 8.24(1H, d, J = 8.5 Hz). |
|---|---|---|

TABLE 85-continued

| 161 | (2E)-3-[1-({5-{(6R)7-Acryloyl-6-ethyl-4,7-diazaspiro[2.5]oct-4-yl]-3-(2-chloro-6-methoxyphenyl)-1,2-oxazol-4-yl}carbonyl)-1H-indol-4-yl]prop-2-enoic acid 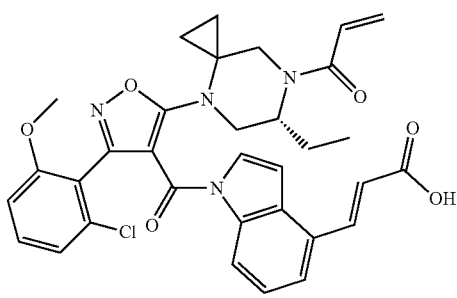 [SMILES: C=CC(=O)N1CC2(CC2)N(c2onc(-c3c(Cl)cccc3OC)c2C(=O)n2ccc3c(/C=C/C(=O)O)cccc32)C[C@H]1CC] | ¹H-NMR(CDCl₃)δ: 0.93(3H, t, J = 7.3 Hz), 1.24-1.34(2H, m), 1.67-2.05 (6H,m), 3.47-3.64(3H, m), 3.87-4.13 (3H, m), 5.72(1H, brs), 6.27-6.62(4H, m), 6.92-7.16(2H, m), 7.23-7.36(3H, m), 7.51(1H, d, J = 7.3 Hz), 8.01(1H, d, J = 15.7 Hz), 8.29(1H, d, J = 7.9 Hz). MS(m/z): 615(M + H)⁺. |
|---|---|---|
| 162 | (2E)-3-[1-({5-[(6R)7-Acryloyl-6-methyl-4,7-diazaspiro[2.5]oct-4-yl]-3-(2-chloro-6-fluorophenyl)-1,2-oxazol-4-yl}carbonyl)-3-methyl-1H-indol-4-yl]prop-2-enoic acid 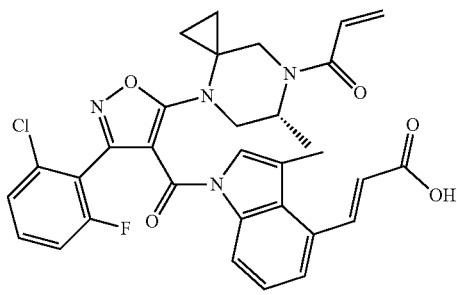 [SMILES: C=CC(=O)N1CC2(CC2)N(c2onc(-c3c(F)cccc3Cl)c2C(=O)n2cc(C)c3c(/C=C/C(=O)O)cccc32)C[C@H]1C] | ¹H-NMR(CDCl₃)δ: 0.74-1.07(4H, m), 1.24-1.40(5H, m), 2.28(3H, s), 2.98-3.07(1H, m), 3.62(1H, d, J = 11.5 Hz), 3.89-4.02(1H, m), 5.73(1H, d, J = 9.7 Hz), 6.27-6.49(3H, m), 6.81-7.01(2H, m), 7.04-7.21(2H, m), 7.24-7.35(2H, m), 7.51(1H, d, J = 7.9 Hz), 8.28(1H, d, J = 8.5 Hz), 8.40(1H, d, J = 15.7 Hz). |

TABLE 86

| 163 | (2E)-3-[1-({5-[(6R)7-Acryloyl-6-ethyl-4,7-diazaspiro[2.5]oct-4-yl]-3-(2,6-dichlorophenyl)-1,2-oxazol-4-yl}carbonyl)-1H-indol-4-yl]prop-2-enoic acid 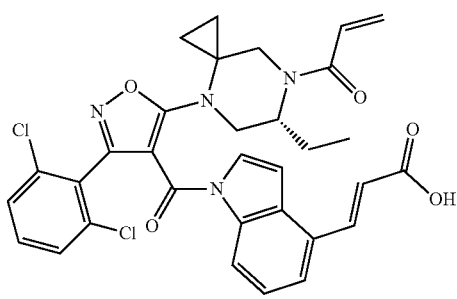 [SMILES: C=CC(=O)N1CC2(CC2)N(c2onc(-c3c(Cl)cccc3Cl)c2C(=O)n2ccc3c(/C=C/C(=O)O)cccc32)C[C@H]1CC] | ¹H-NMR(DMSO-d₆)δ: 0.60-0.81 (5H, m), 0.98-1.66(4H, m), 3.24-3.41(5H, m), 5.67(1H, dd, J = 2.1, 10.6 Hz), 6.12(1H, dd, J = 2.1, 16.6 Hz), 6.55-6.64(1H, m), 6.68-6.83(1H, m), 6.85-6.99 (1H, m), 7.27-7.48(3H, m), 7.51-7.70(3H, m), 7.79-7.91(1H, m), 8.09(1H, d, J = 7.9 Hz), 12.51 (1H, brs). MS(m/z): 619(M + H)⁺. |
|---|---|---|

Example 164

(2E)-3-(3-[5-tert-Butyl-3-(2,4,6-trichlorophenyl)-1,2-oxazol-4-yl]carbonyl}-1-methyl-1H-indol-7-yl)prop-2-enoic acid

[Formula 88]

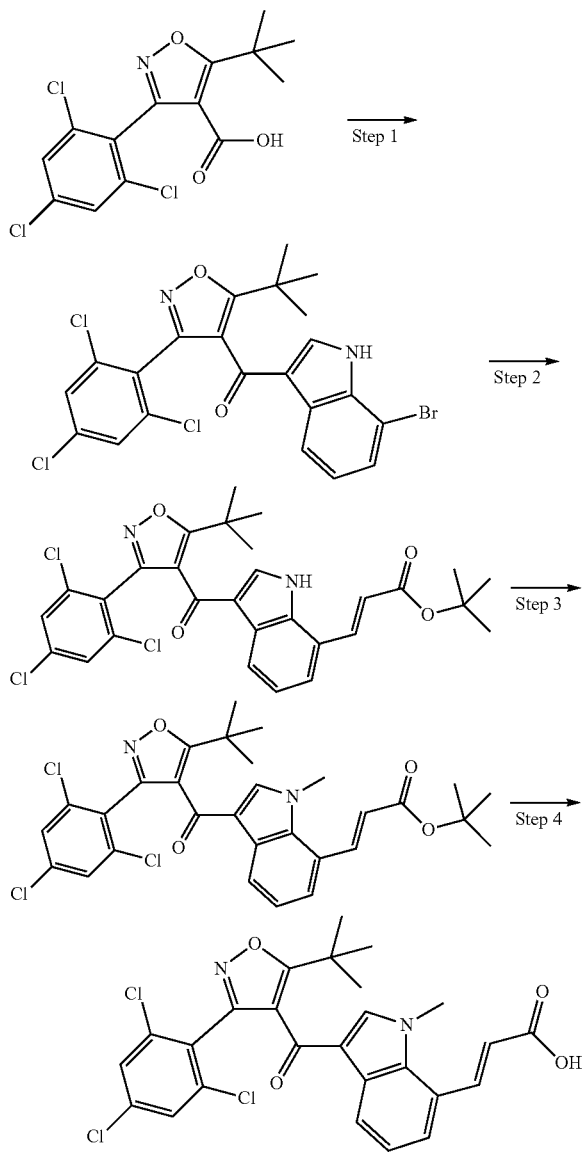

[Step 1] (7-Bromo-1H-indol-3-yl)[5-tert-butyl-3-(2,4,6-trichlorophenyl)-1,2-oxazol-4-yl]methanone To a solution of the compound (1.00 g) obtained in Reference Example X-5 and N,N-dimethylformamide (10 µl) in dichloromethane (20 ml), oxalyl chloride (743 mg) was added, and the mixture was stirred at room temperature for 1 hour. The reaction solution was concentrated under reduced pressure to obtain acid chloride.

To a solution of the acid chloride in dichloromethane (15 ml), aluminum chloride (781 mg) was added under ice cooling under a nitrogen atmosphere, and the mixture was stirred at room temperature for 10 minutes.

To a solution of 7-bromoindole (1.16 g) in dichloromethane (15 ml), the reaction solution was added under a nitrogen atmosphere, and the mixture was stirred at room temperature for 40 minutes. The reaction solution was poured into ice and separated into two layers. The aqueous layer was subjected to extraction with dichloromethane. The organic layers were combined, washed with saturated saline and then dried over anhydrous sodium sulfate. The solvent was distilled off under reduced pressure, and the residue obtained was purified by silica gel column chromatography (n-hexane/ethyl acetate) to obtain the title compound (514 mg).

$^1$H-NMR (CDCl$_3$) δ: 1.43 (9H, s), 7.18 (1H, t, J=7.9 Hz), 7.29 (2H, s), 7.45 (1H, d, J=7.9 Hz), 7.66 (1H, d, J=3.0 Hz), 8.29 (1H, d, J=7.9 Hz), 8.67 (1H, brs).

[Step 2] tert-Butyl (2E)-3-(3-{[5-tert-butyl-3-(2,4,6-trichlorophenyl)-1,2-oxazol-4-yl]carbonyl}-1H-indol-7-yl)prop-2-enoate To a solution of the compound (510 mg) obtained in the preceding step 1, tert-butyl acrylate (186 mg), N,N-di(propan-2-yl)ethylamine (0.33 ml), and tris(2-methylphenyl)phosphine (88 mg) in N,N-dimethylformamide (3.5 ml), palladium acetate (33 mg) was added, and the mixture was stirred at 140° C. for 1 hour using a microwave apparatus. After cooling to room temperature, ethyl acetate and saturated saline were added to the reaction solution, which was then separated into two layers. The organic layer was washed with water and saturated saline in this order and then dried over anhydrous sodium sulfate. The solvent was distilled off under reduced pressure, and the residue obtained was purified by silica gel column chromatography (n-hexane/ethyl acetate) to obtain the title compound (430 mg).

$^1$H-NMR (CDCl$_3$) δ: 1.44 (9H, s), 1.55 (9H, s), 6.42 (1H, d, J=16.9 Hz), 7.28 (2H, s), 7.31 (1H, dd, J=8.2, 4.1 Hz), 7.49 (1H, d, J=7.3 Hz), 7.66 (1H, d, J=2.4 Hz), 7.83 (1H, d, J=15.7 Hz), 8.39 (1H, d, J=7.9 Hz), 8.93 (1H, brs).
MS (m/z): 573 (M+H)$^+$.

[Step 3] tert-Butyl (2E)-3-(3-[5-tert-butyl-3-(2,4,6-trichlorophenyl)-1,2-oxazol-4-yl]carbonyl}-1-methyl-1H-indol-7-yl)prop-2-enoate To a solution of the compound (426 mg) obtained in the preceding step 2 in N,N-dimethylformamide (3 ml), sodium hydride (55% oil, 36 mg) was added under ice cooling under a nitrogen atmosphere, and the mixture was stirred for 5 minutes. Methyl iodide (0.14 ml) was added to the reaction solution, and the mixture was stirred for 1 hour. Ice, water, and ethyl acetate were added to the reaction solution, which was then separated into two layers. The organic layer was washed with water and saturated saline in this order and then dried over anhydrous sodium sulfate. The solvent was distilled off under reduced pressure, and the residue obtained was purified by silica gel column chromatography (n-hexane/ethyl acetate) to obtain the title compound (354 mg).

$^1$H-NMR (CDCl$_3$) δ: 1.45 (9H, s), 1.54 (9H, s), 3.99 (3H, s), 6.32 (1H, d, J=15.7 Hz), 7.25-7.30 (3H, m), 7.44 (2H, d, J=6.7 Hz), 8.32 (1H, d, J=15.7 Hz), 8.40 (1H, d, J=7.9 Hz).
MS (m/z): 587 (M+H)$^+$.

[Step 4] (2E)-3-(3-[5-tert-Butyl-3-(2,4,6-trichlorophenyl)-1,2-oxazol-4-yl]carbonyl}-1-methyl-1H-indol-7-yl)prop-2-enoic acid To a solution of the compound (350 mg) obtained in the preceding step 3 in dichloromethane (5 ml), trifluoroacetic acid (1 ml) was added, and the mixture was stirred overnight at room temperature. The reaction solution was poured into a mixed solution of water and dichloromethane and separated into two layers. The organic layer was washed with water and saturated saline in this order and then dried over anhydrous sodium sulfate. The solvent was distilled off under reduced pressure, and the residue obtained was purified by silica gel column chromatography (n-hexane/ethyl acetate) to obtain the title compound (260 mg).

$^1$H-NMR (CDCl$_3$) δ: 1.46 (9H, s), 4.00 (3H, s), 6.42 (1H, d, J=15.1 Hz), 7.29 (2H, s), 7.32 (1H, t, J=7.9, 3.9 Hz), 7.45 (1H, s), 7.49 (1H, d, J=7.3 Hz), 8.45 (1H, d, J=7.9 Hz), 8.52 (1H, d, J=15.1 Hz).

MS (m/z): 531 (M+H)$^+$.

The following compound was obtained by the same method as in Example 164.

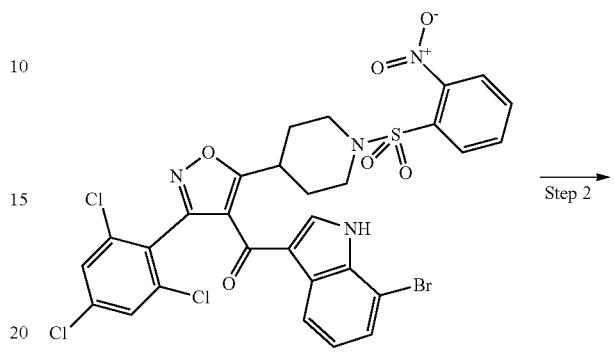
Step 2

TABLE 87

| Example No. | Name and structure | Instrumental data |
|---|---|---|
| 165 | (2E)-3-(1-Methyl-3-{[5-(1-methylcyclopropyl)-3-(2,4,6-trichlorophenyl)-1,2-oxazol-4-yl]carbonyl}-1H-indol-7-yl)prop-2-enoic acid | $^1$H-NMR(CDCl$_3$)δ: 0.87(2H, dd, J = 6.7, 3.3 Hz), 1.37(2H, dd, J = 6.7, 4.8 Hz), 1.43(3H, s), 4.04 (3H, s), 6.43(1H, d, J = 15.7 Hz), 7.29-7.32(3H, m), 7.50-7.52(2H, m), 8.43(1H, d, J = 7.9 Hz), 8.53 (1H, d, J = 15.7 Hz). MS(m/z): 529(M + H)$^+$. |

Example 166

(2E)-3-(3-{[5-(1-Acryloylpiperidin-4-yl)-3-(2,4,6-trichlorophenyl)-1,2-oxazol-4-yl]carbonyl}-1-methyl-1H-indol-7-yl)prop-2-enoic acid

[Formula 89]

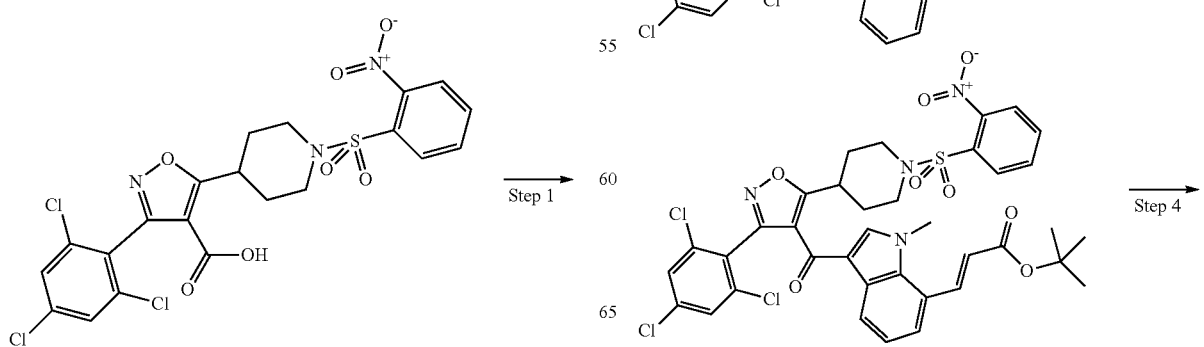

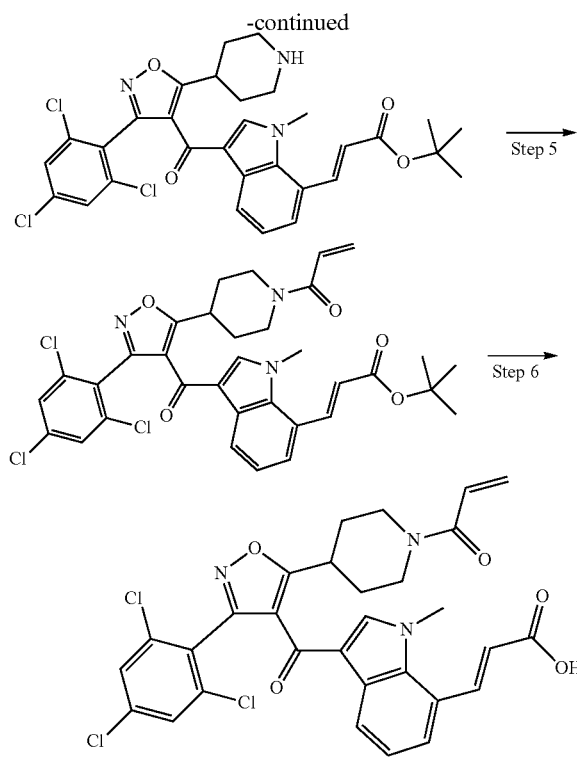

[Step 1] (7-Bromo-1H-indol-3-yl)[5-{1-[(2-nitrophenyl)sulfonyl]piperidin-4-yl}-3-(2,4,6-trichlorophenyl)-1,2-oxazol-4-yl]methanone To a suspension of the compound (500 mg) obtained in Reference Example X-38 in dichloromethane (5.35 ml), N,N-dimethylformamide (28 µl) and oxalyl chloride (0.153 ml) were added under ice cooling under a current of nitrogen, and the mixture was stirred at room temperature for 2 hours. The reaction solution was concentrated under reduced pressure, and the residue obtained was dissolved in dichloromethane (5.35 ml). To this solution, aluminum chloride (238 mg) was added under ice cooling under a current of nitrogen, and the mixture was stirred at room temperature for 15 minutes. 7-Bromoindole (262 mg) was added to the reaction solution under ice cooling, and the mixture was stirred at room temperature for 40 minutes. The reaction solution was added to ice, followed by extraction with dichloromethane. The extract was dried over anhydrous magnesium sulfate. The solvent was distilled off under reduced pressure, and the residue obtained was purified by silica gel column chromatography (n-hexane/ethyl acetate) to obtain the title compound (145 mg).
$^1$H-NMR (CDCl$_3$) δ: 2.08-2.18 (3H, m), 2.86-2.93 (2H, m), 3.25-3.33 (1H, m), 3.59 (1H, dd, J=15.7, 9.1 Hz), 3.97 (2H, d, J=12.7 Hz), 6.90-7.07 (1H, m), 7.20 (1H, q, J=7.9 Hz), 7.35 (2H, dd, J=15.1, 8.5 Hz), 7.45 (1H, t, J=6.3 Hz), 7.53 (1H, t, J=3.9 Hz), 7.59-7.77 (2H, m), 7.99-8.03 (1H, m), 8.22 (1H, d, J=7.9 Hz), 8.64 (1H, s).
MS (m/z): 739 (M+H)$^+$.

[Step 2] tert-Butyl(2E)-3-(3-{[5-{1-[(2-nitrophenyl)sulfonyl]piperidin-4-yl}-3-(2,4,6-trichlorophenyl)-1,2-oxazol-4-yl]carbonyl}-1H-indol-7-yl)prop-2-enoate The title compound (76.7 mg) was obtained by the same method as in step 2 of Example 164 using the compound (145 mg) obtained in the preceding step 1.
$^1$H-NMR (CDCl$_3$) δ: 1.59 (9H, s), 2.08-2.16 (4H, m), 2.85-2.92 (2H, m), 3.26-3.35 (1H, m), 3.97 (2H, d, J=13.4 Hz), 6.41 (1H, d, J=15.8 Hz), 7.30-7.32 (2H, m), 7.48-7.53 (2H, m), 7.61-7.63 (1H, m), 7.69-7.75 (2H, m), 7.81 (1H, d, J=16.4 Hz), 7.98-8.01 (1H, m), 8.31 (1H, d, J=7.3 Hz), 8.90 (1H, s).
MS (m/z): 787 (M+H)$^+$.

[Step 3] tert-Butyl (2E)-3-(1-methyl-3-{[5-{1-[(2-nitrophenyl)sulfonyl]piperidin-4-yl}-3-(2,4,6-trichlorophenyl)-1,2-oxazol-4-yl]carbonyl}-1H-indol-7-yl)prop-2-enoate The title compound (44.7 mg) was obtained by the same method as in step 3 of Example 164 using the compound (76.7 mg) obtained in the preceding step 2.
$^1$H-NMR (CDCl$_3$) δ: 1.54 (9H, s), 2.05-2.12 (4H, m), 2.87-2.94 (2H, m), 3.29-3.39 (1H, m), 3.88-4.04 (5H, m), 6.32 (1H, d, J=15.8 Hz), 7.29-7.33 (3H, m), 7.42-7.46 (1H, m), 7.61-7.72 (4H, m), 8.00 (1H, dd, J=7.3, 1.8 Hz), 8.25-8.35 (2H, m).
MS (m/z): 801 (M+H)$^+$.

[Step 4] tert-Butyl (2E)-3-(1-methyl-3-{[5-(piperidin-4-yl)-3-(2,4,6-trichlorophenyl)-1,2-oxazol-4-yl]carbonyl}-1H-indol-7-yl)prop-2-enoate The title compound (26.9 mg) was obtained by the same method as in step 3 of Example 94 using the compound (44.7 mg) obtained in the preceding step 3.
$^1$H-NMR (CDCl$_3$) δ: 1.54 (9H, s), 2.20-2.30 (4H, m), 2.88-2.97 (2H, m), 3.11 (1H, q, J=7.3 Hz), 3.42-3.51 (3H, m), 3.94 (3H, s), 6.32 (1H, d, J=15.2 Hz), 7.28-7.35 (4H, m), 7.45 (1H, d, J=6.1 Hz), 8.26-8.36 (2H, m).
MS (m/z): 614 (M+H)$^+$.

[Step 5] tert-Butyl (2E)-3-(3-{[5-(1-acryloylpiperidin-4-yl)-3-(2,4,6-trichlorophenyl)-1,2-oxazol-4-yl]carbonyl}-1-methyl-1H-indol-7-yl)prop-2-enoate The title compound (16.6 mg) was obtained by the same method as in step 4 of Example 94 using the compound (26.9 mg) obtained in the preceding step 4.
$^1$H-NMR (CDCl$_3$) δ: 1.54 (9H, s), 1.93-2.10 (4H, m), 2.70-2.90 (1H, m), 3.11-3.22 (1H, m), 3.47-3.52 (1H, m), 3.93 (3H, s), 4.01-4.17 (1H, m), 4.74 (1H, d, J=10.9 Hz), 5.71 (1H, dd, J=10.6, 1.5 Hz), 6.27-6.35 (2H, m), 6.59 (1H, dd, J=16.6, 10.6 Hz), 7.27-7.35 (4H, m), 7.42-7.48 (1H, m), 8.26-8.38 (2H, m).
MS (m/z): 670 (M+H)$^+$.

[Step 6] (2E)-3-(3-{[5-(1-Acryloylpiperidin-4-yl)-3-(2,4,6-trichlorophenyl)-1,2-oxazol-4-yl]carbonyl}-1-methyl-1H-indol-7-yl)prop-2-enoic acid The title compound (10.1 mg) was obtained by the same method as in step 3 of Example 10 using the compound (16.6 mg) obtained in the preceding step 5.
$^1$H-NMR (DMSO-d$_6$) δ: 1.61-1.77 (2H, m), 2.00 (2H, d, J=12.1 Hz), 2.60-2.74 (1H, m), 3.01-3.14 (1H, m), 3.33-3.39 (1H, m), 3.98-4.11 (4H, m), 4.33-4.45 (1H, m), 5.63 (1H, dd, J=10.9, 2.4 Hz), 6.06 (1H, dd, J=16.6, 2.1 Hz), 6.37 (1H, d, J=15.7 Hz), 6.77 (1H, dd, J=16.6, 10.6 Hz), 7.23 (1H, t, J=7.6 Hz), 7.51 (1H, d, J=7.9 Hz), 7.76-7.80 (2H, m), 8.01 (1H, s), 8.12 (1H, d, J=7.9 Hz), 8.33 (1H, t, J=16.0 Hz), 13.5 (1H, brs).
MS (m/z): 614 (M+H)$^+$.

Example 167

3-{[5-tert-Butyl-3-(2,4,6-trichlorophenyl)-1,2-oxazol-4-yl]carbonyl}-1-methyl-1H-benzo[g]indole-8-carboxylic acid

[Formula 90]

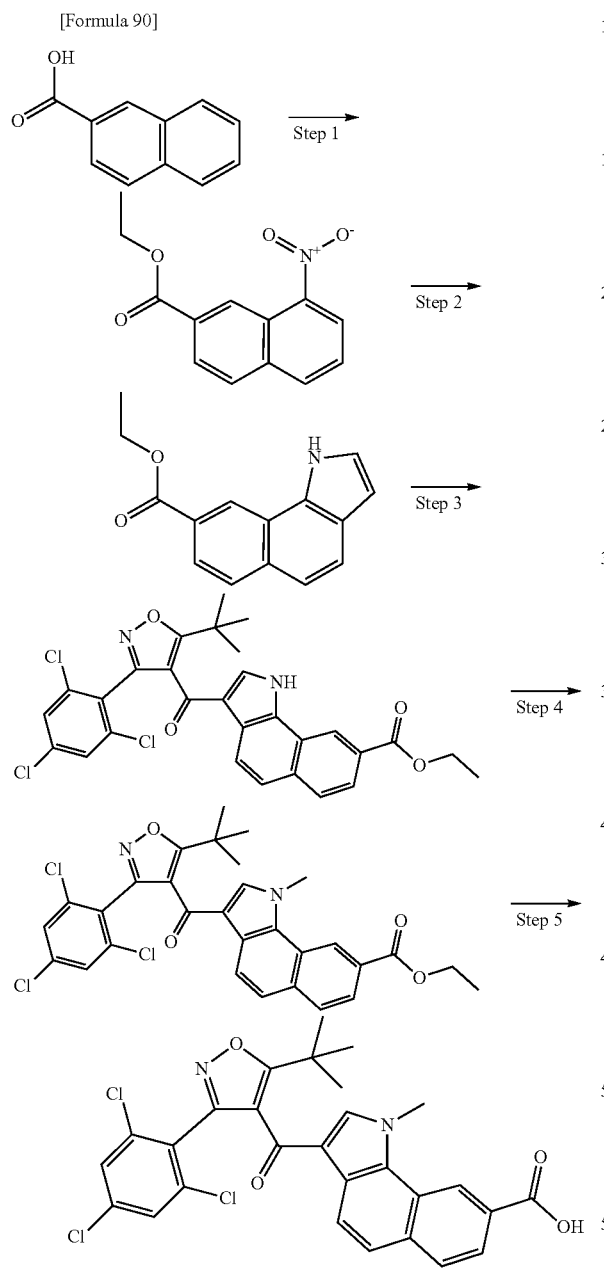

[Step 1] Ethyl 8-nitronaphthalene-2-carboxylate

A solution of naphthalene-2-carboxylic acid (10 g) in acetic anhydride (105 ml) was cooled to −10° C., and a solution of fuming nitric acid (2.71 ml) in acetic anhydride (13 ml) was added dropwise thereto over 10 minutes. The reaction solution was stirred at room temperature for 5 hours and then poured into ice. The insoluble matter was collected by filtration and dried under reduced pressure to obtain a mixture of 5- and 8-nitronaphthalene-2-carboxylic acids (12.6 g). Ethanol (110 ml) and concentrated sulfuric acid (1.2 ml) were added to the solid obtained, and the mixture was heated to reflux for 18 hours. The reaction solution was concentrated under reduced pressure, and ethanol was added to the residue. The resulting solid was collected by filtration. The crude product obtained was purified by silica gel column chromatography (n-hexane/ethyl acetate) to obtain the title compound (2.96 g).

$^1$H-NMR (CDCl$_3$) δ: 1.46 (3H, t, J=7.3 Hz), 4.47 (2H, q, J=7.3 Hz), 7.66 (1H, t, J=7.9 Hz), 8.02 (1H, d, J=9.1 Hz), 8.16 (1H, d, J=8.5 Hz), 8.22 (1H, dd, J=8.8, 1.5 Hz), 8.27 (1H, t, J=3.9 Hz), 9.27 (1H, s).

[Step 2] Ethyl 1H-benzo[g]indole-8-carboxylate

To a solution of the compound (1.0 g) obtained in the preceding step 1 in tetrahydrofuran (20 ml), vinyl magnesium chloride (14% solution in tetrahydrofuran, 13.7 ml) was added dropwise at −45° C., and the mixture was stirred at the same temperature as above for 2 hours. A saturated aqueous solution of ammonium chloride, saturated saline, and ethyl acetate were added to the reaction solution, which was then separated into two layers. The organic layer was concentrated under reduced pressure, and the residue obtained was purified by silica gel column chromatography (n-hexane/ethyl acetate) to obtain the title compound (342 mg).

$^1$H-NMR (CDCl$_3$) δ: 1.44-1.50 (3H, m), 4.48 (2H, q, J=7.3 Hz), 6.73 (1H, t, J=2.7 Hz), 7.33 (1H, t, J=2.7 Hz), 7.55 (1H, d, J=8.5 Hz), 7.84 (1H, d, J=8.5 Hz), 7.96 (1H, d, J=8.5 Hz), 8.04 (1H, dd, J=8.5, 1.2 Hz), 8.86 (1H, s), 9.22 (1H, brs).

[Step 3] Ethyl 3-{[5-tert-butyl-3-(2,4,6-trichlorophenyl)-1,2-oxazol-4-yl]carbonyl}-1H-benzo[g]indole-8-carboxylate To a solution of the compound (382 mg) obtained in Reference Example X-5 in toluene (3.84 ml), N,N-dimethylformamide (14 μl) and thionyl chloride (0.4 ml) were added, and the mixture was stirred at 100° C. for 2 hours. The reaction solution was concentrated under reduced pressure, and the residue obtained was dissolved in dichloromethane (6.58 ml). To the solution, aluminum chloride (219 mg) was added, and the mixture was stirred at room temperature for 20 minutes.

To a solution of the compound (262 mg) obtained in the preceding step 2 in dichloromethane (6.56 ml), the preceding reaction solution was added, and the mixture was stirred at room temperature for 1.5 hours. The reaction solution was poured into ice, followed by extraction with dichloromethane. The extract was dried over anhydrous magnesium sulfate. The solvent was distilled off under reduced pressure, and the residue obtained was purified by silica gel column chromatography (n-hexane/ethyl acetate) to obtain the title compound (61.1 mg).

$^1$H-NMR (CDCl$_3$) δ: 1.41-1.52 (12H, m), 4.46 (2H, q, J=7.1 Hz), 7.69 (1H, d, J=3.0 Hz), 7.73 (1H, d, J=9.1 Hz), 7.99 (1H, d, J=8.5 Hz), 8.10 (1H, d, J=8.5 Hz), 8.50 (1H, d, J=8.5 Hz), 8.79 (1H, s), 9.48 (1H, brs).

[Step 4] Ethyl 3-{[5-tert-butyl-3-(2,4,6-trichlorophenyl)-1,2-oxazol-4-yl]carbonyl}-1-methyl-1H-benzo[g]indole-8-carboxylate The title compound (46 mg) was obtained by the same method as in step 3 of Example 164 using the compound (61.1 mg) obtained in the preceding step 3.

$^1$H-NMR (CDCl$_3$) δ: 1.39-1.52 (0H, m), 4.31 (3H, s), 4.46 (2H, q, J=7.1 Hz), 7.51 (1H, s), 7.73 (1H, d, J=8.5 Hz), 8.01 (1H, d, J=8.5 Hz), 8.09 (1H, t, J=4.2 Hz), 8.55 (1H, d, J=9.1 Hz), 9.17 (1H, s).

[Step 5] 3-{[5-tert-Butyl-3-(2,4,6-trichlorophenyl)-1,2-oxazol-4-yl]carbonyl}-1-methyl-1H-benzo[g]indole-8-carboxylic acid To a mixed solution of the compound (46 mg) obtained in the preceding step 4 in tetrahydrofuran (0.48 ml) and methanol (0.48 ml), an aqueous solution (0.48 ml) of lithium hydroxide (13.4 mg) was added under ice cooling, and the mixture was stirred at 60° C. for 3 hours. The reaction solution was rendered acidic by the addition of 1 N hydrochloric acid under ice cooling, and then, the mixture was concentrated under reduced pressure. The residue obtained was subjected to extraction with ethyl acetate. The extract was dried over anhydrous magnesium sulfate. The solvent was distilled off under reduced pressure, and the residue obtained was purified by silica gel column chromatography (dichloromethane/methanol) to obtain the title compound (37 mg).

$^1$H-NMR (CDCl$_3$) δ: 4.33 (3H, s), 7.27 (1H, s), 7.53 (1H, s), 7.75 (1H, d, J=8.5 Hz), 8.06 (1H, d, J=8.5 Hz), 8.15 (1H, d, J=8.5 Hz), 8.59 (1H, d, J=8.5 Hz), 9.26 (1H, s).

Example 168

(2E)-3-(1-{[5-(2-Fluoropropan-2-yl)-3-(2,4,6-trichlorophenyl)-1,2-oxazol-4-yl]carbonyl}-3-methyl-1H-indol-4-yl)prop-2-enoic acid tert-butylamine salt

[Formula 91]

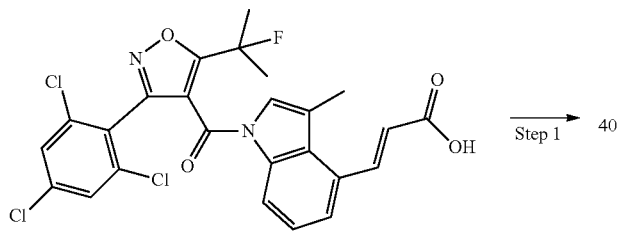

Step 1

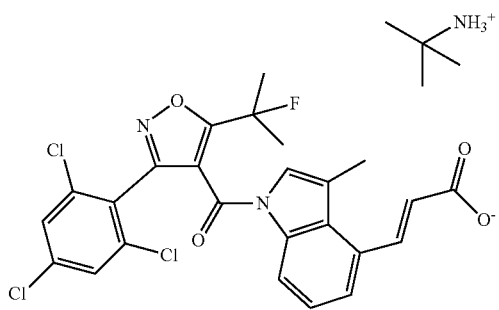

[Step 1] (2E)-3-(1-{[5-(2-Fluoropropan-2-yl)-3-(2,4,6-trichlorophenyl)-1,2-oxazol-4-yl]carbonyl}-3-methyl-1H-indol-4-yl)prop-2-enoic acid tert-butylamine salt To a suspension of the compound (15 g) obtained in step 2 of Example 21 in 2-propanol (150 ml), a solution of tert-butylamine (2.94 ml) in tetrahydrofuran (15 ml) was added under ice cooling, and the mixture was stirred overnight at room temperature. The suspension was filtered, and the solid obtained was dried overnight at 50° C. under reduced pressure to obtain the title compound (15.4 g).

$^1$H-NMR (DMSO-d$_6$) δ: 1.20 (9H, s), 1.83 (6H, d, J=22.4 Hz), 2.35 (3H, s), 6.39 (1H, d, J=15.7 Hz), 7.30 (1H, t, J=7.9 Hz), 7.34 (1H, s), 7.54 (1H, d, J=7.9 Hz), 7.85 (2H, s), 7.93 (1H, d, J=15.7 Hz), 8.17 (1H, d, J=8.5 Hz).

Anal. Calcd for $C_{25}H_{17}Cl_3FN_2O_4 \times C_4H_{12}N$: C, 57.20; H, 4.80; Cl, 17.46; F, 3.12; N, 6.90. Found: C, 57.01; H, 4.93; Cl, 17.65; F, 3.09; N, 6.89.

The following compounds were obtained by the same method as in Example 168.

TABLE 88

| Example No. | Name and structure | Instrumental data |
| --- | --- | --- |
| 169 | (2E)-3-(1-{[3-(2,4-Dichloro-6-fluorophenyl)-5-(2-fluoropropan-2-yl)-1,2-oxazol-4-yl]carbonyl}-3-methyl-1H-indol-4-yl)prop-2-enoic acid tert-butylamine salt | $^1$H-NMR(DMSO-d$_6$)δ: 1.19(9H, s), 1.83(6H, d, J = 23.0 Hz), 2.34(3H, s), 6.40(1H, d, J = 15.7 Hz), 7.31(1H, t, J = 8.2 Hz), 7.37(1H, s), 7.56 (1H, d, J = 7.3 Hz), 7.69-7.72(2H, m), 7.95(1H, d, J = 15.7 Hz), 8.16 (1H, d, J = 8.5 Hz). Anal. Calcd for $C_{25}H_{17}Cl_2F_2N_2O_4 \cdot C_4H_{12}N \cdot 0.25H_2O$: C, 58.35; H, 4.98; Cl, 11.88; F, 6.36; N, 7.04. Found: C, 58.27; H, 5.13; Cl, 11.98; F, 6.45; N, 6.93. |

TABLE 88-continued

| Example No. | Name and structure | Instrumental data |
|---|---|---|
| 170 | (2E)-3-(1-{[3-(4-Chloro-2,6-difluorophenyl)-5-(2-fluoropropan-2-yl)-1,2-oxazol-4-yl]carbonyl}-3-methyl-1H-indol-4-yl)prop-2-enoic acid tert-butylamine salt<br>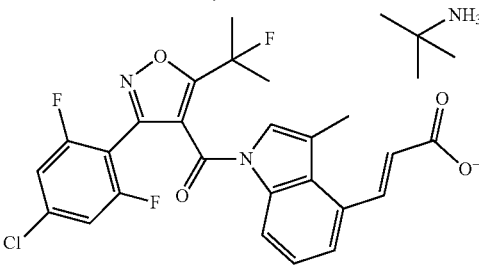 | $^1$H-NMR(DMSO-d$_6$)δ: 1.21(9H, s), 1.72-1.89(6H, m), 6.42(1H, d, J = 15.7 Hz), 7.32(1H, t, J = 7.9 Hz), 7.48(1H, s), 7.56-7.60(3H, m), 7.97(1H, d, J = 15.7 Hz), 8.18(1H, d, J = 7.9 Hz).<br>Anal. Calcd for C$_{25}$H$_{17}$ClF$_3$N$_2$O$_4$·C$_4$H$_{12}$N·0.25H$_2$O:<br>C, 60.00; H, 5.12; Cl, 6.11; F, 9.82; N, 7.24.<br>Found:<br>C, 59.90; H, 4.96; Cl, 6.17; F, 9.72; N, 6.94. |

TABLE 89

| | | |
|---|---|---|
| 171 | (2E)-3-(1-{[3-(4-Chloro-2,6-dimethylphenyl)-5-(2-fluoropropan-2-yl)-1,2-oxazol-4-yl]carbonyl}-3-methyl-1H-indol-4-yl)prop-2-enoic acid tert-butylamine salt<br>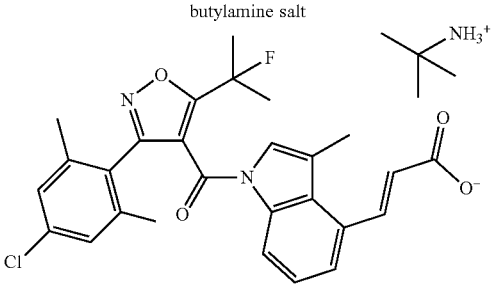 | $^1$H-NMR(DMSO-d$_6$)δ: 1.19(9H, s), 1.81(6H, d, J = 22.4 Hz), 2.15(6H, s), 2.36(3H, s), 6.38(1H, d, J = 15.1 Hz), 7.21(2H, brs), 7.28(1H, t, J = 8.2 Hz), 7.48(1H, s), 7.54(1H, d, J = 7.9 Hz), 7.95(1H, d, J = 15.7 Hz), 8.17(1H, d, J = 8.5 Hz).<br>Anal. Calcd for C$_{27}$H$_{23}$ClF$_2$N$_2$O$_4$·C$_4$H$_{12}$N:<br>C, 65.54; H, 6.21; Cl, 6.24; F, 3.34; N, 7.40.<br>Found:<br>C, 65.50; H, 6.22; Cl, 6.17; F, 3.31; N, 7.41. |
| 172 | (2E)-3-(1-{[3-(2,4-Dichloro-6-methylphenyl)-5-(2-fluoropropan-2-yl)-1,2-oxazol-4-yl]carbonyl}-3-methyl-1H-indol-4-yl)prop-2-enoic acid tert-butylamine salt<br>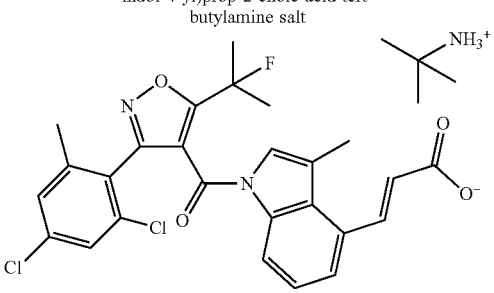 | $^1$H-NMR(DMSO-d$_6$)δ: 1.18(9H, s), 1.83(6H, d, J = 21.2 Hz), 2.25(3H, s), 2.35(3H, s), 6.38(1H, d, J = 15.7 Hz), 7.29(1H, t, J = 7.9 Hz), 7.39(1H, s), 7.45-7.57(3H, m), 7.94(1H, d, J = 15.1 Hz), 8.17(1H, d, J = 7.9 Hz).<br>Anal. Calcd for C$_{26}$H$_{20}$Cl$_2$FN$_2$O$_4$·C$_4$H$_{12}$N:<br>C, 61.22; H, 5.48; Cl, 12.05; F, 3.23; N, 7.14.<br>Found:<br>C, 60.94; H, 5.42; Cl, 11.97; F, 3.20; N, 7.15. |
| 173 | (2E)-3-(1-{[3-(2,4-Dichlorophenyl)-5-(2-fluoropropan-2-yl)-1,2-oxazol-4-yl]carbonyl}-3-methyl-1H-indol-4-yl)prop-2-enoic acid tert-butylamine salt<br>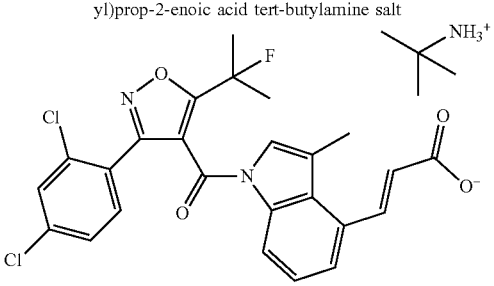 | $^1$H-NMR(DMSO-d$_6$)δ: 1.20(9H, s), 1.82(6H, d, J = 21.8 Hz), 2.30(3H, s), 6.39(1H, d, J = 15.7 Hz), 7.30(1H, t, J = 8.2 Hz), 7.44(1H, s),7.53-7.57 (2H, m), 7.64(1H, d, J = 8.5 Hz), 7.72(1H, d, J = 1.8 Hz), 7.93(1H, d, J = 15.7 Hz), 8.18(1H, d, J = 7.9 Hz).<br>Anal. Calcd for C$_{25}$H$_{18}$Cl$_2$F$_2$N$_2$O$_4$·C$_4$H$_{12}$N:<br>C, 60.63; H, 5.26; Cl, 12.34; F, 3.31; N, 7.31.<br>Found:<br>C, 60.37; H, 5.26; Cl, 12.18; F, 3.26; N, 7.32. |

Example 174

(2E)-[1-{[5-(1-Acryloylpiperidin-4-yl)-3-(2,4,6-trichlorophenyl)-1,2-oxazol-4-yl]carbonyl}-3,4-dihydrobenzo[cd]indol-5(1H)-ylidene]ethanoic acid sodium salt

[Example 175] (2E)-[1-{[5-(1-Acryloylpiperidin-4-yl)-3-(2,4,6-trichlorophenyl)-1,2-oxazol-4-yl]carbonyl}-3,4-dihydrobenzo[cd]indol-5(1H)-ylidene]ethanoic acid tert-butylamine salt

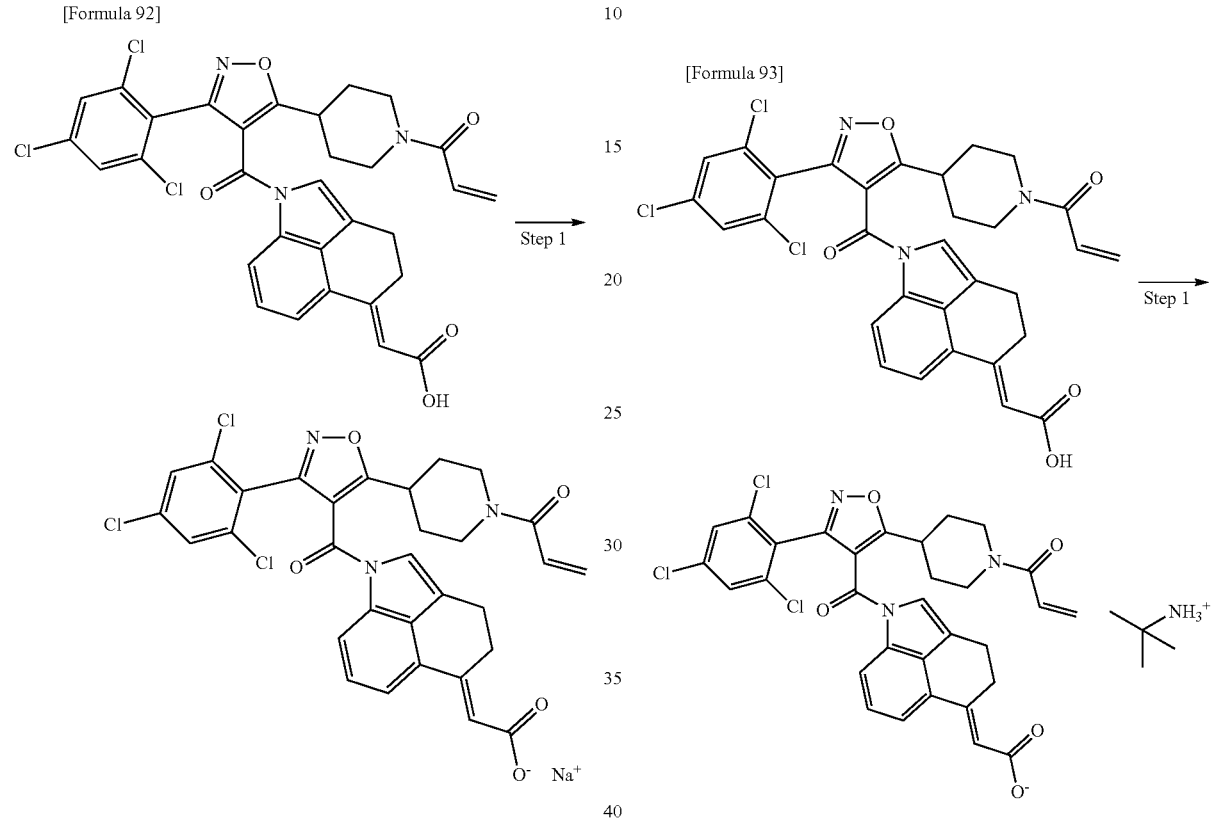

[Formula 92]

[Formula 93]

[Step 1] (2E)-[1-{[5-(1-Acryloylpiperidin-4-yl)-3-(2,4,6-trichlorophenyl)-1,2-oxazol-4-yl]carbonyl}-3,4-dihydrobenzo[cd]indol-5(1H)-ylidene]ethanoic acid sodium salt To a suspension of the compound (1.28 g) obtained in step 5 of Example 94 in tetrahydrofuran (10 ml), a 1 N ethanolic sodium hydroxide solution (1.8 ml) was added, and the mixture was stirred. After confirmation of dissolution, the solvent was distilled off under reduced pressure, and the residue was dried. After addition of ethanol (10 ml) thereto, the solvent was distilled off again under reduced pressure, and the residue was dried. Ethanol (10 ml) was added thereto, and the mixture was stirred overnight at 40° C. Ethyl acetate (20 ml) was added thereto, and the mixture was stirred at room temperature for 1 hour. Then, the solid was collected by filtration and washed with ethyl acetate. The solid obtained was dried in air overnight to obtain the title compound (1.02 g).

$^1$H-NMR (DMSO-$d_6$) δ: 1.63-1.80 (2H, m), 2.03-2.11 (2H, m), 2.60-2.64 (2H, m), 2.71-2.80 (1H, m), 3.11-3.19 (3H, m), 3.42-3.52 (1H, m), 4.09-4.16 (1H, m), 4.44-4.51 (1H, m), 5.67 (1H, dd, J=10.3, 2.4 Hz), 6.10 (1H, dd, J=16.4, 2.4 Hz), 6.38 (1H, s), 6.82 (1H, dd, J=16.4, 10.3 Hz), 7.00 (1H, s), 7.28 (1H, t, J=7.9 Hz), 7.36 (1H, d, J=7.9 Hz), 7.82 (1H, s), 7.84 (1H, d, J=7.9 Hz).

Anal. Calcd for $C_{31}H_{23}Cl_3N_3O_5 \times Na$: C, 57.56; H, 3.58; Cl, 16.44; N, 6.50; Na, 3.55. Found: C, 56.69; H, 3.79; Cl, 16.13; N, 6.28; Na, 3.53.

[Step 1] (2E)-[1-{[5-(1-Acryloylpiperidin-4-yl)-3-(2,4,6-trichlorophenyl)-1,2-oxazol-4-yl]carbonyl}-3,4-dihydrobenzo[cd]indol-5(1H)-ylidene]ethanoic acid tert-butylamine salt To the compound (0.64 g) obtained in step 5 of Example 94, a 1 mol/L solution of tert-butylamine in tetrahydrofuran (1.05 ml) was added, and the compound was dissolved by heating. Ethyl acetate (10 ml) was added thereto, and the mixture was left at room temperature for 3 days with light shielded. The solvent was concentrated under reduced pressure, and the residue was dried. Then, the solid was suspended by the addition of ethyl acetate. The solid was collected by filtration and washed with ethyl acetate. The solid obtained was dried in air to obtain the title compound.

$^1$H-NMR (DMSO-$d_6$) δ: 1.21 (9H, s), 1.68-1.77 (2H, m), 2.03-2.10 (2H, m), 2.67 (2H, t, J=6.7 Hz), 2.71-2.79 (1H, m), 3.11-3.22 (3H, m), 3.42-3.51 (1H, m), 4.13 (1H, d, J=13.4 Hz), 4.47 (1H, d, J=13.4 Hz), 5.67 (1H, dd, J=10.6, 2.1 Hz), 6.10 (1H, d, J=16.4, 2.4 Hz), 6.44 (1H, s), 6.81 (1H, dd, J=17.0, 10.3 Hz), 7.05 (1H, s), 7.30 (1H, t, J=7.9 Hz), 7.45 (1H, d, J=7.3 Hz), 7.81 (2H, s), 7.89 (1H, d, J=7.9 Hz).

Anal. Calcd for $C_{31}H_{23}Cl_3N_3O_5 \times C_4H_{11}N$: C, 60.22; H, 5.05; Cl, 15.24; N, 8.03. Found: C, 59.61; H, 5.05; Cl, 15.29; N, 7.89.

Test Example 1

Evaluation of Inhibitory Activity Against IDH1R132H and IDH1R132C Enzymes

The IDH1R132H protein and the IDH1R132C protein were prepared as follows: the IDH1R132H or IDH1R132C gene was integrated into a pET24b(+) vector (Novagen) to prepare a construct for C-terminal fusion of 6× histidine tag. After transformation of Rosetta 2 (DE3) *E. coli*, the expression of the protein was induced with IPTG. The *E. coli* was collected and homogenized, followed by the affinity purification of the 6× histidine fusion protein using HisTrap HP columns (GE Healthcare Japan Corp.) and gel filtration purification using Superdex 200 columns (GE Healthcare Japan Corp.) to obtain the IDH1R132H or IDH1R132C protein of interest.

IDH1R132H and IDH1R132C each convert 2-oxoglutarate and NADPH to D-2-hydroxyglutarate (2-HG) and NADP+. Therefore, the activity of the IDH1R132H and IDH1R132C enzymes can be measured by detecting NADPH levels.

The enzyme inhibitory activity evaluation was carried out as follows: 40 μL each of reaction solutions containing different concentrations of each compound (100 mM Tris-HCl (pH 7.5), 150 mM NaCl, 20 mM MgCl$_2$, 0.5 mg/mL bovine serum albumin, 1 mM reduced glutathione, 40 μM NADPH, 0.5 mM 2-oxoglutarate, 0.5% dimethyl sulfoxide, 50000 to 0.128 nM compound, and 12 nM IDH1R132H or 10 nM IDH1R132C as the enzyme) was added to each well of 384-well plates (Greiner Bio One International GmbH, #781096) and incubated at room temperature. While NADPH-derived fluorescence was occasionally monitored, the reaction was terminated by the addition of 5 μL of 0.5 M EDTA before consumption of NADPH. 5 μL of WST-8 reagent (Dojindo Laboratories, #CK04) was further added and mixed therewith. 15 minutes later, the absorbance at 450 nm was measured using a plate reader (PerkinElmer, Inc., EnVision). The observed absorbance value reflects the amount of residual NADPH. From the absorbance data, the enzyme inhibitory activity of each compound at each concentration was calculated and analyzed using medical statistical analysis software GraphPad Prism to calculate an IC50 value.

The results are shown in Tables 90 to 93.

TABLE 90

| Example No. | Test Example 1 IDH1 R132H IC50 (nM) | Test Example 1 IDH1 R132C IC50 (nM) | Test Example 2 IC50 (nM) | Test Example 3 IC50 (nM) | Test Example 4 IC50 (nM) | Test Example 5 Ratio (%) |
|---|---|---|---|---|---|---|
| 1 | 10 | 56 | 33 | 33 | 79 | 21 |
| 2 | 7 | 47 | 21 | 18 | 24 | 18 |
| 3 | 7 | 64 |  | 60 |  | 42 |
| 4 | 8 | 56 | 14 | 27 | 25 | 15 |
| 5 | 11 | 62 |  | 42 |  |  |
| 6 | 17 | 151 |  | 459 |  |  |
| 7 | 11 | 152 |  | 787 |  |  |
| 8 | 8 | 55 | 21 | 22 | 68 | 67 |
| 9 | 28 | 107 |  | 1271 |  |  |
| 10 | 18 | 179 | 73 | 50 | 152 | 27 |
| 11 | 13 | 112 | >400 | 345 | >900 | 57 |
| 12 | 16 | 144 | 31 | 24 | 60 | 7 |
| 13 | 18 | 148 | 55 | 51 | 151 | 28 |
| 14 | 14 | 110 |  | 32 |  |  |
| 15 | 12 | 106 |  | 37 |  |  |
| 16 | 15 | 107 | 73 | 89 | 143 | 32 |
| 17 | 24 | 201 |  | 242 |  |  |
| 18 | 19 | 162 | 121 | 136 | 447 | 56 |
| 19 | 16 | 169 | 96 | 64 | 65 | 79 |
| 20 | 27 | 267 |  | 435 |  |  |
| 21 | 12 | 95 | 49 | 56 | 58 | 14 |
| 22 | 31 | 189 | 110 | 109 | 159 | 13 |
| 23 | 6 | 75 |  | 709 |  |  |
| 24 | 30 | 182 |  | 255 |  |  |
| 25 | 30 | 326 |  | 248 |  |  |
| 26 | 38 | 253 |  | 248 |  |  |
| 27 | 11 | 160 |  | 128 |  |  |
| 28 | 8 | 90 |  | 401 |  |  |
| 29 | 14 | 102 |  | 94 |  | 39 |
| 30 | 12 | 114 |  | 350 |  |  |
| 31 | 7 | 57 |  | 24 |  |  |
| 32 | 43 | 176 |  | 413 |  |  |
| 33 | 20 | 193 | 32 | 43 | 30 | 15 |
| 34 | 53 | 364 |  | 209 |  | 55 |
| 35 | 31 | 161 |  | 244 |  | 64 |
| 36 | 13 | 109 | 137 | 170 | 191 | 43 |
| 37 | 13 | 117 |  | 149 |  | 35 |
| 38 | 34 | 234 |  | 200 |  | 61 |
| 39 | 12 | 168 |  | 389 |  |  |
| 40 | 21 | 159 | 39 | 57 | 62 | 18 |
| 41 | 52 | 280 | 230 | 254 | 320 |  |
| 42 | 50 | 217 |  | 178 |  | 84 |
| 43 | 18 | 139 | 49 | 63 | 72 | 54 |
| 44 | 22 | 189 | 177 | 194 | 257 | 72 |
| 45 | 13 | 114 | 42 | 60 | 78 |  |
| 46 | 28 | 197 | 294 | 459 | 657 | 69 |

TABLE 90-continued

| | Test Example 1 | | Test Example 2 | Test Example 3 | Test Example 4 | Test Example 5 |
|---|---|---|---|---|---|---|
| Example No. | IDH1 R132H IC50 (nM) | IDH1 R132C IC50 (nM) | IC50 (nM) | IC50 (nM) | IC50 (nM) | Ratio (%) |
| 47 | 13 | 98 | 33 | 62 | 42 | 17 |
| 48 | 29 | 193 | 134 | 115 | 216 | 72 |
| 49 | 9 | 79 | 89 | 119 | 51 | 44 |
| 50 | 11 | 104 | 127 | 173 | 175 | 84 |
| 51 | 15 | 115 | 165 | 83 | 271 | 52 |
| 52 | 17 | 136 | | 263 | | 71 |
| 53 | 17 | 163 | | 146 | | 60 |
| 54 | 17 | 109 | 168 | 90 | 172 | 16 |

TABLE 91

| | Test Example 1 | | Test Example 2 | Test Example 3 | Test Example 4 | Test Example 5 |
|---|---|---|---|---|---|---|
| Example No. | IDH1 R132H IC50 (nM) | IDH1 R132C IC50 (nM) | IC50 (nM) | IC50 (nM) | IC50 (nM) | Ratio (%) |
| 55 | 14 | 125 | 96 | 62 | 130 | 15 |
| 56 | 15 | 107 | | 52 | | 28 |
| 57 | 10 | 98 | 37 | 26 | 61 | 12 |
| 58 | 27 | 178 | | 295 | | |
| 59 | 15 | 117 | 52 | 56 | 66 | 10 |
| 60 | 18 | 116 | 126 | 92 | 299 | 9 |
| 61 | 36 | 300 | | 337 | | 63 |
| 62 | 20 | 155 | 165 | 69 | 178 | 10 |
| 63 | 15 | 145 | 184 | 193 | 290 | 31 |
| 64 | 252 | 888 | | > 2000 | | |
| 65 | 22 | 198 | 68 | 93 | 263 | 65 |
| 66 | 14 | 122 | | 59 | | 49 |
| 67 | 17 | 154 | 68 | 95 | 250 | 27 |
| 68 | 15 | 125 | 33 | 32 | 30 | 47 |
| 69 | 18 | 168 | 181 | 197 | 534 | 20 |
| 70 | 16 | 153 | 91 | 71 | 175 | 41 |
| 71 | 81 | 646 | | | | |
| 72 | 25 | 201 | 52 | 59 | 77 | 46 |
| 73 | 43 | 208 | 14 | 7 | 15 | |
| 74 | 20 | 175 | | 118 | | 20 |
| 75 | 11 | 118 | | 138 | | |
| 76 | 6 | 94 | | 118 | | |
| 77 | 8 | 94 | | 428 | | |
| 78 | 33 | 192 | 204 | 281 | 518 | 50 |
| 79 | 21 | 161 | 26 | 35 | 26 | 15 |
| 80 | 49 | 335 | 147 | 99 | 144 | |
| 81 | 26 | 163 | 24 | 31 | 30 | 15 |
| 82 | 13 | 96 | | 10 | | |
| 83 | 11 | 87 | 43 | 33 | 168 | 23 |
| 84 | 15 | 80 | | 15 | | |
| 85 | 14 | 99 | | 9.0 | | |
| 86 | 8 | 79 | | 33 | | |
| 87 | 34 | 145 | | 71 | | 68 |
| 88 | 23 | 158 | 70 | 61 | 190 | |
| 89 | 50 | 185 | | 37 | | |
| 90 | 7 | 59 | 65 | 36 | 372 | |
| 91 | 21 | 120 | | 23 | | |
| 92 | 10 | 80 | | 9 | | |
| 93 | 12 | 85 | 51.0 | 42 | 87 | 119 |
| 94 | 24 | 159 | 32 | 3 | 262 | 1 |
| 95 | 6 | 67 | | 89 | | 44 |
| 96 | 149 | 422 | | 290 | | |
| 97 | 19 | 164 | | 162 | | |
| 98 | 19 | 116 | | 34 | | |
| 99 | 142 | 272 | 167 | 34 | 287 | 15 |
| 100 | 37 | 189 | 41 | 28 | 36 | 75 |
| 101 | 16 | 189 | | 32 | | |
| 102 | 53 | 117 | > 400 | 50 | > 900 | |
| 103 | 25 | 114 | | 506 | | 90 |
| 104 | 32 | 93 | 45 | 7 | 129 | 8 |
| 105 | 519 | 567 | | 32 | | 27 |
| 106 | 64 | 149 | 143 | 23 | 192 | 12 |
| 107 | 66 | 169 | 94 | 11 | 137 | 18 |
| 108 | 35 | 149 | > 400 | 38 | > 900 | 58 |

TABLE 92

| Example No. | Test Example 1 IDH1 R132H IC50 (nM) | Test Example 1 IDH1 R132C IC50 (nM) | Test Example 2 IC50 (nM) | | Test Example 3 IC50 (nM) | | Test Example 4 IC50 (nM) | Test Example 5 Ratio (%) |
|---|---|---|---|---|---|---|---|---|
| 109 | 127 | 243 | | | 45 | | | 23 |
| 110 | 158 | 316 | | | 48 | | | 52 |
| 111 | 69 | 188 | | | 10 | | | |
| 112 | 31 | 115 | 196 | | 12 | > | 900 | 15 |
| 113 | 27 | 104 | 40 | | 2 | | 245 | 13 |
| 114 | 21 | 81 | 34 | | 3 | | 35 | 12 |
| 115 | 147 | 301 | | | 32 | | | 12 |
| 116 | 440 | 471 | | | 42 | | | 57 |
| 117 | 23 | 117 | 32 | | 2 | | 75 | 10 |
| 118 | 509 | 625 | | | 97 | | | 87 |
| 119 | 73 | 190 | | | 30 | | | 12 |
| 120 | 119 | 357 | | | 51 | | | 31 |
| 121 | 43 | 110 | 74 | | 8 | > | 900 | 8 |
| 122 | 32 | 94 | 43 | | 6 | | 141 | 29 |
| 123 | 28 | 149 | 24 | | 13 | > | 900 | |
| 124 | 61 | 125 | 161 | | 22 | > | 900 | |
| 125 | 355 | 454 | | | 78 | | | 72 |
| 126 | 37 | 149 | | | 8 | | | |
| 127 | 46 | 139 | 51 | | 6 | | 133 | 1 |
| 128 | 38 | 91 | 40 | | 3 | > | 900 | 1 |
| 129 | 85 | 182 | 214 | | 10.0 | | 245 | |
| 130 | 60 | 143 | 150 | | 14 | > | 900 | 5 |
| 131 | 62 | 133 | 62 | | 4 | | 272 | 3 |
| 132 | 162 | 279 | | | 28 | | | |
| 133 | 10 | 93 | | | 390 | | | |
| 134 | 31 | 143 | | | 347 | | | |
| 135 | 14 | 122 | | | 376 | | | |
| 136 | 27 | 140 | | | 335 | | | |
| 137 | 28 | 189 | | | 299 | | | |
| 138 | 12 | 88 | | | 288 | | | |
| 139 | 183 | 373 | | | 339 | | | |
| 140 | 256 | 1038 | | | 0 | | | |
| 141 | 160 | 137 | > | 2000 | 190 | > | 900 | 36 |
| 142 | 83 | 123 | | | 134 | | | 56 |
| 143 | 116 | 150 | | | 148 | | | 60 |
| 144 | 71 | 151 | | | 107 | | | 34 |
| 145 | 80 | 214 | | | 820 | | | 56 |
| 146 | 176 | 144 | | | 104 | | | 38 |
| 147 | 20 | 78 | > | 400 | 219 | > | 900 | 18 |
| 148 | 167 | 225 | | | 114 | | | 50 |
| 149 | 16 | 132 | | | 278 | | | 96 |
| 150 | 26 | 98 | 214 | | 41 | > | 900 | 18 |
| 151 | 98 | 168 | | | 41 | | | 60 |
| 152 | 144 | 222 | | | 276 | | | 87 |
| 153 | 88 | 130 | | | 166 | | | |
| 154 | 299 | 235 | | | 294 | | | 45 |
| 155 | 20 | 122 | 245 | | 55 | > | 900 | 41 |
| 156 | 41 | 167 | | | 167 | | | 60 |
| 157 | 314 | 256 | | | 265 | | | 89 |
| 158 | 64 | 179 | | | 178 | | | 62 |
| 159 | 11 | 84 | > | 400 | 138 | > | 900 | 30 |
| 160 | 26 | 81 | > | 400 | 106 | > | 900 | 47 |
| 161 | 35 | 98 | | | 121 | | | 72 |
| 162 | 20 | 95 | > | 400 | 253 | > | 900 | |

TABLE 93

| Example No. | Test Example 1 IDH1 R132H IC50 (nM) | Test Example 1 IDH1 R132C IC50 (nM) | Test Example 2 IC50 (nM) | | Test Example 3 IC50 (nM) | | Test Example 4 IC50 (nM) | Test Example 5 Ratio (%) |
|---|---|---|---|---|---|---|---|---|
| 163 | 16 | 98 | 206 | | 45 | | 498 | 33 |
| 164 | 11 | 95 | 255 | | 330 | | 674 | 89 |
| 165 | 10 | 81 | 127 | | 186 | | 211 | |
| 166 | 54 | 141 | > | 400 | 299 | > | 900 | 81 |
| 167 | 37 | 196 | | | 195 | | | 87 |
| 168 | | | | | | | | 13 |
| 169 | | | | | | | | 17 |
| 170 | | | | | | | | 35 |

TABLE 93-continued

| Example No. | Test Example 1 IDH1 R132H IC50 (nM) | Test Example 1 IDH1 R132C IC50 (nM) | Test Example 2 IC50 (nM) | Test Example 3 IC50 (nM) | Test Example 4 IC50 (nM) | Test Example 5 Ratio (%) |
|---|---|---|---|---|---|---|
| 171 | | | | | | 22 |
| 172 | | | | | | 8 |
| 173 | | | | | | 2 |

Test Example 2

Evaluation of Inhibitory Activity of 2-HG (2-hydroxyglutarate) Production Using IDH1R132H-Expressing TF-1 Cells A human erythroleukemia cell line TF-1 (American Type Culture Collection) was cultured in an RPMI medium (Life Technologies Corp., #11875-093) containing 10% (final concentration) fetal bovine serum (Hyclone, #SH30070.03) and 2 ng/mL human recombinant GM-CSF (granulocyte macrophage colony-stimulating factor) (R&D Systems, Inc., #215-GM-050) (hereinafter, referred to as growth medium A). A TF-1 cell line harboring IDH1R132H was prepared as follows: DNA encoding an IDH1R132H mutant of human IDH1 was cloned into a retroviral vector pMSCVpuro (Clontech Laboratories, Inc., #634-401). PT67 cells (Clontech Laboratories, Inc., #634-401) were transfected with the constructed vector pMSCVpuro-IDH1R132H by use of the lipofection method (Invitrogen Corp., #15338-100) so that viruses were produced and secreted into the supernatant. The virus-containing culture supernatant was centrifuged at 2000 rpm for 20 minutes, and the obtained centrifugation supernatant was used as a virus solution. 1200000 TF-1 cells were suspended in 6 mL of growth medium A and plated on a 10-cm plate (IWAKI, #3020-100). 4 mL of the virus solution mixed with Polybrene (Sigma-Aldrich Corp.) at a final concentration of 4 μg/mL was added thereto. After the viral infection, IDH1R132H-expressing cells were selected in growth medium A containing 2 μg/mL (final concentration) puromycin (Invitrogen Corp., #ant-pr) and subsequently cloned by the limiting dilution method to establish an IDH1R132H-expressing TF-1 cell line TF-1/IDH1R132H.

40000 cells/190 μL of TF-1/IDH1R132H cells in growth medium A were inoculated at 190 μL/well to a 96-well plate (IWAKI, #3860-096). Then, 10 μL of a solution of each compound diluted to a predetermined concentration with growth medium A was added to each well, and the cells were incubated at 37° C. for 2 days under 5% CO2. After the incubation, 100 μL of the culture supernatant was transferred from each well to a 96-well round-bottom plate (Corning Inc., #3799). The plate was centrifuged at 2000 rpm for 3 minutes, and then, 50 μL of the supernatant in each well was dispensed to each 1.5-mL tube (Sarstedt K. K., #72.690.001S). 200 μL of ethanol (Wako Pure Chemical Industries, Ltd., #057-00456) was added to each tube, and the tube was stirred for 30 seconds using a vortex mixer (Pasolina, #NS-8) and then incubated at −80° C. for 1 hour. Then, 150 μL of ultrapure water was further added to each tube, and the tube was stirred for 30 seconds using a vortex mixer and stored at −20° C. The preserved solutions were thawed at room temperature, then diluted with an internal standard (3-hydroxyglutarate (3-HG)) solution, and prepared into samples for concentration measurement by solid-phase extraction (Oasis MAX μElution (Waters Corp.)). 10 μL each of the samples was injected to UPLC (Waters Corp.). 50% methanol containing 0.5% formic acid was used as a mobile phase (flow rate: 0.6 mL/min), and the analyte was separated using an analytical column (Hypercarb (2.0×150 mm, particle size: 5 μm, Thermo Fisher Scientific Inc.)) kept at 40° C., and then introduced to a mass spectrometry apparatus (Xevo TQ MS (Waters Corp.). Product ions with a mass-to-charge ratio of 129 (retention time: 1.0 min) generated from anions (mass-to-charge ratio: 147) derived from 2-HG ionized by the electrospray ionization method were observed, and 2-HG concentrations in the solutions were calculated from the calibration curve prepared from the 2-HG standard solution. The concentration at which each compound inhibited 50% of 2-HG production (IC50 value) was calculated by a single logarithmic plot of compound concentrations vs. a relative 2-HG concentration at each concentration (% with respect to the 2-HG concentration in cells without the addition of the compound).

The results are shown above in Tables 90 to 93.

Test Example 3

2-HG Production Inhibitory Activity Evaluation Using HT1080 Cell

A human fibrosarcoma cell line HT-1080 (American Type Culture Collection), which expresses an IDH1R132C mutant of IDH1 was cultured in an RPMI medium (Life Technologies Corp., #11875-093) containing 10% (final concentration) fetal bovine serum (Hyclone, #SH30070.03 (hereinafter, referred to as growth medium B). 2000 cells/100 μL of HT-1080 cells in growth medium A were inoculated at 100 μL/well to a 96-well plate (IWAKI, #3860-096). After culture for 1 day, the culture supernatant was removed from each well. 100 μL of growth medium B was added to each well, and the added growth medium B was removed again. Then, 100 μL of growth medium B was added to each well, further 25 μL of a solution of each compound diluted to a predetermined concentration with growth medium B was added to each well, and the cells were incubated at 37° C. for 2 days under 5% CO2. After the incubation, 90 μL of the culture supernatant was transferred from each well to a 96-well round-bottom plate (Corning Inc., #3363). The plate was centrifuged at 2000 rpm at room temperature for 3 minutes, and then, 50 μL of the supernatant in each well was dispensed to each well of 96 Deep well plate (Porvair plc, #219009). The plate was stirred using 200 μL of methanol (Wako Pure Chemical Industries, Ltd., #131-01826) and pipetting and then incubated at −80° C. for 20 to 60 minutes. Then, 150 μL of ultrapure water was further added to each well, and the mixture was stirred by pipetting and stored at −20° C.

The preserved solutions were thawed at room temperature. Then, 2-HG concentrations in the solutions were calculated in the same way as in [Test Example 2]. The concentration at which each compound inhibited 50% of 2-HG production (IC50 value) was calculated by a single logarithmic plot of compound concentrations vs. a relative 2-HG concentration at each concentration (% with respect to the 2-HG concentration in cells without the addition of the compound).

The results are shown above in Tables 90 to 93.

Test Example 4

Evaluation of the Inhibitory Activity of TF-1/IDH1R132H Cell Growth 30 mL of a cell suspension of the TF-1/IDH1R132H cells cultured in growth medium A was dispensed to each 50-mL tube (IWAKI, #2345-050). The tube was centrifuged at 1200 rpm at room temperature for 5 minutes, and the supernatant was removed. The cells were suspended in 30 mL of growth medium B and centrifuged at 1200 rpm at room temperature for 5 minutes, and the supernatant was removed. This operation was further repeated twice. The obtained TF-1/IDH1R132H cells were adjusted to a cell density of 2000 cells/100 µL with growth medium B.

An RPMI medium containing 10% (final concentration) fetal bovine serum and 4.44 pg/mL human recombinant GM-CSF (hereinafter, referred to as growth medium C) was prepared. 90 µL of growth medium C was dispensed to each well of a 96-well plate (COSTAR, #3904). Subsequently, 10 µL of a solution of each compound diluted to a predetermined concentration with growth medium B was added to each well. 100 µL of the prepared TF-1/IDH1R132H cell suspension was further added to each well and incubated at 37° C. for 2 weeks under 5% $CO_2$. After the incubation, the cells were reacted using ATPlite 1 step Luminescence Assay System (PerkinElmer, Inc., #6016739) according to the attached manual. Then, the light emission of each well was measured using a plate reader (PerkinElmer, Inc., EnVision). From the light emissions of a compound addition group (T), a compound non-addition group (C), and a cell non-addition group (B), the cell viability was calculated according to the following expression:

Cell vialibity $\%=(T-B)/(C-B)\times100$

The concentration at which each compound produced 50% inhibition of growth of the TF-1/IDH1R132H cells (GI50 value) was calculated by a single logarithmic plot of compound concentrations vs. the cell viability at each concentration.

The results are shown above in Tables 90 to 93.

Test Example 5

2-HG Production Inhibitory Activity Evaluation Using HT1080 Xenografted Mice

A human fibrosarcoma cell line HT-1080 (American Type Culture Collection) expressing an IDH1R132C mutant of IDH1 was cultured in an RPMI medium (Life Technologies Corp. #11875-093) containing 10% (final concentration) fetal bovine serum (Hyclone #SH30070.03) and penicillin-streptomycin (Life Technologies Corp. #15070-063).

The HT1080 cells were adjusted to a cell density of $4\times10^7$ cells/mL with PBS (Life Technologies Corp., #14190-250) and subcutaneously transplanted at 100 µL/mouse to the right axillary regions of Balb/c nude mice (Charles River Laboratories Japan, Inc.). HT1080 xenografted mice having successfully engrafted tumors were given by oral gavage each compound at 75 mg/kg a total of three times twice a day. The compound was suspended in a vehicle solution at 7.5 mg/mL using a homogenizer. Then, the suspension was stored at −20° C., thawed immediately before the administration, and given to mice. A negative control group for the test was given a vehicle by oral gavage. The body weights of the mice were measured using an automatic balance for small animals. The dosing solution was administered at a dose of 10 mL/kg body weight.

6 hours after the final administration, each mouse was euthanized with carbon dioxide. A portion of a tumor was collected, and its weight was measured using an electronic balance. Then, the tumor was frozen on dry ice. To the frozen tumor, methanol was added in an amount of 14 times the tumor weight. The resulting tumor was homogenized with Beads shocker (Yasui Kikai Corp.) and then incubated for 15 minutes in a freezer at −20° C. After centrifugation at 15000 rpm at 4° C. for 15 minutes using a high-speed refrigerated microcentrifuge, 250 µL of methanol and 400 µL of ultrapure water were added to 150 µL of the obtained supernatant. The prepared samples were subjected to 2-HG measurement. 2-HG concentrations in the solutions were calculated in the same way as in [Test Example 2]. Then, from the 2-HG concentrations of a compound administration group (T) and a negative control group (C), the rate of inhibition of 2-HG production was calculated according to the following expression:

Rate of inhibition of 2-HG production $\%=T/C\times100$

The results are shown above in Tables 90 to 93.

Test Example 6

Establishment of AML Cell Harboring 4 Genes Including IDH1R132H, and Measurement of 2-HG Viruses for gene transduction were prepared as follows: first, vectors given below were prepared for retrovirus preparation. All of the genes used were mutant genes whose mutation is found at high frequency in acute myeloid leukemia (AML). pMy-NPMc-ires-EGFP was prepared by inserting mutant NPM1 gene (cytoplasmic nucleophosmin 1; hereinafter, referred to as NPMc) to the multicloning site of pMy-ires-EGFP vector (Cell Biolabs, Inc., San Diego, Calif., USA). pGCDN-IDH1/R132H-ires-NGFR was prepared by inserting IDH1/R132H mutated gene to the multicloning site of pGCDN-ires-NGFR vector (kindly provided by professor Shimon Sakaguchi, Kyoto University). pMSCV-DNMT3A (DNA methyltransferase 3A)/R882H was prepared by inserting DNMT3A/R882H mutant gene to pMSCVpuro vector (Takara Bio Inc.). pMSCV-FLT3/ITD was prepared by inserting FLT3/ITD mutated gene (FMS-like tyrosine kinase 3/internal tandem duplication) to pMSCVneo vector (Takara Bio Inc.).

PLAT-E cells (kindly provided by professor Toshio Kitamura, The Institute of Medical Science, The University of Tokyo) were transfected with each of these 4 types of retrovirus vectors (pMy-NPMc-ires-EGFP, pGCDN-IDH1/R132H-ires-NGFR, pMSCV-DNMT3A/R882H, and pMSCV-FLT3/ITD) using GeneJuice (Merck KGaA). 48 hours later, 10 ml each of retrovirus-containing culture supernatants was recovered. 3.3 ml of a PEG concentrate (30% PEG-8000, 0.4 M NaCl, and 40 mM HEPES [pH 7.4]) was added thereto, and the mixture was left standing overnight at 4° C. The samples were centrifuged (1500 rpm×45 minutes, 4° C.) to prepare pellets. 50 ng/ml SCF, 10 ng/ml IL-3, and 10 ng/ml OSM were added to Stempro-34 solution (Invitrogen Corp.) (hereinafter, referred to as Stempro medium). The virus pellets were suspended in 200 µl of Stempro medium, and 100 µl each of the suspensions was dispensed, quickly frozen in liquid nitrogen and stored in a freezer of −80° C.

Gene transduction and primary bone marrow transplantation were carried out as follows.

Bone marrow cells were recovered from the lower limb of an 8-week-old NPM$^{+/-}$ mouse (TaconicArtemis GmbH). After hemolysis treatment, c-Kit$^+$cells were recovered using CD117 MACS beads (Miltenyi Biotec K.K.). 100 µl of the concentrated viruses of pMy-NPMc-ires-EGFP was added to each well of a 24-well plate coated with RetroNectin (Takara Bio Inc.), and 4×10$^5$ c-Kit$^+$ cells suspended in 400 µl of Stempro medium were added to each well and cultured in an incubator. After half a day, the cells were recovered using PBS and suspended in 400 µl of Stempro medium. 100 µl of the concentrated viruses of pGCDN-IDH1/R132H-ires-NGFR was added to each well of a 24-well plate coated with RetroNectin (Takara Bio Inc.), and 400 µl of the cells was added to each well and cultured in an incubator. After half a day, viral infection of pMSCV-DNMT3A/R882H was carried out in the same way as above. After half a day, viral infection of pMSCV-FLT3/ITD was carried out in the same way as above to prepare transfected cells harboring the four types of genes.

The virus-infected cells were suspended in 600 µl of Stempro-34 solution. 300 µl of the cell suspension was intravenously injected to the tail of each of two mice exposed to radiation (950 Gy). Peripheral blood was collected every 4 weeks and analyzed by FACS for the expression of EGFP and NGFR. EGFP-positive cells are considered as AML cells. After confirmation of engraftment of the AML cells, bone marrow cells were recovered and suspended at 5×10$^6$ cells/ml in Bambanker (NIPPON Genetics Co., Ltd.) to stock the cells of the primary transplanted mice.

Secondary bone marrow transplantation and compound administration were carried out as follows: the bone marrow cells of each primary transplanted mouse were intravenously injected at 1×10$^5$ cells to the tail of each mouse exposed to radiation (600 Gy). When 4 weeks passed after the secondary transplantation, blood was collected from all of the mice, followed by the FACS analysis of peripheral blood cells. The mice were randomized so as not to offer a disproportionate proportion of EGFP-positive AML cells. When 6 weeks passed after the transplantation, the compounds of Examples 168 and 94 were each suspended at 7.5, 15, and 30 mg/mL (based on the free form) in 0.5% methylcellulose. Each suspension was administered at a dose of 10 mL/kg to the mice. The compound was administered a total of three times at intervals of twice a day. 6, 16, and 24 hours after the final administration, plasma and bone marrow cells were recovered. 80 µL of water was added to 20 µL of the plasma to prepare 100 µL of a solution. 1×10$^6$ bone marrow cells were suspended in 100 µL of PBS. 400 µL of ethanol was added to 100 µL of the solution of the plasma or the bone marrow and mixed therewith, followed by incubation at −20° C. for 1 hour. Then, 300 µL of water was further added thereto. After centrifugation at 15000 rpm at 4° C. for 20 minutes, the supernatants were recovered and preserved at −20° C.

The preserved solutions were treated in the same way as in Test Example 2, and 2-HG was measured.

As shown in FIG. 1, the 2-HG concentration in the plasma and the 2-HG level in the bone marrow cells were remarkably decreased as a result of administering each of the compounds of Examples 168 and 94.

Test Example 7

Measurement of Antitumor Activity Against AML Mouse Model Harboring 4 Genes Including IDH1R132H Feed supplemented with the compound of Example 94 was based on CRF-1 (Oriental Yeast Co., Ltd.) and prepared (Oriental Yeast Co., Ltd.) by adding the compound at a ratio of 0.3% (weight ratio of the free form).

The bone marrow cells of each primary transplanted mouse established in Test Example 6 were intravenously injected at 1×10$^5$ cells to the tail of each mouse exposed to radiation (600 Gy). At 6 weeks after the transplantation, the bone marrow cells of some mice were recovered to confirm the proportion of EGFP-positive AML cells. 80% of the bone marrow cells on average were EGFP-positive. Thus, the transplanted cells were confirmed to increase sufficiently in the bone marrow.

At 8 weeks after the transplantation, blood was collected from all of the mice, followed by the FACS analysis of peripheral blood cells. The mice were randomized (4 mice for control feed and 4 mice for administration of feed supplemented with the compound of Example 94) so as not to offer a disproportionate proportion of EGFP-positive AML cells. The administration of mixed feed was started using the feed supplemented with the compound of Example 94.

After the administration of the mixed feed for 4 weeks, peripheral blood and bone marrow cells were recovered from each mouse and subjected to FACS analysis. The proportion of EGFP signal-positive AML cells was detected.

Figure 2:
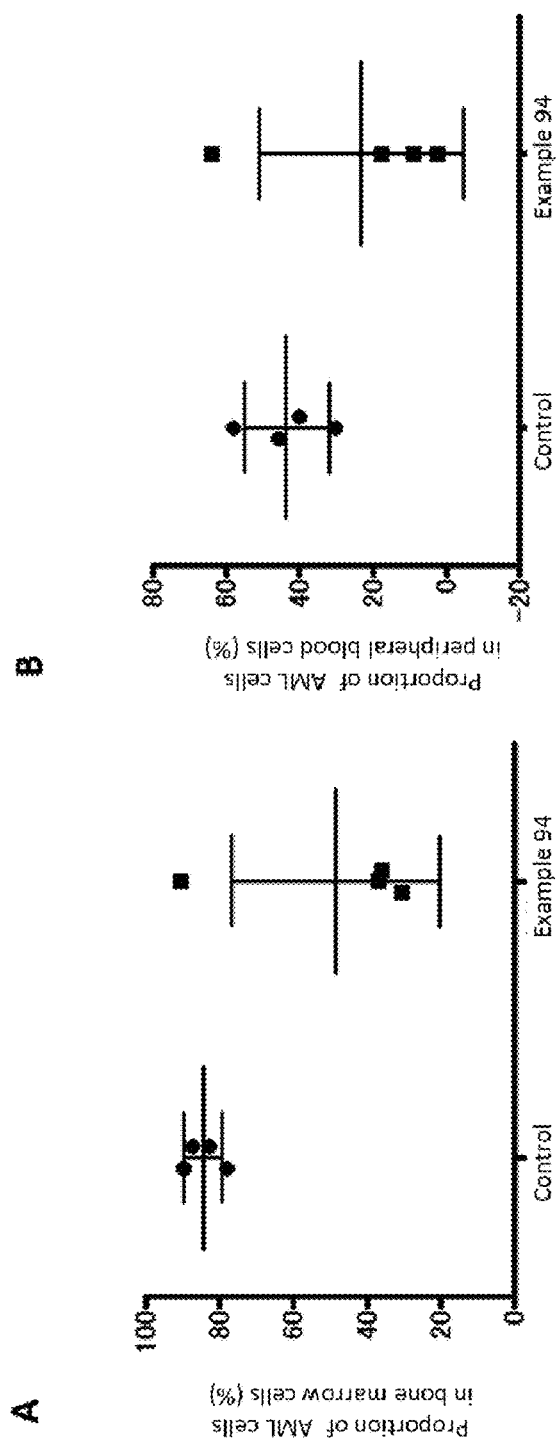
FIG. 2 is a graph showing the results of measuring the antitumor activity of compounds of the present invention in acute myeloid leukemia (AML) mouse models harboring 4 genes including IDH1R132H.

As shown in FIG. 2, it was revealed that the proportion of the EGFP-positive AML cells in the bone marrow and in the peripheral blood was drastically decreased in 3 out of the 4 mice as a result of administering the mixed feed supplemented with the compound of Example 94 for 4 weeks.

Test Example 8

Measurement of Antitumor Activity Against IDH1/R132H Mutant Glioblastoma A1074-Transplanted Mouse Model A subcultured specimen (A1074) of a mouse subcutaneous graft of IDH1/R132H mutant human glioblastoma kindly provided by professor Peter Collins (Department of Pathology, University of Cambridge) was quickly thawed in a water bath of 37° C. according to the method described in the literature (Goike H M: Cryopreservation of viable human glioblastoma xenografts. Neuropathol. Appl. Neurobiol. 26: 172-176, 2000) and diced into 5 mm pieces containing the margin of a tumor mass and the central portion using a surgical knife. Then, these pieces were subcutaneously transplanted to the flank of NOD/SCID mice. When the size of the tumor mass became 1 cm, each mouse was euthanized by cervical dislocation, and the tumor was excised, then transplanted to NOG mice (Central Institute for Experimental Animals), and maintained to establish A1074-transplanted mouse models.

The 5 mm piece divided from the A1074 tumor was subcutaneously transplanted to a flank of each of 15 NOG mice. The tumor size was appropriately measured using calipers. The tumor volume (mm$^3$) was calculated according to the expression (tumor length)×(tumor width)$^2$/2 and used for the confirmation of the growth growth and drug efficacy.

After a lapse of 4 weeks from the transplantation, the mice were divided into 3 groups each involving 5 mice. Then, mixed feed was administered to each group for 4 weeks using feed supplemented with the compound of Example 168, feed supplemented with the compound of Example 94, and control feed. The feed supplemented with each compound was based on CRF-1 (Oriental Yeast Co., Ltd.) and prepared (Oriental Yeast Co., Ltd.) by adding the compound at a ratio of 0.3% (weight ratio of the free form). After the administration of the mixed feed for 4 weeks, each mouse was euthanized by cervical dislocation. The tumor mass was excised, and its weight was measured.

Figure 3:
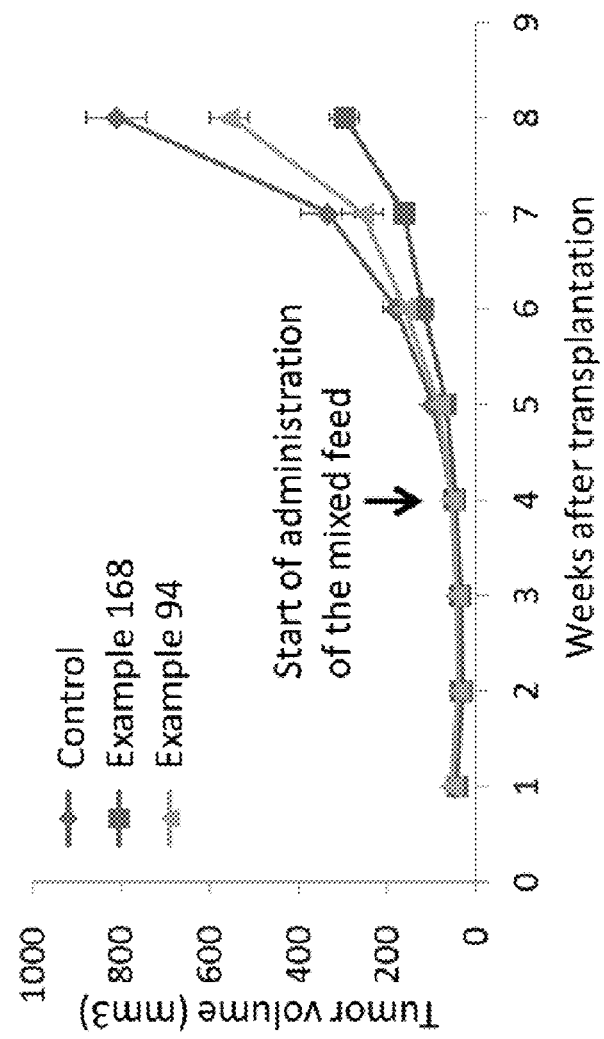
FIG. 3 is a graph showing the results of measuring the antitumor activity of compounds of the present invention in IDH1/R132H mutant glioblastoma A1074-transplanted mouse models. The mean and standard deviation of tumor volumes of each group in this test are shown.
Figure 4:
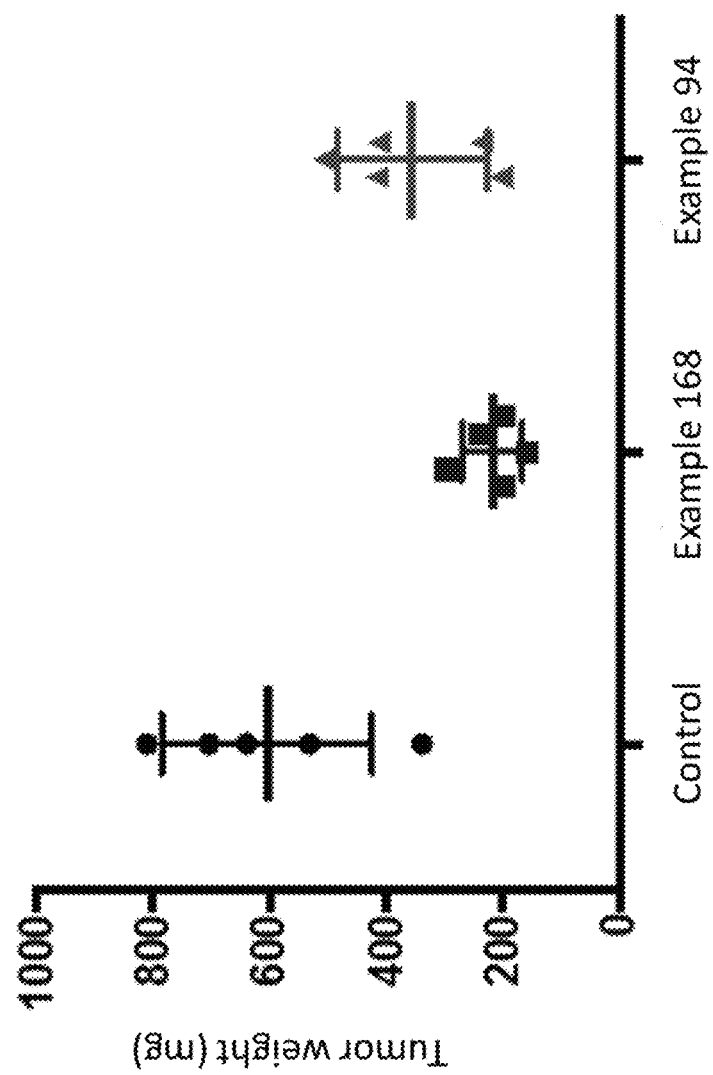
FIG. 4 is a graph showing the results of measuring the antitumor activity of compounds of the present invention in IDH1/R132H mutant glioblastoma A1074-transplanted mouse models. The tumor weights after administration of mixed feed for 4 weeks are shown.

The mean and standard deviation of the tumor volumes of each group in this test are shown in FIG. 3. The tumor weights after the administration of the mixed feed for 4 weeks are shown in FIG. 4. In this experiment, the compound of Example 168 and the compound of Example 94 were found to inhibit tumor growth.

INDUSTRIAL APPLICABILITY

The compound of the present invention or a pharmaceutically acceptable salt thereof can inhibit the growth of a tumor expressing mutant IDH1 protein and as such, can be used particularly as an antitumor agent in the medical field. Also, the compound of the present invention or a pharmaceutically acceptable salt thereof can be used for the purpose of research as a reagent for inhibiting the activity of the mutant IDH1 protein.

The invention claimed is:

1. A compound represented by the general formula (I) or a pharmaceutically acceptable salt thereof:

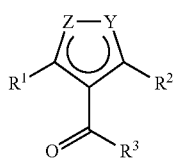
(I)

wherein

Z—Y represents N—O or O—N;

$R^1$ represents a phenyl group optionally having 1 to 3 substituents independently selected from the following group A, or a pyridyl group optionally having 1 to 3 substituents independently selected from the following group A;

$R^2$ represents —$NR^{21}R^{22}$, a $C_1$ to $C_6$ alkyl group optionally having 1 to 3 substituents independently selected from the following group B, a $C_3$ to $C_6$ cycloalkyl group optionally having 1 to 3 substituents independently selected from the following group C, or a 4- to 6-membered heterocyclic group having 1 or 2 heteroatoms independently selected from the group consisting of a nitrogen atom and an oxygen atom in the ring, wherein the 4- to 6-membered heterocyclic group optionally has 1 to 3 substituents independently selected from the following group C, and a bridged structure is optionally bonded within the heterocyclic ring, or one $C_3$ to $C_6$ cycloalkyl ring is optionally bonded onto the heterocyclic ring via a spiro bond;

$R^{21}$ and $R^{22}$ each independently represent a hydrogen atom, a $C_1$ to $C_6$ alkyl group, or —C(=O)$R^{23}$;

$R^{23}$ represents a $C_2$ to $C_6$ alkenyl group or a $C_2$ to $C_6$ alkynyl group;

$R^3$ represents any of the following formulae (II) to (IV):

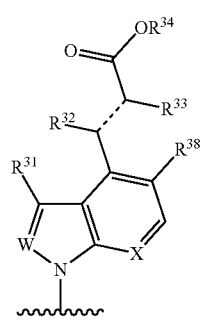
(II)

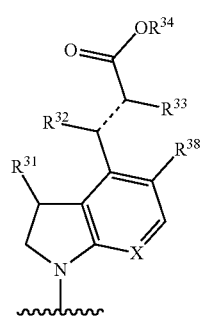
(III)

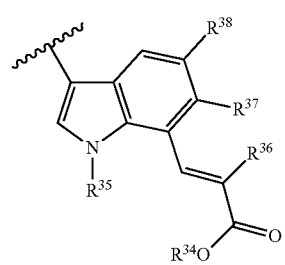
(IV)

wherein $R^{31}$ represents a hydrogen atom, a halogen atom, a $C_1$ to $C_6$ alkyl group optionally substituted by 1 to 3 halogen atoms, a $C_3$ to $C_6$ cycloalkyl group, or a $C_1$ to $C_6$ alkylcarbonyl group, $R^{32}$ represents a hydrogen atom or a $C_1$ to $C_6$ alkyl group, or $R^{31}$ and $R^{32}$ optionally together form a cyclohexane ring, $R^{33}$ represents a hydrogen atom or a $C_1$ to $C_6$ alkyl group, or $R^{32}$ and $R^{33}$ optionally together form a cyclopropane ring, $R^{34}$ represents a hydrogen atom or a $C_1$ to $C_6$ alkyl group, $R^{35}$ represents a $C_1$ to $C_6$ alkyl group, $R^{36}$ represents a hydrogen atom or a $C_1$ to $C_6$ alkyl group, $R^{37}$ represents a hydrogen atom or a $C_1$ to $C_6$ alkyl group, or $R^{36}$ and $R^{37}$ optionally together form a benzene ring, $R^{38}$ represents a hydrogen atom or a halogen atom, X represents a nitrogen atom or CH, W represents a nitrogen atom or CH, and the broken line represents a single bond or a double bond;

group A consists of a halogen atom, a $C_1$ to $C_6$ alkyl group and a $C_1$ to $C_6$ alkoxy group;

group B consists of a halogen atom, a hydroxy group, a $C_1$ to $C_6$ alkoxy group, a $C_1$ to $C_6$ alkylamino group, and a di-$C_1$ to $C_6$ alkylamino group, group C consists of a $C_2$ to $C_6$ alkenyl group, a halogen atom, a hydroxy group, a cyano group, a $C_1$ to $C_6$ alkyl group optionally having 1 to 3 substituents independently selected from the following group D, a $C_1$ to $C_6$ alkoxy group, $-NR^{211}R^{212}$, $-C(=O)R^{213}$, and $-SO_2R^{213}$;

$R^{211}$ and $R^{212}$ each independently represent a hydrogen atom or a $C_1$ to $C_6$ alkyl group;

$R^{213}$ represents a $C_2$ to $C_6$ alkenyl group or a $C_2$ to $C_6$ alkynyl group; and group D consists of an amino group, a $C_1$ to $C_6$ alkoxy group, a di-$C_1$ to $C_6$ alkylamino group, an oxo group, and a $C_3$ to $C_6$ cycloalkyl group.

2. A compound according to claim 1 or a pharmaceutically acceptable salt thereof, wherein in the formula (I), $R^1$ represents a phenyl group optionally having 1 to 3 substituents independently selected from the group A.

3. A compound according to claim 1 or a pharmaceutically acceptable salt thereof, wherein in the formula (I), $R^2$ represents a $C_1$ to $C_6$ alkyl group optionally having 1 to 3 substituents independently selected from the group B, or a 4- to 6-membered aliphatic heterocyclic group having 1 or 2 heteroatoms independently selected from the group consisting of a nitrogen atom and an oxygen atom in the ring, wherein the 4- to 6-membered aliphatic heterocyclic group optionally has 1 to 3 substituents independently selected from the group C.

4. A compound according to any one of claims 1 or a pharmaceutically acceptable salt thereof, wherein in the formula (I), $R^2$ represents any of the following formulae:

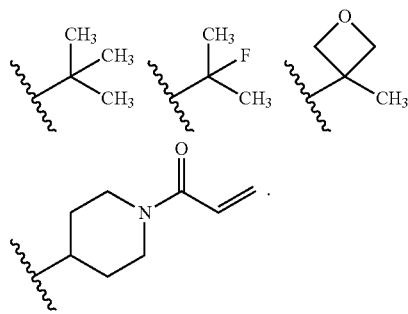

5. A compound according to any one of claims 1 or a pharmaceutically acceptable salt thereof, wherein in the formula (I), $R^3$ represents the following formula (IV) or (V):

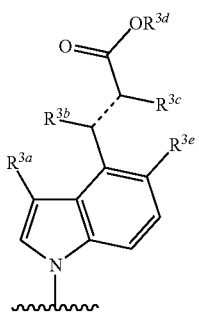
(IV)

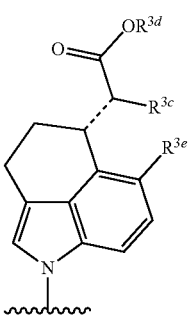
(V)

wherein $R^{3a}$ represents a hydrogen atom or a $C_1$ to $C_6$ alkyl group optionally substituted by 1 to 3 halogen atoms, $R^{3b}$ represents a hydrogen atom or a $C_1$ to $C_6$ alkyl group, $R^{3c}$ represents a hydrogen atom or a $C_1$ to $C_6$ alkyl group, $R^{3d}$ represents a hydrogen atom or a $C_1$ to $C_6$ alkyl group, $R^{3e}$ represents a hydrogen atom or a halogen atom, and the broken line represents a single bond or a double bond.

6. A compound according to any one of claims 1 or a pharmaceutically acceptable salt thereof, wherein in the formula (I), $R^3$ represents any of the following formulae:

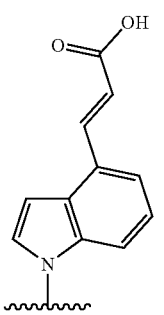

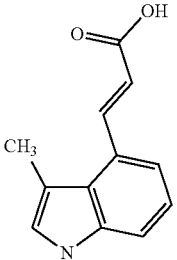

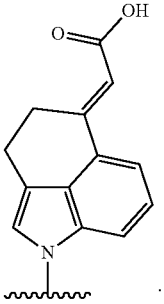

7. A compound represented by the general formula VI or a pharmaceutically acceptable salt thereof:

(VI)

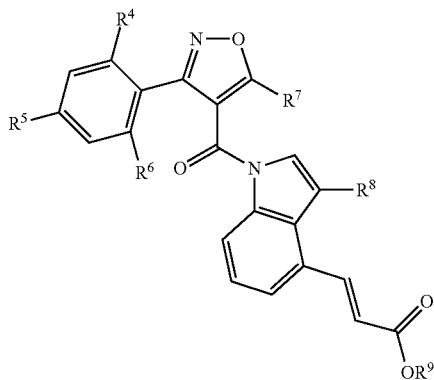

wherein

R⁴, R⁵, and R⁶ each independently represent a hydrogen atom or a halogen atom,

R⁷ represents any of the following formulae:

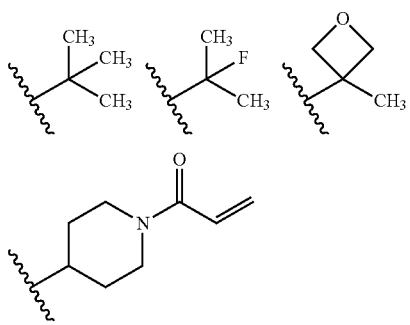

and

R⁸ and R⁹ each independently represent a hydrogen atom or a $C_1$ to $C_6$ alkyl group.

8. A compound represented by the general formula VII or a pharmaceutically acceptable salt thereof:

(VII)

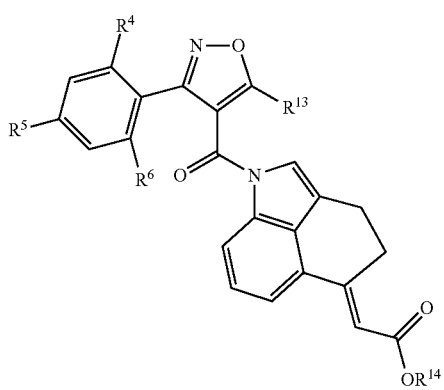

wherein $R^{10}$, $R^{11}$, and $R^{12}$ each independently represent a hydrogen atom or a halogen atom, $R^{13}$ represents any of the following formulae:

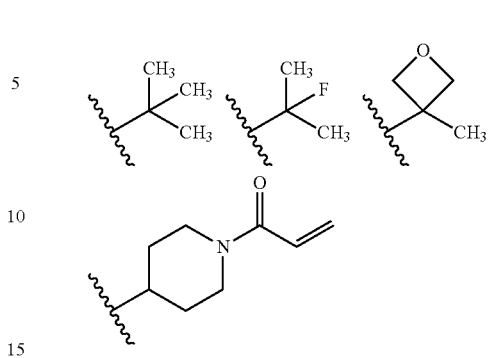

and $R^{14}$ each independently represents a hydrogen atom or a $C_1$ to $C_6$ alkyl group.

9. A compound selected from the following group or a pharmaceutically acceptable salt thereof:

(2E)-3-(1-{[5-(3-methyloxetan-3-yl)-3-(2,4,6-trichlorophenyl)-1,2-oxazol-4-yl]carbonyl}-1H-indol-4-yl)prop-2-enoic acid, (2E)-3-(1-{[5-(2-fluoropropan-2-yl)-3-(2,4,6-trichlorophenyl)-1,2-oxazol-4-yl]carbonyl}-3-methyl-1H-indol-4-yl)prop-2-enoic acid, (2E)-3-(1-{[5-(tert-butyl)-3-(2,4,6-trichlorophenyl)-1,2-oxazol-4-yl]carbonyl}-1H-indol-4-yl)prop-2-enoic acid, (2E)-3-(1-{[3-(2,4-dichloro-6-fluorophenyl)-5-(2-fluoropropan-2-yl)-1,2-oxazol-4-yl]carbonyl}-3-methyl-1H-indol-4-yl)prop-2-enoic acid, (2E)-3-(1-{[3-(2,4-dichlorophenyl)-5-(2-fluoropropan-2-yl)-1,2-oxazol-4-yl]carbonyl}-3-methyl-1H-indol-4-yl)prop-2-enoic acid, (2E)-[1-{[5-(1-acryloylpiperidin-4-yl)-3-(2,4,6-trichlorophenyl)-1,2-oxazol-4-yl]carbonyl}-3,4-dihydrobenzo[cd]indol-5(1H)-ylidene]ethanoic acid, (2E)-3-(1-{[5-(1-acryloylpiperidin-4-yl)-3-(2,4,6-trichlorophenyl)-1,2-oxazol-4-yl]carbonyl}-3-methyl-1H-indol-4-yl)prop-2-enoic acid, (2E)-[1-{[5-(1-acryloylpiperidin-4-yl)-3-(2,4-dichloro-6-fluorophenyl)-1,2-oxazol-4-yl]carbonyl}-3,4-dihydrobenzo[cd]indol-5(1H)-ylidene]ethanoic acid, (2E)-[1-{[5-(1-acryloylpiperidin-4-yl)-3-(2,4-dichloro-5-fluorophenyl)-1,2-oxazol-4-yl]carbonyl}-3,4-dihydrobenzo[cd]indol-5(1H)-ylidene]ethanoic acid, and (2E)-[1-{[5-(1-acryloylpiperidin-4-yl)-3-(2,4-dichlorophenyl)-1,2-oxazol-4-yl]carbonyl}-3,4-dihydrobenzo[cd]indol-5(1H)-ylidene]ethanoic acid.

10. (2E)-3-(1-{[5-(2-Fluoropropan-2-yl)-3-(2,4,6-trichlorophenyl)-1,2-oxazol-4-yl]carbonyl}-3-methyl-1H-indol-4-yl)prop-2-enoic acid or a pharmaceutically acceptable salt thereof.

11. (2E)-3-(1-{[5-(2-Fluoropropan-2-yl)-3-(2,4,6-trichlorophenyl)-1,2-oxazol-4-yl]carbonyl}-3-methyl-1H-indol-4-yl)prop-2-enoic acid tert-butylamine salt.

12. (2E)-[1-{[5-(1-Acryloylpiperidin-4-yl)-3-(2,4,6-trichlorophenyl)-1,2-oxazol-4-yl]carbonyl}-3,4-dihydrobenzo[cd]indol-5(1H)-ylidene]ethanoic acid or a pharmaceutically acceptable salt thereof.

13. (2E)-[1-{[5-(1-Acryloylpiperidin-4-yl)-3-(2,4,6-trichlorophenyl)-1,2-oxazol-4-yl]carbonyl}-3,4-dihydrobenzo[cd]indol-5(1H)-ylidene]ethanoic acid tert-butylamine salt.

14. A pharmaceutical composition comprising a compound according to claim 1 or a pharmaceutically acceptable salt thereof as an active ingredient.

15. A method for treating a tumor having an isocitrate dehydrogenase 1 gene mutation, comprising administering to subject in need thereof a therapeutically effective amount of a compound according to claim 1 or a pharmaceutically acceptable salt thereof, wherein the tumor is glioma, acute myeloid leukemia, myelodysplastic syndrome, myeloproliferative tumor, peripheral T-cell lymphoma, chondrosarcoma, osteosarcoma, bile duct cancer, primitive neuroectodermal tumor, B-cell lymphoblastic lymphoma, malignant melanoma, prostate cancer, colorectal cancer, or thyroidal cancer.

* * * * *

UNITED STATES PATENT AND TRADEMARK OFFICE
CERTIFICATE OF CORRECTION

PATENT NO. : 10,040,791 B2
APPLICATION NO. : 15/516362
DATED : August 7, 2018
INVENTOR(S) : S. Saito et al.

It is certified that error appears in the above-identified patent and that said Letters Patent is hereby corrected as shown below:

In the Claims

| Column | Line | Error |
| --- | --- | --- |
| 295 (Claim 4, Line 1) | 30 | "to any one of claims" should read --to claim-- |
| 295 (Claim 5, Line 1) | 49 | "to any one of claims" should read --to claim-- |
| 296 (Claim 6, Line 1) | 24 | "to any one of claims" should read --to claim-- |
| 296 (Claim 7, Line 1) | 66 | "the general formula" should read --the formula-- |
| 297 (Claim 8, Line 1) | 44 | "the general formula" should read --the formula-- |

Signed and Sealed this
Sixth Day of November, 2018

Andrei Iancu
*Director of the United States Patent and Trademark Office*

CERTIFICATE OF CORRECTION (continued)
U.S. Pat. No. 10,040,791 B2

| 297 (Claim 8, Line 3) | 50 | "Formula (VII) 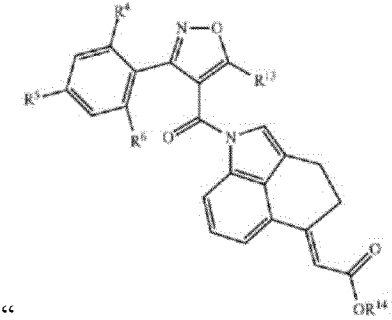 " should read -- 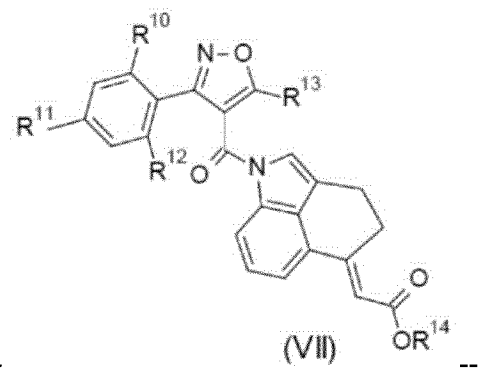 -- |
|---|---|---|
| 298 (Claim 8, Line 8) | 18 | "R14 each independently represents" should read --R14 represents-- |